(12) United States Patent
Ervasti et al.

(10) Patent No.: US 7,863,017 B2
(45) Date of Patent: Jan. 4, 2011

(54) TAT-UTROPHIN AS A PROTEIN THERAPY FOR DYSTROPHINOPATHIES

(75) Inventors: James M. Ervasti, Shoreview, MN (US); Kevin J. Sonnemann, Minneapolis, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 89 days.

(21) Appl. No.: 11/998,798

(22) Filed: Nov. 30, 2007

(65) Prior Publication Data

US 2009/0054327 A1 Feb. 26, 2009

Related U.S. Application Data

(60) Provisional application No. 60/868,119, filed on Dec. 1, 2006.

(51) Int. Cl.
*C07K 19/00* (2006.01)
*C12N 15/62* (2006.01)

(52) U.S. Cl. .......................... 435/69.7; 514/2; 530/350; 536/23.4

(58) Field of Classification Search ........................ None
See application file for complete search history.

(56) References Cited

U.S. PATENT DOCUMENTS

| | | | | |
|---|---|---|---|---|
| 5,011,912 A * | 4/1991 | Hopp et al. | ............... | 530/387.9 |
| 2002/0192710 A1 | 12/2002 | Kaufman | | |
| 2005/0069985 A1 | 3/2005 | Kaufman | | |
| 2005/0158281 A1* | 7/2005 | Chamberlain et al. | ...... | 424/93.2 |
| 2006/0073586 A1 | 4/2006 | Xiao | | |

OTHER PUBLICATIONS

Schwarze et al., In Vivo Protein Transduction: Delivery of a Biologically Active Protein into the Mouse, Sep. 3, 1999, Science 285:1569-1572.*
Rybakova et al. Utropin Binds Laterally along Actin Filaments and Can Couple Costameric Actin with Sarcolemma When Overexpressed in Dystrophin-deficient Muscle, May 2002, Molecular Biology of the Cell 13:1512-1521.*
Sonnemannetal. Functional Substitution by TAT-Utrophin in Dystrophin-Deficient Mice, May 2009, PLoS Medicine 6(5):e1000083, pp. 1-10.*
Amann et al. (1999). Utrophin lacks the rod domain actin binding activity of dystrophin. *J. Biol. Chem.* 274:35375-35380.
Amann et al. (1998). A cluster of basic repeats in the dystrophin rod domain binds F-actin through an electrostatic interaction. *J. Biol. Chem.* 273:28419-28423.
Barchi et al. (1979). Characteristics of saxitoxin binding to the sodium channel of sarcolemma isolated from rat skeletal muscle. *J. Physiol.* 295:383-396.
Blake et al. (1996). Utrophin: A structural and functional comparison to dystrophin. *Brain Pathol.* 6:37-47.
Deconinck et al. (1997a). Utrophin-dystrophin-deficient mice as a model for Duchenne muscular dystrophy. *Cell* 90:717-727.

Deconinck et al. (1997b). Expression of truncated utrophin leads to major functional improvements in dystrophin-deficient muscles of mice. *Nature Med.* 3:1216-1221.
Eddinger et al. (1986). Mechanical and histochemical characterization of skeletal muscles from senescent rats. *Am. J. Physiol.* 251:C421-C430.
Ervasti et al. (1991). Purification of dystrophin from skeletal muscle. *J. Biol. Chem.* 266:9161-9165.
Gregorevic et al. (2003). Gene therapy for muscular dystrophy—a review of promising progress. *Expert. Opin. Biol. Ther.* 3:803-814.
Guo et al. (1996). Cloning and expression of full length mouse utrophin: The differential association of utrophin and dystrophin with AChR clusters. *FEBS Lett.* 398:259-264.
Hoffman et al. (1987). Dystrophin: the protein product of the Duchenne muscular dystrophy locus. *Cell* 51:919-928.
Ishikawa-Sakurai et al. (2004). ZZ domain is essentially required for the physiological binding of dystrophin and utrophin to beta-dystroglycan. *Hum. Mol. Genet.* 13:693-702.
Kramarcy et al. (1994). Association of utrophin and multiple dystrophin short forms with the mammalian $M_r$ 58,000 dystrophin-associated protein (syntrophin). *J. Biol. Chem.* 269:2870-2876.
Kuppuswamy et al. (1989). Multiple functional domains of Tat, the trans-activator of HIV-1, defined by mutational analysis. *Nucleic Acids Research,* 17(9):3551-3561.
Lindsay, M.A. (2002). Peptide-mediated cell delivery: application in protein target validation. *Curr. Opin. Pharmacol.* 2:587-594.
Marriott et al. (1988). Spectroscopic and functional characterization of an environmentally sensitive fluorescent actin conjugate. *Biochemistry* 27:6214-6220.
Matsumura et al. (1992). Association of dystrophin-related protein with dystrophin-associated proteins in *mdx* mouse muscle. *Nature* 360:588-591.
Miyata et al. (1997). Cooperative association of actin protomers and crosslinked actin oligomers in filaments at low ionic strength. *J. Biochem.* (Tokyo) 121:527-533.
Moens et al. (1993). Increased susceptibility of EDL muscles from mdx mice to damage induced by contractions with stretch. *J. Muscle Res. Cell Motil.* 14:446-451.
Petrof et al. (1993). Dystrophin protects the sarcolemma from stresses developed during muscle contraction. *Proc. Natl. Acad. Sci. U.S.A.* 90:3710-3714.
Rybakova et al. (1996). A new model for the interaction of dystrophin with F-actin. *J. Cell Biol.* 135:661-672.

(Continued)

*Primary Examiner*—John D Ulm
(74) *Attorney, Agent, or Firm*—Joseph T. Leone, Esq.; DeWitt Ross & Stevens S.C.

(57) ABSTRACT

Disclosed is a fusion protein including a full-length TAT-utrophin or an anti-dystrophinopathic fragment thereof, a method of treating dystrophinopathies (including Duchenne muscular dystrophy) using the fusion protein, a pharmaceutical composition for treating dystrophinopathies in mammals comprising the fusion protein, and nucleic acid constructs for expressing the fusion protein.

35 Claims, 12 Drawing Sheets

OTHER PUBLICATIONS

Rybakova et al. (1997). Dystrophin-glycoprotein complex is monomeric and stabilizes actin filaments in vitro through a lateral association. *J. Biol. Chem.* 272:28771-28778.

Rybakova et al. (2006) Dystrophin and utrophin bind actin through distinct modes of contact. *J. Biol Chem.* 281 (15): 9996-10001.

Snyder et al. (2004). Cell penetrating peptides in drug delivery. *Pharm. Res.* 21:389-393.

Tinsley et al. (1998). Expression of full-length utrophin prevents muscular dystrophy in *mdx* mice. *Nature Med.* 4:1441-1444.

Tinsley et al. (1992). Primary structure of dystrophin-related protein. *Nature* 360:591-593.

Winder et al. (1995). Utrophin actin binding domain: analysis of actin binding and cellular targeting. *J. Cell Sci.* 108:63-71.

* cited by examiner

| $K_d$ (μM) | $B_{max}$ | Protect? | Protein |
|---|---|---|---|
| 0.2 | 1:14 | Yes | rUTR |
| 0.6 | 1:12 | Yes | UTRN-R10 |
| 1.4 | 1:10 | Yes | UTRN-R9 |
| 1.5 | 1:5 | Partial | UTRN-R6 |
| 2 | 1:3 | No | UTRN-R3 |
| 16 | 1:1 | No | UTR261 |
| No Binding Activity | | | UTRR1-R10 |

FIG. 2

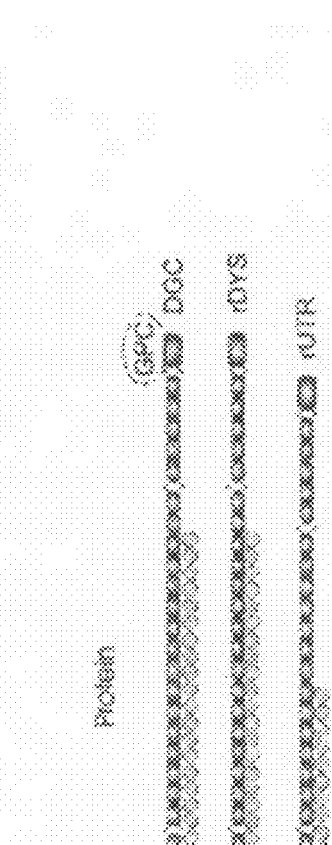
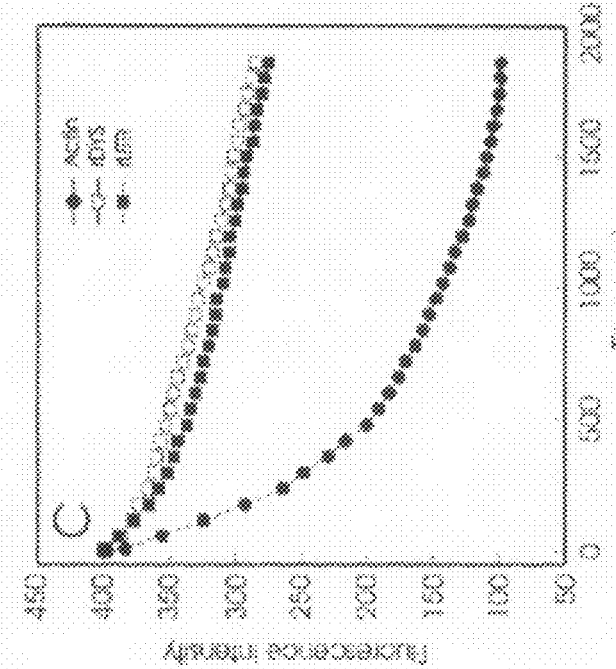
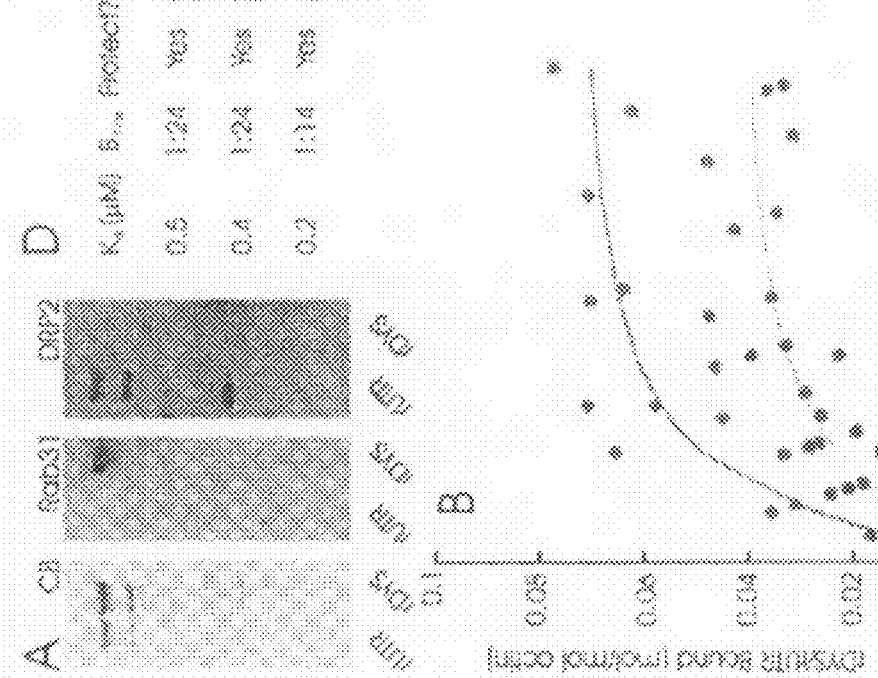
FIG. 3A  FIG. 3B  FIG. 3C  FIG. 3D

| Line/Protein | % Total Protein | % Dys |
|---|---|---|
| WT/Dystrophin | 0.02 | 100 |
| WT/Utrophin | 0.0006 | 3 |
| mdx/Utrophin | 0.0013 | 7 |
| Fiona/Utrophin | 0.014 | 70 |

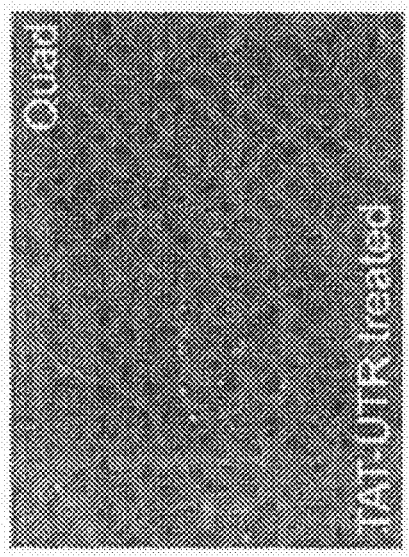
FIG. 7B
FIG. 7C
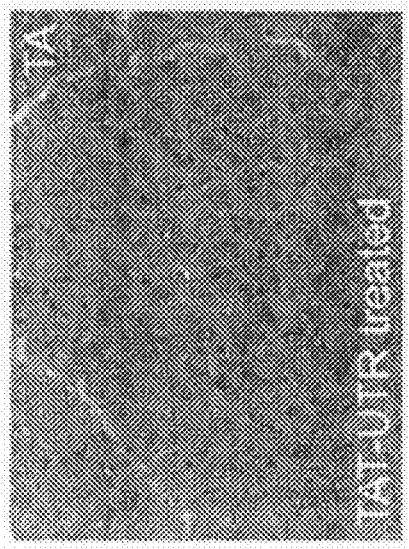
FIG. 7B
FIG. 7E
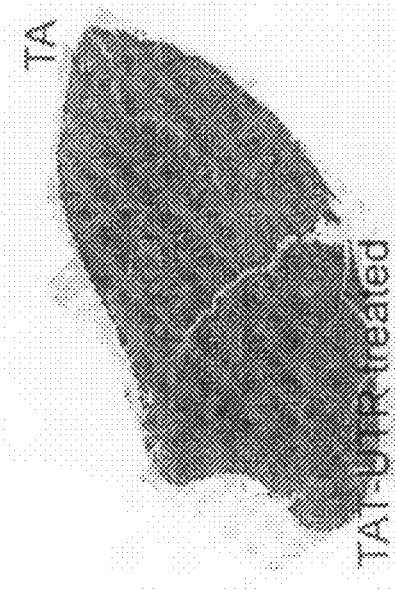
FIG. 7A
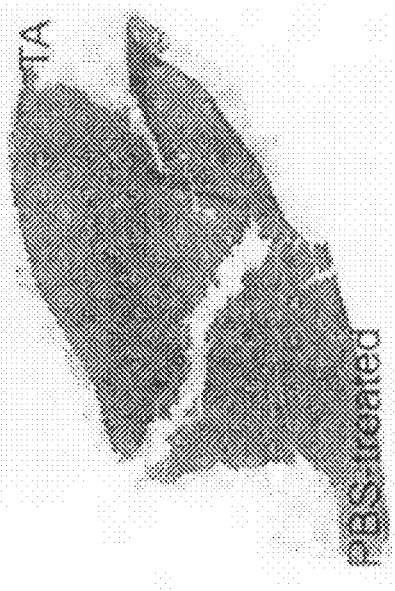
FIG. 7D
FIG. 7F

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Synthetic "FLAG"-type polypeptide binding tag

<400> SEQUENCE: 1

Asp Tyr Lys Asp Asp Asp Asp Lys
1               5

<210> SEQ ID NO 2
<211> LENGTH: 86
<212> TYPE: PRT
<213> ORGANISM: Human immunodeficiency virus type 1
<220> FEATURE:
<221> NAME/KEY: MISC_FEATURE
<222> LOCATION: (47)..(57)
<223> OTHER INFORMATION: Protein Transduction Sequence

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 3
<211> LENGTH: 9181
<212> TYPE: DNA
<213> ORGANISM: Human immunodeficiency virus type 1
<220> FEATURE:
<221> NAME/KEY: gene
<222> LOCATION: (5377)..(5591)
<220> FEATURE:
<221> NAME/KEY: gene
<222> LOCATION: (7925)..(7970)
```

<400> SEQUENCE: 3

```
ggtctctctg gttagaccag atctgagcct gggagctctc tggctaacta gggaacccac    60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca   180
gtggcgcccg aacagggacc tgaaagcgaa agggaaacca gaggagctct ctcgacgcag   240
gactcggctt gctgaagcgc gcacggcaag aggcgagggg cggcgactgg tgagtacgcc   300
aaaaattttg actagcggag gctagaagga gagagatggg tgcgagagcg tcagtattaa   360
gcggggagaa attagatcga tgggaaaaaa ttcggttaag gccaggggga aagaaaaaat   420
ataaattaaa acatatagta tgggcaagca gggagctaga acgattcgca gttaatcctg   480
gcctgttaga acatcagaa ggctgtagac aaatactggg acagctacaa ccatcccttc    540
agacaggatc agaagaactt agatcattat ataatacagt agcaaccctc tattgtgtgc   600
atcaaaggat agagataaaa gacaccaagg aagctttaga caagatagag gaagagcaaa   660
acaaaagtaa gaaaaaagca cagcaagcag cagctgacac aggacacagc aatcaggtca   720
gccaaaatta ccctatagtg cagaacatcc aggggcaaat ggtacatcag gccatatcac   780
ctagaacttt aaatgcatgg gtaaaagtag tagaagagaa ggctttcagc ccagaagtga   840
tacccatgtt ttcagcatta tcagaaggag ccaccccaca gatttaaac accatgctaa    900
acacagtggg gggacatcaa gcagccatgc aaatgttaaa agagaccatc aatgaggaag   960
ctgcagaatg ggatagagtg catccagtgc atgcagggcc tattgcacca ggccagatga  1020
gagaaccaag gggaagtgac atagcaggaa ctactagtac ccttcaggaa caaataggat  1080
ggatgacaaa taatccacct atcccagtag gagaaattta aaagatgg ataatcctgg    1140
gattaaataa aatagtaaga atgtatagcc ctaccagcat tctggacata agacaaggac  1200
caaaggaacc ctttagagac tatgtagacc ggttctataa aactctaaga gccgagcaag  1260
cttcacagga ggtaaaaaat tggatgacag aaaccttgtt ggtccaaaat gcgaacccag  1320
attgtaagac tatttaaaa gcattgggac cagcggctac actagaagaa atgatgacag  1380
catgtcaggg agtaggagga cccggccata aggcaagagt tttggctgaa gcaatgagcc  1440
aagtaacaaa ttcagctacc ataatgatgc agagaggcaa ttttaggaac caaagaaaga  1500
ttgttaagtg tttcaattgt ggcaaagaag ggcacacagc cagaaattgc agggccccta  1560
ggaaaaaggg ctgttggaaa tgtggaaagg aaggacacca aatgaaagat tgtactgaga  1620
gacaggctaa ttttttaggg aagatctggc cttcctacaa gggaaggcca gggaattttc  1680
ttcagagcag accagagcca acagccccac cagaagagag cttcaggtct ggggtagaga  1740
caacaactcc ccctcagaag caggagccga tagacaagga actgtatcct ttaacttccc  1800
tcaggtcact ctttggcaac gacccctcgt cacaataaag atagggggggc aactaaagga  1860
agctctatta gatacaggag cagatgatac agtattagaa gaaatgagtt tgccaggaag  1920
atggaaacca aaaatgatag ggggaattgg aggttttatc aaagtaagac agtatgatca  1980
gatactcata gaaatctgtg gacataaagc tataggtaca gtattagtag gacctacacc  2040
tgtcaacata attggaagaa atctgttgac tcagattggt tgcactttaa attttcccat  2100
tagccctatt gagactgtac cagtaaaatt aaagccagga atggatggcc caaaagttaa  2160
acaatggcca ttgacagaag aaaaaataaa agcattagta gaaatttgta cagagatgga  2220
aaaggaaggg aaaatttcaa aaattgggcc tgaaaatcca tacaatactc cagtatttgc  2280
```

```
cataaagaaa aaagacagta ctaaatggag aaaattagta gatttcagag aacttaataa    2340
gagaactcaa gacttctggg aagttcaatt aggaatacca catcccgcag ggttaaaaaa    2400
gaaaaaatca gtaacagtac tggatgtggg tgatgcatat ttttcagttc ccttagatga    2460
agacttcagg aagtatactg catttaccat acctagtata aacaatgaga caccagggat    2520
tagatatcag tacaatgtgc ttccacaggg atggaaagga tcaccagcaa tattccaaag    2580
tagcatgaca aaaatcttag agccttttag aaaacaaaat ccagacatag ttatctatca    2640
atacatggat gatttgtatg taggatctga cttagaaata gggcagcata gaacaaaaat    2700
agaggagctg agacaacatc tgttgaggtg gggacttacc acaccagaca aaaaacatca    2760
gaaagaacct ccattccttt ggatgggtta tgaactccat cctgataaat ggacagtaca    2820
gcctatagtg ctgccagaaa aagacagctg gactgtcaat gacatacaga agttagtggg    2880
gaaattgaat tgggcaagtc agatttaccc agggattaaa gtaaggcaat tatgtaaact    2940
ccttagagga accaaagcac taacagaagt aataccacta acagaagaag cagagctaga    3000
actggcagaa aacagagaga ttctaaaaga accagtacat ggagtgtatt atgacccatc    3060
aaaagactta atagcagaaa tacagaagca ggggcaaggc caatggacat atcaaattta    3120
tcaagagcca tttaaaaatc tgaaaacagg aaaatatgca agaatgaggg gtgcccacac    3180
taatgatgta aaacaattaa cagaggcagt gcaaaaaata accacagaaa gcatagtaat    3240
atggggaaag actcctaaat ttaaactgcc catacaaaag gaaacatggg aaacatggtg    3300
gacagagtat tggcaagcca cctggattcc tgagtgggag tttgttaata cccctccctt    3360
agtgaaatta tggtaccagt tagagaaaga acccatagta ggagcagaaa ccttctatgt    3420
agatggggca gctaacaggg agactaaatt aggaaaagca ggatatgtta ctaatagagg    3480
aagacaaaaa gttgtcaccc taactgacac aacaaatcag aagactgagt tacaagcaat    3540
ttatctagct ttgcaggatt cgggattaga agtaaacata gtaacagact cacaatatgc    3600
attaggaatc attcaagcac aaccagatca aagtgaatca gagttagtca atcaaataat    3660
agagcagtta ataaaaaagg aaaaggtcta tctggcatgg gtaccagcac acaaaggaat    3720
tggaggaaat gaacaagtag ataaattagt cagtgctgga atcaggaaag tactattttt    3780
agatggaata gataaggccc aagatgaaca tgagaaatat cacagtaatt ggagagcaat    3840
ggctagtgat tttaacctgc cacctgtagt agcaaaagaa atagtagcca gctgtgataa    3900
atgtcagcta aaaggagaag ccatgcatgg acaagtagac tgtagtccag gaatatggca    3960
actagattgt acacatttag aaggaaaagt tatcctggta gcagttcatg tagccagtgg    4020
atatatagaa gcagaagtta ttccagcaga aacagggcag gaaacagcat attttctttt    4080
aaaattagca ggaagatggc cagtaaaaac aatacatact gacaatggca gcaatttcac    4140
cggtgctacg gttagggccg cctgttggtg ggcgggaatc aagcaggaat ttggaattcc    4200
ctacaatccc caaagtcaag gagtagtaga atctatgaat aaagaattaa agaaaattat    4260
aggacaggta agagatcagg ctgaacatct taagacagca gtacaaatgg cagtattcat    4320
ccacaatttt aaaagaaaag gggggattgg ggggtacagt gcaggggaaa gaatagtaga    4380
cataatagca acagacatac aaactaaaga attacaaaaa caaattacaa aaattcaaaa    4440
ttttcgggtt tattacaggg acagcagaaa tccactttgg aaaggaccag caaagctcct    4500
ctggaaaggt gaaggggcag tagtaataca agataatagt gacataaaag tagtgccaag    4560
aagaaaagca aagatcatta gggattatgg aaaacagatg gcaggtgatg attgtgtggc    4620
aagtagacag gatgaggatt agaacatgga aaagtttagt aaaacaccat atgtatgttt    4680
```

```
cagggaaagc tagggatgg ttttatagac atcactatga aagccctcat ccaagaataa    4740
gttcagaagt acacatccca ctaggggatg ctagattggt aataacaaca tattggggtc    4800
tgcatacagg agaaagagac tggcatttgg gtcagggagt ctccatagaa tggaggaaaa    4860
agagatatag cacacaagta gaccctgaac tagcagacca actaattcat ctgtattact    4920
ttgactgttt ttcagactct gctataagaa aggccttatt aggacacata gttagcccta    4980
ggtgtgaata tcaagcagga cataacaagg taggatctct acaatacttg cactagcag     5040
cattaataac accaaaaaag ataaagccac ctttgcctag tgttacgaaa ctgacagagg    5100
atagatggaa caagccccag aagaccaagg gccacagagg gagccacaca atgaatggac    5160
actgagagctt ttagaggagc ttaagaatga agctgttaga cattttccta ggatttggct   5220
ccatggctta gggcaacata tctatgaaac ttatggggat acttgggcag gagtggaagc    5280
cataataaga attctgcaac aactgctgtt tatccatttt cagaattggg tgtcgacata    5340
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca agtttgtttc ataacaaaag ccttaggcat ctcctatggc    5520
aggaagaagc ggagacagcg acgaagagct catcagaaca gtcagactca tcaagcttct    5580
ctatcaaagc agtaagtagt acatgtaatg caacctatac caatagtagc aatagtagca    5640
ttagtagtag caataataat agcaatagtt gtgtggtcca tagtaatcat agaatatagg    5700
aaaatattaa gacaaagaaa aatagacagg ttaattgata gactaataga aagagcagaa    5760
gacagtggca atgagagtga aggagaaata tcagcacttg tggagatggg ggtggagatg    5820
gggcaccatg ctccttggga tgttgatgat ctgtagtgct acagaaaaat tgtgggtcac    5880
agtctattat ggggtacctg tgtggaagga agcaaccacc actctatttt gtgcatcaga    5940
tgctaaagca tatgatacag aggtacataa tgtttgggcc acacatgcct gtgtacccac    6000
agacccccaac ccacaagaag tagtattggt aaatgtgaca gaaaatttta acatgtggaa   6060
aaatgacatg gtagaacaga tgcatgagga tataatcagt ttatgggatc aaagcctaaa    6120
gccatgtgta aaattaaccc cactctgtgt tagtttaaag tgcactgatt tgaagaatga    6180
tactaatacc aatagtagta gcgggagaat gataatggag aaaggagaga taaaaaactg    6240
ctctttcaat atcagcacaa gcataagagg taaggtgcag aaagaatatg catttttttta   6300
taaacttgat ataataccaa tagataatga tactaccagc tataagttga caagttgtaa    6360
cacctcagtc attacacagg cctgtccaaa ggtatccttt gagccaattc ccatacatta    6420
ttgtgccccg gctggttttg cgattctaaa atgtaataat aagacgttca atggaacagg    6480
accatgtaca aatgtcagca cagtacaatg tacacatgga attaggccag tagtatcaac    6540
tcaactgctg ttaaatggca gtctagcaga agaaggta gtaattagat ctgtcaattt      6600
cacggacaat gctaaaacca atatagtaca gctgaacaca tctgtagaaa ttaattgtac    6660
aagacccaac aacaatacaa gaaaagaat ccgtatccag agaggaccag ggagagcatt     6720
tgttacaata ggaaaaatag gaaatatgag acaagcacat tgtaacatta gtagagcaaa    6780
atggaataac actttaaaac agatagctag caaattaaga gaacaatttg gaaataataa    6840
aacaataatc tttaagcaat cctcaggagg ggacccagaa attgtaacgc acagttttaa    6900
ttgtggaggg gaattttct actgtaattc aacacaactg tttaatagta cttggtttaa     6960
tagtacttgg agtactgaag ggtcaaataa cactgaagga agtgacacaa tcaccctccc    7020
```

-continued

| | |
|---|---|
| atgcagaata aaacaaatta taaacatgtg gcagaaagta ggaaaagcaa tgtatgcccc | 7080 |
| tcccatcagt ggacaaatta gatgttcatc aaatattaca gggctgctat taacaagaga | 7140 |
| tggtggtaat agcaacaatg agtccgagat cttcagacct ggaggaggag atatgaggga | 7200 |
| caattggaga agtgaattat ataaatataa agtagtaaaa attgaaccat taggagtagc | 7260 |
| acccaccaag gcaaagagaa gagtggtgca gagagaaaaa agagcagtgg gaataggagc | 7320 |
| tttgttcctt gggttcttgg gagcagcagg aagcactatg ggcgcagcct caatgacgct | 7380 |
| gacggtacag gccagacaat tattgtctgg tatagtgcag cagcagaaca atttgctgag | 7440 |
| ggctattgag gcgcaacagc atctgttgca actcacagtc tggggcatca agcagctcca | 7500 |
| ggcaagaatc ctggctgtgg aaagatacct aaaggatcaa cagctcctgg ggatttgggg | 7560 |
| ttgctctgga aaactcattt gcaccactgc tgtgccttgg aatgctagtt ggagtaataa | 7620 |
| atctctggaa cagatttgga atcacacgac ctggatggag tgggacagag aaattaacaa | 7680 |
| ttacacaagc ttaatacact ccttaattga agaatcgcaa aaccagcaag aaaagaatga | 7740 |
| acaagaatta ttggaattag ataaatgggc aagtttgtgg aattggttta acataacaaa | 7800 |
| ttggctgtgg tatataaaat tattcataat gatagtagga ggcttggtag gtttaagaat | 7860 |
| agtttttgct gtactttcta tagtgaatag agttaggcag ggatattcac cattatcgtt | 7920 |
| tcagacccac ctcccaaccc cgaggggacc cgacaggccc gaaggaatag aagaagaagg | 7980 |
| tggagagaga gacagagaca gatccattcg attagtgaac ggatccttgg cacttatctg | 8040 |
| ggacgatctg cggagcctgt gcctcttcag ctaccaccgc ttgagagact tactcttgat | 8100 |
| tgtaacgagg attgtggaac ttctgggacg caggggtgg gaagccctca aatattggtg | 8160 |
| gaatctccta cagtattgga gtcaggaact aaagaatagt gctgttagct tgctcaatgc | 8220 |
| cacagccata gcagtagctg aggggacaga tagggttata gaagtagtac aaggagcttg | 8280 |
| tagagctatt cgccacatac ctagaagaat aagacagggc ttggaaagga ttttgctata | 8340 |
| agatgggtgg caagtggtca aaaagtagtg tgattggatg gcctactgta agggaaagaa | 8400 |
| tgagacgagc tgagccagca gcagataggg tgggagcagc atctcgagac ctggaaaaac | 8460 |
| atggagcaat cacaagtagc aatacagcag ctaccaatgc tgcttgtgcc tggctagaag | 8520 |
| cacaagagga ggaggaggtg ggttttccag tcacacctca ggtaccttta agaccaatga | 8580 |
| cttacaaggc agctgtagat cttagccact tttaaaaga aaaggggga ctggaagggc | 8640 |
| taattcactc ccaaagaaga caagatatcc ttgatctgtg gatctaccac acacaaggct | 8700 |
| acttccctga ttagcagaac tacacaccag gccagggt cagatatcca ctgacctttg | 8760 |
| gatggtgcta caagctagta ccagttgagc cagataagat agaagaggcc aataaaggag | 8820 |
| agaacaccag cttgttacac cctgtgagcc tgcatggat ggatgacccg gagagagaag | 8880 |
| tgttagagtg gaggtttgac agccgcctag catttcatca cgtggcccga gagctgcatc | 8940 |
| cggagtactt caagaactgc tgacatcgag cttgctacaa gggactttcc gctgggact | 9000 |
| ttccagggag gcgtggcctg ggcgggactg gggagtggcg agccctcaga tcctgcatat | 9060 |
| aagcagctgc ttttgcctg tactgggtct ctctggttag accagatctg agcctgggag | 9120 |
| ctctctggct aactagggaa cccactgctt aagcctcaat aaagcttgcc ttgagtgctt | 9180 |
| c | 9181 |

<210> SEQ ID NO 4
<211> LENGTH: 4776
<212> TYPE: DNA
<213> ORGANISM: Artificial Sequence
<220> FEATURE:
<223> OTHER INFORMATION: Plasmid pFastBac 1

<400> SEQUENCE: 4

| | | | | | |
|---|---|---|---|---|---:|
| gacgcgccct | gtagcggcgc | attaagcgcg | gcgggtgtgg | tggttacgcg | cagcgtgacc | 60 |
| gctacacttg | ccagcgccct | agcgcccgct | cctttcgctt | tcttcccttc | ctttctcgcc | 120 |
| acgttcgccg | gctttccccg | tcaagctcta | aatcggggc | tccctttagg | gttccgattt | 180 |
| agtgctttac | ggcacctcga | ccccaaaaaa | cttgattagg | gtgatggttc | acgtagtggg | 240 |
| ccatcgccct | gatagacggt | ttttcgccct | ttgacgttgg | agtccacgtt | ctttaatagt | 300 |
| ggactcttgt | tccaaactgg | aacaacactc | aaccctatct | cggtctattc | ttttgattta | 360 |
| taagggattt | tgccgatttc | ggcctattgg | ttaaaaaatg | agctgattta | acaaaaattt | 420 |
| aacgcgaatt | ttaacaaaat | attaacgttt | acaatttcag | gtggcacttt | tcggggaaat | 480 |
| gtgcgcggaa | cccctatttg | tttatttttc | taaatacatt | caaatatgta | tccgctcatg | 540 |
| agacaataac | cctgataaat | gcttcaataa | tattgaaaaa | ggaagagtat | gagtattcaa | 600 |
| catttccgtg | tcgcccttat | tcccttttt | gcggcatttt | gccttcctgt | ttttgctcac | 660 |
| ccagaaacgc | tggtgaaagt | aaaagatgct | gaagatcagt | tgggtgcacg | agtgggttac | 720 |
| atcgaactgg | atctcaacag | cggtaagatc | cttgagagtt | ttcgccccga | agaacgtttt | 780 |
| ccaatgatga | gcacttttaa | agttctgcta | tgtggcgcgg | tattatcccg | tattgacgcc | 840 |
| gggcaagagc | aactcggtcg | ccgcatacac | tattctcaga | atgacttggt | tgagtactca | 900 |
| ccagtcacag | aaaagcatct | tacgatggc | atgacagtaa | agaattatg | cagtgctgcc | 960 |
| ataaccatga | gtgataacac | tgcggccaac | ttacttctga | caacgatcgg | aggaccgaag | 1020 |
| gagctaaccg | cttttttgca | caacatgggg | gatcatgtaa | ctcgccttga | tcgttgggaa | 1080 |
| ccggagctga | atgaagccat | accaaacgac | gagcgtgaca | ccacgatgcc | tgtagcaatg | 1140 |
| gcaacaacgt | tgcgcaaact | attaactggc | gaactactta | ctctagcttc | ccggcaacaa | 1200 |
| ttaatagact | ggatggaggc | ggataaagtt | gcaggaccac | ttctgcgctc | ggcccttccg | 1260 |
| gctggctggt | ttattgctga | taaatctgga | gccggtgagc | gtgggtctcg | cggtatcatt | 1320 |
| gcagcactgg | ggccagatgg | taagccctcc | cgtatcgtag | ttatctacac | gacggggagt | 1380 |
| caggcaacta | tggatgaacg | aaatagacag | atcgctgaga | taggtgcctc | actgattaag | 1440 |
| cattggtaac | tgtcagacca | agtttactca | tatatacttt | agattgattt | aaaacttcat | 1500 |
| ttttaattta | aaaggatcta | ggtgaagatc | ctttttgata | atctcatgac | caaaatccct | 1560 |
| taacgtgagt | tttcgttcca | ctgagcgtca | gaccccgtag | aaaagatcaa | aggatcttct | 1620 |
| tgagatcctt | ttttctgcg | cgtaatctgc | tgcttgcaaa | caaaaaaacc | accgctacca | 1680 |
| gcggtggttt | gtttgccgga | tcaagagcta | ccaactcttt | ttccgaaggt | aactggcttc | 1740 |
| agcagagcgc | agataccaaa | tactgtcctt | ctagtgtagc | cgtagttagg | ccaccacttc | 1800 |
| aagaactctg | tagcaccgcc | tacatacctc | gctctgctaa | tcctgttacc | agtggctgct | 1860 |
| gccagtggcg | ataagtcgtg | tcttaccggg | ttggactcaa | gacgatagtt | accggataag | 1920 |
| gcgcagcggt | cgggctgaac | ggggggttcg | tgcacacagc | ccagcttgga | gcgaacgacc | 1980 |
| tacaccgaac | tgagatacct | acagcgtgag | cattgagaaa | gcgccacgct | tcccgaaggg | 2040 |
| agaaaggcgg | acaggtatcc | ggtaagcggc | agggtcggaa | caggagagcg | cacgagggag | 2100 |
| cttccagggg | gaaacgcctg | gtatctttat | agtcctgtcg | ggtttcgcca | cctctgactt | 2160 |
| gagcgtcgat | ttttgtgatg | ctcgtcaggg | gggcggagcc | tatggaaaaa | cgccagcaac | 2220 |

```
gcggccttttt tacggttcct ggccttttgc tggccttttg ctcacatgtt ctttcctgcg    2280
ttatcccctg attctgtgga taaccgtatt accgcctttg agtgagctga taccgctcgc    2340
cgcagccgaa cgaccgagcg cagcgagtca gtgagcgagg aagcggaaga gcgcctgatg    2400
cggtattttc tccttacgca tctgtgcggt atttcacacc gcagaccagc cgcgtaacct    2460
ggcaaaatcg gttacggttg agtaataaat ggatgccctg cgtaagcggg tgtgggcgga    2520
caataaagtc ttaaactgaa caaaatagat ctaaactatg acaataaagt cttaaactag    2580
acagaatagt tgtaaactga atcagtcca gttatgctgt gaaaaagcat actggacttt    2640
tgttatggct aaagcaaact cttcattttc tgaagtgcaa attgcccgtc gtattaaaga    2700
ggggcgtggc aagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgccctgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccggatgaag tggttcgcat cctcggtttt ctggaaggcg agcatcgttt    3840
gttcgcccag gactctagct atagttctag tggttggcta cgtatactcc ggaatattaa    3900
tagatcatgg agataattaa aatgataacc atctcgcaaa taaataagta ttttactgtt    3960
ttcgtaacag ttttgtaata aaaaaaccta taaatattcc ggattattca taccgtccca    4020
ccatcgggcg cggatcccgg tccgaagcgc gcggaattca aaggcctacg tcgacgagct    4080
cactagtcgc ggccgctttc gaatctagag cctgcagtct cgaggcatgc ggtaccaagc    4140
ttgtcgagaa gtactagagg atcataatca gccataccac atttgtagag gttttacttg    4200
ctttaaaaaa cctcccacac ctccccctga acctgaaaca taaaatgaat gcaattgttg    4260
ttgttaactt gtttattgca gcttataatg gttacaaata aagcaatagc atcacaaatt    4320
tcacaaataa agcattttt tcactgcatt ctagttgtgg tttgtccaaa ctcatcaatg    4380
tatcttatca tgtctggatc tgatcactgc ttgagcctag gagatccgaa ccagataagt    4440
gaaatctagt tccaaactat tttgtcattt ttaattttcg tattagctta cgacgctaca    4500
cccagttccc atctattttg tcactcttcc ctaaataatc cttaaaaact ccatttccac    4560
ccctcccagt tcccaactat tttgtccgcc cacagcgggg cattttttctt cctgttatgt    4620
```

-continued

```
ttttaatcaa acatcctgcc aactccatgt gacaaaccgt catcttcggc tacttttcct      4680
ctgtcacaga atgaaaattt ttctgtcatc tcttcgttat taatgtttgt aattgactga      4740
atatcaacgc ttatttgcag cctgaatggc gaatgg                                4776
```

<210> SEQ ID NO 5
<211> LENGTH: 11
<212> TYPE: PRT
<213> ORGANISM: Human immunodeficiency virus type 1

<400> SEQUENCE: 5

Tyr Gly Arg Lys Lys Arg Arg Gln Arg Arg Arg
1               5                   10

<210> SEQ ID NO 6
<211> LENGTH: 12436
<212> TYPE: DNA
<213> ORGANISM: Homo sapiens

<400> SEQUENCE: 6

```
gtattgatgt caagctgaac catcgtagga agttgaaagc cttagaaaga ggacttggta        60 aagttttttgg attatcttga aactctggca agatggccaa gtatggagaa catgaagcca      120
gtcctgacaa tgggcagaac gaattcagtg atatcattaa gtccagatct gatgaacaca      180
atgacgtaca gaagaaaacc tttaccaaat ggataaatgc tcgatttttca aagagtggga      240 aaccacccat caatgatatg ttcacagacc tcaaagatgg aaggaagcta ttggatcttc      300
tagaaggcct cacaggaaca tcactgccaa ggaacgtgg ttccacaagg gtacatgcct       360
taaataacgt caacagagtg ctgcaggttt tacatcagaa caatgtggaa ttagtgaata      420 taggggggaac tgacattgtg gatggaaatc acaaactgac tttggggtta ctttggagca    480 tcatttttgca ctggcaggtg aaagatgtca tgaaggatgt catgtcggac ctgcagcaga    540
cgaacagtga aagatcctg ctcagctggg tgcgtcagac caccaggccc tacagccaag      600
tcaacgtcct caacttcacc accagctgga cagatggact cgcctttaat gctgtcctcc     660
accgacataa acctgatctc ttcagctggg ataaagttgt caaaatgtca ccaattgaga     720
gacttgaaca tgccttcagc aaggctcaaa cttatttggg aattgaaaag ctgttagatc     780
ctgaagatgt tgccgttcag cttcctgaca agaaatccat aattatgtat ttaacatctt     840
tgtttgaggt gctacctcag caagtccacca tagacgccat ccgtgaggta gagacactcc    900
caaggaaata taaaaagaa tgtgaagaag aggcaattaa tatacagagt acagcgcctg      960
aggaggagca tgagagtccc cgagctgaaa ctcccagcac tgtcactgag gttgacatgg    1020
atctggacag ctatcagatt gcgttggagg aagtgctgac ctggttgctt tctgctgagg    1080 acacttttcca ggagcaggat gatatttctg atgatgttga agaagtcaaa gaccagtttg   1140
caacccatga agcttttatg atggaactga ctgcacacca gagcagtgtg ggcagcgtcc    1200
tgcaggcagg caaccaactg ataacacaag gaactctgtc agacgaagaa gaatttgaga    1260
ttcaggaaca gatgacctg ctgaatgcta atgggaggc tcttagggtg gagagtatgg       1320
acagacagtc ccggctgcac gatgtgctga tggaactgca gaagaagcaa ctgcagcagc    1380
tctccgcctg gttaacactc acagaggagc gcattcagaa gatggaaact tgccccctgg     1440
atgatgatgt aaaatctcta caaaagctgc tagaagaaca taaaagtttg caaagtgatc    1500
ttgaggctga acaggtgaaa gtaaattcac taactcacat ggtggtcatt gttgatgaaa    1560
acagtggtga gagtgctaca gctatcctag aagaccagtt acagaaactt ggtgagcgct    1620
```

```
ggacagcagt atgccgttgg actgaagaac gctggaatag gttacaagaa atcaatatat   1680
tgtggcagga attattggaa gaacagtgct tgttgaaagc ttggttaacc gaaaagaag    1740
aggctttaaa taaagtccag acaagcaact tcaaagacca aaaggaacta agtgtcagtg   1800
ttcgacgtct ggctattttg aaggaagaca tggaaatgaa gcgtcaaaca ttggatcagc   1860
tgagtgagat tggccaggat gtgggacaat tacttgataa ttccaaggca tctaagaaga   1920
tcaacagtga ctcagaggaa ctgactcaaa gatgggattc tttggttcag agactagaag   1980
attcctccaa ccaggtgact caggctgtag caaagctggg gatgtctcag attcctcaga   2040
aggacctttt ggagactgtt cgtgtaagag aacaagcaat tacaaaaaaa tctaagcagg   2100
aactgcctcc tcctcctccc ccaaagaaga gacagatcca tgtggatatt gaagctaaga   2160
aaagtttga tgctataagt gcagagctgt tgaactggat tttgaaatgg aaaactgcca   2220
ttcagaccac agagataaaa gagtatatga agatgcaaga cacttccgaa atgaaaaaga   2280
agttgaaggc attagaaaaa gaacagagag aaagaatccc cagagcagat gaattaaacc   2340
aaactggaca aatccttgtg gagcaaatgg gaaaagaagg ccttcctact gaagaaataa   2400
aaaatgttct ggagaaggtt tcatcagaat ggaagaatgt atctcaacat ttggaagatc   2460
tagaaagaaa gattcagcta caggaagata taaatgctta tttcaagcag cttgatgagc   2520
ttgaaaaggt catcaagaca aaggaggagt gggtaaaaca cacttccatt tctgaatctt   2580
cccggcagtc cttgccaagc ttgaaggatt cctgtcagcg ggaattgaca aatcttcttg   2640
gccttcaccc caaaattgaa atggctcgtg caagctgctc ggccctgatg tctcagcctt   2700
ctgccccaga ttttgtccag cggggcttcg atagctttct gggccgctac caagctgtac   2760
aagaggctgt agaggatcgt caacaacatc tagagaatga actgaagggc caacctggac   2820
atgcatatct ggaaacattg aaaacactga agatgtgct aaatgattca gaaaataagg   2880
cccaggtgtc tctgaatgtc cttaatgatc ttgccaaggt ggagaaggcc ctgcaagaaa   2940
aaagacccct tgatgaaatc cttgagaatc agaaacctgc attacataaa cttgcagaag   3000
aaacaaaggc tctggagaaa aatgttcatc ctgatgtaga aaaattatat aagcaagaat   3060
ttgatgatgt gcaaggaaag tggaacaagc taaggtctt ggtttccaaa gatctacatt   3120
tgcttgagga aattgctctc acactcagag cttttgaggc cgattcaaca gtcattgaga   3180
agtggatgga tggcgtgaaa gacttcttaa tgaaacagca ggctgcccaa ggagacgacg   3240
caggtctaca gaggcagtta gaccagtgct ctgcatttgt taatgaaata gaaacaattg   3300
aatcatctct gaaaaacatg aaggaaatag agactaatct tcgaagtggt ccagttgctg   3360
gaataaaaac ttgggtgcag acaagactag gtgactacca aactcaactg gagaaactta   3420
gcaaggagat cgctactcaa aaaagtaggt tgtctgaaag tcaagaaaaa gctgcgaacc   3480
tgaagaaaga cttggcagag atgcaggaat ggatgaccca ggccgaggaa gaatatttgg   3540
agcgggattt tgagtacaag tcaccagaag agcttgagag tgctgtggaa gagatgaaga   3600
gggcaaaaga ggatgtgttg cagaaggagg tgagagtgaa gattctcaag gacaacatca   3660
agttattagc tgccaaggtg ccctctggtg gccaggagtt gacgtctgag ctgaatgttg   3720
tgctggagaa ttaccaactt cttttgtaata gaattcgagg aaagtgccac acgctagagg   3780
aggtctggtc ttgttggatt gaactgcttc actatttgga tcttgaaact acctggttaa   3840
acactttgga agagcggatg aagagcacag aggtcctgcc tgagaagacg gatgctgtca   3900
acgaagccct ggagtctctg gaatctgttc tgcgccaccc ggcagataat cgcacccaga   3960
```

-continued

```
ttcgagagct tggccagact ctgattgatg gggggatcct ggatgatata atcagtgaga    4020
aactggaggc tttcaacagc cgatatgaag atctaagtca cctggcagag agcaagcaga    4080
tttctttgga aaagcaactc caggtgctgc gggaaactga ccagatgctt caagtcttgc    4140
aagagagctt gggggagctg gacaaacagc tcaccacata cctgactgac aggatagatg    4200
ctttccaagt tccacaggaa gctcagaaaa tccaagcaga gatctcagcc catgagctaa    4260
ccctagagga gttgagaaga aatatgcgtt ctcagcccct gacctcccca gagagtagga    4320
ctgccagagg aggaagtcag atggatgtgc tacagaggaa actccgagag gtgtccacaa    4380
agttccagct tttccagaag ccagctaact tcgagcagcg catgctggac tgcaagcgtg    4440
tgctggatgg cgtgaaagca gaacttcacg ttctggatgt gaaggacgta gaccctgacg    4500
tcatacagac gcacctggac aagtgtatga aactgtataa aactttgagt gaagtcaaac    4560
ttgaagtgga aactgtgatt aaaacaggaa gacatattgt ccagaaacag caaacggaca    4620
acccaaaagg gatggatgag cagctgactt ccctgaaggt tctttacaat gacctgggcg    4680
cacaggtgac agaaggaaaa caggatctgg aaagagcatc acagttggcc cggaaaatga    4740
agaaagaggc tgcttctctc tctgaatggc tttctgctac tgaaactgaa ttggtacaga    4800
agtccacttc agaaggtctg cttggtgact tggatacaga aatttcctgg gctaaaaatg    4860
ttctgaagga tctggaaaag agaaaagctg atttaaatac catcacagag agtagtgctg    4920
ccctgcaaaa cttgattgag ggcagtgagc ctattttaga agagaggctc tgcgtcctta    4980
acgctgggtg gagccgagtt cgtacctgga ctgaagattg gtgcaatacc ttgatgaacc    5040
atcagaacca gctagaaata tttgatggga acgtggctca cataagtacc tggctttatc    5100
aagctgaagc tctattggat gaaattgaaa agaaaccaac aagtaaacag gaagaaattg    5160
tgaagcgttt agtatctgag ctggatgatg ccaacctcca ggttgaaaat gtccgcgatc    5220
aagcccttat tttgatgaat gcccgtggaa gctcaagcag ggagcttgta gaaccaaagt    5280
tagctgagct gaataggaac tttgaaaagg tgtctcaaca tatcaaaagt gccaaattgc    5340
taattgctca ggaaccatta taccaatgtt tggtcaccac tgaaacattt gaaactggtg    5400
tgcctttctc tgacttggaa aaattagaaa atgacataga aaatatgtta aaatttgtgg    5460
aaaaacactt ggaatccagt gatgaagatg aaaagatgga tgaggagagt gcccagattg    5520
aggaagttct acaaagagga gaagaaatgt tacatcaacc tatggaagat aataaaaaag    5580
aaaagatccg tttgcaatta ttacttttgc atactagata caacaaaatt aaggcaatcc    5640
ctattcaaca gaggaaaatg ggtcaacttg cttctggaat tagatcatca cttcttccta    5700
cagattatct ggttgaaatt aacaaaattt tactttgcat ggatgatgtt gaattatcgc    5760
ttaatgttcc agagctcaac actgctattt acgaagactt ctcttttcag gaagactctc    5820
tgaagaatat caaagaccaa ctggacaaac ttggagagca gattgcagtc attcatgaaa    5880
aacagccaga tgtcatcctt gaagcctctg gacctgaagc cattcagatc agagatacac    5940
ttactcagct gaatgcaaaa tgggacagaa ttaatagaat gtacagtgat cggaaaggtt    6000
gttttgacag ggcaatggaa gaatgggacg agttccattg tgaccttaat gacctcacac    6060
agtggataac agaggctgaa gaattactgg ttgatacctg tgctccaggt ggcagcctgg    6120
acttagaaaa agccaggata catcagcagg aacttgaggt gggcatcagc agccaccagc    6180
ccagttttgc agcactaaac cgaactgggg atgggattgt gcagaaactc tcccaggcag    6240
atggaagctt cttgaaagaa aaactggcag gtttaaacca acgctgggat gcaattgttg    6300
cagaagtgaa ggataggcag ccaaggctaa aaggagaaag taagcaggtg atgaagtaca    6360
```

```
ggcatcagct agatgagatt atctgttggt taacaaaggc tgagcatgct atgcaaaaga    6420
gatcaaccac cgaattggga gaaaacctgc aagaattaag agacttaact caagaaatgg    6480
aagtacatgc tgaaaaactc aaatggctga atagaactga attggagatg ctttcagata    6540
aaagtctgag tttacctgaa agggataaaa tttcagaaag cttaaggact gtaaatatga    6600
catggaataa gatttgcaga gaggtgccta ccaccctgaa ggaatgcatc caggagccca    6660
gttctgtttc acagacaagg attgctgctc atcctaatgt ccaaaaggtg gtgctagtat    6720
catctgcgtc agatattcct gttcagtctc atcgtacttc ggaaatttca attcctgctg    6780
atcttgataa aactataaca gaactagccg actggctggt attaatcgac cagatgctga    6840
agtccaacat tgtcactgtt ggggatgtag aagagatcaa taagaccgtt tcccgaatga    6900
aaattacaaa ggctgactta aacagcgcc atcctcagct ggattatgtt tttacattgg     6960
cacagaattt gaaaaataaa gcttccagtt cagatatgag aacagcaatt acagaaaaat    7020
tggaaagggt caagaaccag tgggatggca cccagcatgg cgttgagcta agacagcagc    7080
agcttgagga catgattatt gacagtcttc agtgggatga ccatagggag gagactgaag    7140
aactgatgag aaaatatgag gctcgactct atattcttca gcaagcccga cgggatccac    7200
tcaccaaaca aatttctgat aaccaaatac tgcttcaaga actgggtcct ggagatggta    7260
tcgtcatggc gttcgataac gtcctgcaga aactcctgga ggaatatggg agtgatgaca    7320
caaggaatgt gaaagaaacc acagagtact aaaaacatc atggatcaat ctcaaacaaa     7380
gtattgctga cagacagaac gccttggagg ctgagtggag gacggtgcag gcctctcgca    7440
gagatctgga aaacttcctg aagtggatcc aagaagcaga gaccacagtg aatgtgcttg    7500
tggatgcctc tcatcgggag aatgctcttc aggatagtat cttggccagg gaactcaaac    7560
agcagatgca ggacatccag gcagaaattg atgcccacaa tgacatattt aaaagcattg    7620
acggaaacag gcagaagatg gtaaaagctt tgggaaattc tgaagaggct actatgcttc    7680
aacatcgact ggatgatatg aaccaaagat ggaatgactt aaaagcaaaa tctgctagca    7740
tcagggccca tttggaggcc agcgctgaga agtggaacag gttgctgatg tccttagaag    7800
aactgatcaa atggctgaat atgaaagatg aagagcttaa gaaacaaatg cctattggag    7860
gagatgttcc agccttacag ctccagtatg accattgtaa ggccctgaga cgggagttaa    7920
aggagaaaga atattctgtc ctgaatgctg tcgaccaggc ccgagttttc ttggctgatc    7980
agccaattga ggcccctgaa gagccaagaa gaaacctaca atcaaaaaca gaattaactc    8040
ctgaggagag agcccaaaag attgccaaag ccatgcgcaa acagtcttct gaagtcaaag    8100
aaaaatggga aagtctaaat gctgtaacta gcaattggca aaagcaagtg gacaaggcat    8160 tggagaaaact cagagacctg cagggagcta tggatgacct ggacgctgac atgaaggagg    8220
cagagtccgt gcggaatggc tggaagcccg tgggagactt actcattgac tcgctgcagg    8280
atcacattga aaaaatcatg gcatttagag aagaaattgc accaatcaac tttaaagtta    8340
aaacggtgaa tgatttatcc agtcagctgt ctccacttga cctgcatccc tctctaaaga    8400
tgtctcgcca gctagatgac cttaatatgc gatggaaact tttacaggtt tctgtggatg    8460
atcgccttaa acagcttcag gaagcccaca gagattttgg accatcctct cagcatttc     8520 tctctacgtc agtccagctg ccgtggcaaa gatccatttc acataataaa gtgccctatt    8580
acatcaacca tcaaacacag accacctgtt gggaccatcc taaaatgacc gaactctttc    8640
aatcccttgc tgacctgaat aatgtacgtt tttctgccta ccgtacagca atcaaaatcc    8700
```

```
gaagactaca aaaagcacta tgtttggatc tcttagagtt gagtacaaca aatgaaattt    8760
tcaaacagca caagttgaac caaaatgacc agctcctcag tgttccagat gtcatcaact    8820
gtctgacaac aacttatgat ggacttgagc aaatgcataa ggacctggtc aacgttccac    8880
tctgtgttga tatgtgtctc aattggttgc tcaatgtcta tgacacgggt cgaactggaa    8940
aaattagagt gcagagtctg aagattggat taatgtctct ctccaaaggt ctcttggaag    9000
aaaaatacag atatctcttt aaggaagttg cagggccaac agaaatgtgt gaccagaggc    9060
agctgggcct gttacttcat gatgccatcc agatccccg gcagctaggt gaagtagcag     9120
cttttggagg cagtaatatt gagcctagtg ttcgcagctg cttccaacag aataacaata    9180
aaccagaaat aagtgtgaaa gagtttatag attggatgca tttggaacca cagtccatgg    9240
tttggctccc agttttacat cgagtggcag cagcggagc tgcaaaacat caggccaaat     9300
gcaacatctg taaagaatgt ccaattgtcg ggttcaggta tagaagcctt aagcatttta    9360
actatgatgt ctgccagagt tgtttctttt cgggtcgaac agcaaaggt cacaaattac     9420 attcccaat ggtggaatat tgtataccta acatctgg ggaagatgta cgagacttca       9480
caaaggtact taagaacaag ttcaggtcga agaagtactt tgccaaacac cctcgacttg    9540
gttacctgcc tgtccagaca gttcttgaag gtgacaactt agagactcct atcacactca    9600
tcagtatgtg gccagagcac tatgacccct cacaatctcc tcaactgttt catgatgaca    9660
cccattcaag aatagaacaa tatgccacac gactggccca gatggaaagg actaatgggt    9720
cttttctcac tgatagcagc tccaccacag gaagtgtgga agacgagcac gccctcatcc    9780
agcagtattg ccaaacactc ggaggagagt ccccagtgag ccagccgcag agcccagctc    9840
agatcctgaa gtcagtagag agggaagaac gtggagaact ggagaggatc attgctgacc    9900
tggaggaaga acaaagaaat ctacaggtgg agtatgagca gctgaaggac cagcacctcc    9960 gaaggggct ccctgtcggt tcaccgccag agtcgattat atctccccat cacacgtctg     10020
aggattcaga acttatagca gaagcaaaac tcctcaggca gcacaaaggt cggctggagg    10080
ctaggatgca gattttagaa gatcacaata aacagctgga gtctcagctc caccgcctcc    10140
gacagctgct ggagcagcct gaatctgatt cccgaatcaa tggtgtttcc ccatgggctt    10200
ctcctcagca ttctgcactg agctactcgc ttgatccaga tgcctccggc ccacagttcc    10260
accaggcagc gggagaggac ctgctggccc caccgcacga caccagcacg atctcacgg    10320 aggtcatgga gcagattcac agcacgtttc catcttgctg cccaaatgtt cccagcaggc    10380
cacaggcaat gtgaagtatt catccggcca accaatgttt cctgacgtac agtgttgccc    10440
ttttcagcaa atgccaattc caagttccat taaatcagaa gctccatggc tccttggccc    10500
acgatgttga gtgctgactg tgtgttctac tgaaagagta aaacactgac tatccaagga    10560
gaaatggata ttttgttttt ataataacca tatattattg ttttcttctt cccttctat    10620 gcaagtgtaa attaatgaac agagaggtat ttggaaatgg taatacattt gtcacggatt    10680
tgtataatgt atacagcatt gggaaagtgg gtggggct tctaatatga taccgtcttt      10740
ttaataacta tgacaaagct tacataagaa ttagaagacc actttacatt tttacattcc    10800
ttctgctgtt catattaacc ttgcacaatt acttcatttt ttctttgact cttttaccac    10860
aatgttttgg ttatttataa tttatcagcc atatgtttat cagccatata accaactaga    10920
tcccaaatag atccatgtat ttgtttccgt gatttggcca cattaataaa ttcataaatt    10980
tcaatcaaat atcttatata tacacacata tggtttaagc tacagccctg tgtatgccgt    11040
ttaactttat ttgacgttgc ccacttactt ctttgctgac cacttggata accgtaataa    11100
```

-continued

```
aaatcctata agcctaaatg gcatttcttt tgggatattt ttcctgcatt ttattccctt    11160
tttatataag taggaattaa ttatttattt tatgtcttaa tctatttgat aaagaagact    11220
acattataat aatctcaaag atcatattac caaaggttgc ccacttgagc atattttcat    11280
tttgacacag aaacaaaatt tagtacaacc tttcctagtt cccatgtctt gattttcatc    11340
attacatgca cagcagacct ttacctattg tgataccaga acacatcatt gtctttggtt    11400
cccttcaaag agaatttat tgttgttttg tattttcaag tccttaatag ttcttgaaac     11460
tcctagttgt tttcttgttg aaagcagaca cacatttagt gcacggctta ttttacccttt   11520 cgggtgaaag atcagatgtt tttatacct tcacttgatc aatatatttg gaaagaatgt     11580
ttatcaaaag tctatgtcac tgcttctaca gaagaatgaa attaatgctt aggtgatggt    11640
acctccacct acatcttttt gagtgcattc aattatgtat tttggtttag cttctgattt    11700
aacatttaat tgattcagtt taaacatgtt acttaattag caatgtaga ggaaccaaaa     11760 aaaggtgaaa ataatatgtt ttgattcaaa cctaaagaca taaaaacata aagacattt     11820 aactttgggt tctctttagc tgggatctgg ccagaaggag cttaaagtt agaaattgct     11880 attatttag aataggttgg gtgggttggg gggcaagggt gtctatttgc agcagagata     11940 tttgaaaag aagaaaattg ttttatataa aaaggaaagc catgaccacc tttctacctc     12000
agatccatct tcatccattg cattggaaac tgctttatgc tgctgcagtc tgcaaagtct    12060 agagcttta tcaggccatg tcataccccaa gaaagcacct atttaaagaa aaaacaattc    12120
cctgagctct caactccaag ttgtagattt ggtgtcttcc ttgttcttac tttaaaaagt    12180
catgtgttaa ttttttttct gcctgtattt gtatgcaaaa tgtcctctat ctgctattaa    12240
agaaaagcta cgtaaaacac tacattgtaa ccttctaagt aataataaat aaaaagaaat    12300
atattgcagt aacaatggga agtaagtatg tagttctttt gaaatatgtg gtaaagaact    12360
aatcacagac tatcatctaa tctggttaca tattgtattt ttcatcctga ataaaagtaa    12420
ttttaacaca aaaaaa                                                   12436
```

<210> SEQ ID NO 7
<211> LENGTH: 3433
<212> TYPE: PRT
<213> ORGANISM: Homo sapiens

<400> SEQUENCE: 7

```
Met Ala Lys Tyr Gly Glu His Glu Ala Ser Pro Asp Asn Gly Gln Asn
1               5                   10                  15

Glu Phe Ser Asp Ile Ile Lys Ser Arg Ser Asp Glu His Asn Asp Val
            20                  25                  30

Gln Lys Lys Thr Phe Thr Lys Trp Ile Asn Ala Arg Phe Ser Lys Ser
        35                  40                  45

Gly Lys Pro Pro Ile Asn Asp Met Phe Thr Asp Leu Lys Asp Gly Arg
    50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Asn Val Glu Leu Val Asn Ile Gly Gly
            100                 105                 110

Thr Asp Ile Val Asp Gly Asn His Lys Leu Thr Leu Gly Leu Leu Trp
        115                 120                 125
```

Ser Ile Ile Leu His Trp Gln Val Lys Asp Val Met Lys Asp Val Met
130             135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Lys Val Val Lys Met Ser Pro Ile
        195                 200                 205

Glu Arg Leu Glu His Ala Phe Ser Lys Ala Gln Thr Tyr Leu Gly Ile
    210                 215                 220

Glu Lys Leu Leu Asp Pro Glu Asp Val Ala Val Gln Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Glu Thr Leu Pro Arg Lys
                260                 265                 270

Tyr Lys Lys Glu Cys Glu Glu Ala Ile Asn Ile Gln Ser Thr Ala
            275                 280                 285

Pro Glu Glu His Glu Ser Pro Arg Ala Glu Thr Pro Ser Thr Val
    290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Asp Gln Phe Ala Thr His
                340                 345                 350

Glu Ala Phe Met Met Glu Leu Thr Ala His Gln Ser Ser Val Gly Ser
            355                 360                 365

Val Leu Gln Ala Gly Asn Gln Leu Ile Thr Gln Gly Thr Leu Ser Asp
370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Asp Arg Gln Ser Arg Leu His
                405                 410                 415

Asp Val Leu Met Glu Leu Gln Lys Lys Gln Leu Gln Gln Leu Ser Ala
            420                 425                 430

Trp Leu Thr Leu Thr Glu Glu Arg Ile Gln Lys Met Glu Thr Cys Pro
    435                 440                 445

Leu Asp Asp Asp Val Lys Ser Leu Gln Lys Leu Leu Glu Glu His Lys
450                 455                 460

Ser Leu Gln Ser Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Ile Leu Glu Asp Gln Leu Gln Lys Leu Gly Glu Arg Trp Thr Ala
            500                 505                 510

Val Cys Arg Trp Thr Glu Glu Arg Trp Asn Arg Leu Gln Glu Ile Asn
    515                 520                 525

Ile Leu Trp Gln Glu Leu Leu Glu Glu Gln Cys Leu Leu Lys Ala Trp
530                 535                 540

Leu Thr Glu Lys Glu Glu Ala Leu Asn Lys Val Gln Thr Ser Asn Phe

-continued

```
            545                 550                 555                 560
Lys Asp Gln Lys Glu Leu Ser Val Ser Val Arg Arg Leu Ala Ile Leu
                565                 570                 575
Lys Glu Asp Met Glu Met Lys Arg Gln Thr Leu Asp Gln Leu Ser Glu
            580                 585                 590
Ile Gly Gln Asp Val Gly Gln Leu Leu Asp Asn Ser Lys Ala Ser Lys
            595                 600                 605
Lys Ile Asn Ser Asp Ser Glu Leu Thr Gln Arg Trp Asp Ser Leu
            610                 615                 620
Val Gln Arg Leu Glu Asp Ser Ser Asn Gln Val Thr Gln Ala Val Ala
625                 630                 635                 640
Lys Leu Gly Met Ser Gln Ile Pro Gln Lys Asp Leu Leu Glu Thr Val
                645                 650                 655
Arg Val Arg Glu Gln Ala Ile Thr Lys Lys Ser Lys Gln Glu Leu Pro
                660                 665                 670
Pro Pro Pro Pro Pro Lys Lys Arg Gln Ile His Val Asp Ile Glu Ala
                675                 680                 685
Lys Lys Lys Phe Asp Ala Ile Ser Ala Glu Leu Leu Asn Trp Ile Leu
            690                 695                 700
Lys Trp Lys Thr Ala Ile Gln Thr Thr Glu Ile Lys Glu Tyr Met Lys
705                 710                 715                 720
Met Gln Asp Thr Ser Glu Met Lys Lys Lys Leu Lys Ala Leu Glu Lys
                725                 730                 735
Glu Gln Arg Glu Arg Ile Pro Arg Ala Asp Glu Leu Asn Gln Thr Gly
                740                 745                 750
Gln Ile Leu Val Glu Gln Met Gly Lys Glu Gly Leu Pro Thr Glu Glu
            755                 760                 765
Ile Lys Asn Val Leu Glu Lys Val Ser Ser Glu Trp Lys Asn Val Ser
            770                 775                 780
Gln His Leu Glu Asp Leu Glu Arg Lys Ile Gln Leu Gln Glu Asp Ile
785                 790                 795                 800
Asn Ala Tyr Phe Lys Gln Leu Asp Glu Leu Glu Lys Val Ile Lys Thr
                805                 810                 815
Lys Glu Glu Trp Val Lys His Thr Ser Ile Ser Glu Ser Ser Arg Gln
            820                 825                 830
Ser Leu Pro Ser Leu Lys Asp Ser Cys Gln Arg Glu Leu Thr Asn Leu
            835                 840                 845
Leu Gly Leu His Pro Lys Ile Glu Met Ala Arg Ala Ser Cys Ser Ala
            850                 855                 860
Leu Met Ser Gln Pro Ser Ala Pro Asp Phe Val Gln Arg Gly Phe Asp
865                 870                 875                 880
Ser Phe Leu Gly Arg Tyr Gln Ala Val Gln Glu Ala Val Glu Asp Arg
                885                 890                 895
Gln Gln His Leu Glu Asn Glu Leu Lys Gly Gln Pro His Ala Tyr
            900                 905                 910
Leu Glu Thr Leu Lys Thr Leu Lys Asp Val Leu Asn Asp Ser Glu Asn
            915                 920                 925
Lys Ala Gln Val Ser Leu Asn Val Leu Asn Asp Leu Ala Lys Val Glu
            930                 935                 940
Lys Ala Leu Gln Glu Lys Lys Thr Leu Asp Glu Ile Leu Glu Asn Gln
945                 950                 955                 960
Lys Pro Ala Leu His Lys Leu Ala Glu Glu Thr Lys Ala Leu Glu Lys
                965                 970                 975
```

```
Asn Val His Pro Asp Val Glu Lys Leu Tyr Lys Gln Glu Phe Asp Asp
            980                 985                 990

Val Gln Gly Lys Trp Asn Lys Leu Lys Val Leu Val Ser Lys Asp Leu
        995                 1000                1005

His Leu Leu Glu Glu Ile Ala Leu Thr Leu Arg Ala Phe Glu Ala
    1010                1015                1020

Asp Ser Thr Val Ile Glu Lys Trp Met Asp Gly Val Lys Asp Phe
    1025                1030                1035

Leu Met Lys Gln Gln Ala Ala Gln Gly Asp Asp Ala Gly Leu Gln
    1040                1045                1050

Arg Gln Leu Asp Gln Cys Ser Ala Phe Val Asn Glu Ile Glu Thr
    1055                1060                1065

Ile Glu Ser Ser Leu Lys Asn Met Lys Glu Ile Glu Thr Asn Leu
    1070                1075                1080

Arg Ser Gly Pro Val Ala Gly Ile Lys Thr Trp Val Gln Thr Arg
    1085                1090                1095

Leu Gly Asp Tyr Gln Thr Gln Leu Glu Lys Leu Ser Lys Glu Ile
    1100                1105                1110

Ala Thr Gln Lys Ser Arg Leu Ser Glu Ser Gln Glu Lys Ala Ala
    1115                1120                1125

Asn Leu Lys Lys Asp Leu Ala Glu Met Gln Glu Trp Met Thr Gln
    1130                1135                1140

Ala Glu Glu Glu Tyr Leu Glu Arg Asp Phe Glu Tyr Lys Ser Pro
    1145                1150                1155

Glu Glu Leu Glu Ser Ala Val Glu Glu Met Lys Arg Ala Lys Glu
    1160                1165                1170

Asp Val Leu Gln Lys Glu Val Arg Val Lys Ile Leu Lys Asp Asn
    1175                1180                1185

Ile Lys Leu Leu Ala Ala Lys Val Pro Ser Gly Gly Gln Glu Leu
    1190                1195                1200

Thr Ser Glu Leu Asn Val Val Leu Glu Asn Tyr Gln Leu Leu Cys
    1205                1210                1215

Asn Arg Ile Arg Gly Lys Cys His Thr Leu Glu Glu Val Trp Ser
    1220                1225                1230

Cys Trp Ile Glu Leu Leu His Tyr Leu Asp Leu Glu Thr Thr Trp
    1235                1240                1245

Leu Asn Thr Leu Glu Glu Arg Met Lys Ser Thr Glu Val Leu Pro
    1250                1255                1260

Glu Lys Thr Asp Ala Val Asn Glu Ala Leu Glu Ser Leu Glu Ser
    1265                1270                1275

Val Leu Arg His Pro Ala Asp Asn Arg Thr Gln Ile Arg Glu Leu
    1280                1285                1290

Gly Gln Thr Leu Ile Asp Gly Gly Ile Leu Asp Asp Ile Ile Ser
    1295                1300                1305

Glu Lys Leu Glu Ala Phe Asn Ser Arg Tyr Glu Asp Leu Ser His
    1310                1315                1320

Leu Ala Glu Ser Lys Gln Ile Ser Leu Glu Lys Gln Leu Gln Val
    1325                1330                1335

Leu Arg Glu Thr Asp Gln Met Leu Gln Val Leu Gln Glu Ser Leu
    1340                1345                1350

Gly Glu Leu Asp Lys Gln Leu Thr Thr Tyr Leu Thr Asp Arg Ile
    1355                1360                1365
```

-continued

```
Asp Ala Phe Gln Val Pro Gln Glu Ala Gln Lys Ile Gln Ala Glu
    1370            1375            1380

Ile Ser Ala His Glu Leu Thr Leu Glu Leu Arg Arg Asn Met
    1385            1390            1395

Arg Ser Gln Pro Leu Thr Ser Pro Glu Ser Arg Thr Ala Arg Gly
    1400            1405            1410

Gly Ser Gln Met Asp Val Leu Gln Arg Lys Leu Arg Glu Val Ser
    1415            1420            1425

Thr Lys Phe Gln Leu Phe Gln Lys Pro Ala Asn Phe Glu Gln Arg
    1430            1435            1440

Met Leu Asp Cys Lys Arg Val Leu Asp Gly Val Lys Ala Glu Leu
    1445            1450            1455

His Val Leu Asp Val Lys Asp Val Asp Pro Asp Val Ile Gln Thr
    1460            1465            1470

His Leu Asp Lys Cys Met Lys Leu Tyr Lys Thr Leu Ser Glu Val
    1475            1480            1485

Lys Leu Glu Val Glu Thr Val Ile Lys Thr Gly Arg His Ile Val
    1490            1495            1500

Gln Lys Gln Gln Thr Asp Asn Pro Lys Gly Met Asp Glu Gln Leu
    1505            1510            1515

Thr Ser Leu Lys Val Leu Tyr Asn Asp Leu Gly Ala Gln Val Thr
    1520            1525            1530

Glu Gly Lys Gln Asp Leu Glu Arg Ala Ser Gln Leu Ala Arg Lys
    1535            1540            1545

Met Lys Lys Glu Ala Ala Ser Leu Ser Glu Trp Leu Ser Ala Thr
    1550            1555            1560

Glu Thr Glu Leu Val Gln Lys Ser Thr Ser Glu Gly Leu Leu Gly
    1565            1570            1575

Asp Leu Asp Thr Glu Ile Ser Trp Ala Lys Asn Val Leu Lys Asp
    1580            1585            1590

Leu Glu Lys Arg Lys Ala Asp Leu Asn Thr Ile Thr Glu Ser Ser
    1595            1600            1605

Ala Ala Leu Gln Asn Leu Ile Glu Gly Ser Glu Pro Ile Leu Glu
    1610            1615            1620

Glu Arg Leu Cys Val Leu Asn Ala Gly Trp Ser Arg Val Arg Thr
    1625            1630            1635

Trp Thr Glu Asp Trp Cys Asn Thr Leu Met Asn His Gln Asn Gln
    1640            1645            1650

Leu Glu Ile Phe Asp Gly Asn Val Ala His Ile Ser Thr Trp Leu
    1655            1660            1665

Tyr Gln Ala Glu Ala Leu Leu Asp Glu Ile Glu Lys Lys Pro Thr
    1670            1675            1680

Ser Lys Gln Glu Glu Ile Val Lys Arg Leu Val Ser Glu Leu Asp
    1685            1690            1695

Asp Ala Asn Leu Gln Val Glu Asn Val Arg Asp Gln Ala Leu Ile
    1700            1705            1710

Leu Met Asn Ala Arg Gly Ser Ser Ser Arg Glu Leu Val Glu Pro
    1715            1720            1725

Lys Leu Ala Glu Leu Asn Arg Asn Phe Glu Lys Val Ser Gln His
    1730            1735            1740

Ile Lys Ser Ala Lys Leu Leu Ile Ala Gln Glu Pro Leu Tyr Gln
    1745            1750            1755

Cys Leu Val Thr Thr Glu Thr Phe Glu Thr Gly Val Pro Phe Ser
```

-continued

```
        1760                1765                1770

Asp Leu Glu Lys Leu Glu Asn Asp Ile Glu Asn Met Leu Lys Phe
    1775                1780                1785

Val Glu Lys His Leu Glu Ser Ser Asp Glu Asp Lys Met Asp
    1790                1795                1800

Glu Glu Ser Ala Gln Ile Glu Glu Val Leu Gln Arg Gly Glu Glu
    1805                1810                1815

Met Leu His Gln Pro Met Glu Asp Asn Lys Lys Glu Lys Ile Arg
    1820                1825                1830

Leu Gln Leu Leu Leu Leu His Thr Arg Tyr Asn Lys Ile Lys Ala
    1835                1840                1845

Ile Pro Ile Gln Gln Arg Lys Met Gly Gln Leu Ala Ser Gly Ile
    1850                1855                1860

Arg Ser Ser Leu Leu Pro Thr Asp Tyr Leu Val Glu Ile Asn Lys
    1865                1870                1875

Ile Leu Leu Cys Met Asp Asp Val Glu Leu Ser Leu Asn Val Pro
    1880                1885                1890

Glu Leu Asn Thr Ala Ile Tyr Glu Asp Phe Ser Phe Gln Glu Asp
    1895                1900                1905

Ser Leu Lys Asn Ile Lys Asp Gln Leu Asp Lys Leu Gly Glu Gln
    1910                1915                1920

Ile Ala Val Ile His Glu Lys Gln Pro Asp Val Ile Leu Glu Ala
    1925                1930                1935

Ser Gly Pro Glu Ala Ile Gln Ile Arg Asp Thr Leu Thr Gln Leu
    1940                1945                1950

Asn Ala Lys Trp Asp Arg Ile Asn Arg Met Tyr Ser Asp Arg Lys
    1955                1960                1965

Gly Cys Phe Asp Arg Ala Met Glu Glu Trp Arg Gln Phe His Cys
    1970                1975                1980

Asp Leu Asn Asp Leu Thr Gln Trp Ile Thr Glu Ala Glu Glu Leu
    1985                1990                1995

Leu Val Asp Thr Cys Ala Pro Gly Gly Ser Leu Asp Leu Glu Lys
    2000                2005                2010

Ala Arg Ile His Gln Gln Glu Leu Glu Val Gly Ile Ser Ser His
    2015                2020                2025

Gln Pro Ser Phe Ala Ala Leu Asn Arg Thr Gly Asp Gly Ile Val
    2030                2035                2040

Gln Lys Leu Ser Gln Ala Asp Gly Ser Phe Leu Lys Glu Lys Leu
    2045                2050                2055

Ala Gly Leu Asn Gln Arg Trp Asp Ala Ile Val Ala Glu Val Lys
    2060                2065                2070

Asp Arg Gln Pro Arg Leu Lys Gly Glu Ser Lys Gln Val Met Lys
    2075                2080                2085

Tyr Arg His Gln Leu Asp Glu Ile Ile Cys Trp Leu Thr Lys Ala
    2090                2095                2100

Glu His Ala Met Gln Lys Arg Ser Thr Thr Glu Leu Gly Glu Asn
    2105                2110                2115

Leu Gln Glu Leu Arg Asp Leu Thr Gln Glu Met Glu Val His Ala
    2120                2125                2130

Glu Lys Leu Lys Trp Leu Asn Arg Thr Glu Leu Glu Met Leu Ser
    2135                2140                2145

Asp Lys Ser Leu Ser Leu Pro Glu Arg Asp Lys Ile Ser Glu Ser
    2150                2155                2160
```

```
Leu Arg Thr Val Asn Met Thr Trp Asn Lys Ile Cys Arg Glu Val
2165                 2170                 2175

Pro Thr Thr Leu Lys Glu Cys Ile Gln Glu Pro Ser Ser Val Ser
2180                 2185                 2190

Gln Thr Arg Ile Ala Ala His Pro Asn Val Gln Lys Val Val Leu
2195                 2200                 2205

Val Ser Ser Ala Ser Asp Ile Pro Val Gln Ser His Arg Thr Ser
2210                 2215                 2220

Glu Ile Ser Ile Pro Ala Asp Leu Asp Lys Thr Ile Thr Glu Leu
2225                 2230                 2235

Ala Asp Trp Leu Val Leu Ile Asp Gln Met Leu Lys Ser Asn Ile
2240                 2245                 2250

Val Thr Val Gly Asp Val Glu Glu Ile Asn Lys Thr Val Ser Arg
2255                 2260                 2265

Met Lys Ile Thr Lys Ala Asp Leu Glu Gln Arg His Pro Gln Leu
2270                 2275                 2280

Asp Tyr Val Phe Thr Leu Ala Gln Asn Leu Lys Asn Lys Ala Ser
2285                 2290                 2295

Ser Ser Asp Met Arg Thr Ala Ile Thr Glu Lys Leu Glu Arg Val
2300                 2305                 2310

Lys Asn Gln Trp Asp Gly Thr Gln His Gly Val Glu Leu Arg Gln
2315                 2320                 2325

Gln Gln Leu Glu Asp Met Ile Ile Asp Ser Leu Gln Trp Asp Asp
2330                 2335                 2340

His Arg Glu Glu Thr Glu Glu Leu Met Arg Lys Tyr Glu Ala Arg
2345                 2350                 2355

Leu Tyr Ile Leu Gln Gln Ala Arg Arg Asp Pro Leu Thr Lys Gln
2360                 2365                 2370

Ile Ser Asp Asn Gln Ile Leu Leu Gln Glu Leu Gly Pro Gly Asp
2375                 2380                 2385

Gly Ile Val Met Ala Phe Asp Asn Val Leu Gln Lys Leu Leu Glu
2390                 2395                 2400

Glu Tyr Gly Ser Asp Asp Thr Arg Asn Val Lys Glu Thr Thr Glu
2405                 2410                 2415

Tyr Leu Lys Thr Ser Trp Ile Asn Leu Lys Gln Ser Ile Ala Asp
2420                 2425                 2430

Arg Gln Asn Ala Leu Glu Ala Glu Trp Arg Thr Val Gln Ala Ser
2435                 2440                 2445

Arg Arg Asp Leu Glu Asn Phe Leu Lys Trp Ile Gln Glu Ala Glu
2450                 2455                 2460

Thr Thr Val Asn Val Leu Val Asp Ala Ser His Arg Glu Asn Ala
2465                 2470                 2475

Leu Gln Asp Ser Ile Leu Ala Arg Glu Leu Lys Gln Gln Met Gln
2480                 2485                 2490

Asp Ile Gln Ala Glu Ile Asp Ala His Asn Asp Ile Phe Lys Ser
2495                 2500                 2505

Ile Asp Gly Asn Arg Gln Lys Met Val Lys Ala Leu Gly Asn Ser
2510                 2515                 2520

Glu Glu Ala Thr Met Leu Gln His Arg Leu Asp Asp Met Asn Gln
2525                 2530                 2535

Arg Trp Asn Asp Leu Lys Ala Lys Ser Ala Ser Ile Arg Ala His
2540                 2545                 2550
```

-continued

| | | | | | | | | | | | | |
|---|---|---|---|---|---|---|---|---|---|---|---|---|
|Leu|Glu|Ala|Ser|Ala|Glu|Lys|Trp|Asn|Arg|Leu|Leu|Met|Ser|Leu|
| |2555| | | |2560| | | |2565| | | | | |

Leu Glu Ala Ser Ala Glu Lys Trp Asn Arg Leu Leu Met Ser Leu
        2555              2560              2565

Glu Glu Leu Ile Lys Trp Leu Asn Met Lys Asp Glu Glu Leu Lys
        2570              2575              2580

Lys Gln Met Pro Ile Gly Gly Asp Val Pro Ala Leu Gln Leu Gln
        2585              2590              2595

Tyr Asp His Cys Lys Ala Leu Arg Arg Glu Leu Lys Glu Lys Glu
        2600              2605              2610

Tyr Ser Val Leu Asn Ala Val Asp Gln Ala Arg Val Phe Leu Ala
        2615              2620              2625

Asp Gln Pro Ile Glu Ala Pro Glu Glu Pro Arg Arg Asn Leu Gln
        2630              2635              2640

Ser Lys Thr Glu Leu Thr Pro Glu Glu Arg Ala Gln Lys Ile Ala
        2645              2650              2655

Lys Ala Met Arg Lys Gln Ser Ser Glu Val Lys Glu Lys Trp Glu
        2660              2665              2670

Ser Leu Asn Ala Val Thr Ser Asn Trp Gln Lys Gln Val Asp Lys
        2675              2680              2685

Ala Leu Glu Lys Leu Arg Asp Leu Gln Gly Ala Met Asp Asp Leu
        2690              2695              2700

Asp Ala Asp Met Lys Glu Ala Glu Ser Val Arg Asn Gly Trp Lys
        2705              2710              2715

Pro Val Gly Asp Leu Leu Ile Asp Ser Leu Gln Asp His Ile Glu
        2720              2725              2730

Lys Ile Met Ala Phe Arg Glu Glu Ile Ala Pro Ile Asn Phe Lys
        2735              2740              2745

Val Lys Thr Val Asn Asp Leu Ser Ser Gln Leu Ser Pro Leu Asp
        2750              2755              2760

Leu His Pro Ser Leu Lys Met Ser Arg Gln Leu Asp Asp Leu Asn
        2765              2770              2775

Met Arg Trp Lys Leu Leu Gln Val Ser Val Asp Asp Arg Leu Lys
        2780              2785              2790

Gln Leu Gln Glu Ala His Arg Asp Phe Gly Pro Ser Ser Gln His
        2795              2800              2805

Phe Leu Ser Thr Ser Val Gln Leu Pro Trp Gln Arg Ser Ile Ser
        2810              2815              2820

His Asn Lys Val Pro Tyr Tyr Ile Asn His Gln Thr Gln Thr Thr
        2825              2830              2835

Cys Trp Asp His Pro Lys Met Thr Glu Leu Phe Gln Ser Leu Ala
        2840              2845              2850

Asp Leu Asn Asn Val Arg Phe Ser Ala Tyr Arg Thr Ala Ile Lys
        2855              2860              2865

Ile Arg Arg Leu Gln Lys Ala Leu Cys Leu Asp Leu Leu Glu Leu
        2870              2875              2880

Ser Thr Thr Asn Glu Ile Phe Lys Gln His Lys Leu Asn Gln Asn
        2885              2890              2895

Asp Gln Leu Leu Ser Val Pro Asp Val Ile Asn Cys Leu Thr Thr
        2900              2905              2910

Thr Tyr Asp Gly Leu Glu Gln Met His Lys Asp Leu Val Asn Val
        2915              2920              2925

Pro Leu Cys Val Asp Met Cys Leu Asn Trp Leu Leu Asn Val Tyr
        2930              2935              2940

Asp Thr Gly Arg Thr Gly Lys Ile Arg Val Gln Ser Leu Lys Ile

-continued

```
            2945                2950                2955

Gly Leu Met Ser Leu Ser Lys Gly Leu Glu Glu Lys Tyr Arg
    2960                2965                2970

Tyr Leu Phe Lys Glu Val Ala Gly Pro Thr Glu Met Cys Asp Gln
    2975                2980                2985

Arg Gln Leu Gly Leu Leu Leu His Asp Ala Ile Gln Ile Pro Arg
    2990                2995                3000

Gln Leu Gly Glu Val Ala Ala Phe Gly Gly Ser Asn Ile Glu Pro
    3005                3010                3015

Ser Val Arg Ser Cys Phe Gln Gln Asn Asn Asn Lys Pro Glu Ile
    3020                3025                3030

Ser Val Lys Glu Phe Ile Asp Trp Met His Leu Glu Pro Gln Ser
    3035                3040                3045

Met Val Trp Leu Pro Val Leu His Arg Val Ala Ala Ala Glu Thr
    3050                3055                3060

Ala Lys His Gln Ala Lys Cys Asn Ile Cys Lys Glu Cys Pro Ile
    3065                3070                3075

Val Gly Phe Arg Tyr Arg Ser Leu Lys His Phe Asn Tyr Asp Val
    3080                3085                3090

Cys Gln Ser Cys Phe Phe Ser Gly Arg Thr Ala Lys Gly His Lys
    3095                3100                3105

Leu His Tyr Pro Met Val Glu Tyr Cys Ile Pro Thr Thr Ser Gly
    3110                3115                3120

Glu Asp Val Arg Asp Phe Thr Lys Val Leu Lys Asn Lys Phe Arg
    3125                3130                3135

Ser Lys Lys Tyr Phe Ala Lys His Pro Arg Leu Gly Tyr Leu Pro
    3140                3145                3150

Val Gln Thr Val Leu Glu Gly Asp Asn Leu Glu Thr Pro Ile Thr
    3155                3160                3165

Leu Ile Ser Met Trp Pro Glu His Tyr Asp Pro Ser Gln Ser Pro
    3170                3175                3180

Gln Leu Phe His Asp Asp Thr His Ser Arg Ile Glu Gln Tyr Ala
    3185                3190                3195

Thr Arg Leu Ala Gln Met Glu Arg Thr Asn Gly Ser Phe Leu Thr
    3200                3205                3210

Asp Ser Ser Ser Thr Thr Gly Ser Val Glu Asp Glu His Ala Leu
    3215                3220                3225

Ile Gln Gln Tyr Cys Gln Thr Leu Gly Gly Glu Ser Pro Val Ser
    3230                3235                3240

Gln Pro Gln Ser Pro Ala Gln Ile Leu Lys Ser Val Glu Arg Glu
    3245                3250                3255

Glu Arg Gly Glu Leu Glu Arg Ile Ile Ala Asp Leu Glu Glu Glu
    3260                3265                3270

Gln Arg Asn Leu Gln Val Glu Tyr Glu Gln Leu Lys Asp Gln His
    3275                3280                3285

Leu Arg Arg Gly Leu Pro Val Gly Ser Pro Pro Glu Ser Ile Ile
    3290                3295                3300

Ser Pro His His Thr Ser Glu Asp Ser Glu Leu Ile Ala Glu Ala
    3305                3310                3315

Lys Leu Leu Arg Gln His Lys Gly Arg Leu Glu Ala Arg Met Gln
    3320                3325                3330

Ile Leu Glu Asp His Asn Lys Gln Leu Glu Ser Gln Leu His Arg
    3335                3340                3345
```

-continued

```
Leu Arg Gln Leu Leu Glu Gln Pro Glu Ser Asp Ser Arg Ile Asn
    3350                3355                3360
Gly Val Ser Pro Trp Ala Ser Pro Gln His Ser Ala Leu Ser Tyr
    3365                3370                3375
Ser Leu Asp Pro Asp Ala Ser Gly Pro Gln Phe His Gln Ala Ala
    3380                3385                3390
Gly Glu Asp Leu Leu Ala Pro Pro His Asp Thr Ser Thr Asp Leu
    3395                3400                3405
Thr Glu Val Met Glu Gln Ile His Ser Thr Phe Pro Ser Cys Cys
    3410                3415                3420
Pro Asn Val Pro Ser Arg Pro Gln Ala Met
    3425                3430

<210> SEQ ID NO 8
<211> LENGTH: 12382
<212> TYPE: DNA
<213> ORGANISM: Mus musculus

<400> SEQUENCE: 8
gtattcatgc tagcctggac cattttcag atttagcctt cagaagagga tctgggaaag      60
cctttggatt atactgaaac tcattcaaga tggccaagta tggggacctt gaagccaggc    120
ctgatgatgg gcagaacgaa ttcagtgaca tcattaagtc cagatctgat gaacacaatg    180
atgtacagaa gaaaaccttt accaaatgga taaacgctcg attttccaag agtgggaaac    240
cacccatcag tgatatgttc tcagacctca agatgtggga aaagctcttg gatcttctcg    300
aaggcctcac aggaacatca ttgccaaagg aacgtggttc cacaagggtg catgccttaa    360
acaatgtcaa ccgagtgcta caggttttac atcagaacaa tgtggacttg gtgaatattg    420
gaggcacgga cattgtggat ggaaatccca agctgacttt agggttactc tggagcatca    480
ttctgcactg gcaggtgaag gatgtcatga agatatcat gtcagacctg cagcagacaa    540
acagcgagaa gatcctgctg agctgggtgc ggcagaccac caggccctac agtcaagtca    600
acgtcctcaa cttcaccacc agctggaccg atggactcgc gttcaacgcc gtgctccacc    660
ggcacaaacc agatctcttc agctgggaca gagtggtcaa aatgtcccca attgagagac    720
ttgaacatgc tttagcaag gcccacactt atttgggaat tgaaaagctt ctagatcctg    780
aagatgttgc tgtgcatctc cctgacaaga atccataat tatgtattta acgtctctgt    840
ttgaggtgct tcctcagcaa gtcacgatag atgccatccg agaggtggag actctcccaa    900
ggaagtataa gaaagaatgt gaagaggaag aaattcatat ccagagtgca gtgctggcag    960
aggaaggcca gagtccccga gctgagaccc tagcaccgt cactgaagtg acatggatt   1020 tggacagcta ccagatagcg ctagaggaag tgctgacgtg gctgctgtcc gcggaggaca   1080
cgttccagga gcaagatgac atttctgatg atgtcgaaga agtcaaagag cagttttgcta   1140 cccatgaaac ttttatgatg gagctgacag cacaccagag cagcgtgggg agcgtcctgc   1200
aggctggcaa ccagctgatg acacaaggga ctctgtcaga ggaggaggag tttgagatcc   1260
aggaacagat gaccttgctg aatgcaaggt gggaggcgct ccgggtggag agcatggaga   1320
ggcagtcccg gctgcacgac gctctgatgg agctgcagaa gaacagctg cagcagctct   1380 caagctggct ggccctcaca gaagagcgca ttcagaagat ggagagcctc ccgctgggtg   1440
atgacctgcc ctccctgcag aagctgcttc aagaacataa agtttgcaa atgaccttg   1500 aagctgaaca ggtgaaggta aattcttaa ctcacatggt ggtgattgtg gatgaaaaca   1560
```

```
gtggggagag tgccacagct cttctggaag atcagttaca gaaactgggt gagcgctgga    1620
cagctgtatg ccgctggact gaagaacgtt ggaacaggtt gcaagaaatc agtattctgt    1680
ggcaggaatt attggaagag cagtgtctgt tggaggcttg gctcaccgaa aaggaagagg    1740
ctttgaataa agttcaaacc agcaacttta agaccagaa ggaactaagt gtcagtgtcc     1800
ggcgtctggc tatattgaag gaagacatgg aaatgaagag gcagactctg gatcaactga    1860
gtgagattgg ccaggatgtg ggccaattac tcagtaatcc caaggcatct aagaagatga    1920
acagtgactc tgaggagcta acacagagat gggattctct ggttcagaga ctcgaagact    1980
cttctaacca ggtgactcag gcggtagcga agctcggcat gtcccagatt ccacagaagg    2040
acctattgga gaccgttcat gtgagagaac aagggatggt gaagaagccc aagcaggaac    2100
tgcctcctcc tcccccacca aagaagagac agattcacgt ggacgtggag gccaagaaaa    2160
agtttgatgc tataagtaca gagctgctga actggatttt gaaatcaaag actgccattc    2220
agaacacaga gatgaaagaa tataagaagt cgcaggagac ctcaggaatg aaaaagaaat    2280
tgaagggatt agagaaagaa cagaaggaaa atctgccccg actggacgaa ctgaatcaaa    2340
ccggacaaac cctccgggag caaatgggaa agaaggcct ttccactgaa gaagtaaacg      2400
atgttctgga aagggtttcg ttggagtgga agatgatatc tcagcagcta aagatctgg     2460 gaaggaagat ccagctgcag gaagatataa atgcttattt taagcagctt gatgccattg    2520
aggagaccat caaggagaag gaagagtggc tgagggcac acccatttct gaatcgcccc     2580
ggcagccctt gccaggctta aaggattctt gccagaggga actgacagat ctccttggcc    2640
ttcaccccag aattgagacg ctgtgtgcaa gctgttcagc cctgaagtct cagccctgtg    2700
tcccaggttt tgtccagcag ggttttgacg accttcgaca tcattaccag gctgtgcgga    2760
aggctttaga ggaataccaa caacaactag aaaatgagct gaagagccag cctggacccg    2820
cgtatttgga cacactgaat accctgaaaa aaatgctaag cgagtcagaa aaggcggccc    2880
aggcctctct gaatgccctg aacgatccca tagcggtgga gcaggccctg caggagaaaa    2940
aggcccttga tgaaaccctt gagaatcaga acatacgtt acataagctt tcagaagaaa     3000
cgaagacttt ggagaaaaat atgcttcctg atgtgggaa aatgtataaa caagaatttg     3060
atgatgtcca aggcagatgg aataaagtaa agaccaaggt ttccagagac ttacacttgc    3120
tcgaggaaat caccccaga ctccgagatt ttgaggctga ttcagaagtc attgagaagt     3180
gggtgagtgg catcaaagac ttcctcatga agaacaggc tgctcaagga gacgctgctg     3240
cgctgcagag ccagcttgac caatgtgcta cgtttgctaa tgaaatcgaa accatcgagt    3300
catctctgaa gaacatgagg gaagtagaga ctagccttca gaggtgtcca gtcactggag    3360
tcaagacatg ggtacaggca agactagtgg attaccaatc ccaactggag aaattcagca    3420
aagagattgc tattcaaaaa agcaggctgt cagatagtca agaaaaagcc ctgaacttga    3480
aaaggatttt ggctgagatg caggagtgga tgcacaggc tgaagaggac tacctggaga    3540
gggacttcga gtacaaatct ccagaagaac tcgagagtgc ggtggaggaa atgaagaggg    3600
caaaagagga ggtgctgcag aaggaggtga gggtgaaaat tctgaaggac agcatcaagc    3660
tggtggctgc caaggtgccc tctggtggcc aggagttgac gtcggaattc aacgaggtgc    3720
tggagagcta ccagcttctg tgcaatagaa ttcgagggaa gtgccacaca ctggaggagg    3780
tctggtcttg ctgggtggag ctgcttcact atctggacct ggagaccacg tggttgaaca    3840
ccttggagga gcgcgtgagg agcacggagg ccctgcctga gagggcagaa gctgttcatg    3900
aagctctgga gtctcttgag tctgttttgc gccatccggc ggataatcgc acccagattc    3960
```

```
gggaacttgg gcagactctg attgatggtg gaatcctgga tgacataatc agcgagaagc    4020
tggaggcttt taacagccgc tacgaagagc tgagtcactt ggcggagagc aaacagattt    4080
ctttggagaa gcaactccag gtcctccgcg aaactgacca catgcttcag gtgctgaagg    4140
agagcctggg ggagctggac aaacagctta ccacatacct gacggacagg atcgatgcct    4200
tccaactgcc acaggaagct cagaagatcc aagccgaaat ctcagcccat gagctcaccc    4260
tggaggagct gaggaagaat gtgcgctccc agcccccgac gtccctgag ggcagggcca    4320 ccagaggagg aagtcagatg gacatgctac agaggaaact tcgagaggtc tccaccaaat    4380
tccagctttt ccagaagccc gcaaatttcg agcagcggat gctggactgc aagcgtgtgt    4440
tggagggagt gaaggccgag cttcatgtcc tcgatgtgag ggatgtggac cctgacgtca    4500
ttcaggccca cttggacaag tgcatgaaac tatataaaac gttgagtgaa gtcaaacttg    4560
aagttgagac tgtcatcaaa acagggaggc acattgtcca gaagcagcag acggacaacc    4620
cgaaaagcat ggacgaacag cttacatctc tgaaagtcct ctacaatgac ctgggcgcac    4680
aggtgacaga agggaagcaa gacctggaaa gagcctcaca gctgtccagg aagatgaaga    4740
aggaggctgc cgtcctctct gaatggctct ctgccacaga ggcagaacta gtgcagaaat    4800
ccacatcaga aggcgtgatt ggtgacctgg cacagaaaat ctcctgggct aaaagtattc    4860
tcaaggatct ggaaaagagg aaagttgact taaatggcat tacagagagc agtgccgccc    4920
ttcagcactt ggtcttgggc agtgagtctg ttctggaaga gaacctctgt gtgctcaatg    4980
ctggatggag ccgagtgcgg acgtggaccg aagactggtg caacaccttg ctgaaccatc    5040
aaaaccagct ggagctattt gatggacacg tcgctcacat cagtacctgg ctctatcaag    5100
ccgaagctct gctggatgag atcgaaaaga accagcgag taaacaggaa gaaattgtga    5160
agcgtttact gtctgaattg gatgatgcca gcctccaggt tgagaatgtt cgggaacaag    5220
ccatcatctt ggtgaatgct cgtggaagcg ccagcaggga actcgtgaa ccaaaattag    5280 ccgagctgag caggaacttt gaaaaggtgt cccagcacat aaagagcgcc cgaatgctga    5340
ttggtcagga ccccttcatcc taccaaggct tggaccctgc tggaactgtt caagctgctg    5400
agtctttctc tgacttggaa aacttagaac aagacataga aacatgttg aaagttgtgg    5460 aaaagcactt ggaccccaat aacgatgaga agatggatga ggagcaagcc cagattgagg    5520
aagttctaca agagggggag catttgttac atgaacctat ggaggacagt aagaaagaaa    5580
agatccgctt gcagttgtta cttttgcata ctcgttacaa caaaattaag acaatcccta    5640
tccagcagag aaaaacaatt ccagtttctt ctggaattac atcatcagcc ctccctgcag    5700
attatttggt tgaaattaat aaaattttac tcactctgga tgacattgaa ttatcactta    5760
atatgccgga gctaaacacc actgtctaca aagacttctc tttccaggaa gactctctga    5820
agagtatcaa aggtcaactg gacagacttg gagagcagat tgcagttgtt cacgagaagc    5880
agccggatgt catcgtggaa gcctctggcc ctgaggccat tcagatcagg gacatgctcg    5940
ctcagctgaa tgcaaaatgg gaccgagtga atagagtgta cagtgatcgg agagggtcct    6000
ttgccagggc tgtggaggaa tggaggcagt tccaccatga ccttgatgac cttacacagt    6060
ggctatctga agctgaagac ctgctggtag acacttgtgc tccagatggt agcctggacc    6120
tggagaaagc cagggcacag cagctggaac tggaagaggg cctcagcagc caccagccca    6180
gcctgatcaa ggttaaccga aaggggggagg accttgttca gagactccgc ccctcggagg    6240
caagcttcct gaaggagaag ctggcaggtt tcaaccagcg ctggagcact cttgtagctg    6300
```

```
aggtggaggc tttgcagccc aggctaaaag gagaaagtca gcaggtgttg gggtataaga    6360
gacggctaga tgaggtcacc tgctggttaa cgaaagtgga gagtgctgtg cagaagagat    6420 caaccccctga cccggaagaa agcccacagg aattaacaga tttagcccaa gagacggaag    6480
ttcaagctga aaacattaag tggctgaaca gagcagaact ggaaatgctt tcagacaaaa    6540
atctgagttt gcgtgaaaga gagaaacttt cggaaagttt aaggaatgta aacacaacat    6600
ggaccaaggt atgcagagaa gtgcctagcc tcctgaagac acgcacccaa gacccctgct    6660
ctgccccaca gatgaggatg gctgctcatc ccaacgtcca aaaggtggtg ctagtatcat    6720
ctgcatcaga tgctcctctg cgtggcggcc tggaaatctc ggttcctgct gatttggata    6780
aaaccatcac agaactggct gactggctgg tattgatcga ccaaatgctg aagtccaaca    6840
ttgtcactgt gggggacgtg aaagagatca ataagacagt ttcccggatg aaaatcacaa    6900
aggctgattt agaacaacgc catcctcagc ttgattgtgt atttaccttg gcccaaaatt    6960
tgaaaaacaa agcttccagt tcagatgtga ggacagcaat cacagaaaaa ttggaaaagc    7020
tgaagaccca gtgggagagt actcagcatg gtgtggagct gcggcggcag cagctggagg    7080
acatggttgt ggacagcctg cagtgggacg accacaggga agagactgaa gagctcatga    7140
gaaaatacga ggctcgcttc tacatgctgc agcaggcccg ccgggaccca cttagcaaac    7200
aagtttctga taatcaacta ttgcttcaag agctggggtc tggcgatggt gtcatcatgg    7260
cgtttgataa tgtcctgcag aaacttctgg aagaatacag tggcgatgac acaaggaatg    7320
tggaagaaac cacggagtac ttgaaaacat catgggtcaa tctcaaacaa agcatcgctg    7380
atagacagag tgccttggag gctgagctac agacagtgca gacttctcgt agagacctgg    7440
agaactttgt caagtggctt caggaagcag aaaccacagc aaatgtgctg gccgatgcct    7500
ctcagcggga gaatgctctt caggacagtg tcctggcccg gcagctccga cagcagatgc    7560
tggacatcca ggcagaaatt gatgcccaca atgacatatt taaaagcatc gatggaaacc    7620
ggcagaagat ggtgaaagct ctggggaatt ctgaggaagc aacaatgctt cagcatcgac    7680
tggatgacat gaaccaaaga tggaatgatt tgaaggcaaa atctgctagc atcagggccc    7740
atttggaggc cagtgctgag aaatggaacc ggttgctggc atcgctggaa gagctgatca    7800
aatggctcaa tatgaaagat gaggagctta agaagcagat gcccattgga ggggacgtcc    7860
ctgccttaca gctccagtat gaccactgca aggtgctgag acgtgagcta aaggagaaag    7920
agtattctgt gctgaacgcc gtagatcaag ctcgagtttt tctggctgat cagccaatag    7980
aggcccccga agaaccaaga agaaacccac aatcaaagac agagttgact cctgaggaga    8040
gagcccagaa gatcgcccaaa gccatgcgca agcagtcttc tgaagtccga gagaagtggg    8100
aaaatctaaa tgctgtcact agcaactggc aaaagcaagt agggaaggcg ttagagaaac    8160
tccgagacct gcagggagct atggacgacc tggacgcaga catgaaggag gtggaggctg    8220
tgcggaatgg ctggaagccc gtgggagacc tgcttataga ctccctgcag gatcacatcg    8280
agaaaaccct ggcgtttaga gaagaaattg caccaatcaa cttaaaagta aaaacaatga    8340
atgacctgtc cagtcagctg tctccacttg acttgcatcc atctctaaag atgtctcgcc    8400
agctggatga ccttaatatg cgatggaaac ttctacaggt ttccgtggac gatcgcctta    8460
agcagctcca ggaagcccac agagattttg ggccatcttc tcaacacttt ctgtccactt    8520
cagtccagct gccgtggcag agatccattt cacataataa agtgccctat tacatcaacc    8580
atcaaacaca gacaacctgt tgggatcatc ctaaaatgac tgagctcttc caatcccttg    8640
ctgatctgaa taatgtacgt ttctctgcct accgcacagc aatcaaaatt cgaaggctgc    8700
```

```
aaaaagcatt atgtctggat ctcttagagc tgaatacgac gaatgaagtt ttcaagcagc    8760
acaaactgaa ccaaaatgat cagctcctga gtgtcccaga cgtcatcaac tgtctgacca    8820
ccacttacga tgggcttgag cagctgcaca aggacttggt caatgttcca ctctgcgtcg    8880
atatgtgtct caactggctg ctcaacgtat acgacacggg ccggactgga aaaattcggg    8940
tacagagtct gaagattgga ttgatgtctc tctccaaagg cctcttagaa gagaaataca    9000
gatgtctctt taaggaggtg gcagggccaa cagagatgtg tgaccagcgg cagcttggcc    9060
tgctacttca cgatgccatc cagatcccta ggcagctggg ggaagtagca gcctttgggg    9120
gcagtaacat tgagcccagt gtccgcagct gcttccagca gaataacaac aagccagaaa    9180
tcagtgtgaa ggagtttata gactggatgc atttggaacc ccagtccatg gtgtggttgc    9240
cggttctgca tcgggtcgca gctgctgaga ctgcaaaaca tcaggccaaa tgcaacatct    9300
gcaaagaatg cccgattgtt gggttcagat acaggagcct aaagcatttt aattatgatg    9360
tctgccagag ttgcttcttt tctggaagaa cagcaaaggg ccacaagtta cattacccga    9420
tggtagaata ctgcataccg acaacatctg gggaagatgt gagagatttc actaaggtgc    9480
tgaagaacaa gttcaggtcc aagaaatatt ttgccaaaca tcctcggctt ggctacctgc    9540
ctgtccagac cgtgctggaa ggggacaact tagaaactcc tatcacgctc atcagtatgt    9600
ggccagagca ctatgacccc tcccagtccc ctcagctgtt tcatgatgac acccactcaa    9660
gaatagagca atacgctaca cgactggccc agatggaaag gacaaacggg tccttcctaa    9720
ctgatagcag ctctacaaca ggaagcgtgg aggatgagca tgccctcatc cagcagtact    9780
gccagaccct gggcggggag tcacctgtga gtcagccgca gagtccagct cagatcctga    9840
agtccgtgga gagggaagag cgtggggaac tggagcggat cattgctgac ttggaggaag    9900
agcaaagaaa tctgcaggtg gagtatgagc agctgaagga gcagcaccta agaagggggtc    9960
tccctgtggg ctcccctcca gactccatcg tatctcctca ccacacatct gaggactcag   10020
aacttatagc agaagctaaa ctcctgcggc agcacaaagg gcggctggag gcgaggatgc   10080
aaatttttgga agatcacaat aaacagctgg agtctcagct gcaccgcctc agacagctcc   10140
tggagcagcc tgactctgac tcccgcatca atggtgtctc ccctgggct tccccacagc    10200
attctgcatt gagctactca cttgacactg acccaggccc acagttccac caggcagcat   10260
ctgaggacct gctggcccca cctcacgaca ctagcacgga cctcacggac gtgatggagc   10320
agatcaacag cacgtttccc tcttgcagct caaatgtccc cagcaggcca caggcaatgt   10380
gagcatctat ccagccagcc aacatttccc gaccttcagt attgccctct tctgcaaatg   10440
ccaatcccaa gacccattca accccaaagc tccgtggctc cacgcacaa gctgttgagt     10500
gcttactggg tgttctactg agggaaccaa acactgacta tccaaagaga aaggatatt     10560
ttggttttct aataacgtat attattgttt tcttctcccc tttctatgca actgtaaatt    10620
aatgaacaga gaagtatttg gaggtggtaa agcatttgtc actgatttgt ataatatata    10680
cagccatggg aaagtgggtg ggggcttttct aatatgaaac tgtcttttta ataaccaaga    10740
gaaaaaattg cataagaatt agaccacttt acattattac attccttctg ctgttcacat    10800
taaccttgta caataacttc acttattatt tgactgtttt accattatgt tttggttatt    10860
tataaatttta tcagccatac aaacaaatag attctatgta tttgtttcta taatctggcc    10920
aaattcctaa gttcatatat ttgaatcaaa tattttacat atgtggagta ggcaggcatt    10980
ctgaagatac tatttaactt tagttgacgt cacacacacc atcctttagt aaccactgga    11040
```

-continued

```
tgactacact aaaaatcctg tggactttaa cggcaagctg ctggggtatt tttcctcctg    11100
tttttattcc ttttttgtaa gtagatcttg acgtctttat ttatttcatc ttgcaatctc    11160
tataataaag aagactgtat tgtaatagtc tcaaaaaatt attttaccaa gggttaccat    11220
ttaagcatat tttcattttg attcagaaac caaagttggt acaacctctc ctagtacttg    11280
caaccttggt tttcatgaga aaacacacgg caggctttgc ccattgtgag gagagcacac    11340
atcatgctct tcagtttcct tgaatagac ttttattgtt gttttgtat ttttcgagtc      11400
ctgtgtaagt tttgaaagct ctggttgttt cctttgtgaa agcaggcaga tacttattgg    11460
ctgtctcatt tgaagctttg gagcagatag tcagatgtct catgacccct cacttggcca    11520
gcagcacatc cgagaaggat gtcactcaca agcctacacc acggcttctc tagaatgaaa    11580
tcagtgctcg gatgattgta tccctgcctc tacttctgag tgtgttcaac taggtattgg    11640
cttctttttc ttttctttt cttttttttt taatttaaca cttaattgcc gattttagag      11700
aaaccaaaaa taaggtgaa ggtaatatgt tttgattcaa acatatatgc ttttaaaaca      11760
tcaggacatg ctaactttgg gttctctttc actgggatct ggccagaagg aggctgaaag    11820
ttagaaattg ctattctttt aggatcggtt gggtgggttg gggggcaagg gtgtctatt     11880
gcagcataga tattttgaga cgaagaaaat tgttttatat aaggggagag ccatgatcac    11940
ctttctacct cagaaccacc ttcctccatt gtgttggaca tagctttata tgccgcagtg    12000
tgcaaaacct agggctgtag tcaggccttt ccatacccag gaagcacctg tgtaaagaag    12060
atcaacagaa actcccggaa ctcagaaccc caagttgtag atttggtgtc gtccttgttc    12120
ttgctttgag gagtcatgta ttcttttatt tcctgcctgt atttgtatgc aaaatgatct    12180
ctatctgcta ttacagaaaa agctacacaa aacactacat tgtaaccttc tgagtaataa    12240
ataagaggaa atatattaca gtaaccatga tgagaaataa gtgtattgtt cttttgaaat    12300
atgtggttaa tcgcagactg tcatctaatc tgttacatac cgtattttc atcctgaata     12360
aaagtaattt taacacaaaa tg                                              12382
```

<210> SEQ ID NO 9
<211> LENGTH: 3430
<212> TYPE: PRT
<213> ORGANISM: Mus musculus

<400> SEQUENCE: 9

```
Met Ala Lys Tyr Gly Asp Leu Glu Ala Arg Pro Asp Asp Gly Gln Asn
1               5                   10                  15

Glu Phe Ser Asp Ile Ile Lys Ser Arg Ser Asp Glu His Asn Asp Val
            20                  25                  30

Gln Lys Lys Thr Phe Thr Lys Trp Ile Asn Ala Arg Phe Ser Lys Ser
        35                  40                  45

Gly Lys Pro Pro Ile Ser Asp Met Phe Ser Asp Leu Lys Asp Gly Arg
    50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Asn Val Asp Leu Val Asn Ile Gly Gly
            100                 105                 110

Thr Asp Ile Val Asp Gly Asn Pro Lys Leu Thr Leu Gly Leu Leu Trp
        115                 120                 125

Ser Ile Ile Leu His Trp Gln Val Lys Asp Val Met Lys Asp Ile Met
```

-continued

```
            130                 135                 140
Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Ile
                195                 200                 205

Glu Arg Leu Glu His Ala Phe Ser Lys Ala His Thr Tyr Leu Gly Ile
210                 215                 220

Glu Lys Leu Leu Asp Pro Glu Asp Val Ala Val His Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Glu Thr Leu Pro Arg Lys
                260                 265                 270

Tyr Lys Lys Glu Cys Glu Glu Glu Ile His Ile Gln Ser Ala Val
                275                 280                 285

Leu Ala Glu Glu Gly Gln Ser Pro Arg Ala Glu Thr Pro Ser Thr Val
290                 295                 300

Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
                325                 330                 335

Asp Ile Ser Asp Asp Val Glu Glu Val Lys Glu Gln Phe Ala Thr His
                340                 345                 350

Glu Thr Phe Met Met Glu Leu Thr Ala His Gln Ser Ser Val Gly Ser
            355                 360                 365

Val Leu Gln Ala Gly Asn Gln Leu Met Thr Gln Gly Thr Leu Ser Glu
            370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Glu Arg Gln Ser Arg Leu His
                405                 410                 415

Asp Ala Leu Met Glu Leu Gln Lys Lys Gln Leu Gln Leu Ser Ser
                420                 425                 430

Trp Leu Ala Leu Thr Glu Glu Arg Ile Gln Lys Met Glu Ser Leu Pro
                435                 440                 445

Leu Gly Asp Asp Leu Pro Ser Leu Gln Lys Leu Leu Gln Glu His Lys
            450                 455                 460

Ser Leu Gln Asn Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Leu Leu Glu Asp Gln Leu Gln Lys Leu Gly Glu Arg Trp Thr Ala
                500                 505                 510

Val Cys Arg Trp Thr Glu Glu Arg Trp Asn Arg Leu Gln Glu Ile Ser
            515                 520                 525

Ile Leu Trp Gln Glu Leu Leu Glu Glu Gln Cys Leu Leu Glu Ala Trp
            530                 535                 540

Leu Thr Glu Lys Glu Glu Ala Leu Asn Lys Val Gln Thr Ser Asn Phe
545                 550                 555                 560
```

```
Lys Asp Gln Lys Glu Leu Ser Val Ser Val Arg Arg Leu Ala Ile Leu
                565                 570                 575
Lys Glu Asp Met Glu Met Lys Arg Gln Thr Leu Asp Gln Leu Ser Glu
            580                 585                 590
Ile Gly Gln Asp Val Gly Gln Leu Leu Ser Asn Pro Lys Ala Ser Lys
        595                 600                 605
Lys Met Asn Ser Asp Ser Glu Glu Leu Thr Gln Arg Trp Asp Ser Leu
    610                 615                 620
Val Gln Arg Leu Glu Asp Ser Ser Asn Gln Val Thr Gln Ala Val Ala
625                 630                 635                 640
Lys Leu Gly Met Ser Gln Ile Pro Gln Lys Asp Leu Leu Glu Thr Val
                645                 650                 655
His Val Arg Glu Gln Gly Met Val Lys Lys Pro Lys Gln Glu Leu Pro
            660                 665                 670
Pro Pro Pro Pro Pro Lys Lys Arg Gln Ile His Val Asp Val Glu Ala
        675                 680                 685
Lys Lys Lys Phe Asp Ala Ile Ser Thr Glu Leu Leu Asn Trp Ile Leu
    690                 695                 700
Lys Ser Lys Thr Ala Ile Gln Asn Thr Glu Met Lys Glu Tyr Lys Lys
705                 710                 715                 720
Ser Gln Glu Thr Ser Gly Met Lys Lys Leu Lys Gly Leu Glu Lys
                725                 730                 735
Glu Gln Lys Glu Asn Leu Pro Arg Leu Asp Glu Leu Asn Gln Thr Gly
            740                 745                 750
Gln Thr Leu Arg Glu Gln Met Gly Lys Glu Gly Leu Ser Thr Glu Glu
        755                 760                 765
Val Asn Asp Val Leu Glu Arg Val Ser Leu Glu Trp Lys Met Ile Ser
    770                 775                 780
Gln Gln Leu Glu Asp Leu Gly Arg Lys Ile Gln Leu Gln Glu Asp Ile
785                 790                 795                 800
Asn Ala Tyr Phe Lys Gln Leu Asp Ala Ile Glu Glu Thr Ile Lys Glu
                805                 810                 815
Lys Glu Glu Trp Leu Arg Gly Thr Pro Ile Ser Glu Ser Pro Arg Gln
            820                 825                 830
Pro Leu Pro Gly Leu Lys Asp Ser Cys Gln Arg Glu Leu Thr Asp Leu
        835                 840                 845
Leu Gly Leu His Pro Arg Ile Glu Thr Leu Cys Ala Ser Cys Ser Ala
    850                 855                 860
Leu Lys Ser Gln Pro Cys Val Pro Gly Phe Val Gln Gly Phe Asp
865                 870                 875                 880
Asp Leu Arg His His Tyr Gln Ala Val Arg Lys Ala Leu Glu Glu Tyr
                885                 890                 895
Gln Gln Gln Leu Glu Asn Glu Leu Lys Ser Gln Pro Gly Pro Ala Tyr
            900                 905                 910
Leu Asp Thr Leu Asn Thr Leu Lys Lys Met Leu Ser Glu Ser Glu Lys
        915                 920                 925
Ala Ala Gln Ala Ser Leu Asn Ala Leu Asn Asp Pro Ile Ala Val Glu
    930                 935                 940
Gln Ala Leu Gln Glu Lys Lys Ala Leu Asp Glu Thr Leu Glu Asn Gln
945                 950                 955                 960
Lys His Thr Leu His Lys Leu Ser Glu Glu Thr Lys Thr Leu Glu Lys
                965                 970                 975
```

-continued

```
Asn Met Leu Pro Asp Val Gly Lys Met Tyr Lys Gln Glu Phe Asp Asp
            980                 985                 990

Val Gln Gly Arg Trp Asn Lys Val Lys Thr Lys Val Ser Arg Asp Leu
            995                 1000                1005

His Leu Leu Glu Glu Ile Thr Pro Arg Leu Arg Asp Phe Glu Ala
            1010                1015                1020

Asp Ser Glu Val Ile Glu Lys Trp Val Ser Gly Ile Lys Asp Phe
            1025                1030                1035

Leu Met Lys Glu Gln Ala Ala Gln Gly Asp Ala Ala Ala Leu Gln
            1040                1045                1050

Ser Gln Leu Asp Gln Cys Ala Thr Phe Ala Asn Glu Ile Glu Thr
            1055                1060                1065

Ile Glu Ser Ser Leu Lys Asn Met Arg Glu Val Glu Thr Ser Leu
            1070                1075                1080

Gln Arg Cys Pro Val Thr Gly Val Lys Thr Trp Val Gln Ala Arg
            1085                1090                1095

Leu Val Asp Tyr Gln Ser Gln Leu Glu Lys Phe Ser Lys Glu Ile
            1100                1105                1110

Ala Ile Gln Lys Ser Arg Leu Ser Asp Ser Gln Glu Lys Ala Leu
            1115                1120                1125

Asn Leu Lys Lys Asp Leu Ala Glu Met Gln Glu Trp Met Ala Gln
            1130                1135                1140

Ala Glu Glu Asp Tyr Leu Glu Arg Asp Phe Glu Tyr Lys Ser Pro
            1145                1150                1155

Glu Glu Leu Glu Ser Ala Val Glu Glu Met Lys Arg Ala Lys Glu
            1160                1165                1170

Glu Val Leu Gln Lys Glu Val Arg Val Lys Ile Leu Lys Asp Ser
            1175                1180                1185

Ile Lys Leu Val Ala Ala Lys Val Pro Ser Gly Gly Gln Glu Leu
            1190                1195                1200

Thr Ser Glu Phe Asn Glu Val Leu Glu Ser Tyr Gln Leu Leu Cys
            1205                1210                1215

Asn Arg Ile Arg Gly Lys Cys His Thr Leu Glu Glu Val Trp Ser
            1220                1225                1230

Cys Trp Val Glu Leu Leu His Tyr Leu Asp Leu Glu Thr Thr Trp
            1235                1240                1245

Leu Asn Thr Leu Glu Glu Arg Val Arg Ser Thr Glu Ala Leu Pro
            1250                1255                1260

Glu Arg Ala Glu Ala Val His Glu Ala Leu Glu Ser Leu Glu Ser
            1265                1270                1275

Val Leu Arg His Pro Ala Asp Asn Arg Thr Gln Ile Arg Glu Leu
            1280                1285                1290

Gly Gln Thr Leu Ile Asp Gly Gly Ile Leu Asp Asp Ile Ile Ser
            1295                1300                1305

Glu Lys Leu Glu Ala Phe Asn Ser Arg Tyr Glu Glu Leu Ser His
            1310                1315                1320

Leu Ala Glu Ser Lys Gln Ile Ser Leu Glu Lys Gln Leu Gln Val
            1325                1330                1335

Leu Arg Glu Thr Asp His Met Leu Gln Val Leu Lys Glu Ser Leu
            1340                1345                1350

Gly Glu Leu Asp Lys Gln Leu Thr Thr Tyr Leu Thr Asp Arg Ile
            1355                1360                1365

Asp Ala Phe Gln Leu Pro Gln Glu Ala Gln Lys Ile Gln Ala Glu
```

-continued

```
            1370                1375                1380

Ile Ser Ala His Glu Leu Thr Leu Glu Glu Leu Arg Lys Asn Val
    1385                1390                1395

Arg Ser Gln Pro Pro Thr Ser Pro Glu Gly Arg Ala Thr Arg Gly
    1400                1405                1410

Gly Ser Gln Met Asp Met Leu Gln Arg Lys Leu Arg Glu Val Ser
    1415                1420                1425

Thr Lys Phe Gln Leu Phe Gln Lys Pro Ala Asn Phe Glu Gln Arg
    1430                1435                1440

Met Leu Asp Cys Lys Arg Val Leu Glu Gly Val Lys Ala Glu Leu
    1445                1450                1455

His Val Leu Asp Val Arg Asp Val Asp Pro Asp Val Ile Gln Ala
    1460                1465                1470

His Leu Asp Lys Cys Met Lys Leu Tyr Lys Thr Leu Ser Glu Val
    1475                1480                1485

Lys Leu Glu Val Glu Thr Val Ile Lys Thr Gly Arg His Ile Val
    1490                1495                1500

Gln Lys Gln Gln Thr Asp Asn Pro Lys Ser Met Asp Glu Gln Leu
    1505                1510                1515

Thr Ser Leu Lys Val Leu Tyr Asn Asp Leu Gly Ala Gln Val Thr
    1520                1525                1530

Glu Gly Lys Gln Asp Leu Glu Arg Ala Ser Gln Leu Ser Arg Lys
    1535                1540                1545

Met Lys Lys Glu Ala Ala Val Leu Ser Glu Trp Leu Ser Ala Thr
    1550                1555                1560

Glu Ala Glu Leu Val Gln Lys Ser Thr Ser Glu Gly Val Ile Gly
    1565                1570                1575

Asp Leu Asp Thr Glu Ile Ser Trp Ala Lys Ser Ile Leu Lys Asp
    1580                1585                1590

Leu Glu Lys Arg Lys Val Asp Leu Asn Gly Ile Thr Glu Ser Ser
    1595                1600                1605

Ala Ala Leu Gln His Leu Val Leu Gly Ser Glu Ser Val Leu Glu
    1610                1615                1620

Glu Asn Leu Cys Val Leu Asn Ala Gly Trp Ser Arg Val Arg Thr
    1625                1630                1635

Trp Thr Glu Asp Trp Cys Asn Thr Leu Leu Asn His Gln Asn Gln
    1640                1645                1650

Leu Glu Leu Phe Asp Gly His Val Ala His Ile Ser Thr Trp Leu
    1655                1660                1665

Tyr Gln Ala Glu Ala Leu Leu Asp Glu Ile Glu Lys Lys Pro Ala
    1670                1675                1680

Ser Lys Gln Glu Glu Ile Val Lys Arg Leu Leu Ser Glu Leu Asp
    1685                1690                1695

Asp Ala Ser Leu Gln Val Glu Asn Val Arg Glu Gln Ala Ile Ile
    1700                1705                1710

Leu Val Asn Ala Arg Gly Ser Ala Ser Arg Glu Leu Val Glu Pro
    1715                1720                1725

Lys Leu Ala Glu Leu Ser Arg Asn Phe Glu Lys Val Ser Gln His
    1730                1735                1740

Ile Lys Ser Ala Arg Met Leu Ile Gly Gln Asp Pro Ser Ser Tyr
    1745                1750                1755

Gln Gly Leu Asp Pro Ala Gly Thr Val Gln Ala Ala Glu Ser Phe
    1760                1765                1770
```

-continued

Ser Asp Leu Glu Asn Leu Glu Gln Asp Ile Glu Asn Met Leu Lys
    1775              1780              1785

Val Val Glu Lys His Leu Asp Pro Asn Asp Glu Lys Met Asp
1790              1795              1800

Glu Glu Gln Ala Gln Ile Glu Glu Val Leu Gln Arg Gly Glu His
    1805              1810              1815

Leu Leu His Glu Pro Met Glu Asp Ser Lys Lys Glu Lys Ile Arg
    1820              1825              1830

Leu Gln Leu Leu Leu Leu His Thr Arg Tyr Asn Lys Ile Lys Thr
    1835              1840              1845

Ile Pro Ile Gln Gln Arg Lys Thr Ile Pro Val Ser Ser Gly Ile
    1850              1855              1860

Thr Ser Ser Ala Leu Pro Ala Asp Tyr Leu Val Glu Ile Asn Lys
    1865              1870              1875

Ile Leu Leu Thr Leu Asp Asp Ile Glu Leu Ser Leu Asn Met Pro
    1880              1885              1890

Glu Leu Asn Thr Thr Val Tyr Lys Asp Phe Ser Phe Gln Glu Asp
    1895              1900              1905

Ser Leu Lys Ser Ile Lys Gly Gln Leu Asp Arg Leu Gly Glu Gln
    1910              1915              1920

Ile Ala Val Val His Glu Lys Gln Pro Asp Val Ile Val Glu Ala
    1925              1930              1935

Ser Gly Pro Glu Ala Ile Gln Ile Arg Asp Met Leu Ala Gln Leu
    1940              1945              1950

Asn Ala Lys Trp Asp Arg Val Asn Arg Val Tyr Ser Asp Arg Arg
    1955              1960              1965

Gly Ser Phe Ala Arg Ala Val Glu Glu Trp Arg Gln Phe His His
    1970              1975              1980

Asp Leu Asp Asp Leu Thr Gln Trp Leu Ser Glu Ala Glu Asp Leu
    1985              1990              1995

Leu Val Asp Thr Cys Ala Pro Asp Gly Ser Leu Asp Leu Glu Lys
    2000              2005              2010

Ala Arg Ala Gln Gln Leu Glu Leu Glu Glu Gly Leu Ser Ser His
    2015              2020              2025

Gln Pro Ser Leu Ile Lys Val Asn Arg Lys Gly Glu Asp Leu Val
    2030              2035              2040

Gln Arg Leu Arg Pro Ser Glu Ala Ser Phe Leu Lys Glu Lys Leu
    2045              2050              2055

Ala Gly Phe Asn Gln Arg Trp Ser Thr Leu Val Ala Glu Val Glu
    2060              2065              2070

Ala Leu Gln Pro Arg Leu Lys Gly Glu Ser Gln Gln Val Leu Gly
    2075              2080              2085

Tyr Lys Arg Arg Leu Asp Glu Val Thr Cys Trp Leu Thr Lys Val
    2090              2095              2100

Glu Ser Ala Val Gln Lys Arg Ser Thr Pro Asp Pro Glu Glu Ser
    2105              2110              2115

Pro Gln Glu Leu Thr Asp Leu Ala Gln Glu Thr Glu Val Gln Ala
    2120              2125              2130

Glu Asn Ile Lys Trp Leu Asn Arg Ala Glu Leu Glu Met Leu Ser
    2135              2140              2145

Asp Lys Asn Leu Ser Leu Arg Glu Arg Glu Lys Leu Ser Glu Ser
    2150              2155              2160

-continued

```
Leu Arg Asn Val Asn Thr Thr Trp Thr Lys Val Cys Arg Glu Val
2165                2170                2175

Pro Ser Leu Leu Lys Thr Arg Thr Gln Asp Pro Cys Ser Ala Pro
2180                2185                2190

Gln Met Arg Met Ala Ala His Pro Asn Val Gln Lys Val Val Leu
2195                2200                2205

Val Ser Ser Ala Ser Asp Ala Pro Leu Arg Gly Gly Leu Glu Ile
2210                2215                2220

Ser Val Pro Ala Asp Leu Asp Lys Thr Ile Thr Glu Leu Ala Asp
2225                2230                2235

Trp Leu Val Leu Ile Asp Gln Met Leu Lys Ser Asn Ile Val Thr
2240                2245                2250

Val Gly Asp Val Lys Glu Ile Asn Lys Thr Val Ser Arg Met Lys
2255                2260                2265

Ile Thr Lys Ala Asp Leu Glu Gln Arg His Pro Gln Leu Asp Cys
2270                2275                2280

Val Phe Thr Leu Ala Gln Asn Leu Lys Asn Lys Ala Ser Ser Ser
2285                2290                2295

Asp Val Arg Thr Ala Ile Thr Glu Lys Leu Glu Lys Leu Lys Thr
2300                2305                2310

Gln Trp Glu Ser Thr Gln His Gly Val Glu Leu Arg Arg Gln Gln
2315                2320                2325

Leu Glu Asp Met Val Val Asp Ser Leu Gln Trp Asp Asp His Arg
2330                2335                2340

Glu Glu Thr Glu Glu Leu Met Arg Lys Tyr Glu Ala Arg Phe Tyr
2345                2350                2355

Met Leu Gln Gln Ala Arg Arg Asp Pro Leu Ser Lys Gln Val Ser
2360                2365                2370

Asp Asn Gln Leu Leu Leu Gln Glu Leu Gly Ser Gly Asp Gly Val
2375                2380                2385

Ile Met Ala Phe Asp Asn Val Leu Gln Lys Leu Leu Glu Glu Tyr
2390                2395                2400

Ser Gly Asp Asp Thr Arg Asn Val Glu Glu Thr Thr Glu Tyr Leu
2405                2410                2415

Lys Thr Ser Trp Val Asn Leu Lys Gln Ser Ile Ala Asp Arg Gln
2420                2425                2430

Ser Ala Leu Glu Ala Glu Leu Gln Thr Val Gln Thr Ser Arg Arg
2435                2440                2445

Asp Leu Glu Asn Phe Val Lys Trp Leu Gln Glu Ala Glu Thr Thr
2450                2455                2460

Ala Asn Val Leu Ala Asp Ala Ser Gln Arg Glu Asn Ala Leu Gln
2465                2470                2475

Asp Ser Val Leu Ala Arg Gln Leu Arg Gln Gln Met Leu Asp Ile
2480                2485                2490

Gln Ala Glu Ile Asp Ala His Asn Asp Ile Phe Lys Ser Ile Asp
2495                2500                2505

Gly Asn Arg Gln Lys Met Val Lys Ala Leu Gly Asn Ser Glu Glu
2510                2515                2520

Ala Thr Met Leu Gln His Arg Leu Asp Asp Met Asn Gln Arg Trp
2525                2530                2535

Asn Asp Leu Lys Ala Lys Ser Ala Ser Ile Arg Ala His Leu Glu
2540                2545                2550

Ala Ser Ala Glu Lys Trp Asn Arg Leu Leu Ala Ser Leu Glu Glu
```

-continued

```
            2555                2560                2565

Leu Ile Lys Trp Leu Asn Met Lys Asp Glu Glu Leu Lys Lys Gln
        2570                2575                2580

Met Pro Ile Gly Gly Asp Val Pro Ala Leu Gln Leu Gln Tyr Asp
    2585                2590                2595

His Cys Lys Val Leu Arg Arg Glu Leu Lys Glu Lys Glu Tyr Ser
    2600                2605                2610

Val Leu Asn Ala Val Asp Gln Ala Arg Val Phe Leu Ala Asp Gln
    2615                2620                2625

Pro Ile Glu Ala Pro Glu Glu Pro Arg Arg Asn Pro Gln Ser Lys
    2630                2635                2640

Thr Glu Leu Thr Pro Glu Glu Arg Ala Gln Lys Ile Ala Lys Ala
    2645                2650                2655

Met Arg Lys Gln Ser Ser Glu Val Arg Glu Lys Trp Glu Asn Leu
    2660                2665                2670

Asn Ala Val Thr Ser Asn Trp Gln Lys Gln Val Gly Lys Ala Leu
    2675                2680                2685

Glu Lys Leu Arg Asp Leu Gln Gly Ala Met Asp Asp Leu Asp Ala
    2690                2695                2700

Asp Met Lys Glu Val Glu Ala Val Arg Asn Gly Trp Lys Pro Val
    2705                2710                2715

Gly Asp Leu Leu Ile Asp Ser Leu Gln Asp His Ile Glu Lys Thr
    2720                2725                2730

Leu Ala Phe Arg Glu Glu Ile Ala Pro Ile Asn Leu Lys Val Lys
    2735                2740                2745

Thr Met Asn Asp Leu Ser Ser Gln Leu Ser Pro Leu Asp Leu His
    2750                2755                2760

Pro Ser Leu Lys Met Ser Arg Gln Leu Asp Asp Leu Asn Met Arg
    2765                2770                2775

Trp Lys Leu Leu Gln Val Ser Val Asp Asp Arg Leu Lys Gln Leu
    2780                2785                2790

Gln Glu Ala His Arg Asp Phe Gly Pro Ser Ser Gln His Phe Leu
    2795                2800                2805

Ser Thr Ser Val Gln Leu Pro Trp Gln Arg Ser Ile Ser His Asn
    2810                2815                2820

Lys Val Pro Tyr Tyr Ile Asn His Gln Thr Gln Thr Thr Cys Trp
    2825                2830                2835

Asp His Pro Lys Met Thr Glu Leu Phe Gln Ser Leu Ala Asp Leu
    2840                2845                2850

Asn Asn Val Arg Phe Ser Ala Tyr Arg Thr Ala Ile Lys Ile Arg
    2855                2860                2865

Arg Leu Gln Lys Ala Leu Cys Leu Asp Leu Leu Glu Leu Asn Thr
    2870                2875                2880

Thr Asn Glu Val Phe Lys Gln His Lys Leu Asn Gln Asn Asp Gln
    2885                2890                2895

Leu Leu Ser Val Pro Asp Val Ile Asn Cys Leu Thr Thr Thr Tyr
    2900                2905                2910

Asp Gly Leu Glu Gln Leu His Lys Asp Leu Val Asn Val Pro Leu
    2915                2920                2925

Cys Val Asp Met Cys Leu Asn Trp Leu Leu Asn Val Tyr Asp Thr
    2930                2935                2940

Gly Arg Thr Gly Lys Ile Arg Val Gln Ser Leu Lys Ile Gly Leu
    2945                2950                2955
```

-continued

```
Met Ser Leu Ser Lys Gly Leu Leu Glu Glu Lys Tyr Arg Cys Leu
    2960                2965                2970

Phe Lys Glu Val Ala Gly Pro Thr Glu Met Cys Asp Gln Arg Gln
    2975                2980                2985

Leu Gly Leu Leu Leu His Asp Ala Ile Gln Ile Pro Arg Gln Leu
    2990                2995                3000

Gly Glu Val Ala Ala Phe Gly Gly Ser Asn Ile Glu Pro Ser Val
    3005                3010                3015

Arg Ser Cys Phe Gln Gln Asn Asn Asn Lys Pro Glu Ile Ser Val
    3020                3025                3030

Lys Glu Phe Ile Asp Trp Met His Leu Glu Pro Gln Ser Met Val
    3035                3040                3045

Trp Leu Pro Val Leu His Arg Val Ala Ala Glu Thr Ala Lys
    3050                3055                3060

His Gln Ala Lys Cys Asn Ile Cys Lys Glu Cys Pro Ile Val Gly
    3065                3070                3075

Phe Arg Tyr Arg Ser Leu Lys His Phe Asn Tyr Asp Val Cys Gln
    3080                3085                3090

Ser Cys Phe Phe Ser Gly Arg Thr Ala Lys Gly His Lys Leu His
    3095                3100                3105

Tyr Pro Met Val Glu Tyr Cys Ile Pro Thr Thr Ser Gly Glu Asp
    3110                3115                3120

Val Arg Asp Phe Thr Lys Val Leu Lys Asn Lys Phe Arg Ser Lys
    3125                3130                3135

Lys Tyr Phe Ala Lys His Pro Arg Leu Gly Tyr Leu Pro Val Gln
    3140                3145                3150

Thr Val Leu Glu Gly Asp Asn Leu Glu Thr Pro Ile Thr Leu Ile
    3155                3160                3165

Ser Met Trp Pro Glu His Tyr Asp Pro Ser Gln Ser Pro Gln Leu
    3170                3175                3180

Phe His Asp Asp Thr His Ser Arg Ile Glu Gln Tyr Ala Thr Arg
    3185                3190                3195

Leu Ala Gln Met Glu Arg Thr Asn Gly Ser Phe Leu Thr Asp Ser
    3200                3205                3210

Ser Ser Thr Thr Gly Ser Val Glu Asp Glu His Ala Leu Ile Gln
    3215                3220                3225

Gln Tyr Cys Gln Thr Leu Gly Gly Glu Ser Pro Val Ser Gln Pro
    3230                3235                3240

Gln Ser Pro Ala Gln Ile Leu Lys Ser Val Glu Arg Glu Glu Arg
    3245                3250                3255

Gly Glu Leu Glu Arg Ile Ile Ala Asp Leu Glu Glu Glu Gln Arg
    3260                3265                3270

Asn Leu Gln Val Glu Tyr Glu Gln Leu Lys Glu Gln His Leu Arg
    3275                3280                3285

Arg Gly Leu Pro Val Gly Ser Pro Pro Asp Ser Ile Val Ser Pro
    3290                3295                3300

His His Thr Ser Glu Asp Ser Glu Leu Ile Ala Glu Ala Lys Leu
    3305                3310                3315

Leu Arg Gln His Lys Gly Arg Leu Glu Ala Arg Met Gln Ile Leu
    3320                3325                3330

Glu Asp His Asn Lys Gln Leu Glu Ser Gln Leu His Arg Leu Arg
    3335                3340                3345
```

-continued

```
Gln Leu Leu Glu Gln Pro Asp Ser Asp Ser Arg Ile Asn Gly Val
    3350            3355            3360

Ser Pro Trp Ala Ser Pro Gln His Ser Ala Leu Ser Tyr Ser Leu
    3365            3370            3375

Asp Thr Asp Pro Gly Pro Gln Phe His Gln Ala Ala Ser Glu Asp
    3380            3385            3390

Leu Leu Ala Pro Pro His Asp Thr Ser Thr Asp Leu Thr Asp Val
    3395            3400            3405

Met Glu Gln Ile Asn Ser Thr Phe Pro Ser Cys Ser Ser Asn Val
    3410            3415            3420

Pro Ser Arg Pro Gln Ala Met
    3425            3430

<210> SEQ ID NO 10
<211> LENGTH: 4083
<212> TYPE: DNA
<213> ORGANISM: Homo sapiens
<220> FEATURE:
<221> NAME/KEY: CDS
<222> LOCATION: (1)..(4083)
<220> FEATURE:
<221> NAME/KEY: misc_feature
<222> LOCATION: (1)..(117)
<223> OTHER INFORMATION: TAT and epitope tag coding region

<400> SEQUENCE: 10 atg gac tac aag gac gac gat gac aag ggc tac ggc cgc aag aaa cgc      48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac      96
Arg Gln Arg Arg Arg Gly Gly Ser Thr Met Ser Gly Tyr Pro Tyr Asp
                20                  25                  30 gtc cca gac tat gct ggc tcc atg gcc aag tat gga gaa cat gaa gcc     144
Val Pro Asp Tyr Ala Gly Ser Met Ala Lys Tyr Gly Glu His Glu Ala
            35                  40                  45 agt cct gac aat ggg cag aac gaa ttc agt gat atc att aag tcc aga     192
Ser Pro Asp Asn Gly Gln Asn Glu Phe Ser Asp Ile Ile Lys Ser Arg
        50                  55                  60 tct gat gaa cac aat gac gta cag aag aaa acc ttt acc aaa tgg ata     240
Ser Asp Glu His Asn Asp Val Gln Lys Lys Thr Phe Thr Lys Trp Ile
65                  70                  75                  80 aat gct cga ttt tca aag agt ggg aaa cca ccc atc aat gat atg ttc     288
Asn Ala Arg Phe Ser Lys Ser Gly Lys Pro Pro Ile Asn Asp Met Phe
                85                  90                  95 aca gac ctc aaa gat gga agg aag cta ttg gat ctt cta gaa ggc ctc     336
Thr Asp Leu Lys Asp Gly Arg Lys Leu Leu Asp Leu Leu Glu Gly Leu
            100                 105                 110 aca gga aca tca ctg cca aag gaa cgt ggt tcc aca agg gta cat gcc     384
Thr Gly Thr Ser Leu Pro Lys Glu Arg Gly Ser Thr Arg Val His Ala
        115                 120                 125 tta aat aac gtc aac aga gtg ctg cag gtt tta cat cag aac aat gtg     432
Leu Asn Asn Val Asn Arg Val Leu Gln Val Leu His Gln Asn Asn Val
    130                 135                 140 gaa tta gtg aat ata ggg gga act gac att gtg gat gga aat cac aaa     480
Glu Leu Val Asn Ile Gly Gly Thr Asp Ile Val Asp Gly Asn His Lys
145                 150                 155                 160 ctg act ttg ggg tta ctt tgg agc atc att ttg cac tgg cag gtg aaa     528
Leu Thr Leu Gly Leu Leu Trp Ser Ile Ile Leu His Trp Gln Val Lys
                165                 170                 175 gat gtc atg aag gat gtc atg tcg gac ctg cag cag acg aac agt gag     576
Asp Val Met Lys Asp Val Met Ser Asp Leu Gln Gln Thr Asn Ser Glu
```

-continued

```
              180                 185                 190
aag atc ctg ctc agc tgg gtg cgt cag acc acc agg ccc tac agc caa     624
Lys Ile Leu Leu Ser Trp Val Arg Gln Thr Thr Arg Pro Tyr Ser Gln
        195                 200                 205 gtc aac gtc ctc aac ttc acc acc agc tgg aca gat gga ctc gcc ttt     672
Val Asn Val Leu Asn Phe Thr Thr Ser Trp Thr Asp Gly Leu Ala Phe
210                 215                 220 aat gct gtc ctc cac cga cat aaa cct gat ctc ttc agc tgg gat aaa     720
Asn Ala Val Leu His Arg His Lys Pro Asp Leu Phe Ser Trp Asp Lys
225                 230                 235                 240 gtt gtc aaa atg tca cca att gag aga ctt gaa cat gcc ttc agc aag     768
Val Val Lys Met Ser Pro Ile Glu Arg Leu Glu His Ala Phe Ser Lys
                245                 250                 255 gct caa act tat ttg gga att gaa aag ctg tta gat cct gaa gat gtt     816
Ala Gln Thr Tyr Leu Gly Ile Glu Lys Leu Leu Asp Pro Glu Asp Val
            260                 265                 270 gcc gtt cag ctt cct gac aag aaa tcc ata att atg tat tta aca tct     864
Ala Val Gln Leu Pro Asp Lys Lys Ser Ile Ile Met Tyr Leu Thr Ser
        275                 280                 285 ttg ttt gag gtg cta cct cag caa gtc acc ata gac gcc atc cgt gag     912
Leu Phe Glu Val Leu Pro Gln Gln Val Thr Ile Asp Ala Ile Arg Glu
290                 295                 300 gta gag aca ctc cca agg aaa tat aaa aaa gaa tgt gaa gaa gag gca     960
Val Glu Thr Leu Pro Arg Lys Tyr Lys Lys Glu Cys Glu Glu Glu Ala
305                 310                 315                 320 att aat ata cag agt aca gcg cct gag gag gag cat gag agt ccc cga    1008
Ile Asn Ile Gln Ser Thr Ala Pro Glu Glu Glu His Glu Ser Pro Arg
                325                 330                 335 gct gaa act ccc agc act gtc act gag gtt gac atg gat ctg gac agc    1056
Ala Glu Thr Pro Ser Thr Val Thr Glu Val Asp Met Asp Leu Asp Ser
            340                 345                 350 tat cag att gcg ttg gag gaa gtg ctg acc tgg ttg ctt tct gct gag    1104
Tyr Gln Ile Ala Leu Glu Glu Val Leu Thr Trp Leu Leu Ser Ala Glu
        355                 360                 365 gac act ttc cag gag cag gat gat att tct gat gat gtt gaa gaa gtc    1152
Asp Thr Phe Gln Glu Gln Asp Asp Ile Ser Asp Asp Val Glu Glu Val
370                 375                 380 aaa gac cag ttt gca acc cat gaa gct ttt atg atg gaa ctg act gca    1200
Lys Asp Gln Phe Ala Thr His Glu Ala Phe Met Met Glu Leu Thr Ala
385                 390                 395                 400 cac cag agc agt gtg ggc agc gtc ctg cag gca ggc aac caa ctg ata    1248
His Gln Ser Ser Val Gly Ser Val Leu Gln Ala Gly Asn Gln Leu Ile
                405                 410                 415 aca caa gga act ctg tca gac gaa gaa gaa ttt gag att cag gaa cag    1296
Thr Gln Gly Thr Leu Ser Asp Glu Glu Glu Phe Glu Ile Gln Glu Gln
            420                 425                 430 atg acc ctg ctg aat gct aga tgg gag gct ctt agg gtg gag agt atg    1344
Met Thr Leu Leu Asn Ala Arg Trp Glu Ala Leu Arg Val Glu Ser Met
        435                 440                 445 gac aga cag tcc cgg ctg cac gat gtg ctg atg gaa ctg cag aag aag    1392
Asp Arg Gln Ser Arg Leu His Asp Val Leu Met Glu Leu Gln Lys Lys
450                 455                 460 caa ctg cag cag ctc tcc gcc tgg tta aca ctc aca gag gag cgc att    1440
Gln Leu Gln Gln Leu Ser Ala Trp Leu Thr Leu Thr Glu Glu Arg Ile
465                 470                 475                 480 cag aag atg gaa act tgc ccc ctg gat gat gat gta aaa tct cta caa    1488
Gln Lys Met Glu Thr Cys Pro Leu Asp Asp Asp Val Lys Ser Leu Gln
                485                 490                 495 aag ctg cta gaa gaa cat aaa agt ttg caa agt gat ctt gag gct gaa    1536
```

```
                Lys Leu Leu Glu Glu His Lys Ser Leu Gln Ser Asp Leu Glu Ala Glu
                                500                 505                 510 cag gtg aaa gta aat tca cta act cac atg gtg gtc att gtt gat gaa              1584
Gln Val Lys Val Asn Ser Leu Thr His Met Val Val Ile Val Asp Glu
        515                 520                 525 aac agt ggt gag agt gct aca gct atc cta gaa gac cag tta cag aaa              1632
Asn Ser Gly Glu Ser Ala Thr Ala Ile Leu Glu Asp Gln Leu Gln Lys
530                 535                 540 ctt ggt gag cgc tgg aca gca gta tgc cgt tgg act gaa gaa cgc tgg              1680
Leu Gly Glu Arg Trp Thr Ala Val Cys Arg Trp Thr Glu Glu Arg Trp
545                 550                 555                 560 aat agg tta caa gaa atc aat ata ttg tgg cag gaa tta ttg gaa gaa              1728
Asn Arg Leu Gln Glu Ile Asn Ile Leu Trp Gln Glu Leu Leu Glu Glu
                565                 570                 575 cag tgc ttg ttg aaa gct tgg tta acc gaa aaa gaa gag gct tta aat              1776
Gln Cys Leu Leu Lys Ala Trp Leu Thr Glu Lys Glu Glu Ala Leu Asn
            580                 585                 590 aaa gtc cag aca agc aac ttc aaa gac caa aag gaa cta agt gtc agt              1824
Lys Val Gln Thr Ser Asn Phe Lys Asp Gln Lys Glu Leu Ser Val Ser
        595                 600                 605 gtt cga cgt ctg gct att ttg aag gaa gac atg gaa atg aag cgt caa              1872
Val Arg Arg Leu Ala Ile Leu Lys Glu Asp Met Glu Met Lys Arg Gln
610                 615                 620 aca ttg gat cag ctg agt gag att ggc cag gat gtg gga caa tta ctt              1920
Thr Leu Asp Gln Leu Ser Glu Ile Gly Gln Asp Val Gly Gln Leu Leu
625                 630                 635                 640 gat aat tcc aag gca tct aag aag atc aac agt gac tca gag gaa ctg              1968
Asp Asn Ser Lys Ala Ser Lys Lys Ile Asn Ser Asp Ser Glu Glu Leu
                645                 650                 655 act caa aga tgg gat tct ttg gtt cag aga cta gaa gat tcc tcc aac              2016
Thr Gln Arg Trp Asp Ser Leu Val Gln Arg Leu Glu Asp Ser Ser Asn
            660                 665                 670 cag gtg act cag gct gta gca aag ctg ggg atg tct cag att cct cag              2064
Gln Val Thr Gln Ala Val Ala Lys Leu Gly Met Ser Gln Ile Pro Gln
        675                 680                 685 aag gac ctt ttg gag act gtt cgt gta aga gaa caa gca att aca aaa              2112
Lys Asp Leu Leu Glu Thr Val Arg Val Arg Glu Gln Ala Ile Thr Lys
690                 695                 700 aaa tct aag cag gaa ctg cct cct cct cct ccc cca aag aag aga cag              2160
Lys Ser Lys Gln Glu Leu Pro Pro Pro Pro Pro Pro Lys Lys Arg Gln
705                 710                 715                 720 atc cat gtg gat gcc cac aga gat ttt gga cca tcc tct cag cat ttt              2208
Ile His Val Asp Ala His Arg Asp Phe Gly Pro Ser Ser Gln His Phe
                725                 730                 735 ctc tct acg tca gtc cag ctg ccg tgg caa aga tcc att tca cat aat              2256
Leu Ser Thr Ser Val Gln Leu Pro Trp Gln Arg Ser Ile Ser His Asn
            740                 745                 750 aaa gtg ccc tat tac atc aac cat caa aca cag acc acc tgt tgg gac              2304
Lys Val Pro Tyr Tyr Ile Asn His Gln Thr Gln Thr Thr Cys Trp Asp
        755                 760                 765 cat cct aaa atg acc gaa ctc ttt caa tcc ctt gct gac ctg aat aat              2352
His Pro Lys Met Thr Glu Leu Phe Gln Ser Leu Ala Asp Leu Asn Asn
770                 775                 780 gta cgt ttt tct gcc tac cgt aca gca atc aaa atc cga aga cta caa              2400
Val Arg Phe Ser Ala Tyr Arg Thr Ala Ile Lys Ile Arg Arg Leu Gln
785                 790                 795                 800 aaa gca cta tgt ttg gat ctc tta gag ttg agt aca aca aat gaa att              2448
Lys Ala Leu Cys Leu Asp Leu Leu Glu Leu Ser Thr Thr Asn Glu Ile
                805                 810                 815
```

```
ttc aaa cag cac aag ttg aac caa aat gac cag ctc ctc agt gtt cca      2496
Phe Lys Gln His Lys Leu Asn Gln Asn Asp Gln Leu Leu Ser Val Pro
            820                 825                 830 gat gtc atc aac tgt ctg aca aca act tat gat gga ctt gag caa atg      2544
Asp Val Ile Asn Cys Leu Thr Thr Thr Tyr Asp Gly Leu Glu Gln Met
        835                 840                 845 cat aag gac ctg gtc aac gtt cca ctc tgt gtt gat atg tgt ctc aat      2592
His Lys Asp Leu Val Asn Val Pro Leu Cys Val Asp Met Cys Leu Asn
    850                 855                 860 tgg ttg ctc aat gtc tat gac acg ggt cga act gga aaa att aga gtg      2640
Trp Leu Leu Asn Val Tyr Asp Thr Gly Arg Thr Gly Lys Ile Arg Val
865                 870                 875                 880 cag agt ctg aag att gga tta atg tct ctc tcc aaa ggt ctc ttg gaa      2688
Gln Ser Leu Lys Ile Gly Leu Met Ser Leu Ser Lys Gly Leu Leu Glu
                885                 890                 895 gaa aaa tac aga tat ctc ttt aag gaa gtt gca ggg cca aca gaa atg      2736
Glu Lys Tyr Arg Tyr Leu Phe Lys Glu Val Ala Gly Pro Thr Glu Met
            900                 905                 910 tgt gac cag agg cag ctg ggc ctg tta ctt cat gat gcc atc cag atc      2784
Cys Asp Gln Arg Gln Leu Gly Leu Leu Leu His Asp Ala Ile Gln Ile
        915                 920                 925 ccc cgg cag cta ggt gaa gta gca gct ttt gga ggc agt aat att gag      2832
Pro Arg Gln Leu Gly Glu Val Ala Ala Phe Gly Gly Ser Asn Ile Glu
    930                 935                 940 cct agt gtt cgc agc tgc ttc caa cag aat aac aat aaa cca gaa ata      2880
Pro Ser Val Arg Ser Cys Phe Gln Gln Asn Asn Asn Lys Pro Glu Ile
945                 950                 955                 960 agt gtg aaa gag ttt ata gat tgg atg cat ttg gaa cca cag tcc atg      2928
Ser Val Lys Glu Phe Ile Asp Trp Met His Leu Glu Pro Gln Ser Met
                965                 970                 975 gtt tgg ctc cca gtt tta cat cga gtg gca gca gcg gag act gca aaa      2976
Val Trp Leu Pro Val Leu His Arg Val Ala Ala Ala Glu Thr Ala Lys
            980                 985                 990 cat cag gcc aaa tgc aac atc tgt aaa gaa tgt cca att gtc ggg ttc      3024
His Gln Ala Lys Cys Asn Ile Cys Lys Glu Cys Pro Ile Val Gly Phe
        995                 1000                1005 agg tat aga agc ctt aag cat ttt aac tat gat gtc tgc cag agt         3069
Arg Tyr Arg Ser Leu Lys His Phe Asn Tyr Asp Val Cys Gln Ser
    1010                1015                1020 tgt ttc ttt tcg ggt cga aca gca aaa ggt cac aaa tta cat tac         3114
Cys Phe Phe Ser Gly Arg Thr Ala Lys Gly His Lys Leu His Tyr
1025                1030                1035 cca atg gtg gaa tat tgt ata cct aca aca tct ggg gaa gat gta         3159
Pro Met Val Glu Tyr Cys Ile Pro Thr Thr Ser Gly Glu Asp Val
    1040                1045                1050 cga gac ttc aca aag gta ctt aag aac aag ttc agg tcg aag aag         3204
Arg Asp Phe Thr Lys Val Leu Lys Asn Lys Phe Arg Ser Lys Lys
    1055                1060                1065 tac ttt gcc aaa cac cct cga ctt ggt tac ctg cct gtc cag aca         3249
Tyr Phe Ala Lys His Pro Arg Leu Gly Tyr Leu Pro Val Gln Thr
    1070                1075                1080 gtt ctt gaa ggt gac aac tta gag act cct atc aca ctc atc agt         3294
Val Leu Glu Gly Asp Asn Leu Glu Thr Pro Ile Thr Leu Ile Ser
    1085                1090                1095 atg tgg cca gag cac tat gac ccc tca caa tct cct caa ctg ttt         3339
Met Trp Pro Glu His Tyr Asp Pro Ser Gln Ser Pro Gln Leu Phe
    1100                1105                1110 cat gat gac acc cat tca aga ata gaa caa tat gcc aca cga ctg         3384
His Asp Asp Thr His Ser Arg Ile Glu Gln Tyr Ala Thr Arg Leu
    1115                1120                1125
```

| | | |
|---|---|---|
| gcc cag atg gaa agg act aat ggg tct ttt ctc act gat agc agc<br>Ala Gln Met Glu Arg Thr Asn Gly Ser Phe Leu Thr Asp Ser Ser<br>      1130                    1135                 1140 | | 3429 |
| tcc acc aca gga agt gtg gaa gac gag cac gcc ctc atc cag cag<br>Ser Thr Thr Gly Ser Val Glu Asp Glu His Ala Leu Ile Gln Gln<br>      1145                    1150                 1155 | | 3474 |
| tat tgc caa aca ctc gga gga gag tcc cca gtg agc cag ccg cag<br>Tyr Cys Gln Thr Leu Gly Gly Glu Ser Pro Val Ser Gln Pro Gln<br>      1160                    1165                 1170 | | 3519 |
| agc cca gct cag atc ctg aag tca gta gag agg gaa gaa cgt gga<br>Ser Pro Ala Gln Ile Leu Lys Ser Val Glu Arg Glu Glu Arg Gly<br>      1175                    1180                 1185 | | 3564 |
| gaa ctg gag agg atc att gct gac ctg gag gaa gaa caa aga aat<br>Glu Leu Glu Arg Ile Ile Ala Asp Leu Glu Glu Glu Gln Arg Asn<br>      1190                    1195                 1200 | | 3609 |
| cta cag gtg gag tat gag cag ctg aag gac cag cac ctc cga agg<br>Leu Gln Val Glu Tyr Glu Gln Leu Lys Asp Gln His Leu Arg Arg<br>      1205                    1210                 1215 | | 3654 |
| ggg ctc cct gtc ggt tca ccg cca gag tcg att ata tct ccc cat<br>Gly Leu Pro Val Gly Ser Pro Pro Glu Ser Ile Ile Ser Pro His<br>      1220                    1225                 1230 | | 3699 |
| cac acg tct gag gat tca gaa ctt ata gca gaa gca aaa ctc ctc<br>His Thr Ser Glu Asp Ser Glu Leu Ile Ala Glu Ala Lys Leu Leu<br>      1235                    1240                 1245 | | 3744 |
| agg cag cac aaa ggt cgg ctg gag gct agg atg cag att tta gaa<br>Arg Gln His Lys Gly Arg Leu Glu Ala Arg Met Gln Ile Leu Glu<br>      1250                    1255                 1260 | | 3789 |
| gat cac aat aaa cag ctg gag tct cag ctc cac cgc ctc cga cag<br>Asp His Asn Lys Gln Leu Glu Ser Gln Leu His Arg Leu Arg Gln<br>      1265                    1270                 1275 | | 3834 |
| ctg ctg gag cag cct gaa tct gat tcc cga atc aat ggt gtt tcc<br>Leu Leu Glu Gln Pro Glu Ser Asp Ser Arg Ile Asn Gly Val Ser<br>      1280                    1285                 1290 | | 3879 |
| cca tgg gct tct cct cag cat tct gca ctg agc tac tcg ctt gat<br>Pro Trp Ala Ser Pro Gln His Ser Ala Leu Ser Tyr Ser Leu Asp<br>      1295                    1300                 1305 | | 3924 |
| cca gat gcc tcc ggc cca cag ttc cac cag gca gcg gga gag gac<br>Pro Asp Ala Ser Gly Pro Gln Phe His Gln Ala Ala Gly Glu Asp<br>      1310                    1315                 1320 | | 3969 |
| ctg ctg gcc cca ccg cac gac acc agc acg gat ctc acg gag gtc<br>Leu Leu Ala Pro Pro His Asp Thr Ser Thr Asp Leu Thr Glu Val<br>      1325                    1330                 1335 | | 4014 |
| atg gag cag att cac agc acg ttt cca tct tgc tgc cca aat gtt<br>Met Glu Gln Ile His Ser Thr Phe Pro Ser Cys Cys Pro Asn Val<br>      1340                    1345                 1350 | | 4059 |
| ccc agc agg cca cag gca atg tga<br>Pro Ser Arg Pro Gln Ala Met<br>      1355                    1360 | | 4083 |

<210> SEQ ID NO 11
<211> LENGTH: 1360
<212> TYPE: PRT
<213> ORGANISM: Homo sapiens

<400> SEQUENCE: 11

Met Asp Tyr Lys Asp Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
                20                  25                  30

-continued

```
Val Pro Asp Tyr Ala Gly Ser Met Ala Lys Tyr Gly Glu His Glu Ala
        35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270

Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Ala
305                 310                 315                 320

Ile Asn Ile Gln Ser Thr Ala Pro Glu Glu His Glu Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln Asp Asp Ile Ser Asp Val Glu Glu Val
    370                 375                 380

Lys Asp Gln Phe Ala Thr His Glu Ala Phe Met Met Glu Leu Thr Ala
385                 390                 395                 400

His Gln Ser Ser Val Gly Ser Val Leu Gln Ala Gly Asn Gln Leu Ile
                405                 410                 415

Thr Gln Gly Thr Leu Ser Asp Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Asp Arg Gln Ser Arg Leu His Asp Val Leu Met Glu Leu Gln Lys Lys
```

-continued

```
            450                 455                 460
Gln Leu Gln Gln Leu Ser Ala Trp Leu Thr Leu Thr Glu Glu Arg Ile
465                 470                 475                 480
Gln Lys Met Glu Thr Cys Pro Leu Asp Asp Asp Val Lys Ser Leu Gln
                485                 490                 495
Lys Leu Leu Glu Glu His Lys Ser Leu Gln Ser Asp Leu Glu Ala Glu
            500                 505                 510
Gln Val Lys Val Asn Ser Leu Thr His Met Val Val Ile Val Asp Glu
            515                 520                 525
Asn Ser Gly Glu Ser Ala Thr Ala Ile Leu Glu Asp Gln Leu Gln Lys
            530                 535                 540
Leu Gly Glu Arg Trp Thr Ala Val Cys Arg Trp Thr Glu Glu Arg Trp
545                 550                 555                 560
Asn Arg Leu Gln Glu Ile Asn Ile Leu Trp Gln Glu Leu Leu Glu Glu
                565                 570                 575
Gln Cys Leu Leu Lys Ala Trp Leu Thr Glu Lys Glu Glu Ala Leu Asn
            580                 585                 590
Lys Val Gln Thr Ser Asn Phe Lys Asp Gln Lys Glu Leu Ser Val Ser
            595                 600                 605
Val Arg Arg Leu Ala Ile Leu Lys Glu Asp Met Glu Met Lys Arg Gln
610                 615                 620
Thr Leu Asp Gln Leu Ser Glu Ile Gly Gln Asp Val Gly Gln Leu Leu
625                 630                 635                 640
Asp Asn Ser Lys Ala Ser Lys Lys Ile Asn Ser Asp Ser Glu Glu Leu
                645                 650                 655
Thr Gln Arg Trp Asp Ser Leu Val Gln Arg Leu Glu Asp Ser Ser Asn
            660                 665                 670
Gln Val Thr Gln Ala Val Ala Lys Leu Gly Met Ser Gln Ile Pro Gln
            675                 680                 685
Lys Asp Leu Leu Glu Thr Val Arg Val Arg Glu Gln Ala Ile Thr Lys
            690                 695                 700
Lys Ser Lys Gln Glu Leu Pro Pro Pro Pro Pro Lys Lys Arg Gln
705                 710                 715                 720
Ile His Val Asp Ala His Arg Asp Phe Gly Pro Ser Ser Gln His Phe
                725                 730                 735
Leu Ser Thr Ser Val Gln Leu Pro Trp Gln Arg Ser Ile Ser His Asn
            740                 745                 750
Lys Val Pro Tyr Tyr Ile Asn His Gln Thr Gln Thr Thr Cys Trp Asp
            755                 760                 765
His Pro Lys Met Thr Glu Leu Phe Gln Ser Leu Ala Asp Leu Asn Asn
770                 775                 780
Val Arg Phe Ser Ala Tyr Arg Thr Ala Ile Lys Ile Arg Arg Leu Gln
785                 790                 795                 800
Lys Ala Leu Cys Leu Asp Leu Leu Glu Leu Ser Thr Thr Asn Glu Ile
                805                 810                 815
Phe Lys Gln His Lys Leu Asn Gln Asn Asp Gln Leu Leu Ser Val Pro
            820                 825                 830
Asp Val Ile Asn Cys Leu Thr Thr Thr Tyr Asp Gly Leu Glu Gln Met
            835                 840                 845
His Lys Asp Leu Val Asn Val Pro Leu Cys Val Asp Met Cys Leu Asn
            850                 855                 860
Trp Leu Leu Asn Val Tyr Asp Thr Gly Arg Thr Gly Lys Ile Arg Val
865                 870                 875                 880
```

-continued

```
Gln Ser Leu Lys Ile Gly Leu Met Ser Leu Ser Lys Gly Leu Leu Glu
            885                 890                 895
Glu Lys Tyr Arg Tyr Leu Phe Lys Glu Val Ala Gly Pro Thr Glu Met
            900                 905                 910
Cys Asp Gln Arg Gln Leu Gly Leu Leu His Asp Ala Ile Gln Ile
            915                 920                 925
Pro Arg Gln Leu Gly Glu Val Ala Ala Phe Gly Gly Ser Asn Ile Glu
        930                 935                 940
Pro Ser Val Arg Ser Cys Phe Gln Gln Asn Asn Asn Lys Pro Glu Ile
945                 950                 955                 960
Ser Val Lys Glu Phe Ile Asp Trp Met His Leu Glu Pro Gln Ser Met
            965                 970                 975
Val Trp Leu Pro Val Leu His Arg Val Ala Ala Glu Thr Ala Lys
            980                 985                 990
His Gln Ala Lys Cys Asn Ile Cys  Lys Glu Cys Pro Ile Val Gly Phe
            995                 1000                1005
Arg Tyr  Arg Ser Leu Lys His  Phe Asn Tyr Asp Val  Cys Gln Ser
    1010                1015                1020
Cys Phe  Phe Ser Gly Arg Thr  Ala Lys Gly His Lys  Leu His Tyr
    1025                1030                1035
Pro Met  Val Glu Tyr Cys Ile  Pro Thr Thr Ser Gly  Glu Asp Val
    1040                1045                1050
Arg Asp  Phe Thr Lys Val Leu  Lys Asn Lys Phe Arg  Ser Lys Lys
    1055                1060                1065
Tyr Phe  Ala Lys His Pro Arg  Leu Gly Tyr Leu Pro  Val Gln Thr
    1070                1075                1080
Val Leu  Glu Gly Asp Asn Leu  Glu Thr Pro Ile Thr  Leu Ile Ser
    1085                1090                1095
Met Trp  Pro Glu His Tyr Asp  Pro Ser Gln Ser Pro  Gln Leu Phe
    1100                1105                1110
His Asp  Asp Thr His Ser Arg  Ile Glu Gln Tyr Ala  Thr Arg Leu
    1115                1120                1125
Ala Gln  Met Glu Arg Thr Asn  Gly Ser Phe Leu Thr  Asp Ser Ser
    1130                1135                1140
Ser Thr  Thr Gly Ser Val Glu  Asp Glu His Ala Leu  Ile Gln Gln
    1145                1150                1155
Tyr Cys  Gln Thr Leu Gly Gly  Glu Ser Pro Val Ser  Gln Pro Gln
    1160                1165                1170
Ser Pro  Ala Gln Ile Leu Lys  Ser Val Glu Arg Glu  Glu Arg Gly
    1175                1180                1185
Glu Leu  Glu Arg Ile Ile Ala  Asp Leu Glu Glu Glu  Gln Arg Asn
    1190                1195                1200
Leu Gln  Val Glu Tyr Glu Gln  Leu Lys Asp Gln His  Leu Arg Arg
    1205                1210                1215
Gly Leu  Pro Val Gly Ser Pro  Pro Glu Ser Ile Ile  Ser Pro His
    1220                1225                1230
His Thr  Ser Glu Asp Ser Glu  Leu Ile Ala Glu Ala  Lys Leu Leu
    1235                1240                1245
Arg Gln  His Lys Gly Arg Leu  Glu Ala Arg Met Gln  Ile Leu Glu
    1250                1255                1260
Asp His  Asn Lys Gln Leu Glu  Ser Gln Leu His Arg  Leu Arg Gln
    1265                1270                1275
```

-continued

```
Leu Leu Glu Gln Pro Glu Ser Asp Ser Arg Ile Asn Gly Val Ser
    1280                1285                1290

Pro Trp Ala Ser Pro Gln His Ser Ala Leu Ser Tyr Ser Leu Asp
    1295                1300                1305

Pro Asp Ala Ser Gly Pro Gln Phe His Gln Ala Ala Gly Glu Asp
    1310                1315                1320

Leu Leu Ala Pro Pro His Asp Thr Ser Thr Asp Leu Thr Glu Val
    1325                1330                1335

Met Glu Gln Ile His Ser Thr Phe Pro Ser Cys Cys Pro Asn Val
    1340                1345                1350

Pro Ser Arg Pro Gln Ala Met
    1355                1360

<210> SEQ ID NO 12
<211> LENGTH: 5070
<212> TYPE: DNA
<213> ORGANISM: Homo sapiens
<220> FEATURE:
<221> NAME/KEY: CDS
<222> LOCATION: (1)..(5070)
<220> FEATURE:
<221> NAME/KEY: misc_feature
<222> LOCATION: (1)..(117)
<223> OTHER INFORMATION: TAT and epitope tag coding sequence

<400> SEQUENCE: 12 atg gac tac aag gac gac gat gac aag ggc tac ggc cgc aag aaa cgc      48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac      96
Arg Gln Arg Arg Arg Gly Gly Ser Thr Met Ser Gly Tyr Pro Tyr Asp
            20                  25                  30 gtc cca gac tat gct ggc tcc atg gcc aag tat gga gaa cat gaa gcc     144
Val Pro Asp Tyr Ala Gly Ser Met Ala Lys Tyr Gly Glu His Glu Ala
        35                  40                  45 agt cct gac aat ggg cag aac gaa ttc agt gat atc att aag tcc aga     192
Ser Pro Asp Asn Gly Gln Asn Glu Phe Ser Asp Ile Ile Lys Ser Arg
    50                  55                  60 tct gat gaa cac aat gac gta cag aag aaa acc ttt acc aaa tgg ata     240
Ser Asp Glu His Asn Asp Val Gln Lys Lys Thr Phe Thr Lys Trp Ile
65                  70                  75                  80 aat gct cga ttt tca aag agt ggg aaa cca ccc atc aat gat atg ttc     288
Asn Ala Arg Phe Ser Lys Ser Gly Lys Pro Pro Ile Asn Asp Met Phe
                85                  90                  95 aca gac ctc aaa gat gga agg aag cta ttg gat ctt cta gaa ggc ctc     336
Thr Asp Leu Lys Asp Gly Arg Lys Leu Leu Asp Leu Leu Glu Gly Leu
            100                 105                 110 aca gga aca tca ctg cca aag gaa cgt ggt tcc aca agg gta cat gcc     384
Thr Gly Thr Ser Leu Pro Lys Glu Arg Gly Ser Thr Arg Val His Ala
        115                 120                 125 tta aat aac gtc aac aga gtg ctg cag gtt tta cat cag aac aat gtg     432
Leu Asn Asn Val Asn Arg Val Leu Gln Val Leu His Gln Asn Asn Val
    130                 135                 140 gaa tta gtg aat ata ggg gga act gac att gtg gat gga aat cac aaa     480
Glu Leu Val Asn Ile Gly Gly Thr Asp Ile Val Asp Gly Asn His Lys
145                 150                 155                 160 ctg act ttg ggg tta ctt tgg agc atc att ttg cac tgg cag gtg aaa     528
Leu Thr Leu Gly Leu Leu Trp Ser Ile Ile Leu His Trp Gln Val Lys
                165                 170                 175 gat gtc atg aag gat gtc atg tcg gac ctg cag cag acg aac agt gag     576
Asp Val Met Lys Asp Val Met Ser Asp Leu Gln Gln Thr Asn Ser Glu
```

-continued

```
                  180             185             190
aag atc ctg ctc agc tgg gtg cgt cag acc acc agg ccc tac agc caa      624
Lys Ile Leu Leu Ser Trp Val Arg Gln Thr Thr Arg Pro Tyr Ser Gln
        195             200             205 gtc aac gtc ctc aac ttc acc acc agc tgg aca gat gga ctc gcc ttt      672
Val Asn Val Leu Asn Phe Thr Thr Ser Trp Thr Asp Gly Leu Ala Phe
210             215             220 aat gct gtc ctc cac cga cat aaa cct gat ctc ttc agc tgg gat aaa      720
Asn Ala Val Leu His Arg His Lys Pro Asp Leu Phe Ser Trp Asp Lys
225             230             235             240 gtt gtc aaa atg tca cca att gag aga ctt gaa cat gcc ttc agc aag      768
Val Val Lys Met Ser Pro Ile Glu Arg Leu Glu His Ala Phe Ser Lys
            245             250             255 gct caa act tat ttg gga att gaa aag ctg tta gat cct gaa gat gtt      816
Ala Gln Thr Tyr Leu Gly Ile Glu Lys Leu Leu Asp Pro Glu Asp Val
        260             265             270 gcc gtt cag ctt cct gac aag aaa tcc ata att atg tat tta aca tct      864
Ala Val Gln Leu Pro Asp Lys Lys Ser Ile Ile Met Tyr Leu Thr Ser
    275             280             285 ttg ttt gag gtg cta cct cag caa gtc acc ata gac gcc atc cgt gag      912
Leu Phe Glu Val Leu Pro Gln Gln Val Thr Ile Asp Ala Ile Arg Glu
290             295             300 gta gag aca ctc cca agg aaa tat aaa aaa gaa tgt gaa gaa gag gca      960
Val Glu Thr Leu Pro Arg Lys Tyr Lys Lys Glu Cys Glu Glu Glu Ala
305             310             315             320 att aat ata cag agt aca gcg cct gag gag gag cat gag agt ccc cga     1008
Ile Asn Ile Gln Ser Thr Ala Pro Glu Glu Glu His Glu Ser Pro Arg
            325             330             335 gct gaa act ccc agc act gtc act gag gtt gac atg gat ctg gac agc     1056
Ala Glu Thr Pro Ser Thr Val Thr Glu Val Asp Met Asp Leu Asp Ser
        340             345             350 tat cag att gcg ttg gag gaa gtg ctg acc tgg ttg ctt tct gct gag     1104
Tyr Gln Ile Ala Leu Glu Glu Val Leu Thr Trp Leu Leu Ser Ala Glu
    355             360             365 gac act ttc cag gag cag gat gat att tct gat gat gtt gaa gaa gtc     1152
Asp Thr Phe Gln Glu Gln Asp Asp Ile Ser Asp Asp Val Glu Glu Val
370             375             380 aaa gac cag ttt gca acc cat gaa gct ttt atg atg gaa ctg act gca     1200
Lys Asp Gln Phe Ala Thr His Glu Ala Phe Met Met Glu Leu Thr Ala
385             390             395             400 cac cag agc agt gtg ggc agc gtc ctg cag gca ggc aac caa ctg ata     1248
His Gln Ser Ser Val Gly Ser Val Leu Gln Ala Gly Asn Gln Leu Ile
            405             410             415 aca caa gga act ctg tca gac gaa gaa gaa ttt gag att cag gaa cag     1296
Thr Gln Gly Thr Leu Ser Asp Glu Glu Glu Phe Glu Ile Gln Glu Gln
        420             425             430 atg acc ctg ctg aat gct aga tgg gag gct ctt agg gtg gag agt atg     1344
Met Thr Leu Leu Asn Ala Arg Trp Glu Ala Leu Arg Val Glu Ser Met
    435             440             445 gac aga cag tcc cgg ctg cac gat gtg ctg atg gaa ctg cag aag aag     1392
Asp Arg Gln Ser Arg Leu His Asp Val Leu Met Glu Leu Gln Lys Lys
450             455             460 caa ctg cag cag ctc tcc gcc tgg tta aca ctc aca gag gag cgc att     1440
Gln Leu Gln Gln Leu Ser Ala Trp Leu Thr Leu Thr Glu Glu Arg Ile
465             470             475             480 cag aag atg gaa act tgc ccc ctg gat gat gat gta aaa tct cta caa     1488
Gln Lys Met Glu Thr Cys Pro Leu Asp Asp Asp Val Lys Ser Leu Gln
            485             490             495 aag ctg cta gaa gaa cat aaa agt ttg caa agt gat ctt gag gct gaa     1536
```

```
Lys Leu Leu Glu Glu His Lys Ser Leu Gln Ser Asp Leu Glu Ala Glu
            500                 505                 510 cag gtg aaa gta aat tca cta act cac atg gtg gtc att gtt gat gaa      1584
Gln Val Lys Val Asn Ser Leu Thr His Met Val Val Ile Val Asp Glu
        515                 520                 525 aac agt ggt gag agt gct aca gct atc cta gaa gac cag tta cag aaa      1632
Asn Ser Gly Glu Ser Ala Thr Ala Ile Leu Glu Asp Gln Leu Gln Lys
530                 535                 540 ctt ggt gag cgc tgg aca gca gta tgc cgt tgg act gaa gaa cgc tgg      1680
Leu Gly Glu Arg Trp Thr Ala Val Cys Arg Trp Thr Glu Glu Arg Trp
545                 550                 555                 560 aat agg tta caa gaa atc aat ata ttg tgg cag gaa tta ttg gaa gaa      1728
Asn Arg Leu Gln Glu Ile Asn Ile Leu Trp Gln Glu Leu Leu Glu Glu
            565                 570                 575 cag tgc ttg ttg aaa gct tgg tta acc gaa aaa gaa gag gct tta aat      1776
Gln Cys Leu Leu Lys Ala Trp Leu Thr Glu Lys Glu Glu Ala Leu Asn
        580                 585                 590 aaa gtc cag aca agc aac ttc aaa gac caa aag gaa cta agt gtc agt      1824
Lys Val Gln Thr Ser Asn Phe Lys Asp Gln Lys Glu Leu Ser Val Ser
    595                 600                 605 gtt cga cgt ctg gct att ttg aag gaa gac atg gaa atg aag cgt caa      1872
Val Arg Arg Leu Ala Ile Leu Lys Glu Asp Met Glu Met Lys Arg Gln
610                 615                 620 aca ttg gat cag ctg agt gag att ggc cag gat gtg gga caa tta ctt      1920
Thr Leu Asp Gln Leu Ser Glu Ile Gly Gln Asp Val Gly Gln Leu Leu
625                 630                 635                 640 gat aat tcc aag gca tct aag aag atc aac agt gac tca gag gaa ctg      1968
Asp Asn Ser Lys Ala Ser Lys Lys Ile Asn Ser Asp Ser Glu Glu Leu
            645                 650                 655 act caa aga tgg gat tct ttg gtt cag aga cta gaa gat tcc tcc aac      2016
Thr Gln Arg Trp Asp Ser Leu Val Gln Arg Leu Glu Asp Ser Ser Asn
        660                 665                 670 cag gtg act cag gct gta gca aag ctg ggg atg tct cag att cct cag      2064
Gln Val Thr Gln Ala Val Ala Lys Leu Gly Met Ser Gln Ile Pro Gln
    675                 680                 685 aag gac ctt ttg gag act gtt cgt gta aga gaa caa gca att aca aaa      2112
Lys Asp Leu Leu Glu Thr Val Arg Val Arg Glu Gln Ala Ile Thr Lys
690                 695                 700 aaa tct aag cag gaa ctg cct cct cct cct ccc cca aag aag aga cag      2160
Lys Ser Lys Gln Glu Leu Pro Pro Pro Pro Pro Pro Lys Lys Arg Gln
705                 710                 715                 720 atc cat gtg gat att gaa gct aag aaa aag ttt gat gct ata agt gca      2208
Ile His Val Asp Ile Glu Ala Lys Lys Lys Phe Asp Ala Ile Ser Ala
            725                 730                 735 gag ctg ttg aac tgg att ttg aaa tgg aaa act gcc att cag acc aca      2256
Glu Leu Leu Asn Trp Ile Leu Lys Trp Lys Thr Ala Ile Gln Thr Thr
        740                 745                 750 gag ata aaa gag tat atg aag atg caa gac act tcc gaa atg aaa aag      2304
Glu Ile Lys Glu Tyr Met Lys Met Gln Asp Thr Ser Glu Met Lys Lys
    755                 760                 765 aag ttg aag gca tta gaa aaa gaa cag aga gaa aga atc ccc aga gca      2352
Lys Leu Lys Ala Leu Glu Lys Glu Gln Arg Glu Arg Ile Pro Arg Ala
770                 775                 780 gat gaa tta aac caa act gga caa atc ctt gtg gag caa atg gga aaa      2400
Asp Glu Leu Asn Gln Thr Gly Gln Ile Leu Val Glu Gln Met Gly Lys
785                 790                 795                 800 gaa ggc ctt cct act gaa gaa ata aaa aat gtt ctg gag aag gtt tca      2448
Glu Gly Leu Pro Thr Glu Glu Ile Lys Asn Val Leu Glu Lys Val Ser
            805                 810                 815
```

-continued

| | |
|---|---|
| tca gaa tgg aag aat gta tct caa cat ttg gaa gat cta gaa aga aag<br>Ser Glu Trp Lys Asn Val Ser Gln His Leu Glu Asp Leu Glu Arg Lys<br>820                        825                    830 | 2496 |
| att cag cta cag gaa gat ata aat gct tat ttc aag cag ctt gat gag<br>Ile Gln Leu Gln Glu Asp Ile Asn Ala Tyr Phe Lys Gln Leu Asp Glu<br>    835                    840                  845 | 2544 |
| ctt gaa aag gtc atc aag aca aag gag gag tgg gta aaa cac act tcc<br>Leu Glu Lys Val Ile Lys Thr Lys Glu Glu Trp Val Lys His Thr Ser<br>850                        855                    860 | 2592 |
| att tct gaa tct tcc cgg cag tcc ttg cca agc ttg aag gat tcc tgt<br>Ile Ser Glu Ser Ser Arg Gln Ser Leu Pro Ser Leu Lys Asp Ser Cys<br>865                        870                  875                880 | 2640 |
| cag cgg gaa ttg aca aat ctt ctt ggc ctt cac ccc aaa att gaa atg<br>Gln Arg Glu Leu Thr Asn Leu Leu Gly Leu His Pro Lys Ile Glu Met<br>                    885                  890                  895 | 2688 |
| gct cgt gca agc tgc tcg gcc ctg atg tct cag cct tct gcc cca gat<br>Ala Arg Ala Ser Cys Ser Ala Leu Met Ser Gln Pro Ser Ala Pro Asp<br>900                        905                    910 | 2736 |
| ttt gtc cag cgg ggc ttc gat agc ttt ctg ggc cgc tac caa gct gta<br>Phe Val Gln Arg Gly Phe Asp Ser Phe Leu Gly Arg Tyr Gln Ala Val<br>    915                    920                  925 | 2784 |
| caa gag gct gta gag gat cgt caa caa cat cta gag aat gaa ctg aag<br>Gln Glu Ala Val Glu Asp Arg Gln Gln His Leu Glu Asn Glu Leu Lys<br>930                        935                    940 | 2832 |
| ggc caa cct gga cat gca tat ctg gaa aca ttg aaa aca ctg aaa gat<br>Gly Gln Pro Gly His Ala Tyr Leu Glu Thr Leu Lys Thr Leu Lys Asp<br>945                        950                  955                960 | 2880 |
| gtg cta aat gat tca gaa aat aag gcc cag gtg tct ctg aat gtc ctt<br>Val Leu Asn Asp Ser Glu Asn Lys Ala Gln Val Ser Leu Asn Val Leu<br>                    965                  970                  975 | 2928 |
| aat gat ctt gcc aag gtg gag aag gcc ctg caa gaa aaa aag acc ctt<br>Asn Asp Leu Ala Lys Val Glu Lys Ala Leu Gln Glu Lys Lys Thr Leu<br>980                        985                    990 | 2976 |
| gat gaa atc ctt gag aat cag aaa cct gca tta cat aaa ctt gca gaa<br>Asp Glu Ile Leu Glu Asn Gln Lys Pro Ala Leu His Lys Leu Ala Glu<br>    995                    1000                 1005 | 3024 |
| gaa aca aag gct ctg gag aaa aat gtt cat cct gat gta gaa aaa<br>Glu Thr Lys Ala Leu Glu Lys Asn Val His Pro Asp Val Glu Lys<br>1010                     1015                 1020 | 3069 |
| tta tat aag caa gaa ttt gat gat gtg caa gga aag tgg aac aag<br>Leu Tyr Lys Gln Glu Phe Asp Asp Val Gln Gly Lys Trp Asn Lys<br>1025                     1030                 1035 | 3114 |
| cta aag gtc ttg gtt tcc aaa gat cta cat ttg ctt gag gaa att<br>Leu Lys Val Leu Val Ser Lys Asp Leu His Leu Leu Glu Glu Ile<br>1040                     1045                 1050 | 3159 |
| gcc cac aga gat ttt gga cca tcc tct cag cat ttt ctc tct acg<br>Ala His Arg Asp Phe Gly Pro Ser Ser Gln His Phe Leu Ser Thr<br>1055                     1060                 1065 | 3204 |
| tca gtc cag ctg ccg tgg caa aga tcc att tca cat aat aaa gtg<br>Ser Val Gln Leu Pro Trp Gln Arg Ser Ile Ser His Asn Lys Val<br>1070                     1075                 1080 | 3249 |
| ccc tat tac atc aac cat caa aca cag acc acc tgt tgg gac cat<br>Pro Tyr Tyr Ile Asn His Gln Thr Gln Thr Thr Cys Trp Asp His<br>1085                     1090                 1095 | 3294 |
| cct aaa atg acc gaa ctc ttt caa tcc ctt gct gac ctg aat aat<br>Pro Lys Met Thr Glu Leu Phe Gln Ser Leu Ala Asp Leu Asn Asn<br>1100                     1105                 1110 | 3339 |
| gta cgt ttt tct gcc tac cgt aca gca atc aaa atc cga aga cta<br>Val Arg Phe Ser Ala Tyr Arg Thr Ala Ile Lys Ile Arg Arg Leu<br>1115                     1120                 1125 | 3384 |

| | | |
|---|---|---|
| caa aaa gca cta tgt ttg gat ctc tta gag ttg agt aca aca aat<br>Gln Lys Ala Leu Cys Leu Asp Leu Leu Glu Leu Ser Thr Thr Asn<br>1130                      1135                      1140 | | 3429 |
| gaa att ttc aaa cag cac aag ttg aac caa aat gac cag ctc ctc<br>Glu Ile Phe Lys Gln His Lys Leu Asn Gln Asn Asp Gln Leu Leu<br>1145                      1150                      1155 | | 3474 |
| agt gtt cca gat gtc atc aac tgt ctg aca aca act tat gat gga<br>Ser Val Pro Asp Val Ile Asn Cys Leu Thr Thr Thr Tyr Asp Gly<br>1160                      1165                      1170 | | 3519 |
| ctt gag caa atg cat aag gac ctg gtc aac gtt cca ctc tgt gtt<br>Leu Glu Gln Met His Lys Asp Leu Val Asn Val Pro Leu Cys Val<br>1175                      1180                      1185 | | 3564 |
| gat atg tgt ctc aat tgg ttg ctc aat gtc tat gac acg ggt cga<br>Asp Met Cys Leu Asn Trp Leu Leu Asn Val Tyr Asp Thr Gly Arg<br>1190                      1195                      1200 | | 3609 |
| act gga aaa att aga gtg cag agt ctg aag att gga tta atg tct<br>Thr Gly Lys Ile Arg Val Gln Ser Leu Lys Ile Gly Leu Met Ser<br>1205                      1210                      1215 | | 3654 |
| ctc tcc aaa ggt ctc ttg gaa gaa aaa tac aga tat ctc ttt aag<br>Leu Ser Lys Gly Leu Leu Glu Glu Lys Tyr Arg Tyr Leu Phe Lys<br>1220                      1225                      1230 | | 3699 |
| gaa gtt gca ggg cca aca gaa atg tgt gac cag agg cag ctg ggc<br>Glu Val Ala Gly Pro Thr Glu Met Cys Asp Gln Arg Gln Leu Gly<br>1235                      1240                      1245 | | 3744 |
| ctg tta ctt cat gat gcc atc cag atc ccc cgg cag cta ggt gaa<br>Leu Leu Leu His Asp Ala Ile Gln Ile Pro Arg Gln Leu Gly Glu<br>1250                      1255                      1260 | | 3789 |
| gta gca gct ttt gga ggc agt aat att gag cct agt gtt cgc agc<br>Val Ala Ala Phe Gly Gly Ser Asn Ile Glu Pro Ser Val Arg Ser<br>1265                      1270                      1275 | | 3834 |
| tgc ttc caa cag aat aac aat aaa cca gaa ata agt gtg aaa gag<br>Cys Phe Gln Gln Asn Asn Asn Lys Pro Glu Ile Ser Val Lys Glu<br>1280                      1285                      1290 | | 3879 |
| ttt ata gat tgg atg cat ttg gaa cca cag tcc atg gtt tgg ctc<br>Phe Ile Asp Trp Met His Leu Glu Pro Gln Ser Met Val Trp Leu<br>1295                      1300                      1305 | | 3924 |
| cca gtt tta cat cga gtg gca gca gcg gag act gca aaa cat cag<br>Pro Val Leu His Arg Val Ala Ala Ala Glu Thr Ala Lys His Gln<br>1310                      1315                      1320 | | 3969 |
| gcc aaa tgc aac atc tgt aaa gaa tgt cca att gtc ggg ttc agg<br>Ala Lys Cys Asn Ile Cys Lys Glu Cys Pro Ile Val Gly Phe Arg<br>1325                      1330                      1335 | | 4014 |
| tat aga agc ctt aag cat ttt aac tat gat gtc tgc cag agt tgt<br>Tyr Arg Ser Leu Lys His Phe Asn Tyr Asp Val Cys Gln Ser Cys<br>1340                      1345                      1350 | | 4059 |
| ttc ttt tcg ggt cga aca gca aaa ggt cac aaa tta cat tac cca<br>Phe Phe Ser Gly Arg Thr Ala Lys Gly His Lys Leu His Tyr Pro<br>1355                      1360                      1365 | | 4104 |
| atg gtg gaa tat tgt ata cct aca aca tct ggg gaa gat gta cga<br>Met Val Glu Tyr Cys Ile Pro Thr Thr Ser Gly Glu Asp Val Arg<br>1370                      1375                      1380 | | 4149 |
| gac ttc aca aag gta ctt aag aac aag ttc agg tcg aag aag tac<br>Asp Phe Thr Lys Val Leu Lys Asn Lys Phe Arg Ser Lys Lys Tyr<br>1385                      1390                      1395 | | 4194 |
| ttt gcc aaa cac cct cga ctt ggt tac ctg cct gtc cag aca gtt<br>Phe Ala Lys His Pro Arg Leu Gly Tyr Leu Pro Val Gln Thr Val<br>1400                      1405                      1410 | | 4239 |
| ctt gaa ggt gac aac tta gag act cct atc aca ctc atc agt atg<br>Leu Glu Gly Asp Asn Leu Glu Thr Pro Ile Thr Leu Ile Ser Met | | 4284 |

|  |  |  |  |  |  |  |  |  |  |  |
|---|---|---|---|---|---|---|---|---|---|---|
|  | 1415 |  |  | 1420 |  |  |  | 1425 |  |  |

| tgg | cca | gag | cac | tat | gac | ccc | tca | caa | tct | cct | caa | ctg | ttt | cat | 4329 |
|---|---|---|---|---|---|---|---|---|---|---|---|---|---|---|---|
| Trp | Pro | Glu | His | Tyr | Asp | Pro | Ser | Gln | Ser | Pro | Gln | Leu | Phe | His |  |
| 1430 |  |  |  |  | 1435 |  |  |  |  | 1440 |  |  |  |  |  |

| gat | gac | acc | cat | tca | aga | ata | gaa | caa | tat | gcc | aca | cga | ctg | gcc | 4374 |
|---|---|---|---|---|---|---|---|---|---|---|---|---|---|---|---|
| Asp | Asp | Thr | His | Ser | Arg | Ile | Glu | Gln | Tyr | Ala | Thr | Arg | Leu | Ala |  |
| 1445 |  |  |  |  | 1450 |  |  |  |  | 1455 |  |  |  |  |  |

| cag | atg | gaa | agg | act | aat | ggg | tct | ttt | ctc | act | gat | agc | agc | tcc | 4419 |
|---|---|---|---|---|---|---|---|---|---|---|---|---|---|---|---|
| Gln | Met | Glu | Arg | Thr | Asn | Gly | Ser | Phe | Leu | Thr | Asp | Ser | Ser | Ser |  |
| 1460 |  |  |  |  | 1465 |  |  |  |  | 1470 |  |  |  |  |  |

| acc | aca | gga | agt | gtg | gaa | gac | gag | cac | gcc | ctc | atc | cag | cag | tat | 4464 |
|---|---|---|---|---|---|---|---|---|---|---|---|---|---|---|---|
| Thr | Thr | Gly | Ser | Val | Glu | Asp | Glu | His | Ala | Leu | Ile | Gln | Gln | Tyr |  |
| 1475 |  |  |  |  | 1480 |  |  |  |  | 1485 |  |  |  |  |  |

| tgc | caa | aca | ctc | gga | gga | gag | tcc | cca | gtg | agc | cag | ccg | cag | agc | 4509 |
|---|---|---|---|---|---|---|---|---|---|---|---|---|---|---|---|
| Cys | Gln | Thr | Leu | Gly | Gly | Glu | Ser | Pro | Val | Ser | Gln | Pro | Gln | Ser |  |
| 1490 |  |  |  |  | 1495 |  |  |  |  | 1500 |  |  |  |  |  |

| cca | gct | cag | atc | ctg | aag | tca | gta | gag | agg | gaa | gaa | cgt | gga | gaa | 4554 |
|---|---|---|---|---|---|---|---|---|---|---|---|---|---|---|---|
| Pro | Ala | Gln | Ile | Leu | Lys | Ser | Val | Glu | Arg | Glu | Glu | Arg | Gly | Glu |  |
| 1505 |  |  |  |  | 1510 |  |  |  |  | 1515 |  |  |  |  |  |

| ctg | gag | agg | atc | att | gct | gac | ctg | gag | gaa | gaa | caa | aga | aat | cta | 4599 |
|---|---|---|---|---|---|---|---|---|---|---|---|---|---|---|---|
| Leu | Glu | Arg | Ile | Ile | Ala | Asp | Leu | Glu | Glu | Glu | Gln | Arg | Asn | Leu |  |
| 1520 |  |  |  |  | 1525 |  |  |  |  | 1530 |  |  |  |  |  |

| cag | gtg | gag | tat | gag | cag | ctg | aag | gac | cag | cac | ctc | cga | agg | ggg | 4644 |
|---|---|---|---|---|---|---|---|---|---|---|---|---|---|---|---|
| Gln | Val | Glu | Tyr | Glu | Gln | Leu | Lys | Asp | Gln | His | Leu | Arg | Arg | Gly |  |
| 1535 |  |  |  |  | 1540 |  |  |  |  | 1545 |  |  |  |  |  |

| ctc | cct | gtc | ggt | tca | ccg | cca | gag | tcg | att | ata | tct | ccc | cat | cac | 4689 |
|---|---|---|---|---|---|---|---|---|---|---|---|---|---|---|---|
| Leu | Pro | Val | Gly | Ser | Pro | Pro | Glu | Ser | Ile | Ile | Ser | Pro | His | His |  |
| 1550 |  |  |  |  | 1555 |  |  |  |  | 1560 |  |  |  |  |  |

| acg | tct | gag | gat | tca | gaa | ctt | ata | gca | gaa | gca | aaa | ctc | ctc | agg | 4734 |
|---|---|---|---|---|---|---|---|---|---|---|---|---|---|---|---|
| Thr | Ser | Glu | Asp | Ser | Glu | Leu | Ile | Ala | Glu | Ala | Lys | Leu | Leu | Arg |  |
| 1565 |  |  |  |  | 1570 |  |  |  |  | 1575 |  |  |  |  |  |

| cag | cac | aaa | ggt | cgg | ctg | gag | gct | agg | atg | cag | att | tta | gaa | gat | 4779 |
|---|---|---|---|---|---|---|---|---|---|---|---|---|---|---|---|
| Gln | His | Lys | Gly | Arg | Leu | Glu | Ala | Arg | Met | Gln | Ile | Leu | Glu | Asp |  |
| 1580 |  |  |  |  | 1585 |  |  |  |  | 1590 |  |  |  |  |  |

| cac | aat | aaa | cag | ctg | gag | tct | cag | ctc | cac | cgc | ctc | cga | cag | ctg | 4824 |
|---|---|---|---|---|---|---|---|---|---|---|---|---|---|---|---|
| His | Asn | Lys | Gln | Leu | Glu | Ser | Gln | Leu | His | Arg | Leu | Arg | Gln | Leu |  |
| 1595 |  |  |  |  | 1600 |  |  |  |  | 1605 |  |  |  |  |  |

| ctg | gag | cag | cct | gaa | tct | gat | tcc | cga | atc | aat | ggt | gtt | tcc | cca | 4869 |
|---|---|---|---|---|---|---|---|---|---|---|---|---|---|---|---|
| Leu | Glu | Gln | Pro | Glu | Ser | Asp | Ser | Arg | Ile | Asn | Gly | Val | Ser | Pro |  |
| 1610 |  |  |  |  | 1615 |  |  |  |  | 1620 |  |  |  |  |  |

| tgg | gct | tct | cct | cag | cat | tct | gca | ctg | agc | tac | tcg | ctt | gat | cca | 4914 |
|---|---|---|---|---|---|---|---|---|---|---|---|---|---|---|---|
| Trp | Ala | Ser | Pro | Gln | His | Ser | Ala | Leu | Ser | Tyr | Ser | Leu | Asp | Pro |  |
| 1625 |  |  |  |  | 1630 |  |  |  |  | 1635 |  |  |  |  |  |

| gat | gcc | tcc | ggc | cca | cag | ttc | cac | cag | gca | gcg | gga | gag | gac | ctg | 4959 |
|---|---|---|---|---|---|---|---|---|---|---|---|---|---|---|---|
| Asp | Ala | Ser | Gly | Pro | Gln | Phe | His | Gln | Ala | Ala | Gly | Glu | Asp | Leu |  |
| 1640 |  |  |  |  | 1645 |  |  |  |  | 1650 |  |  |  |  |  |

| ctg | gcc | cca | ccg | cac | gac | acc | agc | acg | gat | ctc | acg | gag | gtc | atg | 5004 |
|---|---|---|---|---|---|---|---|---|---|---|---|---|---|---|---|
| Leu | Ala | Pro | Pro | His | Asp | Thr | Ser | Thr | Asp | Leu | Thr | Glu | Val | Met |  |
| 1655 |  |  |  |  | 1660 |  |  |  |  | 1665 |  |  |  |  |  |

| gag | cag | att | cac | agc | acg | ttt | cca | tct | tgc | tgc | cca | aat | gtt | ccc | 5049 |
|---|---|---|---|---|---|---|---|---|---|---|---|---|---|---|---|
| Glu | Gln | Ile | His | Ser | Thr | Phe | Pro | Ser | Cys | Cys | Pro | Asn | Val | Pro |  |
| 1670 |  |  |  |  | 1675 |  |  |  |  | 1680 |  |  |  |  |  |

| agc | agg | cca | cag | gca | atg | tga |  |  |  |  |  |  |  |  | 5070 |
|---|---|---|---|---|---|---|---|---|---|---|---|---|---|---|---|
| Ser | Arg | Pro | Gln | Ala | Met |  |  |  |  |  |  |  |  |  |  |
| 1685 |  |  |  |  |  |  |  |  |  |  |  |  |  |  |  |

<210> SEQ ID NO 13
<211> LENGTH: 1689
<212> TYPE: PRT
<213> ORGANISM: Homo sapiens

<400> SEQUENCE: 13

```
Met Asp Tyr Lys Asp Asp Asp Lys Gly Tyr Gly Arg Lys Lys Arg
1               5                   10                  15
Arg Gln Arg Arg Arg Gly Gly Ser Thr Met Ser Gly Tyr Pro Tyr Asp
            20                  25                  30
Val Pro Asp Tyr Ala Gly Ser Met Ala Lys Tyr Gly Glu His Glu Ala
            35                  40                  45
Ser Pro Asp Asn Gly Gln Asn Glu Phe Ser Asp Ile Ile Lys Ser Arg
    50                  55                  60
Ser Asp Glu His Asn Asp Val Gln Lys Lys Thr Phe Thr Lys Trp Ile
65                  70                  75                  80
Asn Ala Arg Phe Ser Lys Ser Gly Lys Pro Pro Ile Asn Asp Met Phe
                85                  90                  95
Thr Asp Leu Lys Asp Gly Arg Lys Leu Leu Asp Leu Leu Glu Gly Leu
            100                 105                 110
Thr Gly Thr Ser Leu Pro Lys Glu Arg Gly Ser Thr Arg Val His Ala
            115                 120                 125
Leu Asn Asn Val Asn Arg Val Leu Gln Val Leu His Gln Asn Asn Val
    130                 135                 140
Glu Leu Val Asn Ile Gly Gly Thr Asp Ile Val Asp Gly Asn His Lys
145                 150                 155                 160
Leu Thr Leu Gly Leu Leu Trp Ser Ile Ile Leu His Trp Gln Val Lys
                165                 170                 175
Asp Val Met Lys Asp Val Met Ser Asp Leu Gln Gln Thr Asn Ser Glu
            180                 185                 190
Lys Ile Leu Leu Ser Trp Val Arg Gln Thr Thr Arg Pro Tyr Ser Gln
            195                 200                 205
Val Asn Val Leu Asn Phe Thr Thr Ser Trp Thr Asp Gly Leu Ala Phe
    210                 215                 220
Asn Ala Val Leu His Arg His Lys Pro Asp Leu Phe Ser Trp Asp Lys
225                 230                 235                 240
Val Val Lys Met Ser Pro Ile Glu Arg Leu Glu His Ala Phe Ser Lys
                245                 250                 255
Ala Gln Thr Tyr Leu Gly Ile Glu Lys Leu Leu Asp Pro Glu Asp Val
            260                 265                 270
Ala Val Gln Leu Pro Asp Lys Lys Ser Ile Ile Met Tyr Leu Thr Ser
            275                 280                 285
Leu Phe Glu Val Leu Pro Gln Gln Val Thr Ile Asp Ala Ile Arg Glu
    290                 295                 300
Val Glu Thr Leu Pro Arg Lys Tyr Lys Lys Glu Cys Glu Glu Glu Ala
305                 310                 315                 320
Ile Asn Ile Gln Ser Thr Ala Pro Glu Glu His Glu Ser Pro Arg
                325                 330                 335
Ala Glu Thr Pro Ser Thr Val Thr Glu Val Asp Met Asp Leu Asp Ser
            340                 345                 350
Tyr Gln Ile Ala Leu Glu Glu Val Leu Thr Trp Leu Leu Ser Ala Glu
            355                 360                 365
Asp Thr Phe Gln Glu Gln Asp Asp Ile Ser Asp Val Glu Glu Val
    370                 375                 380
Lys Asp Gln Phe Ala Thr His Glu Ala Phe Met Met Glu Leu Thr Ala
385                 390                 395                 400
His Gln Ser Ser Val Gly Ser Val Leu Gln Ala Gly Asn Gln Leu Ile
```

-continued

```
                405                 410                 415
Thr Gln Gly Thr Leu Ser Asp Glu Glu Phe Glu Ile Gln Glu Gln
            420                 425                 430

Met Thr Leu Leu Asn Ala Arg Trp Glu Ala Leu Arg Val Glu Ser Met
            435                 440                 445

Asp Arg Gln Ser Arg Leu His Asp Val Leu Met Glu Leu Gln Lys Lys
            450                 455                 460

Gln Leu Gln Gln Leu Ser Ala Trp Leu Thr Leu Thr Glu Glu Arg Ile
465                 470                 475                 480

Gln Lys Met Glu Thr Cys Pro Leu Asp Asp Val Lys Ser Leu Gln
            485                 490                 495

Lys Leu Leu Glu Glu His Lys Ser Leu Gln Ser Asp Leu Glu Ala Glu
            500                 505                 510

Gln Val Lys Val Asn Ser Leu Thr His Met Val Val Ile Val Asp Glu
            515                 520                 525

Asn Ser Gly Glu Ser Ala Thr Ala Ile Leu Glu Asp Gln Leu Gln Lys
            530                 535                 540

Leu Gly Glu Arg Trp Thr Ala Val Cys Arg Trp Thr Glu Glu Arg Trp
545                 550                 555                 560

Asn Arg Leu Gln Glu Ile Asn Ile Leu Trp Gln Glu Leu Leu Glu Glu
            565                 570                 575

Gln Cys Leu Leu Lys Ala Trp Leu Thr Glu Lys Glu Glu Ala Leu Asn
            580                 585                 590

Lys Val Gln Thr Ser Asn Phe Lys Asp Gln Lys Glu Leu Ser Val Ser
            595                 600                 605

Val Arg Arg Leu Ala Ile Leu Lys Glu Asp Met Glu Met Lys Arg Gln
            610                 615                 620

Thr Leu Asp Gln Leu Ser Glu Ile Gly Gln Asp Val Gly Gln Leu Leu
625                 630                 635                 640

Asp Asn Ser Lys Ala Ser Lys Lys Ile Asn Ser Asp Ser Glu Glu Leu
            645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
            675                 680                 685

Lys Asp Leu Leu Glu Thr Val Arg Val Arg Glu Gln Ala Ile Thr Lys
            690                 695                 700

Lys Ser Lys Gln Glu Leu Pro Pro Pro Pro Lys Lys Arg Gln
705                 710                 715                 720

Ile His Val Asp Ile Glu Ala Lys Lys Phe Asp Ala Ile Ser Ala
            725                 730                 735

Glu Leu Leu Asn Trp Ile Leu Lys Trp Lys Thr Ala Ile Gln Thr Thr
            740                 745                 750

Glu Ile Lys Glu Tyr Met Lys Met Gln Asp Thr Ser Glu Met Lys Lys
            755                 760                 765

Lys Leu Lys Ala Leu Glu Lys Glu Gln Arg Glu Arg Ile Pro Arg Ala
            770                 775                 780

Asp Glu Leu Asn Gln Thr Gly Gln Ile Leu Val Glu Gln Met Gly Lys
785                 790                 795                 800

Glu Gly Leu Pro Thr Glu Glu Ile Lys Asn Val Leu Glu Lys Val Ser
            805                 810                 815

Ser Glu Trp Lys Asn Val Ser Gln His Leu Glu Asp Leu Glu Arg Lys
            820                 825                 830
```

```
Ile Gln Leu Gln Glu Asp Ile Asn Ala Tyr Phe Lys Gln Leu Asp Glu
    835                 840                 845

Leu Glu Lys Val Ile Lys Thr Lys Glu Glu Trp Val Lys His Thr Ser
850                 855                 860

Ile Ser Glu Ser Ser Arg Gln Ser Leu Pro Ser Leu Lys Asp Ser Cys
865                 870                 875                 880

Gln Arg Glu Leu Thr Asn Leu Leu Gly Leu His Pro Lys Ile Glu Met
                885                 890                 895

Ala Arg Ala Ser Cys Ser Ala Leu Met Ser Gln Pro Ser Ala Pro Asp
            900                 905                 910

Phe Val Gln Arg Gly Phe Asp Ser Phe Leu Gly Arg Tyr Gln Ala Val
        915                 920                 925

Gln Glu Ala Val Glu Asp Arg Gln Gln His Leu Glu Asn Glu Leu Lys
    930                 935                 940

Gly Gln Pro Gly His Ala Tyr Leu Glu Thr Leu Lys Thr Leu Lys Asp
945                 950                 955                 960

Val Leu Asn Asp Ser Glu Asn Lys Ala Gln Val Ser Leu Asn Val Leu
                965                 970                 975

Asn Asp Leu Ala Lys Val Glu Lys Ala Leu Gln Glu Lys Lys Thr Leu
            980                 985                 990

Asp Glu Ile Leu Glu Asn Gln Lys Pro Ala Leu His Lys Leu Ala Glu
        995                 1000                1005

Glu Thr Lys Ala Leu Glu Lys Asn Val His Pro Asp Val Glu Lys
    1010                1015                1020

Leu Tyr Lys Gln Glu Phe Asp Val Gln Gly Lys Trp Asn Lys
    1025                1030                1035

Leu Lys Val Leu Val Ser Lys Asp Leu His Leu Leu Glu Glu Ile
    1040                1045                1050

Ala His Arg Asp Phe Gly Pro Ser Ser Gln His Phe Leu Ser Thr
    1055                1060                1065

Ser Val Gln Leu Pro Trp Gln Arg Ser Ile Ser His Asn Lys Val
    1070                1075                1080

Pro Tyr Tyr Ile Asn His Gln Thr Gln Thr Thr Cys Trp Asp His
    1085                1090                1095

Pro Lys Met Thr Glu Leu Phe Gln Ser Leu Ala Asp Leu Asn Asn
    1100                1105                1110

Val Arg Phe Ser Ala Tyr Arg Thr Ala Ile Lys Ile Arg Arg Leu
    1115                1120                1125

Gln Lys Ala Leu Cys Leu Asp Leu Leu Glu Leu Ser Thr Thr Asn
    1130                1135                1140

Glu Ile Phe Lys Gln His Lys Leu Asn Gln Asn Asp Gln Leu Leu
    1145                1150                1155

Ser Val Pro Asp Val Ile Asn Cys Leu Thr Thr Thr Tyr Asp Gly
    1160                1165                1170

Leu Glu Gln Met His Lys Asp Leu Val Asn Val Pro Leu Cys Val
    1175                1180                1185

Asp Met Cys Leu Asn Trp Leu Leu Asn Val Tyr Asp Thr Gly Arg
    1190                1195                1200

Thr Gly Lys Ile Arg Val Gln Ser Leu Lys Ile Gly Leu Met Ser
    1205                1210                1215

Leu Ser Lys Gly Leu Leu Glu Glu Lys Tyr Arg Tyr Leu Phe Lys
    1220                1225                1230
```

-continued

```
Glu Val Ala Gly Pro Thr Glu Met Cys Asp Gln Arg Gln Leu Gly
    1235                1240                1245

Leu Leu Leu His Asp Ala Ile Gln Ile Pro Arg Gln Leu Gly Glu
    1250                1255                1260

Val Ala Ala Phe Gly Gly Ser Asn Ile Glu Pro Ser Val Arg Ser
    1265                1270                1275

Cys Phe Gln Gln Asn Asn Asn Lys Pro Glu Ile Ser Val Lys Glu
    1280                1285                1290

Phe Ile Asp Trp Met His Leu Glu Pro Gln Ser Met Val Trp Leu
    1295                1300                1305

Pro Val Leu His Arg Val Ala Ala Glu Thr Ala Lys His Gln
    1310                1315                1320

Ala Lys Cys Asn Ile Cys Lys Glu Cys Pro Ile Val Gly Phe Arg
    1325                1330                1335

Tyr Arg Ser Leu Lys His Phe Asn Tyr Asp Val Cys Gln Ser Cys
    1340                1345                1350

Phe Phe Ser Gly Arg Thr Ala Lys Gly His Lys Leu His Tyr Pro
    1355                1360                1365

Met Val Glu Tyr Cys Ile Pro Thr Thr Ser Gly Glu Asp Val Arg
    1370                1375                1380

Asp Phe Thr Lys Val Leu Lys Asn Lys Phe Arg Ser Lys Lys Tyr
    1385                1390                1395

Phe Ala Lys His Pro Arg Leu Gly Tyr Leu Pro Val Gln Thr Val
    1400                1405                1410

Leu Glu Gly Asp Asn Leu Glu Thr Pro Ile Thr Leu Ile Ser Met
    1415                1420                1425

Trp Pro Glu His Tyr Asp Pro Ser Gln Ser Pro Gln Leu Phe His
    1430                1435                1440

Asp Asp Thr His Ser Arg Ile Glu Gln Tyr Ala Thr Arg Leu Ala
    1445                1450                1455

Gln Met Glu Arg Thr Asn Gly Ser Phe Leu Thr Asp Ser Ser Ser
    1460                1465                1470

Thr Thr Gly Ser Val Glu Asp Glu His Ala Leu Ile Gln Gln Tyr
    1475                1480                1485

Cys Gln Thr Leu Gly Gly Glu Ser Pro Val Ser Gln Pro Gln Ser
    1490                1495                1500

Pro Ala Gln Ile Leu Lys Ser Val Glu Arg Glu Glu Arg Gly Glu
    1505                1510                1515

Leu Glu Arg Ile Ile Ala Asp Leu Glu Glu Glu Gln Arg Asn Leu
    1520                1525                1530

Gln Val Glu Tyr Glu Gln Leu Lys Asp Gln His Leu Arg Arg Gly
    1535                1540                1545

Leu Pro Val Gly Ser Pro Pro Glu Ser Ile Ile Ser Pro His His
    1550                1555                1560

Thr Ser Glu Asp Ser Glu Leu Ile Ala Glu Ala Lys Leu Leu Arg
    1565                1570                1575

Gln His Lys Gly Arg Leu Glu Ala Arg Met Gln Ile Leu Glu Asp
    1580                1585                1590

His Asn Lys Gln Leu Glu Ser Gln Leu His Arg Leu Arg Gln Leu
    1595                1600                1605

Leu Glu Gln Pro Glu Ser Asp Ser Arg Ile Asn Gly Val Ser Pro
    1610                1615                1620

Trp Ala Ser Pro Gln His Ser Ala Leu Ser Tyr Ser Leu Asp Pro
```

-continued

```
              1625                1630                1635

Asp Ala Ser Gly Pro Gln Phe His Gln Ala Ala Gly Glu Asp Leu
        1640                1645                1650

Leu Ala Pro Pro His Asp Thr Ser Thr Asp Leu Thr Glu Val Met
    1655                1660                1665

Glu Gln Ile His Ser Thr Phe Pro Ser Cys Cys Pro Asn Val Pro
1670                1675                1680

Ser Arg Pro Gln Ala Met
    1685

<210> SEQ ID NO 14
<211> LENGTH: 6033
<212> TYPE: DNA
<213> ORGANISM: Homo sapiens
<220> FEATURE:
<221> NAME/KEY: CDS
<222> LOCATION: (1)..(6033)
<220> FEATURE:
<221> NAME/KEY: misc_feature
<222> LOCATION: (1)..(117)
<223> OTHER INFORMATION: TAT and epitope tag coding sequence

<400> SEQUENCE: 14 atg gac tac aag gac gac gat gac aag ggc tac ggc cgc aag aaa cgc    48
Met Asp Tyr Lys Asp Asp Asp Asp Lys Gly Tyr Gly Arg Lys Lys Arg
 1               5                  10                  15 cgc cag cgc cgc cgc ggt gga tcc acc atg tcc ggc tat cca tat gac    96
Arg Gln Arg Arg Arg Gly Gly Ser Thr Met Ser Gly Tyr Pro Tyr Asp
            20                  25                  30 gtc cca gac tat gct ggc tcc atg gcc aag tat gga gaa cat gaa gcc   144
Val Pro Asp Tyr Ala Gly Ser Met Ala Lys Tyr Gly Glu His Glu Ala
        35                  40                  45 agt cct gac aat ggg cag aac gaa ttc agt gat atc att aag tcc aga   192
Ser Pro Asp Asn Gly Gln Asn Glu Phe Ser Asp Ile Ile Lys Ser Arg
    50                  55                  60 tct gat gaa cac aat gac gta cag aag aaa acc ttt acc aaa tgg ata   240
Ser Asp Glu His Asn Asp Val Gln Lys Lys Thr Phe Thr Lys Trp Ile
65                  70                  75                  80 aat gct cga ttt tca aag agt ggg aaa cca ccc atc aat gat atg ttc   288
Asn Ala Arg Phe Ser Lys Ser Gly Lys Pro Pro Ile Asn Asp Met Phe
                85                  90                  95 aca gac ctc aaa gat gga agg aag cta ttg gat ctt cta gaa ggc ctc   336
Thr Asp Leu Lys Asp Gly Arg Lys Leu Leu Asp Leu Leu Glu Gly Leu
            100                 105                 110 aca gga aca tca ctg cca aag gaa cgt ggt tcc aca agg gta cat gcc   384
Thr Gly Thr Ser Leu Pro Lys Glu Arg Gly Ser Thr Arg Val His Ala
        115                 120                 125 tta aat aac gtc aac aga gtg ctg cag gtt tta cat cag aac aat gtg   432
Leu Asn Asn Val Asn Arg Val Leu Gln Val Leu His Gln Asn Asn Val
    130                 135                 140 gaa tta gtg aat ata ggg gga act gac att gtg gat gga aat cac aaa   480
Glu Leu Val Asn Ile Gly Gly Thr Asp Ile Val Asp Gly Asn His Lys
145                 150                 155                 160 ctg act ttg ggg tta ctt tgg agc atc att ttg cac tgg cag gtg aaa   528
Leu Thr Leu Gly Leu Leu Trp Ser Ile Ile Leu His Trp Gln Val Lys
                165                 170                 175 gat gtc atg aag gat gtc atg tcg gac ctg cag cag acg aac agt gag   576
Asp Val Met Lys Asp Val Met Ser Asp Leu Gln Gln Thr Asn Ser Glu
            180                 185                 190 aag atc ctg ctc agc tgg gtg cgt cag acc acc agg ccc tac agc caa   624
Lys Ile Leu Leu Ser Trp Val Arg Gln Thr Thr Arg Pro Tyr Ser Gln
```

```
            195                 200                 205
gtc aac gtc ctc aac ttc acc acc agc tgg aca gat gga ctc gcc ttt      672
Val Asn Val Leu Asn Phe Thr Thr Ser Trp Thr Asp Gly Leu Ala Phe
    210                 215                 220 aat gct gtc ctc cac cga cat aaa cct gat ctc ttc agc tgg gat aaa      720
Asn Ala Val Leu His Arg His Lys Pro Asp Leu Phe Ser Trp Asp Lys
225                 230                 235                 240 gtt gtc aaa atg tca cca att gag aga ctt gaa cat gcc ttc agc aag      768
Val Val Lys Met Ser Pro Ile Glu Arg Leu Glu His Ala Phe Ser Lys
                245                 250                 255 gct caa act tat ttg gga att gaa aag ctg tta gat cct gaa gat gtt      816
Ala Gln Thr Tyr Leu Gly Ile Glu Lys Leu Leu Asp Pro Glu Asp Val
        260                 265                 270 gcc gtt cag ctt cct gac aag aaa tcc ata att atg tat tta aca tct      864
Ala Val Gln Leu Pro Asp Lys Lys Ser Ile Ile Met Tyr Leu Thr Ser
            275                 280                 285 ttg ttt gag gtg cta cct cag caa gtc acc ata gac gcc atc cgt gag      912
Leu Phe Glu Val Leu Pro Gln Gln Val Thr Ile Asp Ala Ile Arg Glu
    290                 295                 300 gta gag aca ctc cca agg aaa tat aaa aaa gaa tgt gaa gaa gag gca      960
Val Glu Thr Leu Pro Arg Lys Tyr Lys Lys Glu Cys Glu Glu Glu Ala
305                 310                 315                 320 att aat ata cag agt aca gcg cct gag gag gag cat gag agt ccc cga     1008
Ile Asn Ile Gln Ser Thr Ala Pro Glu Glu Glu His Glu Ser Pro Arg
                325                 330                 335 gct gaa act ccc agc act gtc act gag gtt gac atg gat ctg gac agc     1056
Ala Glu Thr Pro Ser Thr Val Thr Glu Val Asp Met Asp Leu Asp Ser
        340                 345                 350 tat cag att gcg ttg gag gaa gtg ctg acc tgg ttg ctt tct gct gag     1104
Tyr Gln Ile Ala Leu Glu Glu Val Leu Thr Trp Leu Leu Ser Ala Glu
            355                 360                 365 gac act ttc cag gag cag gat gat att tct gat gat gtt gaa gaa gtc     1152
Asp Thr Phe Gln Glu Gln Asp Asp Ile Ser Asp Asp Val Glu Glu Val
    370                 375                 380 aaa gac cag ttt gca acc cat gaa gct ttt atg atg gaa ctg act gca     1200
Lys Asp Gln Phe Ala Thr His Glu Ala Phe Met Met Glu Leu Thr Ala
385                 390                 395                 400 cac cag agc agt gtg ggc agc gtc ctg cag gca ggc aac caa ctg ata     1248
His Gln Ser Ser Val Gly Ser Val Leu Gln Ala Gly Asn Gln Leu Ile
                405                 410                 415 aca caa gga act ctg tca gac gaa gaa gaa ttt gag att cag gaa cag     1296
Thr Gln Gly Thr Leu Ser Asp Glu Glu Glu Phe Glu Ile Gln Glu Gln
        420                 425                 430 atg acc ctg ctg aat gct aga tgg gag gct ctt agg gtg gag agt atg     1344
Met Thr Leu Leu Asn Ala Arg Trp Glu Ala Leu Arg Val Glu Ser Met
            435                 440                 445 gac aga cag tcc cgg ctg cac gat gtg ctg atg gaa ctg cag aag aag     1392
Asp Arg Gln Ser Arg Leu His Asp Val Leu Met Glu Leu Gln Lys Lys
    450                 455                 460 caa ctg cag cag ctc tcc gcc tgg tta aca ctc aca gag gag cgc att     1440
Gln Leu Gln Gln Leu Ser Ala Trp Leu Thr Leu Thr Glu Glu Arg Ile
465                 470                 475                 480 cag aag atg gaa act tgc ccc ctg gat gat gat gta aaa tct cta caa     1488
Gln Lys Met Glu Thr Cys Pro Leu Asp Asp Asp Val Lys Ser Leu Gln
                485                 490                 495 aag ctg cta gaa gaa cat aaa agt ttg caa agt gat ctt gag gct gaa     1536
Lys Leu Leu Glu Glu His Lys Ser Leu Gln Ser Asp Leu Glu Ala Glu
        500                 505                 510 cag gtg aaa gta aat tca cta act cac atg gtg gtc att gtt gat gaa     1584
```

```
                Gln Val Lys Val Asn Ser Leu Thr His Met Val Val Ile Val Asp Glu
                                515                 520                 525 aac agt ggt gag agt gct aca gct atc cta gaa gac cag tta cag aaa            1632
Asn Ser Gly Glu Ser Ala Thr Ala Ile Leu Glu Asp Gln Leu Gln Lys
            530                 535                 540 ctt ggt gag cgc tgg aca gca gta tgc cgt tgg act gaa gaa cgc tgg            1680
Leu Gly Glu Arg Trp Thr Ala Val Cys Arg Trp Thr Glu Glu Arg Trp
545                 550                 555                 560 aat agg tta caa gaa atc aat ata ttg tgg cag gaa tta ttg gaa gaa            1728
Asn Arg Leu Gln Glu Ile Asn Ile Leu Trp Gln Glu Leu Leu Glu Glu
                565                 570                 575 cag tgc ttg ttg aaa gct tgg tta acc gaa aaa gaa gag gct tta aat            1776
Gln Cys Leu Leu Lys Ala Trp Leu Thr Glu Lys Glu Glu Ala Leu Asn
            580                 585                 590 aaa gtc cag aca agc aac ttc aaa gac caa aag gaa cta agt gtc agt            1824
Lys Val Gln Thr Ser Asn Phe Lys Asp Gln Lys Glu Leu Ser Val Ser
        595                 600                 605 gtt cga cgt ctg gct att ttg aag gaa gac atg gaa atg aag cgt caa            1872
Val Arg Arg Leu Ala Ile Leu Lys Glu Asp Met Glu Met Lys Arg Gln
610                 615                 620 aca ttg gat cag ctg agt gag att ggc cag gat gtg gga caa tta ctt            1920
Thr Leu Asp Gln Leu Ser Glu Ile Gly Gln Asp Val Gly Gln Leu Leu
625                 630                 635                 640 gat aat tcc aag gca tct aag aag atc aac agt gac tca gag gaa ctg            1968
Asp Asn Ser Lys Ala Ser Lys Lys Ile Asn Ser Asp Ser Glu Glu Leu
                645                 650                 655 act caa aga tgg gat tct ttg gtt cag aga cta gaa gat tcc tcc aac            2016
Thr Gln Arg Trp Asp Ser Leu Val Gln Arg Leu Glu Asp Ser Ser Asn
            660                 665                 670 cag gtg act cag gct gta gca aag ctg ggg atg tct cag att cct cag            2064
Gln Val Thr Gln Ala Val Ala Lys Leu Gly Met Ser Gln Ile Pro Gln
        675                 680                 685 aag gac ctt ttg gag act gtt cgt gta aga gaa caa gca att aca aaa            2112
Lys Asp Leu Leu Glu Thr Val Arg Val Arg Glu Gln Ala Ile Thr Lys
690                 695                 700 aaa tct aag cag gaa ctg cct cct cct cct ccc cca aag aag aga cag            2160
Lys Ser Lys Gln Glu Leu Pro Pro Pro Pro Pro Lys Lys Arg Gln
705                 710                 715                 720 atc cat gtg gat att gaa gct aag aaa aag ttt gat gct ata agt gca            2208
Ile His Val Asp Ile Glu Ala Lys Lys Lys Phe Asp Ala Ile Ser Ala
                725                 730                 735 gag ctg ttg aac tgg att ttg aaa tgg aaa act gcc att cag acc aca            2256
Glu Leu Leu Asn Trp Ile Leu Lys Trp Lys Thr Ala Ile Gln Thr Thr
            740                 745                 750 gag ata aaa gag tat atg aag atg caa gac act tcc gaa atg aaa aag            2304
Glu Ile Lys Glu Tyr Met Lys Met Gln Asp Thr Ser Glu Met Lys Lys
        755                 760                 765 aag ttg aag gca tta gaa aaa gaa cag aga gaa aga atc ccc aga gca            2352
Lys Leu Lys Ala Leu Glu Lys Glu Gln Arg Glu Arg Ile Pro Arg Ala
770                 775                 780 gat gaa tta aac caa act gga caa atc ctt gtg gag caa atg gga aaa            2400
Asp Glu Leu Asn Gln Thr Gly Gln Ile Leu Val Glu Gln Met Gly Lys
785                 790                 795                 800 gaa ggc ctt cct act gaa gaa ata aaa aat gtt ctg gag aag gtt tca            2448
Glu Gly Leu Pro Thr Glu Glu Ile Lys Asn Val Leu Glu Lys Val Ser
                805                 810                 815 tca gaa tgg aag aat gta tct caa cat ttg gaa gat cta gaa aga aag            2496
Ser Glu Trp Lys Asn Val Ser Gln His Leu Glu Asp Leu Glu Arg Lys
            820                 825                 830
```

```
att cag cta cag gaa gat ata aat gct tat ttc aag cag ctt gat gag    2544
Ile Gln Leu Gln Glu Asp Ile Asn Ala Tyr Phe Lys Gln Leu Asp Glu
            835                 840                 845 ctt gaa aag gtc atc aag aca aag gag gag tgg gta aaa cac act tcc    2592
Leu Glu Lys Val Ile Lys Thr Lys Glu Glu Trp Val Lys His Thr Ser
    850                 855                 860 att tct gaa tct tcc cgg cag tcc ttg cca agc ttg aag gat tcc tgt    2640
Ile Ser Glu Ser Ser Arg Gln Ser Leu Pro Ser Leu Lys Asp Ser Cys
865                 870                 875                 880 cag cgg gaa ttg aca aat ctt ctt ggc ctt cac ccc aaa att gaa atg    2688
Gln Arg Glu Leu Thr Asn Leu Leu Gly Leu His Pro Lys Ile Glu Met
                885                 890                 895 gct cgt gca agc tgc tcg gcc ctg atg tct cag cct tct gcc cca gat    2736
Ala Arg Ala Ser Cys Ser Ala Leu Met Ser Gln Pro Ser Ala Pro Asp
        900                 905                 910 ttt gtc cag cgg ggc ttc gat agc ttt ctg ggc cgc tac caa gct gta    2784
Phe Val Gln Arg Gly Phe Asp Ser Phe Leu Gly Arg Tyr Gln Ala Val
            915                 920                 925 caa gag gct gta gag gat cgt caa caa cat cta gag aat gaa ctg aag    2832
Gln Glu Ala Val Glu Asp Arg Gln Gln His Leu Glu Asn Glu Leu Lys
    930                 935                 940 ggc caa cct gga cat gca tat ctg gaa aca ttg aaa aca ctg aaa gat    2880
Gly Gln Pro Gly His Ala Tyr Leu Glu Thr Leu Lys Thr Leu Lys Asp
945                 950                 955                 960 gtg cta aat gat tca gaa aat aag gcc cag gtg tct ctg aat gtc ctt    2928
Val Leu Asn Asp Ser Glu Asn Lys Ala Gln Val Ser Leu Asn Val Leu
                965                 970                 975 aat gat ctt gcc aag gtg gag aag gcc ctg caa gaa aaa aag acc ctt    2976
Asn Asp Leu Ala Lys Val Glu Lys Ala Leu Gln Glu Lys Lys Thr Leu
        980                 985                 990 gat gaa atc ctt gag aat cag aaa cct gca tta cat aaa ctt gca gaa    3024
Asp Glu Ile Leu Glu Asn Gln Lys Pro Ala Leu His Lys Leu Ala Glu
            995                 1000                1005 gaa aca aag gct ctg gag aaa aat gtt cat cct gat gta gaa aaa        3069
Glu Thr Lys Ala Leu Glu Lys Asn Val His Pro Asp Val Glu Lys
    1010                1015                1020 tta tat aag caa gaa ttt gat gat gtg caa gga aag tgg aac aag        3114
Leu Tyr Lys Gln Glu Phe Asp Asp Val Gln Gly Lys Trp Asn Lys
    1025                1030                1035 cta aag gtc ttg gtt tcc aaa gat cta cat ttg ctt gag gaa att        3159
Leu Lys Val Leu Val Ser Lys Asp Leu His Leu Leu Glu Glu Ile
    1040                1045                1050 gct ctc aca ctc aga gct ttt gag gcc gat tca aca gtc att gag        3204
Ala Leu Thr Leu Arg Ala Phe Glu Ala Asp Ser Thr Val Ile Glu
    1055                1060                1065 aag tgg atg gat ggc gtg aaa gac ttc tta atg aaa cag cag gct        3249
Lys Trp Met Asp Gly Val Lys Asp Phe Leu Met Lys Gln Gln Ala
    1070                1075                1080 gcc caa gga gac gac gca ggt cta cag agg cag tta gac cag tgc        3294
Ala Gln Gly Asp Asp Ala Gly Leu Gln Arg Gln Leu Asp Gln Cys
    1085                1090                1095 tct gca ttt gtt aat gaa ata gaa aca att gaa tca tct ctg aaa        3339
Ser Ala Phe Val Asn Glu Ile Glu Thr Ile Glu Ser Ser Leu Lys
    1100                1105                1110 aac atg aag gaa ata gag act aat ctt cga agt ggt cca gtt gct        3384
Asn Met Lys Glu Ile Glu Thr Asn Leu Arg Ser Gly Pro Val Ala
    1115                1120                1125 gga ata aaa act tgg gtg cag aca aga cta ggt gac tac caa act        3429
Gly Ile Lys Thr Trp Val Gln Thr Arg Leu Gly Asp Tyr Gln Thr
    1130                1135                1140
```

-continued

| | | |
|---|---|---|
| caa ctg gag aaa ctt agc aag gag atc gct act caa aaa agt agg<br>Gln Leu Glu Lys Leu Ser Lys Glu Ile Ala Thr Gln Lys Ser Arg<br>1145                         1150                       1155 | 3474 |
| ttg tct gaa agt caa gaa aaa gct gcg aac ctg aag aaa gac ttg<br>Leu Ser Glu Ser Gln Glu Lys Ala Ala Asn Leu Lys Lys Asp Leu<br>1160                         1165                       1170 | 3519 |
| gca gag atg cag gaa tgg atg acc cag gcc gag gaa gaa tat ttg<br>Ala Glu Met Gln Glu Trp Met Thr Gln Ala Glu Glu Glu Tyr Leu<br>1175                         1180                       1185 | 3564 |
| gag cgg gat ttt gag tac aag tca cca gaa gag ctt gag agt gct<br>Glu Arg Asp Phe Glu Tyr Lys Ser Pro Glu Glu Leu Glu Ser Ala<br>1190                         1195                       1200 | 3609 |
| gtg gaa gag atg aag agg gca aaa gag gat gtg ttg cag aag gag<br>Val Glu Glu Met Lys Arg Ala Lys Glu Asp Val Leu Gln Lys Glu<br>1205                         1210                       1215 | 3654 |
| gtg aga gtg aag att ctc aag gac aac atc aag tta tta gct gcc<br>Val Arg Val Lys Ile Leu Lys Asp Asn Ile Lys Leu Leu Ala Ala<br>1220                         1225                       1230 | 3699 |
| aag gtg ccc tct ggt ggc cag gag ttg acg tct gag ctg aat gtt<br>Lys Val Pro Ser Gly Gly Gln Glu Leu Thr Ser Glu Leu Asn Val<br>1235                         1240                       1245 | 3744 |
| gtg ctg gag aat tac caa ctt ctt tgt aat aga att cga gga aag<br>Val Leu Glu Asn Tyr Gln Leu Leu Cys Asn Arg Ile Arg Gly Lys<br>1250                         1255                       1260 | 3789 |
| tgc cac acg cta gag gag gtc tgg tct tgt tgg att gaa ctg ctt<br>Cys His Thr Leu Glu Glu Val Trp Ser Cys Trp Ile Glu Leu Leu<br>1265                         1270                       1275 | 3834 |
| cac tat ttg gat ctt gaa act acc tgg tta aac act ttg gaa gag<br>His Tyr Leu Asp Leu Glu Thr Thr Trp Leu Asn Thr Leu Glu Glu<br>1280                         1285                       1290 | 3879 |
| cgg atg aag agc aca gag gtc ctg cct gag aag acg gat gct gtc<br>Arg Met Lys Ser Thr Glu Val Leu Pro Glu Lys Thr Asp Ala Val<br>1295                         1300                       1305 | 3924 |
| aac gaa gcc ctg gag tct ctg gaa tct gtt ctg cgc cac ccg gca<br>Asn Glu Ala Leu Glu Ser Leu Glu Ser Val Leu Arg His Pro Ala<br>1310                         1315                       1320 | 3969 |
| gat aat cgc acc cag att cga gag ctt ggc cag act ctg att gat<br>Asp Asn Arg Thr Gln Ile Arg Glu Leu Gly Gln Thr Leu Ile Asp<br>1325                         1330                       1335 | 4014 |
| ggg ggg atc ctg gat gat ata atc agt gag aaa ctg gag gct ttc<br>Gly Gly Ile Leu Asp Asp Ile Ile Ser Glu Lys Leu Glu Ala Phe<br>1340                         1345                       1350 | 4059 |
| aac agc cga tat gaa gat cta agt cac ctg gca gag agc aag cag<br>Asn Ser Arg Tyr Glu Asp Leu Ser His Leu Ala Glu Ser Lys Gln<br>1355                         1360                       1365 | 4104 |
| att tct ttg gaa aag caa gcc cac aga gat ttt gga cca tcc tct<br>Ile Ser Leu Glu Lys Gln Ala His Arg Asp Phe Gly Pro Ser Ser<br>1370                         1375                       1380 | 4149 |
| cag cat ttt ctc tct acg tca gtc cag ctg ccg tgg caa aga tcc<br>Gln His Phe Leu Ser Thr Ser Val Gln Leu Pro Trp Gln Arg Ser<br>1385                         1390                       1395 | 4194 |
| att tca cat aat aaa gtg ccc tat tac atc aac cat caa aca cag<br>Ile Ser His Asn Lys Val Pro Tyr Tyr Ile Asn His Gln Thr Gln<br>1400                         1405                       1410 | 4239 |
| acc acc tgt tgg gac cat cct aaa atg acc gaa ctc ttt caa tcc<br>Thr Thr Cys Trp Asp His Pro Lys Met Thr Glu Leu Phe Gln Ser<br>1415                         1420                       1425 | 4284 |
| ctt gct gac ctg aat aat gta cgt ttt tct gcc tac cgt aca gca<br>Leu Ala Asp Leu Asn Asn Val Arg Phe Ser Ala Tyr Arg Thr Ala | 4329 |

-continued

```
              1430                1435                1440
atc aaa atc cga aga cta caa aaa gca cta tgt ttg gat ctc tta        4374
Ile Lys Ile Arg Arg Leu Gln Lys Ala Leu Cys Leu Asp Leu Leu
    1445                1450                1455 gag ttg agt aca aca aat gaa att ttc aaa cag cac aag ttg aac        4419
Glu Leu Ser Thr Thr Asn Glu Ile Phe Lys Gln His Lys Leu Asn
    1460                1465                1470 caa aat gac cag ctc ctc agt gtt cca gat gtc atc aac tgt ctg        4464
Gln Asn Asp Gln Leu Leu Ser Val Pro Asp Val Ile Asn Cys Leu
    1475                1480                1485 aca aca act tat gat gga ctt gag caa atg cat aag gac ctg gtc        4509
Thr Thr Thr Tyr Asp Gly Leu Glu Gln Met His Lys Asp Leu Val
    1490                1495                1500 aac gtt cca ctc tgt gtt gat atg tgt ctc aat tgg ttg ctc aat        4554
Asn Val Pro Leu Cys Val Asp Met Cys Leu Asn Trp Leu Leu Asn
    1505                1510                1515 gtc tat gac acg ggt cga act gga aaa att aga gtg cag agt ctg        4599
Val Tyr Asp Thr Gly Arg Thr Gly Lys Ile Arg Val Gln Ser Leu
    1520                1525                1530 aag att gga tta atg tct ctc tcc aaa ggt ctc ttg gaa gaa aaa        4644
Lys Ile Gly Leu Met Ser Leu Ser Lys Gly Leu Leu Glu Glu Lys
    1535                1540                1545 tac aga tat ctc ttt aag gaa gtt gca ggg cca aca gaa atg tgt        4689
Tyr Arg Tyr Leu Phe Lys Glu Val Ala Gly Pro Thr Glu Met Cys
    1550                1555                1560 gac cag agg cag ctg ggc ctg tta ctt cat gat gcc atc cag atc        4734
Asp Gln Arg Gln Leu Gly Leu Leu Leu His Asp Ala Ile Gln Ile
    1565                1570                1575 ccc cgg cag cta ggt gaa gta gca gct ttt gga ggc agt aat att        4779
Pro Arg Gln Leu Gly Glu Val Ala Ala Phe Gly Gly Ser Asn Ile
    1580                1585                1590 gag cct agt gtt cgc agc tgc ttc caa cag aat aac aat aaa cca        4824
Glu Pro Ser Val Arg Ser Cys Phe Gln Gln Asn Asn Asn Lys Pro
    1595                1600                1605 gaa ata agt gtg aaa gag ttt ata gat tgg atg cat ttg gaa cca        4869
Glu Ile Ser Val Lys Glu Phe Ile Asp Trp Met His Leu Glu Pro
    1610                1615                1620 cag tcc atg gtt tgg ctc cca gtt tta cat cga gtg gca gca gcg        4914
Gln Ser Met Val Trp Leu Pro Val Leu His Arg Val Ala Ala Ala
    1625                1630                1635 gag act gca aaa cat cag gcc aaa tgc aac atc tgt aaa gaa tgt        4959
Glu Thr Ala Lys His Gln Ala Lys Cys Asn Ile Cys Lys Glu Cys
    1640                1645                1650 cca att gtc ggg ttc agg tat aga agc ctt aag cat ttt aac tat        5004
Pro Ile Val Gly Phe Arg Tyr Arg Ser Leu Lys His Phe Asn Tyr
    1655                1660                1665 gat gtc tgc cag agt tgt ttc ttt tcg ggt cga aca gca aaa ggt        5049
Asp Val Cys Gln Ser Cys Phe Phe Ser Gly Arg Thr Ala Lys Gly
    1670                1675                1680 cac aaa tta cat tac cca atg gtg gaa tat tgt ata cct aca aca        5094
His Lys Leu His Tyr Pro Met Val Glu Tyr Cys Ile Pro Thr Thr
    1685                1690                1695 tct ggg gaa gat gta cga gac ttc aca aag gta ctt aag aac aag        5139
Ser Gly Glu Asp Val Arg Asp Phe Thr Lys Val Leu Lys Asn Lys
    1700                1705                1710 ttc agg tcg aag aag tac ttt gcc aaa cac cct cga ctt ggt tac        5184
Phe Arg Ser Lys Lys Tyr Phe Ala Lys His Pro Arg Leu Gly Tyr
    1715                1720                1725 ctg cct gtc cag aca gtt ctt gaa ggt gac aac tta gag act cct        5229
```

```
                Leu Pro Val Gln Thr Val Leu Glu Gly Asp Asn Leu Glu Thr Pro
                    1730                1735                1740 atc aca ctc atc agt atg tgg cca gag cac tat gac ccc tca caa          5274
Ile Thr Leu Ile Ser Met Trp Pro Glu His Tyr Asp Pro Ser Gln
    1745                1750                1755 tct cct caa ctg ttt cat gat gac acc cat tca aga ata gaa caa          5319
Ser Pro Gln Leu Phe His Asp Asp Thr His Ser Arg Ile Glu Gln
    1760                1765                1770 tat gcc aca cga ctg gcc cag atg gaa agg act aat ggg tct ttt          5364
Tyr Ala Thr Arg Leu Ala Gln Met Glu Arg Thr Asn Gly Ser Phe
    1775                1780                1785 ctc act gat agc agc tcc acc aca gga agt gtg gaa gac gag cac          5409
Leu Thr Asp Ser Ser Ser Thr Thr Gly Ser Val Glu Asp Glu His
    1790                1795                1800 gcc ctc atc cag cag tat tgc caa aca ctc gga gga gag tcc cca          5454
Ala Leu Ile Gln Gln Tyr Cys Gln Thr Leu Gly Gly Glu Ser Pro
    1805                1810                1815 gtg agc cag ccg cag agc cca gct cag atc ctg aag tca gta gag          5499
Val Ser Gln Pro Gln Ser Pro Ala Gln Ile Leu Lys Ser Val Glu
    1820                1825                1830 agg gaa gaa cgt gga gaa ctg gag agg atc att gct gac ctg gag          5544
Arg Glu Glu Arg Gly Glu Leu Glu Arg Ile Ile Ala Asp Leu Glu
    1835                1840                1845 gaa gaa caa aga aat cta cag gtg gag tat gag cag ctg aag gac          5589
Glu Glu Gln Arg Asn Leu Gln Val Glu Tyr Glu Gln Leu Lys Asp
    1850                1855                1860 cag cac ctc cga agg ggg ctc cct gtc ggt tca ccg cca gag tcg          5634
Gln His Leu Arg Arg Gly Leu Pro Val Gly Ser Pro Pro Glu Ser
    1865                1870                1875 att ata tct ccc cat cac acg tct gag gat tca gaa ctt ata gca          5679
Ile Ile Ser Pro His His Thr Ser Glu Asp Ser Glu Leu Ile Ala
    1880                1885                1890 gaa gca aaa ctc ctc agg cag cac aaa ggt cgg ctg gag gct agg          5724
Glu Ala Lys Leu Leu Arg Gln His Lys Gly Arg Leu Glu Ala Arg
    1895                1900                1905 atg cag att tta gaa gat cac aat aaa cag ctg gag tct cag ctc          5769
Met Gln Ile Leu Glu Asp His Asn Lys Gln Leu Glu Ser Gln Leu
    1910                1915                1920 cac cgc ctc cga cag ctg ctg gag cag cct gaa tct gat tcc cga          5814
His Arg Leu Arg Gln Leu Leu Glu Gln Pro Glu Ser Asp Ser Arg
    1925                1930                1935 atc aat ggt gtt tcc cca tgg gct tct cct cag cat tct gca ctg          5859
Ile Asn Gly Val Ser Pro Trp Ala Ser Pro Gln His Ser Ala Leu
    1940                1945                1950 agc tac tcg ctt gat cca gat gcc tcc ggc cca cag ttc cac cag          5904
Ser Tyr Ser Leu Asp Pro Asp Ala Ser Gly Pro Gln Phe His Gln
    1955                1960                1965 gca gcg gga gag gac ctg ctg gcc cca ccg cac gac acc agc acg          5949
Ala Ala Gly Glu Asp Leu Leu Ala Pro Pro His Asp Thr Ser Thr
    1970                1975                1980 gat ctc acg gag gtc atg gag cag att cac agc acg ttt cca tct          5994
Asp Leu Thr Glu Val Met Glu Gln Ile His Ser Thr Phe Pro Ser
    1985                1990                1995 tgc tgc cca aat gtt ccc agc agg cca cag gca atg tga              6033
Cys Cys Pro Asn Val Pro Ser Arg Pro Gln Ala Met
    2000                2005                2010

<210> SEQ ID NO 15
<211> LENGTH: 2010
<212> TYPE: PRT
```

<213> ORGANISM: Homo sapiens

<400> SEQUENCE: 15

```
Met Asp Tyr Lys Asp Asp Asp Lys Gly Tyr Gly Arg Lys Lys Arg
1               5                   10                  15
Arg Gln Arg Arg Arg Gly Gly Ser Thr Met Ser Gly Tyr Pro Tyr Asp
            20                  25                  30
Val Pro Asp Tyr Ala Gly Ser Met Ala Lys Tyr Gly Glu His Glu Ala
        35                  40                  45
Ser Pro Asp Asn Gly Gln Asn Glu Phe Ser Asp Ile Ile Lys Ser Arg
50                  55                  60
Ser Asp Glu His Asn Asp Val Gln Lys Lys Thr Phe Thr Lys Trp Ile
65                  70                  75                  80
Asn Ala Arg Phe Ser Lys Ser Gly Lys Pro Pro Ile Asn Asp Met Phe
                85                  90                  95
Thr Asp Leu Lys Asp Gly Arg Lys Leu Leu Asp Leu Leu Glu Gly Leu
            100                 105                 110
Thr Gly Thr Ser Leu Pro Lys Glu Arg Gly Ser Thr Arg Val His Ala
        115                 120                 125
Leu Asn Asn Val Asn Arg Val Leu Gln Val Leu His Gln Asn Asn Val
130                 135                 140
Glu Leu Val Asn Ile Gly Gly Thr Asp Ile Val Asp Gly Asn His Lys
145                 150                 155                 160
Leu Thr Leu Gly Leu Leu Trp Ser Ile Ile Leu His Trp Gln Val Lys
                165                 170                 175
Asp Val Met Lys Asp Val Met Ser Asp Leu Gln Gln Thr Asn Ser Glu
            180                 185                 190
Lys Ile Leu Leu Ser Trp Val Arg Gln Thr Thr Arg Pro Tyr Ser Gln
        195                 200                 205
Val Asn Val Leu Asn Phe Thr Thr Ser Trp Thr Asp Gly Leu Ala Phe
210                 215                 220
Asn Ala Val Leu His Arg His Lys Pro Asp Leu Phe Ser Trp Asp Lys
225                 230                 235                 240
Val Val Lys Met Ser Pro Ile Glu Arg Leu Glu His Ala Phe Ser Lys
                245                 250                 255
Ala Gln Thr Tyr Leu Gly Ile Glu Lys Leu Leu Asp Pro Glu Asp Val
            260                 265                 270
Ala Val Gln Leu Pro Asp Lys Lys Ser Ile Ile Met Tyr Leu Thr Ser
        275                 280                 285
Leu Phe Glu Val Leu Pro Gln Gln Val Thr Ile Asp Ala Ile Arg Glu
290                 295                 300
Val Glu Thr Leu Pro Arg Lys Tyr Lys Lys Glu Cys Glu Glu Glu Ala
305                 310                 315                 320
Ile Asn Ile Gln Ser Thr Ala Pro Glu Glu His Glu Ser Pro Arg
                325                 330                 335
Ala Glu Thr Pro Ser Thr Val Thr Glu Val Asp Met Asp Leu Asp Ser
            340                 345                 350
Tyr Gln Ile Ala Leu Glu Glu Val Leu Thr Trp Leu Leu Ser Ala Glu
        355                 360                 365
Asp Thr Phe Gln Glu Gln Asp Ile Ser Asp Val Glu Glu Val
370                 375                 380
Lys Asp Gln Phe Ala Thr His Glu Ala Phe Met Met Glu Leu Thr Ala
385                 390                 395                 400
```

-continued

```
His Gln Ser Ser Val Gly Ser Val Leu Gln Ala Gly Asn Gln Leu Ile
                405                 410                 415
Thr Gln Gly Thr Leu Ser Asp Glu Glu Phe Glu Ile Gln Glu Gln
            420                 425                 430
Met Thr Leu Leu Asn Ala Arg Trp Glu Ala Leu Arg Val Glu Ser Met
                435                 440                 445
Asp Arg Gln Ser Arg Leu His Asp Val Leu Met Glu Leu Gln Lys Lys
            450                 455                 460
Gln Leu Gln Gln Leu Ser Ala Trp Leu Thr Leu Thr Glu Glu Arg Ile
465                 470                 475                 480
Gln Lys Met Glu Thr Cys Pro Leu Asp Asp Val Lys Ser Leu Gln
                485                 490                 495
Lys Leu Leu Glu Glu His Lys Ser Leu Gln Ser Asp Leu Glu Ala Glu
                500                 505                 510
Gln Val Lys Val Asn Ser Leu Thr His Met Val Val Ile Val Asp Glu
            515                 520                 525
Asn Ser Gly Glu Ser Ala Thr Ala Ile Leu Glu Asp Gln Leu Gln Lys
            530                 535                 540
Leu Gly Glu Arg Trp Thr Ala Val Cys Arg Trp Thr Glu Glu Arg Trp
545                 550                 555                 560
Asn Arg Leu Gln Glu Ile Asn Ile Leu Trp Gln Leu Leu Glu Glu
                565                 570                 575
Gln Cys Leu Leu Lys Ala Trp Leu Thr Glu Lys Glu Glu Ala Leu Asn
                580                 585                 590
Lys Val Gln Thr Ser Asn Phe Lys Asp Gln Lys Glu Leu Ser Val Ser
            595                 600                 605
Val Arg Arg Leu Ala Ile Leu Lys Glu Asp Met Glu Met Lys Arg Gln
            610                 615                 620
Thr Leu Asp Gln Leu Ser Glu Ile Gly Gln Asp Val Gly Gln Leu Leu
625                 630                 635                 640
Asp Asn Ser Lys Ala Ser Lys Lys Ile Asn Ser Asp Ser Glu Glu Leu
                645                 650                 655
Thr Gln Arg Trp Asp Ser Leu Val Gln Arg Leu Glu Asp Ser Ser Asn
                660                 665                 670
Gln Val Thr Gln Ala Val Ala Lys Leu Gly Met Ser Gln Ile Pro Gln
            675                 680                 685
Lys Asp Leu Leu Glu Thr Val Arg Val Arg Glu Gln Ala Ile Thr Lys
            690                 695                 700
Lys Ser Lys Gln Glu Leu Pro Pro Pro Pro Lys Lys Arg Gln
705                 710                 715                 720
Ile His Val Asp Ile Glu Ala Lys Lys Phe Asp Ala Ile Ser Ala
                725                 730                 735
Glu Leu Leu Asn Trp Ile Leu Lys Trp Lys Thr Ala Ile Gln Thr Thr
            740                 745                 750
Glu Ile Lys Glu Tyr Met Lys Met Gln Asp Thr Ser Glu Met Lys Lys
            755                 760                 765
Lys Leu Lys Ala Leu Glu Lys Glu Gln Arg Glu Arg Ile Pro Arg Ala
            770                 775                 780
Asp Glu Leu Asn Gln Thr Gly Gln Ile Leu Val Glu Gln Met Gly Lys
785                 790                 795                 800
Glu Gly Leu Pro Thr Glu Glu Ile Lys Asn Val Leu Glu Lys Val Ser
                805                 810                 815
Ser Glu Trp Lys Asn Val Ser Gln His Leu Glu Asp Leu Glu Arg Lys
```

-continued

```
                820                 825                 830
Ile Gln Leu Gln Glu Asp Ile Asn Ala Tyr Phe Lys Gln Leu Asp Glu
                835                 840                 845
Leu Glu Lys Val Ile Lys Thr Lys Glu Glu Trp Val Lys His Thr Ser
                850                 855                 860
Ile Ser Glu Ser Ser Arg Gln Ser Leu Pro Ser Leu Lys Asp Ser Cys
865                 870                 875                 880
Gln Arg Glu Leu Thr Asn Leu Leu Gly Leu His Pro Lys Ile Glu Met
                885                 890                 895
Ala Arg Ala Ser Cys Ser Ala Leu Met Ser Gln Pro Ser Ala Pro Asp
                900                 905                 910
Phe Val Gln Arg Gly Phe Asp Ser Phe Leu Gly Arg Tyr Gln Ala Val
                915                 920                 925
Gln Glu Ala Val Glu Asp Arg Gln Gln His Leu Glu Asn Glu Leu Lys
                930                 935                 940
Gly Gln Pro Gly His Ala Tyr Leu Glu Thr Leu Lys Thr Leu Lys Asp
945                 950                 955                 960
Val Leu Asn Asp Ser Glu Asn Lys Ala Gln Val Ser Leu Asn Val Leu
                965                 970                 975
Asn Asp Leu Ala Lys Val Glu Lys Ala Leu Gln Glu Lys Lys Thr Leu
                980                 985                 990
Asp Glu Ile Leu Glu Asn Gln Lys Pro Ala Leu His Lys Leu Ala Glu
                995                1000                1005
Glu Thr Lys Ala Leu Glu Lys Asn Val His Pro Asp Val Glu Lys
                1010                1015                1020
Leu Tyr Lys Gln Glu Phe Asp Asp Val Gln Gly Lys Trp Asn Lys
                1025                1030                1035
Leu Lys Val Leu Val Ser Lys Asp Leu His Leu Leu Glu Glu Ile
                1040                1045                1050
Ala Leu Thr Leu Arg Ala Phe Glu Ala Asp Ser Thr Val Ile Glu
                1055                1060                1065
Lys Trp Met Asp Gly Val Lys Asp Phe Leu Met Lys Gln Gln Ala
                1070                1075                1080
Ala Gln Gly Asp Asp Ala Gly Leu Gln Arg Gln Leu Asp Gln Cys
                1085                1090                1095
Ser Ala Phe Val Asn Glu Ile Glu Thr Ile Glu Ser Ser Leu Lys
                1100                1105                1110
Asn Met Lys Glu Ile Glu Thr Asn Leu Arg Ser Gly Pro Val Ala
                1115                1120                1125
Gly Ile Lys Thr Trp Val Gln Thr Arg Leu Gly Asp Tyr Gln Thr
                1130                1135                1140
Gln Leu Glu Lys Leu Ser Lys Glu Ile Ala Thr Gln Lys Ser Arg
                1145                1150                1155
Leu Ser Glu Ser Gln Glu Lys Ala Ala Asn Leu Lys Lys Asp Leu
                1160                1165                1170
Ala Glu Met Gln Glu Trp Met Thr Gln Ala Glu Glu Tyr Leu
                1175                1180                1185
Glu Arg Asp Phe Glu Tyr Lys Ser Pro Glu Glu Leu Glu Ser Ala
                1190                1195                1200
Val Glu Glu Met Lys Arg Ala Lys Glu Asp Val Leu Gln Lys Glu
                1205                1210                1215
Val Arg Val Lys Ile Leu Lys Asp Asn Ile Lys Leu Leu Ala Ala
                1220                1225                1230
```

-continued

Lys Val Pro Ser Gly Gly Gln Glu Leu Thr Ser Glu Leu Asn Val
1235                1240                    1245

Val Leu Glu Asn Tyr Gln Leu Leu Cys Asn Arg Ile Arg Gly Lys
1250                1255                    1260

Cys His Thr Leu Glu Glu Val Trp Ser Cys Trp Ile Glu Leu Leu
1265                1270                    1275

His Tyr Leu Asp Leu Glu Thr Thr Trp Leu Asn Thr Leu Glu Glu
1280                1285                    1290

Arg Met Lys Ser Thr Glu Val Leu Pro Glu Lys Thr Asp Ala Val
1295                1300                    1305

Asn Glu Ala Leu Glu Ser Leu Glu Ser Val Leu Arg His Pro Ala
1310                1315                    1320

Asp Asn Arg Thr Gln Ile Arg Glu Leu Gly Gln Thr Leu Ile Asp
1325                1330                    1335

Gly Gly Ile Leu Asp Asp Ile Ile Ser Glu Lys Leu Glu Ala Phe
1340                1345                    1350

Asn Ser Arg Tyr Glu Asp Leu Ser His Leu Ala Glu Ser Lys Gln
1355                1360                    1365

Ile Ser Leu Glu Lys Gln Ala His Arg Asp Phe Gly Pro Ser Ser
1370                1375                    1380

Gln His Phe Leu Ser Thr Ser Val Gln Leu Pro Trp Gln Arg Ser
1385                1390                    1395

Ile Ser His Asn Lys Val Pro Tyr Tyr Ile Asn His Gln Thr Gln
1400                1405                    1410

Thr Thr Cys Trp Asp His Pro Lys Met Thr Glu Leu Phe Gln Ser
1415                1420                    1425

Leu Ala Asp Leu Asn Asn Val Arg Phe Ser Ala Tyr Arg Thr Ala
1430                1435                    1440

Ile Lys Ile Arg Arg Leu Gln Lys Ala Leu Cys Leu Asp Leu Leu
1445                1450                    1455

Glu Leu Ser Thr Thr Asn Glu Ile Phe Lys Gln His Lys Leu Asn
1460                1465                    1470

Gln Asn Asp Gln Leu Leu Ser Val Pro Asp Val Ile Asn Cys Leu
1475                1480                    1485

Thr Thr Thr Tyr Asp Gly Leu Glu Gln Met His Lys Asp Leu Val
1490                1495                    1500

Asn Val Pro Leu Cys Val Asp Met Cys Leu Asn Trp Leu Leu Asn
1505                1510                    1515

Val Tyr Asp Thr Gly Arg Thr Gly Lys Ile Arg Val Gln Ser Leu
1520                1525                    1530

Lys Ile Gly Leu Met Ser Leu Ser Lys Gly Leu Leu Glu Glu Lys
1535                1540                    1545

Tyr Arg Tyr Leu Phe Lys Glu Val Ala Gly Pro Thr Glu Met Cys
1550                1555                    1560

Asp Gln Arg Gln Leu Gly Leu Leu Leu His Asp Ala Ile Gln Ile
1565                1570                    1575

Pro Arg Gln Leu Gly Glu Val Ala Ala Phe Gly Gly Ser Asn Ile
1580                1585                    1590

Glu Pro Ser Val Arg Ser Cys Phe Gln Gln Asn Asn Asn Lys Pro
1595                1600                    1605

Glu Ile Ser Val Lys Glu Phe Ile Asp Trp Met His Leu Glu Pro
1610                1615                    1620

-continued

```
Gln Ser Met Val Trp Leu Pro Val Leu His Arg Val Ala Ala Ala
    1625            1630            1635

Glu Thr Ala Lys His Gln Ala Lys Cys Asn Ile Cys Lys Glu Cys
    1640            1645            1650

Pro Ile Val Gly Phe Arg Tyr Arg Ser Leu Lys His Phe Asn Tyr
    1655            1660            1665

Asp Val Cys Gln Ser Cys Phe Phe Ser Gly Arg Thr Ala Lys Gly
    1670            1675            1680

His Lys Leu His Tyr Pro Met Val Glu Tyr Cys Ile Pro Thr Thr
    1685            1690            1695

Ser Gly Glu Asp Val Arg Asp Phe Thr Lys Val Leu Lys Asn Lys
    1700            1705            1710

Phe Arg Ser Lys Lys Tyr Phe Ala Lys His Pro Arg Leu Gly Tyr
    1715            1720            1725

Leu Pro Val Gln Thr Val Leu Glu Gly Asp Asn Leu Glu Thr Pro
    1730            1735            1740

Ile Thr Leu Ile Ser Met Trp Pro Glu His Tyr Asp Pro Ser Gln
    1745            1750            1755

Ser Pro Gln Leu Phe His Asp Asp Thr His Ser Arg Ile Glu Gln
    1760            1765            1770

Tyr Ala Thr Arg Leu Ala Gln Met Glu Arg Thr Asn Gly Ser Phe
    1775            1780            1785

Leu Thr Asp Ser Ser Ser Thr Thr Gly Ser Val Glu Asp Glu His
    1790            1795            1800

Ala Leu Ile Gln Gln Tyr Cys Gln Thr Leu Gly Gly Glu Ser Pro
    1805            1810            1815

Val Ser Gln Pro Gln Ser Pro Ala Gln Ile Leu Lys Ser Val Glu
    1820            1825            1830

Arg Glu Glu Arg Gly Glu Leu Glu Arg Ile Ile Ala Asp Leu Glu
    1835            1840            1845

Glu Glu Gln Arg Asn Leu Gln Val Glu Tyr Glu Gln Leu Lys Asp
    1850            1855            1860

Gln His Leu Arg Arg Gly Leu Pro Val Gly Ser Pro Pro Glu Ser
    1865            1870            1875

Ile Ile Ser Pro His His Thr Ser Glu Asp Ser Glu Leu Ile Ala
    1880            1885            1890

Glu Ala Lys Leu Leu Arg Gln His Lys Gly Arg Leu Glu Ala Arg
    1895            1900            1905

Met Gln Ile Leu Glu Asp His Asn Lys Gln Leu Glu Ser Gln Leu
    1910            1915            1920

His Arg Leu Arg Gln Leu Leu Glu Gln Pro Glu Ser Asp Ser Arg
    1925            1930            1935

Ile Asn Gly Val Ser Pro Trp Ala Ser Pro Gln His Ser Ala Leu
    1940            1945            1950

Ser Tyr Ser Leu Asp Pro Asp Ala Ser Gly Pro Gln Phe His Gln
    1955            1960            1965

Ala Ala Gly Glu Asp Leu Leu Ala Pro Pro His Asp Thr Ser Thr
    1970            1975            1980

Asp Leu Thr Glu Val Met Glu Gln Ile His Ser Thr Phe Pro Ser
    1985            1990            1995

Cys Cys Pro Asn Val Pro Ser Arg Pro Gln Ala Met
    2000            2005            2010
```

-continued

```
<210> SEQ ID NO 16
<211> LENGTH: 6327
<212> TYPE: DNA
<213> ORGANISM: Homo sapiens
<220> FEATURE:
<221> NAME/KEY: CDS
<222> LOCATION: (1)..(6327)
<220> FEATURE:
<221> NAME/KEY: misc_feature
<222> LOCATION: (1)..(117)
<223> OTHER INFORMATION: TAT and epitope tag coding sequence

<400> SEQUENCE: 16 atg gac tac aag gac gac gat gac aag ggc tac ggc cgc aag aaa cgc        48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac        96
Arg Gln Arg Arg Arg Gly Gly Ser Thr Met Ser Gly Tyr Pro Tyr Asp
                20                  25                  30 gtc cca gac tat gct ggc tcc atg gcc aag tat gga gaa cat gaa gcc       144
Val Pro Asp Tyr Ala Gly Ser Met Ala Lys Tyr Gly Glu His Glu Ala
            35                  40                  45 agt cct gac aat ggg cag aac gaa ttc agt gat atc att aag tcc aga       192
Ser Pro Asp Asn Gly Gln Asn Glu Phe Ser Asp Ile Ile Lys Ser Arg
        50                  55                  60 tct gat gaa cac aat gac gta cag aag aaa acc ttt acc aaa tgg ata       240
Ser Asp Glu His Asn Asp Val Gln Lys Lys Thr Phe Thr Lys Trp Ile
65                  70                  75                  80 aat gct cga ttt tca aag agt ggg aaa cca ccc atc aat gat atg ttc       288
Asn Ala Arg Phe Ser Lys Ser Gly Lys Pro Pro Ile Asn Asp Met Phe
                85                  90                  95 aca gac ctc aaa gat gga agg aag cta ttg gat ctt cta gaa ggc ctc       336
Thr Asp Leu Lys Asp Gly Arg Lys Leu Leu Asp Leu Leu Glu Gly Leu
                100                 105                 110 aca gga aca tca ctg cca aag gaa cgt ggt tcc aca agg gta cat gcc       384
Thr Gly Thr Ser Leu Pro Lys Glu Arg Gly Ser Thr Arg Val His Ala
            115                 120                 125 tta aat aac gtc aac aga gtg ctg cag gtt tta cat cag aac aat gtg       432
Leu Asn Asn Val Asn Arg Val Leu Gln Val Leu His Gln Asn Asn Val
        130                 135                 140 gaa tta gtg aat ata ggg gga act gac att gtg gat gga aat cac aaa       480
Glu Leu Val Asn Ile Gly Gly Thr Asp Ile Val Asp Gly Asn His Lys
145                 150                 155                 160 ctg act ttg ggg tta ctt tgg agc atc att ttg cac tgg cag gtg aaa       528
Leu Thr Leu Gly Leu Leu Trp Ser Ile Ile Leu His Trp Gln Val Lys
                165                 170                 175 gat gtc atg aag gat gtc atg tcg gac ctg cag cag acg aac agt gag       576
Asp Val Met Lys Asp Val Met Ser Asp Leu Gln Gln Thr Asn Ser Glu
                180                 185                 190 aag atc ctg ctc agc tgg gtg cgt cag acc acc agg ccc tac agc caa       624
Lys Ile Leu Leu Ser Trp Val Arg Gln Thr Thr Arg Pro Tyr Ser Gln
            195                 200                 205 gtc aac gtc ctc aac ttc acc acc agc tgg aca gat gga ctc gcc ttt       672
Val Asn Val Leu Asn Phe Thr Thr Ser Trp Thr Asp Gly Leu Ala Phe
        210                 215                 220 aat gct gtc ctc cac cga cat aaa cct gat ctc ttc agc tgg gat aaa       720
Asn Ala Val Leu His Arg His Lys Pro Asp Leu Phe Ser Trp Asp Lys
225                 230                 235                 240 gtt gtc aaa atg tca cca att gag aga ctt gaa cat gcc ttc agc aag       768
Val Val Lys Met Ser Pro Ile Glu Arg Leu Glu His Ala Phe Ser Lys
                245                 250                 255 gct caa act tat ttg gga att gaa aag ctg tta gat cct gaa gat gtt       816
Ala Gln Thr Tyr Leu Gly Ile Glu Lys Leu Leu Asp Pro Glu Asp Val
```

```
Ala Gln Thr Tyr Leu Gly Ile Glu Lys Leu Leu Asp Pro Glu Asp Val
            260                 265                 270 gcc gtt cag ctt cct gac aag aaa tcc ata att atg tat tta aca tct    864
Ala Val Gln Leu Pro Asp Lys Lys Ser Ile Ile Met Tyr Leu Thr Ser
        275                 280                 285 ttg ttt gag gtg cta cct cag caa gtc acc ata gac gcc atc cgt gag    912
Leu Phe Glu Val Leu Pro Gln Gln Val Thr Ile Asp Ala Ile Arg Glu
    290                 295                 300 gta gag aca ctc cca agg aaa tat aaa aaa gaa tgt gaa gaa gag gca    960
Val Glu Thr Leu Pro Arg Lys Tyr Lys Lys Glu Cys Glu Glu Glu Ala
305                 310                 315                 320 att aat ata cag agt aca gcg cct gag gag gag cat gag agt ccc cga   1008
Ile Asn Ile Gln Ser Thr Ala Pro Glu Glu Glu His Glu Ser Pro Arg
                325                 330                 335 gct gaa act ccc agc act gtc act gag gtt gac atg gat ctg gac agc   1056
Ala Glu Thr Pro Ser Thr Val Thr Glu Val Asp Met Asp Leu Asp Ser
            340                 345                 350 tat cag att gcg ttg gag gaa gtg ctg acc tgg ttg ctt tct gct gag   1104
Tyr Gln Ile Ala Leu Glu Glu Val Leu Thr Trp Leu Leu Ser Ala Glu
        355                 360                 365 gac act ttc cag gag cag gat gat att tct gat gat gtt gaa gaa gtc   1152
Asp Thr Phe Gln Glu Gln Asp Asp Ile Ser Asp Asp Val Glu Glu Val
    370                 375                 380 aaa gac cag ttt gca acc cat gaa gct ttt atg atg gaa ctg act gca   1200
Lys Asp Gln Phe Ala Thr His Glu Ala Phe Met Met Glu Leu Thr Ala
385                 390                 395                 400 cac cag agc agt gtg ggc agc gtc ctg cag gca ggc aac caa ctg ata   1248
His Gln Ser Ser Val Gly Ser Val Leu Gln Ala Gly Asn Gln Leu Ile
                405                 410                 415 aca caa gga act ctg tca gac gaa gaa gaa ttt gag att cag gaa cag   1296
Thr Gln Gly Thr Leu Ser Asp Glu Glu Glu Phe Glu Ile Gln Glu Gln
            420                 425                 430 atg acc ctg ctg aat gct aga tgg gag gct ctt agg gtg gag agt atg   1344
Met Thr Leu Leu Asn Ala Arg Trp Glu Ala Leu Arg Val Glu Ser Met
        435                 440                 445 gac aga cag tcc cgg ctg cac gat gtg ctg atg gaa ctg cag aag aag   1392
Asp Arg Gln Ser Arg Leu His Asp Val Leu Met Glu Leu Gln Lys Lys
    450                 455                 460 caa ctg cag cag ctc tcc gcc tgg tta aca ctc aca gag gag cgc att   1440
Gln Leu Gln Gln Leu Ser Ala Trp Leu Thr Leu Thr Glu Glu Arg Ile
465                 470                 475                 480 cag aag atg gaa act tgc ccc ctg gat gat gat gta aaa tct cta caa   1488
Gln Lys Met Glu Thr Cys Pro Leu Asp Asp Asp Val Lys Ser Leu Gln
                485                 490                 495 aag ctg cta gaa gaa cat aaa agt ttg caa agt gat ctt gag gct gaa   1536
Lys Leu Leu Glu Glu His Lys Ser Leu Gln Ser Asp Leu Glu Ala Glu
            500                 505                 510 cag gtg aaa gta aat tca cta act cac atg gtg gtc att gtt gat gaa   1584
Gln Val Lys Val Asn Ser Leu Thr His Met Val Val Ile Val Asp Glu
        515                 520                 525 aac agt ggt gag agt gct aca gct atc cta gaa gac cag tta cag aaa   1632
Asn Ser Gly Glu Ser Ala Thr Ala Ile Leu Glu Asp Gln Leu Gln Lys
    530                 535                 540 ctt ggt gag cgc tgg aca gca gta tgc cgt tgg act gaa gaa cgc tgg   1680
Leu Gly Glu Arg Trp Thr Ala Val Cys Arg Trp Thr Glu Glu Arg Trp
545                 550                 555                 560 aat agg tta caa gaa atc aat ata ttg tgg cag gaa tta ttg gaa gaa   1728
Asn Arg Leu Gln Glu Ile Asn Ile Leu Trp Gln Glu Leu Leu Glu Glu
                565                 570                 575
```

```
cag tgc ttg ttg aaa gct tgg tta acc gaa aaa gaa gag gct tta aat    1776
Gln Cys Leu Leu Lys Ala Trp Leu Thr Glu Lys Glu Glu Ala Leu Asn
        580                 585                 590 aaa gtc cag aca agc aac ttc aaa gac caa aag gaa cta agt gtc agt    1824
Lys Val Gln Thr Ser Asn Phe Lys Asp Gln Lys Glu Leu Ser Val Ser
    595                 600                 605 gtt cga cgt ctg gct att ttg aag gaa gac atg gaa atg aag cgt caa    1872
Val Arg Arg Leu Ala Ile Leu Lys Glu Asp Met Glu Met Lys Arg Gln
610                 615                 620 aca ttg gat cag ctg agt gag att ggc cag gat gtg gga caa tta ctt    1920
Thr Leu Asp Gln Leu Ser Glu Ile Gly Gln Asp Val Gly Gln Leu Leu
625                 630                 635                 640 gat aat tcc aag gca tct aag aag atc aac agt gac tca gag gaa ctg    1968
Asp Asn Ser Lys Ala Ser Lys Lys Ile Asn Ser Asp Ser Glu Glu Leu
                645                 650                 655 act caa aga tgg gat tct ttg gtt cag aga cta gaa gat tcc tcc aac    2016
Thr Gln Arg Trp Asp Ser Leu Val Gln Arg Leu Glu Asp Ser Ser Asn
            660                 665                 670 cag gtg act cag gct gta gca aag ctg ggg atg tct cag att cct cag    2064
Gln Val Thr Gln Ala Val Ala Lys Leu Gly Met Ser Gln Ile Pro Gln
        675                 680                 685 aag gac ctt ttg gag act gtt cgt gta aga gaa caa gca att aca aaa    2112
Lys Asp Leu Leu Glu Thr Val Arg Val Arg Glu Gln Ala Ile Thr Lys
    690                 695                 700 aaa tct aag cag gaa ctg cct cct cct cct ccc cca aag aag aga cag    2160
Lys Ser Lys Gln Glu Leu Pro Pro Pro Pro Pro Pro Lys Lys Arg Gln
705                 710                 715                 720 atc cat gtg gat att gaa gct aag aaa aag ttt gat gct ata agt gca    2208
Ile His Val Asp Ile Glu Ala Lys Lys Lys Phe Asp Ala Ile Ser Ala
                725                 730                 735 gag ctg ttg aac tgg att ttg aaa tgg aaa act gcc att cag acc aca    2256
Glu Leu Leu Asn Trp Ile Leu Lys Trp Lys Thr Ala Ile Gln Thr Thr
            740                 745                 750 gag ata aaa gag tat atg aag atg caa gac act tcc gaa atg aaa aag    2304
Glu Ile Lys Glu Tyr Met Lys Met Gln Asp Thr Ser Glu Met Lys Lys
        755                 760                 765 aag ttg aag gca tta gaa aaa gaa cag aga gaa aga atc ccc aga gca    2352
Lys Leu Lys Ala Leu Glu Lys Glu Gln Arg Glu Arg Ile Pro Arg Ala
    770                 775                 780 gat gaa tta aac caa act gga caa atc ctt gtg gag caa atg gga aaa    2400
Asp Glu Leu Asn Gln Thr Gly Gln Ile Leu Val Glu Gln Met Gly Lys
785                 790                 795                 800 gaa ggc ctt cct act gaa gaa ata aaa aat gtt ctg gag aag gtt tca    2448
Glu Gly Leu Pro Thr Glu Glu Ile Lys Asn Val Leu Glu Lys Val Ser
                805                 810                 815 tca gaa tgg aag aat gta tct caa cat ttg gaa gat cta gaa aga aag    2496
Ser Glu Trp Lys Asn Val Ser Gln His Leu Glu Asp Leu Glu Arg Lys
            820                 825                 830 att cag cta cag gaa gat ata aat gct tat ttc aag cag ctt gat gag    2544
Ile Gln Leu Gln Glu Asp Ile Asn Ala Tyr Phe Lys Gln Leu Asp Glu
        835                 840                 845 ctt gaa aag gtc atc aag aca aag gag gag tgg gta aaa cac act tcc    2592
Leu Glu Lys Val Ile Lys Thr Lys Glu Glu Trp Val Lys His Thr Ser
    850                 855                 860 att tct gaa tct tcc cgg cag tcc ttg cca agc ttg aag gat tcc tgt    2640
Ile Ser Glu Ser Ser Arg Gln Ser Leu Pro Ser Leu Lys Asp Ser Cys
865                 870                 875                 880 cag cgg gaa ttg aca aat ctt ctt ggc ctt cac ccc aaa att gaa atg    2688
Gln Arg Glu Leu Thr Asn Leu Leu Gly Leu His Pro Lys Ile Glu Met
                885                 890                 895
```

-continued

| | |
|---|---|
| gct cgt gca agc tgc tcg gcc ctg atg tct cag cct tct gcc cca gat<br>Ala Arg Ala Ser Cys Ser Ala Leu Met Ser Gln Pro Ser Ala Pro Asp<br>            900                      905                910 | 2736 |
| ttt gtc cag cgg ggc ttc gat agc ttt ctg ggc cgc tac caa gct gta<br>Phe Val Gln Arg Gly Phe Asp Ser Phe Leu Gly Arg Tyr Gln Ala Val<br>       915                      920                925 | 2784 |
| caa gag gct gta gag gat cgt caa caa cat cta gag aat gaa ctg aag<br>Gln Glu Ala Val Glu Asp Arg Gln Gln His Leu Glu Asn Glu Leu Lys<br>930                      935                940 | 2832 |
| ggc caa cct gga cat gca tat ctg gaa aca ttg aaa aca ctg aaa gat<br>Gly Gln Pro Gly His Ala Tyr Leu Glu Thr Leu Lys Thr Leu Lys Asp<br>945                950                955              960 | 2880 |
| gtg cta aat gat tca gaa aat aag gcc cag gtg tct ctg aat gtc ctt<br>Val Leu Asn Asp Ser Glu Asn Lys Ala Gln Val Ser Leu Asn Val Leu<br>                  965                970              975 | 2928 |
| aat gat ctt gcc aag gtg gag aag gcc ctg caa gaa aaa aag acc ctt<br>Asn Asp Leu Ala Lys Val Glu Lys Ala Leu Gln Glu Lys Lys Thr Leu<br>       980                    985                990 | 2976 |
| gat gaa atc ctt gag aat cag aaa cct gca tta cat aaa ctt gca gaa<br>Asp Glu Ile Leu Glu Asn Gln Lys Pro Ala Leu His Lys Leu Ala Glu<br>         995                1000             1005 | 3024 |
| gaa aca aag gct ctg gag aaa aat gtt cat cct gat gta gaa aaa<br>Glu Thr Lys Ala Leu Glu Lys Asn Val His Pro Asp Val Glu Lys<br>      1010              1015             1020 | 3069 |
| tta tat aag caa gaa ttt gat gat gtg caa gga aag tgg aac aag<br>Leu Tyr Lys Gln Glu Phe Asp Asp Val Gln Gly Lys Trp Asn Lys<br>      1025              1030             1035 | 3114 |
| cta aag gtc ttg gtt tcc aaa gat cta cat ttg ctt gag gaa att<br>Leu Lys Val Leu Val Ser Lys Asp Leu His Leu Leu Glu Glu Ile<br>      1040              1045             1050 | 3159 |
| gct ctc aca ctc aga gct ttt gag gcc gat tca aca gtc att gag<br>Ala Leu Thr Leu Arg Ala Phe Glu Ala Asp Ser Thr Val Ile Glu<br>      1055              1060             1065 | 3204 |
| aag tgg atg gat ggc gtg aaa gac ttc tta atg aaa cag cag gct<br>Lys Trp Met Asp Gly Val Lys Asp Phe Leu Met Lys Gln Gln Ala<br>      1070              1075             1080 | 3249 |
| gcc caa gga gac gac gca ggt cta cag agg cag tta gac cag tgc<br>Ala Gln Gly Asp Asp Ala Gly Leu Gln Arg Gln Leu Asp Gln Cys<br>      1085              1090             1095 | 3294 |
| tct gca ttt gtt aat gaa ata gaa aca att gaa tca tct ctg aaa<br>Ser Ala Phe Val Asn Glu Ile Glu Thr Ile Glu Ser Ser Leu Lys<br>      1100              1105             1110 | 3339 |
| aac atg aag gaa ata gag act aat ctt cga agt ggt cca gtt gct<br>Asn Met Lys Glu Ile Glu Thr Asn Leu Arg Ser Gly Pro Val Ala<br>      1115              1120             1125 | 3384 |
| gga ata aaa act tgg gtg cag aca aga cta ggt gac tac caa act<br>Gly Ile Lys Thr Trp Val Gln Thr Arg Leu Gly Asp Tyr Gln Thr<br>      1130              1135             1140 | 3429 |
| caa ctg gag aaa ctt agc aag gag atc gct act caa aaa agt agg<br>Gln Leu Glu Lys Leu Ser Lys Glu Ile Ala Thr Gln Lys Ser Arg<br>      1145              1150             1155 | 3474 |
| ttg tct gaa agt caa gaa aaa gct gcg aac ctg aag aaa gac ttg<br>Leu Ser Glu Ser Gln Glu Lys Ala Ala Asn Leu Lys Lys Asp Leu<br>      1160              1165             1170 | 3519 |
| gca gag atg cag gaa tgg atg acc cag gcc gag gaa gaa tat ttg<br>Ala Glu Met Gln Glu Trp Met Thr Gln Ala Glu Glu Glu Tyr Leu<br>      1175              1180             1185 | 3564 |
| gag cgg gat ttt gag tac aag tca cca gaa gag ctt gag agt gct<br>Glu Arg Asp Phe Glu Tyr Lys Ser Pro Glu Glu Leu Glu Ser Ala | 3609 |

```
                                                                    -continued
         1190              1195              1200
gtg gaa gag atg aag agg gca aaa gag gat gtg ttg cag aag gag         3654
Val Glu Glu Met Lys Arg Ala Lys Glu Asp Val Leu Gln Lys Glu
    1205              1210              1215 gtg aga gtg aag att ctc aag gac aac atc aag tta tta gct gcc         3699
Val Arg Val Lys Ile Leu Lys Asp Asn Ile Lys Leu Leu Ala Ala
    1220              1225              1230 aag gtg ccc tct ggt ggc cag gag ttg acg tct gag ctg aat gtt         3744
Lys Val Pro Ser Gly Gly Gln Glu Leu Thr Ser Glu Leu Asn Val
    1235              1240              1245 gtg ctg gag aat tac caa ctt ctt tgt aat aga att cga gga aag         3789
Val Leu Glu Asn Tyr Gln Leu Leu Cys Asn Arg Ile Arg Gly Lys
    1250              1255              1260 tgc cac acg cta gag gag gtc tgg tct tgt tgg att gaa ctg ctt         3834
Cys His Thr Leu Glu Glu Val Trp Ser Cys Trp Ile Glu Leu Leu
    1265              1270              1275 cac tat ttg gat ctt gaa act acc tgg tta aac act ttg gaa gag         3879
His Tyr Leu Asp Leu Glu Thr Thr Trp Leu Asn Thr Leu Glu Glu
    1280              1285              1290 cgg atg aag agc aca gag gtc ctg cct gag aag acg gat gct gtc         3924
Arg Met Lys Ser Thr Glu Val Leu Pro Glu Lys Thr Asp Ala Val
    1295              1300              1305 aac gaa gcc ctg gag tct ctg gaa tct gtt ctg cgc cac ccg gca         3969
Asn Glu Ala Leu Glu Ser Leu Glu Ser Val Leu Arg His Pro Ala
    1310              1315              1320 gat aat cgc acc cag att cga gag ctt ggc cag act ctg att gat         4014
Asp Asn Arg Thr Gln Ile Arg Glu Leu Gly Gln Thr Leu Ile Asp
    1325              1330              1335 ggg ggg atc ctg gat gat ata atc agt gag aaa ctg gag gct ttc         4059
Gly Gly Ile Leu Asp Asp Ile Ile Ser Glu Lys Leu Glu Ala Phe
    1340              1345              1350 aac agc cga tat gaa gat cta agt cac ctg gca gag agc aag cag         4104
Asn Ser Arg Tyr Glu Asp Leu Ser His Leu Ala Glu Ser Lys Gln
    1355              1360              1365 att tct ttg gaa aag caa ctc cag gtg ctg cgg gaa act gac cag         4149
Ile Ser Leu Glu Lys Gln Leu Gln Val Leu Arg Glu Thr Asp Gln
    1370              1375              1380 atg ctt caa gtc ttg caa gag agc ttg ggg gag ctg gac aaa cag         4194
Met Leu Gln Val Leu Gln Glu Ser Leu Gly Glu Leu Asp Lys Gln
    1385              1390              1395 ctc acc aca tac ctg act gac agg ata gat gct ttc caa gtt cca         4239
Leu Thr Thr Tyr Leu Thr Asp Arg Ile Asp Ala Phe Gln Val Pro
    1400              1405              1410 cag gaa gct cag aaa atc caa gca gag atc tca gcc cat gag cta         4284
Gln Glu Ala Gln Lys Ile Gln Ala Glu Ile Ser Ala His Glu Leu
    1415              1420              1425 acc cta gag gag ttg aga aga aat atg cgt tct cag ccc ctg acc         4329
Thr Leu Glu Glu Leu Arg Arg Asn Met Arg Ser Gln Pro Leu Thr
    1430              1435              1440 tcc cca gag agt agg act gcc aga gga gga agt cag atg gat gtg         4374
Ser Pro Glu Ser Arg Thr Ala Arg Gly Gly Ser Gln Met Asp Val
    1445              1450              1455 cta cag agg aaa ctc cga gag gtg tcc aca aag ttc cag ctt gcc         4419
Leu Gln Arg Lys Leu Arg Glu Val Ser Thr Lys Phe Gln Leu Ala
    1460              1465              1470 cac aga gat ttt gga cca tcc tct cag cat ttt ctc tct acg tca         4464
His Arg Asp Phe Gly Pro Ser Ser Gln His Phe Leu Ser Thr Ser
    1475              1480              1485 gtc cag ctg ccg tgg caa aga tcc att tca cat aat aaa gtg ccc         4509
```

```
                                      -continued
Val Gln Leu Pro Trp Gln Arg Ser Ile Ser His Asn Lys Val Pro
    1490            1495            1500 tat tac atc aac cat caa aca cag acc acc tgt tgg gac cat cct      4554
Tyr Tyr Ile Asn His Gln Thr Gln Thr Thr Cys Trp Asp His Pro
1505            1510            1515 aaa atg acc gaa ctc ttt caa tcc ctt gct gac ctg aat aat gta      4599
Lys Met Thr Glu Leu Phe Gln Ser Leu Ala Asp Leu Asn Asn Val
    1520            1525            1530 cgt ttt tct gcc tac cgt aca gca atc aaa atc cga aga cta caa      4644
Arg Phe Ser Ala Tyr Arg Thr Ala Ile Lys Ile Arg Arg Leu Gln
    1535            1540            1545 aaa gca cta tgt ttg gat ctc tta gag ttg agt aca aca aat gaa      4689
Lys Ala Leu Cys Leu Asp Leu Leu Glu Leu Ser Thr Thr Asn Glu
1550            1555            1560 att ttc aaa cag cac aag ttg aac caa aat gac cag ctc ctc agt      4734
Ile Phe Lys Gln His Lys Leu Asn Gln Asn Asp Gln Leu Leu Ser
    1565            1570            1575 gtt cca gat gtc atc aac tgt ctg aca aca act tat gat gga ctt      4779
Val Pro Asp Val Ile Asn Cys Leu Thr Thr Thr Tyr Asp Gly Leu
    1580            1585            1590 gag caa atg cat aag gac ctg gtc aac gtt cca ctc tgt gtt gat      4824
Glu Gln Met His Lys Asp Leu Val Asn Val Pro Leu Cys Val Asp
1595            1600            1605 atg tgt ctc aat tgg ttg ctc aat gtc tat gac acg ggt cga act      4869
Met Cys Leu Asn Trp Leu Leu Asn Val Tyr Asp Thr Gly Arg Thr
    1610            1615            1620 gga aaa att aga gtg cag agt ctg aag att gga tta atg tct ctc      4914
Gly Lys Ile Arg Val Gln Ser Leu Lys Ile Gly Leu Met Ser Leu
    1625            1630            1635 tcc aaa ggt ctc ttg gaa gaa aaa tac aga tat ctc ttt aag gaa      4959
Ser Lys Gly Leu Leu Glu Glu Lys Tyr Arg Tyr Leu Phe Lys Glu
1640            1645            1650 gtt gca ggg cca aca gaa atg tgt gac cag agg cag ctg ggc ctg      5004
Val Ala Gly Pro Thr Glu Met Cys Asp Gln Arg Gln Leu Gly Leu
    1655            1660            1665 tta ctt cat gat gcc atc cag atc ccc cgg cag cta ggt gaa gta      5049
Leu Leu His Asp Ala Ile Gln Ile Pro Arg Gln Leu Gly Glu Val
    1670            1675            1680 gca gct ttt gga ggc agt aat att gag cct agt gtt cgc agc tgc      5094
Ala Ala Phe Gly Gly Ser Asn Ile Glu Pro Ser Val Arg Ser Cys
1685            1690            1695 ttc caa cag aat aac aat aaa cca gaa ata agt gtg aaa gag ttt      5139
Phe Gln Gln Asn Asn Asn Lys Pro Glu Ile Ser Val Lys Glu Phe
    1700            1705            1710 ata gat tgg atg cat ttg gaa cca cag tcc atg gtt tgg ctc cca      5184
Ile Asp Trp Met His Leu Glu Pro Gln Ser Met Val Trp Leu Pro
    1715            1720            1725 gtt tta cat cga gtg gca gca gcg gag act gca aaa cat cag gcc      5229
Val Leu His Arg Val Ala Ala Ala Glu Thr Ala Lys His Gln Ala
1730            1735            1740 aaa tgc aac atc tgt aaa gaa tgt cca att gtc ggg ttc agg tat      5274
Lys Cys Asn Ile Cys Lys Glu Cys Pro Ile Val Gly Phe Arg Tyr
    1745            1750            1755 aga agc ctt aag cat ttt aac tat gat gtc tgc cag agt tgt ttc      5319
Arg Ser Leu Lys His Phe Asn Tyr Asp Val Cys Gln Ser Cys Phe
    1760            1765            1770 ttt tcg ggt cga aca gca aaa ggt cac aaa tta cat tac cca atg      5364
Phe Ser Gly Arg Thr Ala Lys Gly His Lys Leu His Tyr Pro Met
1775            1780            1785
```

```
gtg gaa tat tgt ata cct aca aca tct ggg gaa gat gta cga gac       5409
Val Glu Tyr Cys Ile Pro Thr Thr Ser Gly Glu Asp Val Arg Asp
    1790                1795                1800 ttc aca aag gta ctt aag aac aag ttc agg tcg aag aag tac ttt       5454
Phe Thr Lys Val Leu Lys Asn Lys Phe Arg Ser Lys Lys Tyr Phe
1805                1810                1815 gcc aaa cac cct cga ctt ggt tac ctg cct gtc cag aca gtt ctt       5499
Ala Lys His Pro Arg Leu Gly Tyr Leu Pro Val Gln Thr Val Leu
    1820                1825                1830 gaa ggt gac aac tta gag act cct atc aca ctc atc agt atg tgg       5544
Glu Gly Asp Asn Leu Glu Thr Pro Ile Thr Leu Ile Ser Met Trp
1835                1840                1845 cca gag cac tat gac ccc tca caa tct cct caa ctg ttt cat gat       5589
Pro Glu His Tyr Asp Pro Ser Gln Ser Pro Gln Leu Phe His Asp
    1850                1855                1860 gac acc cat tca aga ata gaa caa tat gcc aca cga ctg gcc cag       5634
Asp Thr His Ser Arg Ile Glu Gln Tyr Ala Thr Arg Leu Ala Gln
1865                1870                1875 atg gaa agg act aat ggg tct ttt ctc act gat agc agc tcc acc       5679
Met Glu Arg Thr Asn Gly Ser Phe Leu Thr Asp Ser Ser Ser Thr
    1880                1885                1890 aca gga agt gtg gaa gac gag cac gcc ctc atc cag cag tat tgc       5724
Thr Gly Ser Val Glu Asp Glu His Ala Leu Ile Gln Gln Tyr Cys
1895                1900                1905 caa aca ctc gga gga gag tcc cca gtg agc cag ccg cag agc cca       5769
Gln Thr Leu Gly Gly Glu Ser Pro Val Ser Gln Pro Gln Ser Pro
    1910                1915                1920 gct cag atc ctg aag tca gta gag agg gaa gaa cgt gga gaa ctg       5814
Ala Gln Ile Leu Lys Ser Val Glu Arg Glu Glu Arg Gly Glu Leu
1925                1930                1935 gag agg atc att gct gac ctg gag gaa gaa caa aga aat cta cag       5859
Glu Arg Ile Ile Ala Asp Leu Glu Glu Glu Gln Arg Asn Leu Gln
    1940                1945                1950 gtg gag tat gag cag ctg aag gac cag cac ctc cga agg ggg ctc       5904
Val Glu Tyr Glu Gln Leu Lys Asp Gln His Leu Arg Arg Gly Leu
1955                1960                1965 cct gtc ggt tca ccg cca gag tcg att ata tct ccc cat cac acg       5949
Pro Val Gly Ser Pro Pro Glu Ser Ile Ile Ser Pro His His Thr
    1970                1975                1980 tct gag gat tca gaa ctt ata gca gaa gca aaa ctc ctc agg cag       5994
Ser Glu Asp Ser Glu Leu Ile Ala Glu Ala Lys Leu Leu Arg Gln
1985                1990                1995 cac aaa ggt cgg ctg gag gct agg atg cag att tta gaa gat cac       6039
His Lys Gly Arg Leu Glu Ala Arg Met Gln Ile Leu Glu Asp His
    2000                2005                2010 aat aaa cag ctg gag tct cag ctc cac cgc ctc cga cag ctg ctg       6084
Asn Lys Gln Leu Glu Ser Gln Leu His Arg Leu Arg Gln Leu Leu
2015                2020                2025 gag cag cct gaa tct gat tcc cga atc aat ggt gtt tcc cca tgg       6129
Glu Gln Pro Glu Ser Asp Ser Arg Ile Asn Gly Val Ser Pro Trp
    2030                2035                2040 gct tct cct cag cat tct gca ctg agc tac tcg ctt gat cca gat       6174
Ala Ser Pro Gln His Ser Ala Leu Ser Tyr Ser Leu Asp Pro Asp
2045                2050                2055 gcc tcc ggc cca cag ttc cac cag gca gcg gga gag gac ctg ctg       6219
Ala Ser Gly Pro Gln Phe His Gln Ala Ala Gly Glu Asp Leu Leu
    2060                2065                2070 gcc cca ccg cac gac acc agc acg gat ctc acg gag gtc atg gag       6264
Ala Pro Pro His Asp Thr Ser Thr Asp Leu Thr Glu Val Met Glu
2075                2080                2085
```

```
cag att cac agc acg ttt cca tct tgc tgc cca aat gtt ccc agc     6309
Gln Ile His Ser Thr Phe Pro Ser Cys Cys Pro Asn Val Pro Ser
    2090                2095                2100 agg cca cag gca atg tga                                          6327
Arg Pro Gln Ala Met
    2105
```

<210> SEQ ID NO 17
<211> LENGTH: 2108
<212> TYPE: PRT
<213> ORGANISM: Homo sapiens

<400> SEQUENCE: 17

```
Met Asp Tyr Lys Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Glu His Glu Ala
                35                  40                  45

Ser Pro Asp Asn Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Asn Asp Met Phe
                85                  90                  95

Thr Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Glu Leu Val Asn Ile Gly Gly Thr Asp Ile Val Asp Gly Asn His Lys
145                 150                 155                 160

Leu Thr Leu Gly Leu Leu Trp Ser Ile Ile Leu His Trp Gln Val Lys
                165                 170                 175

Asp Val Met Lys Asp Val Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Ser Trp Thr Asp Gly Leu Ala Phe
    210                 215                 220

Asn Ala Val Leu His Arg His Lys Pro Asp Leu Phe Ser Trp Asp Lys
225                 230                 235                 240

Val Val Lys Met Ser Pro Ile Glu Arg Leu Glu His Ala Phe Ser Lys
                245                 250                 255

Ala Gln Thr Tyr Leu Gly Ile Glu Lys Leu Leu Asp Pro Glu Asp Val
            260                 265                 270

Ala Val Gln Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Ala
305                 310                 315                 320

Ile Asn Ile Gln Ser Thr Ala Pro Glu Glu His Glu Ser Pro Arg
                325                 330                 335
```

-continued

```
Ala Glu Thr Pro Ser Thr Val Thr Glu Val Asp Met Asp Leu Asp Ser
            340                 345                 350
Tyr Gln Ile Ala Leu Glu Glu Val Leu Thr Trp Leu Leu Ser Ala Glu
        355                 360                 365
Asp Thr Phe Gln Glu Gln Asp Asp Ile Ser Asp Asp Val Glu Glu Val
    370                 375                 380
Lys Asp Gln Phe Ala Thr His Glu Ala Phe Met Met Glu Leu Thr Ala
385                 390                 395                 400
His Gln Ser Ser Val Gly Ser Val Leu Gln Ala Gly Asn Gln Leu Ile
                405                 410                 415
Thr Gln Gly Thr Leu Ser Asp Glu Glu Glu Phe Glu Ile Gln Glu Gln
            420                 425                 430
Met Thr Leu Leu Asn Ala Arg Trp Glu Ala Leu Arg Val Glu Ser Met
        435                 440                 445
Asp Arg Gln Ser Arg Leu His Asp Val Leu Met Glu Leu Gln Lys Lys
    450                 455                 460
Gln Leu Gln Gln Leu Ser Ala Trp Leu Thr Leu Thr Glu Glu Arg Ile
465                 470                 475                 480
Gln Lys Met Glu Thr Cys Pro Leu Asp Asp Asp Val Lys Ser Leu Gln
                485                 490                 495
Lys Leu Leu Glu Glu His Lys Ser Leu Gln Ser Asp Leu Glu Ala Glu
            500                 505                 510
Gln Val Lys Val Asn Ser Leu Thr His Met Val Val Ile Val Asp Glu
        515                 520                 525
Asn Ser Gly Glu Ser Ala Thr Ala Ile Leu Glu Asp Gln Leu Gln Lys
    530                 535                 540
Leu Gly Glu Arg Trp Thr Ala Val Cys Arg Trp Thr Glu Glu Arg Trp
545                 550                 555                 560
Asn Arg Leu Gln Glu Ile Asn Ile Leu Trp Gln Glu Leu Leu Glu Glu
                565                 570                 575
Gln Cys Leu Leu Lys Ala Trp Leu Thr Glu Lys Glu Glu Ala Leu Asn
            580                 585                 590
Lys Val Gln Thr Ser Asn Phe Lys Asp Gln Lys Glu Leu Ser Val Ser
        595                 600                 605
Val Arg Arg Leu Ala Ile Leu Lys Glu Asp Met Glu Met Lys Arg Gln
    610                 615                 620
Thr Leu Asp Gln Leu Ser Glu Ile Gly Gln Asp Val Gly Gln Leu Leu
625                 630                 635                 640
Asp Asn Ser Lys Ala Ser Lys Lys Ile Asn Ser Asp Ser Glu Glu Leu
                645                 650                 655
Thr Gln Arg Trp Asp Ser Leu Val Gln Arg Leu Glu Asp Ser Ser Asn
            660                 665                 670
Gln Val Thr Gln Ala Val Ala Lys Leu Gly Met Ser Gln Ile Pro Gln
        675                 680                 685
Lys Asp Leu Leu Glu Thr Val Arg Val Arg Glu Gln Ala Ile Thr Lys
    690                 695                 700
Lys Ser Lys Gln Glu Leu Pro Pro Pro Pro Pro Lys Lys Arg Gln
705                 710                 715                 720
Ile His Val Asp Ile Glu Ala Lys Lys Phe Asp Ala Ile Ser Ala
                725                 730                 735
Glu Leu Leu Asn Trp Ile Leu Lys Trp Lys Thr Ala Ile Gln Thr Thr
            740                 745                 750
```

```
Glu Ile Lys Glu Tyr Met Lys Met Gln Asp Thr Ser Glu Met Lys Lys
        755                 760                 765

Lys Leu Lys Ala Leu Glu Lys Glu Gln Arg Glu Arg Ile Pro Arg Ala
        770                 775                 780

Asp Glu Leu Asn Gln Thr Gly Gln Ile Leu Val Glu Gln Met Gly Lys
785                 790                 795                 800

Glu Gly Leu Pro Thr Glu Glu Ile Lys Asn Val Leu Glu Lys Val Ser
                805                 810                 815

Ser Glu Trp Lys Asn Val Ser Gln His Leu Glu Asp Leu Glu Arg Lys
                820                 825                 830

Ile Gln Leu Gln Glu Asp Ile Asn Ala Tyr Phe Lys Gln Leu Asp Glu
            835                 840                 845

Leu Glu Lys Val Ile Lys Thr Lys Glu Glu Trp Val Lys His Thr Ser
        850                 855                 860

Ile Ser Glu Ser Ser Arg Gln Ser Leu Pro Ser Leu Lys Asp Ser Cys
865                 870                 875                 880

Gln Arg Glu Leu Thr Asn Leu Gly Leu His Pro Lys Ile Glu Met
                885                 890                 895

Ala Arg Ala Ser Cys Ser Ala Leu Met Ser Gln Pro Ser Ala Pro Asp
                900                 905                 910

Phe Val Gln Arg Gly Phe Asp Ser Phe Leu Gly Arg Tyr Gln Ala Val
        915                 920                 925

Gln Glu Ala Val Glu Asp Arg Gln Gln His Leu Glu Asn Glu Leu Lys
        930                 935                 940

Gly Gln Pro Gly His Ala Tyr Leu Glu Thr Leu Lys Thr Leu Lys Asp
945                 950                 955                 960

Val Leu Asn Asp Ser Glu Asn Lys Ala Gln Val Ser Leu Asn Val Leu
                965                 970                 975

Asn Asp Leu Ala Lys Val Glu Lys Ala Leu Gln Glu Lys Lys Thr Leu
                980                 985                 990

Asp Glu Ile Leu Glu Asn Gln Lys Pro Ala Leu His Lys Leu Ala Glu
            995                 1000                1005

Glu Thr Lys Ala Leu Glu Lys Asn Val His Pro Asp Val Glu Lys
        1010                1015                1020

Leu Tyr Lys Gln Glu Phe Asp Asp Val Gln Gly Lys Trp Asn Lys
        1025                1030                1035

Leu Lys Val Leu Val Ser Lys Asp Leu His Leu Leu Glu Glu Ile
        1040                1045                1050

Ala Leu Thr Leu Arg Ala Phe Glu Ala Asp Ser Thr Val Ile Glu
        1055                1060                1065

Lys Trp Met Asp Gly Val Lys Asp Phe Leu Met Lys Gln Gln Ala
        1070                1075                1080

Ala Gln Gly Asp Asp Ala Gly Leu Gln Arg Gln Leu Asp Gln Cys
        1085                1090                1095

Ser Ala Phe Val Asn Glu Ile Glu Thr Ile Glu Ser Ser Leu Lys
        1100                1105                1110

Asn Met Lys Glu Ile Glu Thr Asn Leu Arg Ser Gly Pro Val Ala
        1115                1120                1125

Gly Ile Lys Thr Trp Val Gln Thr Arg Leu Gly Asp Tyr Gln Thr
        1130                1135                1140

Gln Leu Glu Lys Leu Ser Lys Glu Ile Ala Thr Gln Lys Ser Arg
        1145                1150                1155

Leu Ser Glu Ser Gln Glu Lys Ala Ala Asn Leu Lys Lys Asp Leu
```

```
                1160              1165              1170
Ala Glu Met Gln Glu Trp Met Thr Gln Ala Glu Glu Tyr Leu
    1175              1180              1185

Glu Arg Asp Phe Glu Tyr Lys Ser Pro Glu Glu Leu Glu Ser Ala
    1190              1195              1200

Val Glu Glu Met Lys Arg Ala Lys Glu Asp Val Leu Gln Lys Glu
    1205              1210              1215

Val Arg Val Lys Ile Leu Lys Asp Asn Ile Lys Leu Leu Ala Ala
    1220              1225              1230

Lys Val Pro Ser Gly Gly Gln Glu Leu Thr Ser Glu Leu Asn Val
    1235              1240              1245

Val Leu Glu Asn Tyr Gln Leu Leu Cys Asn Arg Ile Arg Gly Lys
    1250              1255              1260

Cys His Thr Leu Glu Glu Val Trp Ser Cys Trp Ile Glu Leu Leu
    1265              1270              1275

His Tyr Leu Asp Leu Glu Thr Thr Trp Leu Asn Thr Leu Glu Glu
    1280              1285              1290

Arg Met Lys Ser Thr Glu Val Leu Pro Glu Lys Thr Asp Ala Val
    1295              1300              1305

Asn Glu Ala Leu Glu Ser Leu Glu Ser Val Leu Arg His Pro Ala
    1310              1315              1320

Asp Asn Arg Thr Gln Ile Arg Glu Leu Gly Gln Thr Leu Ile Asp
    1325              1330              1335

Gly Gly Ile Leu Asp Asp Ile Ile Ser Glu Lys Leu Glu Ala Phe
    1340              1345              1350

Asn Ser Arg Tyr Glu Asp Leu Ser His Leu Ala Glu Ser Lys Gln
    1355              1360              1365

Ile Ser Leu Glu Lys Gln Leu Gln Val Leu Arg Glu Thr Asp Gln
    1370              1375              1380

Met Leu Gln Val Leu Gln Glu Ser Leu Gly Glu Leu Asp Lys Gln
    1385              1390              1395

Leu Thr Thr Tyr Leu Thr Asp Arg Ile Asp Ala Phe Gln Val Pro
    1400              1405              1410

Gln Glu Ala Gln Lys Ile Gln Ala Glu Ile Ser Ala His Glu Leu
    1415              1420              1425

Thr Leu Glu Glu Leu Arg Arg Asn Met Arg Ser Gln Pro Leu Thr
    1430              1435              1440

Ser Pro Glu Ser Arg Thr Ala Arg Gly Gly Ser Gln Met Asp Val
    1445              1450              1455

Leu Gln Arg Lys Leu Arg Glu Val Ser Thr Lys Phe Gln Leu Ala
    1460              1465              1470

His Arg Asp Phe Gly Pro Ser Ser Gln His Phe Leu Ser Thr Ser
    1475              1480              1485

Val Gln Leu Pro Trp Gln Arg Ser Ile Ser His Asn Lys Val Pro
    1490              1495              1500

Tyr Tyr Ile Asn His Gln Thr Gln Thr Thr Cys Trp Asp His Pro
    1505              1510              1515

Lys Met Thr Glu Leu Phe Gln Ser Leu Ala Asp Leu Asn Asn Val
    1520              1525              1530

Arg Phe Ser Ala Tyr Arg Thr Ala Ile Lys Ile Arg Arg Leu Gln
    1535              1540              1545

Lys Ala Leu Cys Leu Asp Leu Leu Glu Leu Ser Thr Thr Asn Glu
    1550              1555              1560
```

-continued

```
Ile Phe Lys Gln His Lys Leu Asn Gln Asn Asp Gln  Leu Leu Ser
    1565                1570                1575

Val Pro Asp Val Ile Asn Cys Leu Thr Thr Thr Tyr  Asp Gly Leu
    1580                1585                1590

Glu Gln Met His Lys Asp Leu Val Asn Val Pro Leu  Cys Val Asp
    1595                1600                1605

Met Cys Leu Asn Trp Leu Leu Asn Val Tyr Asp Thr  Gly Arg Thr
    1610                1615                1620

Gly Lys Ile Arg Val Gln Ser Leu Lys Ile Gly Leu  Met Ser Leu
    1625                1630                1635

Ser Lys Gly Leu Leu Glu Glu Lys Tyr Arg Tyr Leu  Phe Lys Glu
    1640                1645                1650

Val Ala Gly Pro Thr Glu Met Cys Asp Gln Arg Gln  Leu Gly Leu
    1655                1660                1665

Leu Leu His Asp Ala Ile Gln Ile Pro Arg Gln Leu  Gly Glu Val
    1670                1675                1680

Ala Ala Phe Gly Gly Ser Asn Ile Glu Pro Ser Val  Arg Ser Cys
    1685                1690                1695

Phe Gln Gln Asn Asn Asn Lys Pro Glu Ile Ser Val  Lys Glu Phe
    1700                1705                1710

Ile Asp Trp Met His Leu Glu Pro Gln Ser Met Val  Trp Leu Pro
    1715                1720                1725

Val Leu His Arg Val Ala Ala Ala Glu Thr Ala Lys  His Gln Ala
    1730                1735                1740

Lys Cys Asn Ile Cys Lys Glu Cys Pro Ile Val Gly  Phe Arg Tyr
    1745                1750                1755

Arg Ser Leu Lys His Phe Asn Tyr Asp Val Cys Gln  Ser Cys Phe
    1760                1765                1770

Phe Ser Gly Arg Thr Ala Lys Gly His Lys Leu His  Tyr Pro Met
    1775                1780                1785

Val Glu Tyr Cys Ile Pro Thr Thr Ser Gly Glu Asp  Val Arg Asp
    1790                1795                1800

Phe Thr Lys Val Leu Lys Asn Lys Phe Arg Ser Lys  Lys Tyr Phe
    1805                1810                1815

Ala Lys His Pro Arg Leu Gly Tyr Leu Pro Val Gln  Thr Val Leu
    1820                1825                1830

Glu Gly Asp Asn Leu Glu Thr Pro Ile Thr Leu Ile  Ser Met Trp
    1835                1840                1845

Pro Glu His Tyr Asp Pro Ser Gln Ser Pro Gln Leu  Phe His Asp
    1850                1855                1860

Asp Thr His Ser Arg Ile Glu Gln Tyr Ala Thr Arg  Leu Ala Gln
    1865                1870                1875

Met Glu Arg Thr Asn Gly Ser Phe Leu Thr Asp Ser  Ser Ser Thr
    1880                1885                1890

Thr Gly Ser Val Glu Asp Glu His Ala Leu Ile Gln  Gln Tyr Cys
    1895                1900                1905

Gln Thr Leu Gly Gly Glu Ser Pro Val Ser Gln Pro  Gln Ser Pro
    1910                1915                1920

Ala Gln Ile Leu Lys Ser Val Glu Arg Glu Glu Arg  Gly Glu Leu
    1925                1930                1935

Glu Arg Ile Ile Ala Asp Leu Glu Glu Glu Gln Arg  Asn Leu Gln
    1940                1945                1950
```

```
Val Glu Tyr Glu Gln Leu Lys Asp Gln His Leu Arg Arg Gly Leu
    1955                1960                1965

Pro Val Gly Ser Pro Pro Glu Ser Ile Ile Ser Pro His His Thr
    1970                1975                1980

Ser Glu Asp Ser Glu Leu Ile Ala Glu Ala Lys Leu Leu Arg Gln
    1985                1990                1995

His Lys Gly Arg Leu Glu Ala Arg Met Gln Ile Leu Glu Asp His
    2000                2005                2010

Asn Lys Gln Leu Glu Ser Gln Leu His Arg Leu Arg Gln Leu Leu
    2015                2020                2025

Glu Gln Pro Glu Ser Asp Ser Arg Ile Asn Gly Val Ser Pro Trp
    2030                2035                2040

Ala Ser Pro Gln His Ser Ala Leu Ser Tyr Ser Leu Asp Pro Asp
    2045                2050                2055

Ala Ser Gly Pro Gln Phe His Gln Ala Ala Gly Glu Asp Leu Leu
    2060                2065                2070

Ala Pro Pro His Asp Thr Ser Thr Asp Leu Thr Glu Val Met Glu
    2075                2080                2085

Gln Ile His Ser Thr Phe Pro Ser Cys Cys Pro Asn Val Pro Ser
    2090                2095                2100

Arg Pro Gln Ala Met
    2105

<210> SEQ ID NO 18
<211> LENGTH: 4080
<212> TYPE: DNA
<213> ORGANISM: Mus musculus
<220> FEATURE:
<221> NAME/KEY: CDS
<222> LOCATION: (1)..(4080)
<220> FEATURE:
<221> NAME/KEY: misc_feature
<222> LOCATION: (1)..(117)
<223> OTHER INFORMATION: TAT and epitope tag coding sequence

<400> SEQUENCE: 18 atg gac tac aag gac gac gat gac aag ggc tac ggc cgc aag aaa cgc      48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac      96
Arg Gln Arg Arg Arg Gly Gly Ser Thr Met Ser Gly Tyr Pro Tyr Asp
            20                  25                  30 gtc cca gac tat gct ggc tcc atg gcc aag tat ggg gac ctt gaa gcc     144
Val Pro Asp Tyr Ala Gly Ser Met Ala Lys Tyr Gly Asp Leu Glu Ala
        35                  40                  45 agg cct gat gat ggg cag aac gaa ttc agt gac atc att aag tcc aga     192
Arg Pro Asp Asp Gly Gln Asn Glu Phe Ser Asp Ile Ile Lys Ser Arg
    50                  55                  60 tct gat gaa cac aat gat gta cag aag aaa acc ttt acc aaa tgg ata     240
Ser Asp Glu His Asn Asp Val Gln Lys Lys Thr Phe Thr Lys Trp Ile
65                  70                  75                  80 aac gct cga ttt tcc aag agt ggg aaa cca ccc atc agt gat atg ttc     288
Asn Ala Arg Phe Ser Lys Ser Gly Lys Pro Pro Ile Ser Asp Met Phe
                85                  90                  95 tca gac ctc aaa gat ggg aga aag ctc ttg gat ctt ctc gaa ggc ctc     336
Ser Asp Leu Lys Asp Gly Arg Lys Leu Leu Asp Leu Leu Glu Gly Leu
            100                 105                 110 aca gga aca tca ttg cca aag gaa cgt ggt tcc aca agg gtg cat gcc     384
Thr Gly Thr Ser Leu Pro Lys Glu Arg Gly Ser Thr Arg Val His Ala
        115                 120                 125
```

-continued

| | | |
|---|---|---|
| tta aac aat gtc aac cga gtg cta cag gtt tta cat cag aac aat gtg<br>Leu Asn Asn Val Asn Arg Val Leu Gln Val Leu His Gln Asn Asn Val<br>130                    135                    140 | 432 |
| gac ttg gtg aat att gga ggc acg gac att gtg gct gga aat ccc aag<br>Asp Leu Val Asn Ile Gly Gly Thr Asp Ile Val Ala Gly Asn Pro Lys<br>145                    150                    155                    160 | 480 |
| ctg act tta ggg tta ctc tgg agc atc att ctg cac tgg cag gtg aag<br>Leu Thr Leu Gly Leu Leu Trp Ser Ile Ile Leu His Trp Gln Val Lys<br>                    165                    170                    175 | 528 |
| gat gtc atg aaa gat atc atg tca gac ctg cag cag aca aac agc gag<br>Asp Val Met Lys Asp Ile Met Ser Asp Leu Gln Gln Thr Asn Ser Glu<br>180                    185                    190 | 576 |
| aag atc ctg ctg agc tgg gtg cgg cag acc acc agg ccc tac agt caa<br>Lys Ile Leu Leu Ser Trp Val Arg Gln Thr Thr Arg Pro Tyr Ser Gln<br>                    195                    200                    205 | 624 |
| gtc aac gtc ctc aac ttc acc acc agc tgg acc gat gga ctc gcg ttc<br>Val Asn Val Leu Asn Phe Thr Thr Ser Trp Thr Asp Gly Leu Ala Phe<br>210                    215                    220 | 672 |
| aac gcc gtg ctc cac cgg cac aaa cca gat ctc ttc gac tgg gac gag<br>Asn Ala Val Leu His Arg His Lys Pro Asp Leu Phe Asp Trp Asp Glu<br>225                    230                    235                    240 | 720 |
| atg gtc aaa atg tcc cca att gag aga ctt gac cat gct ttt gac aag<br>Met Val Lys Met Ser Pro Ile Glu Arg Leu Asp His Ala Phe Asp Lys<br>                    245                    250                    255 | 768 |
| gcc cac act tct ttg gga att gaa aag ctc cta agt cct gaa act gtt<br>Ala His Thr Ser Leu Gly Ile Glu Lys Leu Leu Ser Pro Glu Thr Val<br>                    260                    265                    270 | 816 |
| gct gtg cat ctc cct gac aag aaa tcc ata att atg tat tta acg tct<br>Ala Val His Leu Pro Asp Lys Lys Ser Ile Ile Met Tyr Leu Thr Ser<br>275                    280                    285 | 864 |
| ctg ttt gag gtg ctt cct cag caa gtc acg ata gat gcc atc cga gag<br>Leu Phe Glu Val Leu Pro Gln Gln Val Thr Ile Asp Ala Ile Arg Glu<br>290                    295                    300 | 912 |
| gtg gag act ctc cca agg aag tat aag aaa gaa tgt gaa gag gaa gaa<br>Val Glu Thr Leu Pro Arg Lys Tyr Lys Lys Glu Cys Glu Glu Glu Glu<br>305                    310                    315                    320 | 960 |
| att cat atc cag agt gca gtg ctg gca gag gaa ggc cag agt ccc cga<br>Ile His Ile Gln Ser Ala Val Leu Ala Glu Glu Gly Gln Ser Pro Arg<br>                    325                    330                    335 | 1008 |
| gct gag acc cct agc acc gtc act gaa gtg gac atg gat ttg gac agc<br>Ala Glu Thr Pro Ser Thr Val Thr Glu Val Asp Met Asp Leu Asp Ser<br>340                    345                    350 | 1056 |
| tac cag ata gcg cta gag gaa gtg ctg acg tgg ctg ctg tcc gcg gag<br>Tyr Gln Ile Ala Leu Glu Glu Val Leu Thr Trp Leu Leu Ser Ala Glu<br>                    355                    360                    365 | 1104 |
| gac acg ttc cag gag caa cat gac att tct gat gat gtc gaa gaa gtc<br>Asp Thr Phe Gln Glu Gln His Asp Ile Ser Asp Asp Val Glu Glu Val<br>370                    375                    380 | 1152 |
| aaa gag cag ttt gct acc cat gaa act ttt atg atg gag ctg aca gca<br>Lys Glu Gln Phe Ala Thr His Glu Thr Phe Met Met Glu Leu Thr Ala<br>385                    390                    395                    400 | 1200 |
| cac cag agc agc gtg ggg agc gtc ctg cag gct ggc aac cag ctg atg<br>His Gln Ser Ser Val Gly Ser Val Leu Gln Ala Gly Asn Gln Leu Met<br>                    405                    410                    415 | 1248 |
| aca caa ggg act ctg tcc aga gag gag gag ttt gag atc cag gaa cag<br>Thr Gln Gly Thr Leu Ser Arg Glu Glu Glu Phe Glu Ile Gln Glu Gln<br>420                    425                    430 | 1296 |
| atg acc ttg ctg aat gca agg tgg gag gcg ctc cgg gtg gag agc atg<br>Met Thr Leu Leu Asn Ala Arg Trp Glu Ala Leu Arg Val Glu Ser Met | 1344 |

-continued

```
            435                 440                 445
gag agg cag tcc cgg ctg cac gac gct ctg atg gag ctg cag aag aaa     1392
Glu Arg Gln Ser Arg Leu His Asp Ala Leu Met Glu Leu Gln Lys Lys
        450                 455                 460 cag ctg cag cag ctc tca agc tgg ctg gcc ctc aca gaa gag cgc att     1440
Gln Leu Gln Gln Leu Ser Ser Trp Leu Ala Leu Thr Glu Glu Arg Ile
465                 470                 475                 480 cag aag atg gag agc ctc ccg ctg ggt gat gac ctg ccc tcc ctg cag     1488
Gln Lys Met Glu Ser Leu Pro Leu Gly Asp Asp Leu Pro Ser Leu Gln
                485                 490                 495 aag ctg ctt caa gaa cat aaa agt ttg caa aat gac ctt gaa gct gaa     1536
Lys Leu Leu Gln Glu His Lys Ser Leu Gln Asn Asp Leu Glu Ala Glu
            500                 505                 510 cag gtg aag gta aat tcc tta act cac atg gtg gtg att gtg gat gaa     1584
Gln Val Lys Val Asn Ser Leu Thr His Met Val Val Ile Val Asp Glu
        515                 520                 525 aac agt ggg gag agt gcc aca gct ctt ctg gaa gat cag tta cag aaa     1632
Asn Ser Gly Glu Ser Ala Thr Ala Leu Leu Glu Asp Gln Leu Gln Lys
    530                 535                 540 ctg ggt gag cgc tgg aca gct gta tgc cgc tgg act gaa gaa cgt tgg     1680
Leu Gly Glu Arg Trp Thr Ala Val Cys Arg Trp Thr Glu Glu Arg Trp
545                 550                 555                 560 aac agg ttg caa gaa atc agt att ctg tgg cag gaa tta ttg gaa gag     1728
Asn Arg Leu Gln Glu Ile Ser Ile Leu Trp Gln Glu Leu Leu Glu Glu
                565                 570                 575 cag tgt ctg ttg gag gct tgg ctc acc gaa aag gaa gag gct ttg gat     1776
Gln Cys Leu Leu Glu Ala Trp Leu Thr Glu Lys Glu Glu Ala Leu Asp
            580                 585                 590 aaa gtt caa acc agc aac ttt aaa gac cag aag gaa cta agt gtc agt     1824
Lys Val Gln Thr Ser Asn Phe Lys Asp Gln Lys Glu Leu Ser Val Ser
        595                 600                 605 gtc cgg cgt ctg gct ata ttg aag gaa gac atg gaa atg aag agg cag     1872
Val Arg Arg Leu Ala Ile Leu Lys Glu Asp Met Glu Met Lys Arg Gln
    610                 615                 620 act ctg gat caa ctg agt gag att ggc cag gat gtg ggc caa tta ctc     1920
Thr Leu Asp Gln Leu Ser Glu Ile Gly Gln Asp Val Gly Gln Leu Leu
625                 630                 635                 640 agt aat ccc aag gca tct aag aag atg aac agt gac tct gag gag cta     1968
Ser Asn Pro Lys Ala Ser Lys Lys Met Asn Ser Asp Ser Glu Glu Leu
                645                 650                 655 aca cag aga tgg gat tct ctg gtt cag aga ctc gaa gac tct tct aac     2016
Thr Gln Arg Trp Asp Ser Leu Val Gln Arg Leu Glu Asp Ser Ser Asn
            660                 665                 670 cag gtg act cag gcg gta gcg aag ctc ggc atg tcc cag att cca cag     2064
Gln Val Thr Gln Ala Val Ala Lys Leu Gly Met Ser Gln Ile Pro Gln
        675                 680                 685 aag gac cta ttg gag acc gtt cat gtg aga gaa caa ggg atg gtg aag     2112
Lys Asp Leu Leu Glu Thr Val His Val Arg Glu Gln Gly Met Val Lys
    690                 695                 700 aag ccc aag cag gaa ctg cct cct cct ccc cca aag aag aga cag         2160
Lys Pro Lys Gln Glu Leu Pro Pro Pro Pro Pro Lys Lys Arg Gln
705                 710                 715                 720 att cac gtg gac gcc cac aga gat ttt ggg cca tct tct caa cac ttt     2208
Ile His Val Asp Ala His Arg Asp Phe Gly Pro Ser Ser Gln His Phe
                725                 730                 735 ctg tcc act tca gtc cag ctg ccg tgg cag aga tcc att tca cat aat     2256
Leu Ser Thr Ser Val Gln Leu Pro Trp Gln Arg Ser Ile Ser His Asn
            740                 745                 750 aaa gtg ccc tat tac atc aac cat caa aca cag aca acc tgt tgg gat     2304
Lys Val Pro Tyr Tyr Ile Asn His Gln Thr Gln Thr Thr Cys Trp Asp
```

-continued

```
                Lys Val Pro Tyr Tyr Ile Asn His Gln Thr Gln Thr Cys Trp Asp
                            755                 760                 765 cat cct aaa atg act gag ctc ttc caa tcc ctt gct gat ctg aat aat       2352
His Pro Lys Met Thr Glu Leu Phe Gln Ser Leu Ala Asp Leu Asn Asn
        770                 775                 780 gta cgt ttc tct gcc tac cgc aca gca atc aaa att cga agg ctg caa       2400
Val Arg Phe Ser Ala Tyr Arg Thr Ala Ile Lys Ile Arg Arg Leu Gln
785                 790                 795                 800 aaa gca tta tgt ctg gat ctc tta gag ctg aat acg acg aat gaa gtt       2448
Lys Ala Leu Cys Leu Asp Leu Leu Glu Leu Asn Thr Thr Asn Glu Val
                805                 810                 815 ttc aag cag cac aaa ctg aac caa aat gat cag ctc ctg agt gtc cca       2496
Phe Lys Gln His Lys Leu Asn Gln Asn Asp Gln Leu Leu Ser Val Pro
            820                 825                 830 gac gtc atc aac tgt ctg acc acc act tac gat ggg ctt gag cag ctg       2544
Asp Val Ile Asn Cys Leu Thr Thr Thr Tyr Asp Gly Leu Glu Gln Leu
        835                 840                 845 cac aag gac ttg gtc aat gtt cca ctc tgc gtc gat atg tgt ctc aac       2592
His Lys Asp Leu Val Asn Val Pro Leu Cys Val Asp Met Cys Leu Asn
    850                 855                 860 tgg ctg ctc aac gta tac gac acg ggc cgg act gga aaa att cgg gta       2640
Trp Leu Leu Asn Val Tyr Asp Thr Gly Arg Thr Gly Lys Ile Arg Val
865                 870                 875                 880 cag agt ctg aag att gga ttg atg tct ctc tcc aaa ggc ctc tta gaa       2688
Gln Ser Leu Lys Ile Gly Leu Met Ser Leu Ser Lys Gly Leu Leu Glu
                885                 890                 895 gag aaa tac aga tgt ctc ttt aag gag gtg gca ggg cca act gag atg       2736
Glu Lys Tyr Arg Cys Leu Phe Lys Glu Val Ala Gly Pro Thr Glu Met
            900                 905                 910 tgt gac cag cgg cag ctt ggc ctg cta ctt cac gat gcc atc cag atc       2784
Cys Asp Gln Arg Gln Leu Gly Leu Leu Leu His Asp Ala Ile Gln Ile
        915                 920                 925 cct agg cag ctg ggg gaa gta gca gcc ttt ggg ggc agt aac att gag       2832
Pro Arg Gln Leu Gly Glu Val Ala Ala Phe Gly Gly Ser Asn Ile Glu
    930                 935                 940 ccc agt gtc cgc agc tgc ttc cag cag aat aac aac aag cca gaa atc       2880
Pro Ser Val Arg Ser Cys Phe Gln Gln Asn Asn Asn Lys Pro Glu Ile
945                 950                 955                 960 agt gtg aag gag ttt ata gac tgg atg cat ttg gaa ccc cag tcc atg       2928
Ser Val Lys Glu Phe Ile Asp Trp Met His Leu Glu Pro Gln Ser Met
                965                 970                 975 gtg tgg ttg ccg gtt ctg cat cgg gtc gca gct gct gag act gca aaa       2976
Val Trp Leu Pro Val Leu His Arg Val Ala Ala Ala Glu Thr Ala Lys
            980                 985                 990 cat cag gcc aaa tgc aac atc tgc aaa gaa tgc ccg att gtt ggg ttc       3024
His Gln Ala Lys Cys Asn Ile Cys Lys Glu Cys Pro Ile Val Gly Phe
        995                 1000                1005 aga tac agg agc cta aag cat ttt aat tat gat gtc tgc cag agt           3069
Arg Tyr Arg Ser Leu Lys His Phe Asn Tyr Asp Val Cys Gln Ser
    1010                1015                1020 tgc ttc ttt tct gga aga aca gca aag ggc cac aag tta cat tac           3114
Cys Phe Phe Ser Gly Arg Thr Ala Lys Gly His Lys Leu His Tyr
    1025                1030                1035 ccg atg gta gaa tac tgc ata ccg aca aca tct ggg gaa gat gtg           3159
Pro Met Val Glu Tyr Cys Ile Pro Thr Thr Ser Gly Glu Asp Val
    1040                1045                1050 aga gat ttc act aag gtg ctg aag aac aag ttc agg tcc aag aaa           3204
Arg Asp Phe Thr Lys Val Leu Lys Asn Lys Phe Arg Ser Lys Lys
    1055                1060                1065
```

```
tat ttt gcc aaa cat cct cgg ctt ggc tac ctg cct gtc cag acc       3249
Tyr Phe Ala Lys His Pro Arg Leu Gly Tyr Leu Pro Val Gln Thr
    1070            1075                1080 gtg ctg gaa ggg gac aac tta gaa act cct atc acg ctc atc agt       3294
Val Leu Glu Gly Asp Asn Leu Glu Thr Pro Ile Thr Leu Ile Ser
    1085            1090                1095 atg tgg cca gag cac tat gac ccc tcc cag tcc cct cag ctg ttt       3339
Met Trp Pro Glu His Tyr Asp Pro Ser Gln Ser Pro Gln Leu Phe
    1100            1105                1110 cat gat gac acc cac tca aga ata gag caa tac gct aca cga ctg       3384
His Asp Asp Thr His Ser Arg Ile Glu Gln Tyr Ala Thr Arg Leu
    1115            1120                1125 gcc cag atg gaa agg aca aac ggg tcc ttc cta act gat agc agc       3429
Ala Gln Met Glu Arg Thr Asn Gly Ser Phe Leu Thr Asp Ser Ser
    1130            1135                1140 tct aca aca gga agc gtg gag gat gag cat gcc ctc atc cag cag       3474
Ser Thr Thr Gly Ser Val Glu Asp Glu His Ala Leu Ile Gln Gln
    1145            1150                1155 tac tgc cag acc ctg ggc ggg gag tca cct gtg agt cag ccg cag       3519
Tyr Cys Gln Thr Leu Gly Gly Glu Ser Pro Val Ser Gln Pro Gln
    1160            1165                1170 agt cca gct cag atc ctg aag tcc gtg gag agg gaa gag cgt ggg       3564
Ser Pro Ala Gln Ile Leu Lys Ser Val Glu Arg Glu Glu Arg Gly
    1175            1180                1185 gaa ctg gag cgg atc att gct gac ttg gag gaa gag caa aga aat       3609
Glu Leu Glu Arg Ile Ile Ala Asp Leu Glu Glu Glu Gln Arg Asn
    1190            1195                1200 ctg cag gtg gag tat gag cag ctg aag gag cag cac cta aga agg       3654
Leu Gln Val Glu Tyr Glu Gln Leu Lys Glu Gln His Leu Arg Arg
    1205            1210                1215 ggt ctc cct gtg ggc tcc cct cca gac tcc atc gta tct cct cac       3699
Gly Leu Pro Val Gly Ser Pro Pro Asp Ser Ile Val Ser Pro His
    1220            1225                1230 cac aca tct gag gac tca gaa ctt ata gca gaa gct aaa ctc ctg       3744
His Thr Ser Glu Asp Ser Glu Leu Ile Ala Glu Ala Lys Leu Leu
    1235            1240                1245 cgg cag cac aaa ggg cgg ctg gag gcg agg atg caa att ttg gaa       3789
Arg Gln His Lys Gly Arg Leu Glu Ala Arg Met Gln Ile Leu Glu
    1250            1255                1260 gat cac aat aaa cag ctg gag tct cag ctg cac cgc ctc aga cag       3834
Asp His Asn Lys Gln Leu Glu Ser Gln Leu His Arg Leu Arg Gln
    1265            1270                1275 ctc ctg gag cag cct gac tct gac tcc cgc atc aat ggt gtc tcc       3879
Leu Leu Glu Gln Pro Asp Ser Asp Ser Arg Ile Asn Gly Val Ser
    1280            1285                1290 ccc tgg gct tcc cca cag cat tct gca ttg agc tac tca ctt gac       3924
Pro Trp Ala Ser Pro Gln His Ser Ala Leu Ser Tyr Ser Leu Asp
    1295            1300                1305 act gac cca ggc cca cag ttc cac cag gca gca tct gag gac ctg       3969
Thr Asp Pro Gly Pro Gln Phe His Gln Ala Ala Ser Glu Asp Leu
    1310            1315                1320 ctg gcc cca cct cac gac act agc acg gac ctc acg gac gtg atg       4014
Leu Ala Pro Pro His Asp Thr Ser Thr Asp Leu Thr Asp Val Met
    1325            1330                1335 gag cag atc aac agc acg ttt ccc tct tgc agc tca aat gtc ccc       4059
Glu Gln Ile Asn Ser Thr Phe Pro Ser Cys Ser Ser Asn Val Pro
    1340            1345                1350 agc agg cca cag gca atg tga                                       4080
Ser Arg Pro Gln Ala Met
    1355
```

<210> SEQ ID NO 19
<211> LENGTH: 1359
<212> TYPE: PRT
<213> ORGANISM: Mus musculus

<400> SEQUENCE: 19

```
Met Asp Tyr Lys Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
                20                  25                  30

Val Pro Asp Tyr Ala Gly Ser Met Ala Lys Tyr Gly Asp Leu Glu Ala
            35                  40                  45

Arg Pro Asp Asp Gly Gln Asn Glu Phe Ser Asp Ile Ile Lys Ser Arg
        50                  55                  60

Ser Asp Glu His Asn Asp Val Gln Lys Lys Thr Phe Thr Lys Trp Ile
65              70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu
305                 310                 315                 320

Ile His Ile Gln Ser Ala Val Leu Ala Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
        355                 360                 365

Asp Thr Phe Gln Glu Gln His Asp Ile Ser Asp Asp Val Glu Glu Val
```

-continued

```
            370                 375                 380
Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Phe Glu Ile Gln Glu Gln
                420                 425                 430

Met Thr Leu Leu Asn Ala Arg Trp Glu Ala Leu Arg Val Glu Ser Met
                435                 440                 445

Glu Arg Gln Ser Arg Leu His Asp Ala Leu Met Glu Leu Gln Lys Lys
                450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
                500                 505                 510

Gln Val Lys Val Asn Ser Leu Thr His Met Val Val Ile Val Asp Glu
                515                 520                 525

Asn Ser Gly Glu Ser Ala Thr Ala Leu Leu Glu Asp Gln Leu Gln Lys
                530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
                580                 585                 590

Lys Val Gln Thr Ser Asn Phe Lys Asp Gln Lys Glu Leu Ser Val Ser
                595                 600                 605

Val Arg Arg Leu Ala Ile Leu Lys Glu Asp Met Glu Met Lys Arg Gln
                610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
                660                 665                 670

Gln Val Thr Gln Ala Val Ala Lys Leu Gly Met Ser Gln Ile Pro Gln
                675                 680                 685

Lys Asp Leu Leu Glu Thr Val His Val Arg Glu Gln Gly Met Val Lys
                690                 695                 700

Lys Pro Lys Gln Glu Leu Pro Pro Pro Pro Pro Lys Lys Arg Gln
705                 710                 715                 720

Ile His Val Asp Ala His Arg Asp Phe Gly Pro Ser Ser Gln His Phe
                725                 730                 735

Leu Ser Thr Ser Val Gln Leu Pro Trp Gln Arg Ser Ile Ser His Asn
                740                 745                 750

Lys Val Pro Tyr Tyr Ile Asn His Gln Thr Gln Thr Thr Cys Trp Asp
                755                 760                 765

His Pro Lys Met Thr Glu Leu Phe Gln Ser Leu Ala Asp Leu Asn Asn
                770                 775                 780

Val Arg Phe Ser Ala Tyr Arg Thr Ala Ile Lys Ile Arg Arg Leu Gln
785                 790                 795                 800
```

-continued

```
Lys Ala Leu Cys Leu Asp Leu Leu Glu Leu Asn Thr Thr Asn Glu Val
            805                 810                 815
Phe Lys Gln His Lys Leu Asn Gln Asn Asp Gln Leu Leu Ser Val Pro
            820                 825                 830
Asp Val Ile Asn Cys Leu Thr Thr Thr Tyr Asp Gly Leu Glu Gln Leu
            835                 840                 845
His Lys Asp Leu Val Asn Val Pro Leu Cys Val Asp Met Cys Leu Asn
            850                 855                 860
Trp Leu Leu Asn Val Tyr Asp Thr Gly Arg Thr Gly Lys Ile Arg Val
865                 870                 875                 880
Gln Ser Leu Lys Ile Gly Leu Met Ser Leu Ser Lys Gly Leu Leu Glu
            885                 890                 895
Glu Lys Tyr Arg Cys Leu Phe Lys Glu Val Ala Gly Pro Thr Glu Met
            900                 905                 910
Cys Asp Gln Arg Gln Leu Gly Leu Leu Leu His Asp Ala Ile Gln Ile
            915                 920                 925
Pro Arg Gln Leu Gly Glu Val Ala Ala Phe Gly Gly Ser Asn Ile Glu
            930                 935                 940
Pro Ser Val Arg Ser Cys Phe Gln Gln Asn Asn Asn Lys Pro Glu Ile
945                 950                 955                 960
Ser Val Lys Glu Phe Ile Asp Trp Met His Leu Glu Pro Gln Ser Met
            965                 970                 975
Val Trp Leu Pro Val Leu His Arg Val Ala Ala Ala Glu Thr Ala Lys
            980                 985                 990
His Gln Ala Lys Cys Asn Ile Cys  Lys Glu Cys Pro Ile  Val Gly Phe
            995                 1000                    1005
Arg Tyr  Arg Ser Leu Lys His  Phe Asn Tyr Asp Val  Cys Gln Ser
            1010                    1015                1020
Cys Phe  Phe Ser Gly Arg Thr  Ala Lys Gly His Lys  Leu His Tyr
            1025                    1030                1035
Pro Met  Val Glu Tyr Cys Ile  Pro Thr Thr Ser Gly  Glu Asp Val
            1040                    1045                1050
Arg Asp  Phe Thr Lys Val Leu  Lys Asn Lys Phe Arg  Ser Lys Lys
            1055                    1060                1065
Tyr Phe  Ala Lys His Pro Arg  Leu Gly Tyr Leu Pro  Val Gln Thr
            1070                    1075                1080
Val Leu  Glu Gly Asp Asn Leu  Glu Thr Pro Ile Thr  Leu Ile Ser
            1085                    1090                1095
Met Trp  Pro Glu His Tyr Asp  Pro Ser Gln Ser Pro  Gln Leu Phe
            1100                    1105                1110
His Asp  Asp Thr His Ser Arg  Ile Glu Gln Tyr Ala  Thr Arg Leu
            1115                    1120                1125
Ala Gln  Met Glu Arg Thr Asn  Gly Ser Phe Leu Thr  Asp Ser Ser
            1130                    1135                1140
Ser Thr  Thr Gly Ser Val Glu  Asp Glu His Ala Leu  Ile Gln Gln
            1145                    1150                1155
Tyr Cys  Gln Thr Leu Gly Gly  Glu Ser Pro Val Ser  Gln Pro Gln
            1160                    1165                1170
Ser Pro  Ala Gln Ile Leu Lys  Ser Val Glu Arg Glu  Arg Gly
            1175                    1180                    1185
Glu Leu  Glu Arg Ile Ile Ala  Asp Leu Glu Glu Glu  Gln Arg Asn
            1190                    1195                1200
```

```
Leu Gln Val Glu Tyr Glu Gln Leu Lys Glu Gln His Leu Arg Arg
    1205                1210                1215

Gly Leu Pro Val Gly Ser Pro Pro Asp Ser Ile Val Ser Pro His
    1220                1225                1230

His Thr Ser Glu Asp Ser Glu Leu Ile Ala Glu Ala Lys Leu Leu
    1235                1240                1245

Arg Gln His Lys Gly Arg Leu Glu Ala Arg Met Gln Ile Leu Glu
    1250                1255                1260

Asp His Asn Lys Gln Leu Glu Ser Gln Leu His Arg Leu Arg Gln
    1265                1270                1275

Leu Leu Glu Gln Pro Asp Ser Asp Ser Arg Ile Asn Gly Val Ser
    1280                1285                1290

Pro Trp Ala Ser Pro Gln His Ser Ala Leu Ser Tyr Ser Leu Asp
    1295                1300                1305

Thr Asp Pro Gly Pro Gln Phe His Gln Ala Ala Ser Glu Asp Leu
    1310                1315                1320

Leu Ala Pro Pro His Asp Thr Ser Thr Asp Leu Thr Asp Val Met
    1325                1330                1335

Glu Gln Ile Asn Ser Thr Phe Pro Ser Cys Ser Ser Asn Val Pro
    1340                1345                1350

Ser Arg Pro Gln Ala Met
    1355

<210> SEQ ID NO 20
<211> LENGTH: 5067
<212> TYPE: DNA
<213> ORGANISM: Mus musculus
<220> FEATURE:
<221> NAME/KEY: CDS
<222> LOCATION: (1)..(5067)
<220> FEATURE:
<221> NAME/KEY: misc_feature
<222> LOCATION: (1)..(117)
<223> OTHER INFORMATION: TAT and epitope tag coding sequence

<400> SEQUENCE: 20 atg gac tac aag gac gac gat gac aag ggc tac ggc cgc aag aaa cgc        48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac        96
Arg Gln Arg Arg Arg Gly Gly Ser Thr Met Ser Gly Tyr Pro Tyr Asp
            20                  25                  30 gtc cca gac tat gct ggc tcc atg gcc aag tat ggg gac ctt gaa gcc       144
Val Pro Asp Tyr Ala Gly Ser Met Ala Lys Tyr Gly Asp Leu Glu Ala
        35                  40                  45 agg cct gat gat ggg cag aac gaa ttc agt gac atc att aag tcc aga       192
Arg Pro Asp Asp Gly Gln Asn Glu Phe Ser Asp Ile Ile Lys Ser Arg
    50                  55                  60 tct gat gaa cac aat gat gta cag aag aaa acc ttt acc aaa tgg ata       240
Ser Asp Glu His Asn Asp Val Gln Lys Lys Thr Phe Thr Lys Trp Ile
65                  70                  75                  80 aac gct cga ttt tcc aag agt ggg aaa cca ccc atc agt gat atg ttc       288
Asn Ala Arg Phe Ser Lys Ser Gly Lys Pro Pro Ile Ser Asp Met Phe
                85                  90                  95 tca gac ctc aaa gat ggg aga aag ctc ttg gat ctt ctc gaa ggc ctc       336
Ser Asp Leu Lys Asp Gly Arg Lys Leu Leu Asp Leu Leu Glu Gly Leu
            100                 105                 110 aca gga aca tca ttg cca aag gaa cgt ggt tcc aca agg gtg cat gcc       384
Thr Gly Thr Ser Leu Pro Lys Glu Arg Gly Ser Thr Arg Val His Ala
        115                 120                 125
```

```
tta aac aat gtc aac cga gtg cta cag gtt tta cat cag aac aat gtg         432
Leu Asn Asn Val Asn Arg Val Leu Gln Val Leu His Gln Asn Asn Val
        130                 135                 140 gac ttg gtg aat att gga ggc acg gac att gtg gct gga aat ccc aag         480
Asp Leu Val Asn Ile Gly Gly Thr Asp Ile Val Ala Gly Asn Pro Lys
145                 150                 155                 160 ctg act tta ggg tta ctc tgg agc atc att ctg cac tgg cag gtg aag         528
Leu Thr Leu Gly Leu Leu Trp Ser Ile Ile Leu His Trp Gln Val Lys
                165                 170                 175 gat gtc atg aaa gat atc atg tca gac ctg cag cag aca aac agc gag         576
Asp Val Met Lys Asp Ile Met Ser Asp Leu Gln Gln Thr Asn Ser Glu
            180                 185                 190 aag atc ctg ctg agc tgg gtg cgg cag acc acc agg ccc tac agt caa         624
Lys Ile Leu Leu Ser Trp Val Arg Gln Thr Thr Arg Pro Tyr Ser Gln
        195                 200                 205 gtc aac gtc ctc aac ttc acc acc agc tgg acc gat gga ctc gcg ttc         672
Val Asn Val Leu Asn Phe Thr Thr Ser Trp Thr Asp Gly Leu Ala Phe
    210                 215                 220 aac gcc gtg ctc cac cgg cac aaa cca gat ctc ttc gac tgg gac gag         720
Asn Ala Val Leu His Arg His Lys Pro Asp Leu Phe Asp Trp Asp Glu
225                 230                 235                 240 atg gtc aaa atg tcc cca att gag aga ctt gac cat gct ttt gac aag         768
Met Val Lys Met Ser Pro Ile Glu Arg Leu Asp His Ala Phe Asp Lys
                245                 250                 255 gcc cac act tct ttg gga att gaa aag ctc cta agt cct gaa act gtt         816
Ala His Thr Ser Leu Gly Ile Glu Lys Leu Leu Ser Pro Glu Thr Val
            260                 265                 270 gct gtg cat ctc cct gac aag aaa tcc ata att atg tat tta acg tct         864
Ala Val His Leu Pro Asp Lys Lys Ser Ile Ile Met Tyr Leu Thr Ser
        275                 280                 285 ctg ttt gag gtg ctt cct cag caa gtc acg ata gat gcc atc cga gag         912
Leu Phe Glu Val Leu Pro Gln Gln Val Thr Ile Asp Ala Ile Arg Glu
    290                 295                 300 gtg gag act ctc cca agg aag tat aag aaa gaa tgt gaa gag gaa gaa         960
Val Glu Thr Leu Pro Arg Lys Tyr Lys Lys Glu Cys Glu Glu Glu Glu
305                 310                 315                 320 att cat atc cag agt gca gtg ctg gca gag gaa ggc cag agt ccc cga        1008
Ile His Ile Gln Ser Ala Val Leu Ala Glu Glu Gly Gln Ser Pro Arg
                325                 330                 335 gct gag acc cct agc acc gtc act gaa gtg gac atg gat ttg gac agc        1056
Ala Glu Thr Pro Ser Thr Val Thr Glu Val Asp Met Asp Leu Asp Ser
            340                 345                 350 tac cag ata gcg cta gag gaa gtg ctg acg tgg ctg ctg tcc gcg gag        1104
Tyr Gln Ile Ala Leu Glu Glu Val Leu Thr Trp Leu Leu Ser Ala Glu
        355                 360                 365 gac acg ttc cag gag caa cat gac att tct gat gat gtc gaa gaa gtc        1152
Asp Thr Phe Gln Glu Gln His Asp Ile Ser Asp Asp Val Glu Glu Val
    370                 375                 380 aaa gag cag ttt gct acc cat gaa act ttt atg atg gag ctg aca gca        1200
Lys Glu Gln Phe Ala Thr His Glu Thr Phe Met Met Glu Leu Thr Ala
385                 390                 395                 400 cac cag agc agc gtg ggg agc gtc ctg cag gct ggc aac cag ctg atg        1248
His Gln Ser Ser Val Gly Ser Val Leu Gln Ala Gly Asn Gln Leu Met
                405                 410                 415 aca caa ggg act ctg tcc aga gag gag gag ttt gag atc cag gaa cag        1296
Thr Gln Gly Thr Leu Ser Arg Glu Glu Glu Phe Glu Ile Gln Glu Gln
            420                 425                 430 atg acc ttg ctg aat gca agg tgg gag gcg ctc cgg gtg gag agc atg        1344
Met Thr Leu Leu Asn Ala Arg Trp Glu Ala Leu Arg Val Glu Ser Met
```

-continued

```
                435                 440                 445
gag agg cag tcc cgg ctg cac gac gct ctg atg gag ctg cag aag aaa        1392
Glu Arg Gln Ser Arg Leu His Asp Ala Leu Met Glu Leu Gln Lys Lys
        450                 455                 460 cag ctg cag cag ctc tca agc tgg ctg gcc ctc aca gaa gag cgc att        1440
Gln Leu Gln Gln Leu Ser Ser Trp Leu Ala Leu Thr Glu Glu Arg Ile
465                 470                 475                 480 cag aag atg gag agc ctc ccg ctg ggt gat gac ctg ccc tcc ctg cag        1488
Gln Lys Met Glu Ser Leu Pro Leu Gly Asp Asp Leu Pro Ser Leu Gln
                485                 490                 495 aag ctg ctt caa gaa cat aaa agt ttg caa aat gac ctt gaa gct gaa        1536
Lys Leu Leu Gln Glu His Lys Ser Leu Gln Asn Asp Leu Glu Ala Glu
            500                 505                 510 cag gtg aag gta aat tcc tta act cac atg gtg gtg att gtg gat gaa        1584
Gln Val Lys Val Asn Ser Leu Thr His Met Val Val Ile Val Asp Glu
            515                 520                 525 aac agt ggg gag agt gcc aca gct ctt ctg gaa gat cag tta cag aaa        1632
Asn Ser Gly Glu Ser Ala Thr Ala Leu Leu Glu Asp Gln Leu Gln Lys
            530                 535                 540 ctg ggt gag cgc tgg aca gct gta tgc cgc tgg act gaa gaa cgt tgg        1680
Leu Gly Glu Arg Trp Thr Ala Val Cys Arg Trp Thr Glu Glu Arg Trp
545                 550                 555                 560 aac agg ttg caa gaa atc agt att ctg tgg cag gaa tta ttg gaa gag        1728
Asn Arg Leu Gln Glu Ile Ser Ile Leu Trp Gln Glu Leu Leu Glu Glu
                565                 570                 575 cag tgt ctg ttg gag gct tgg ctc acc gaa aag gaa gag gct ttg gat        1776
Gln Cys Leu Leu Glu Ala Trp Leu Thr Glu Lys Glu Glu Ala Leu Asp
            580                 585                 590 aaa gtt caa acc agc aac ttt aaa gac cag aag gaa cta agt gtc agt        1824
Lys Val Gln Thr Ser Asn Phe Lys Asp Gln Lys Glu Leu Ser Val Ser
            595                 600                 605 gtc cgg cgt ctg gct ata ttg aag gaa gac atg gaa atg aag agg cag        1872
Val Arg Arg Leu Ala Ile Leu Lys Glu Asp Met Glu Met Lys Arg Gln
        610                 615                 620 act ctg gat caa ctg agt gag att ggc cag gat gtg ggc caa tta ctc        1920
Thr Leu Asp Gln Leu Ser Glu Ile Gly Gln Asp Val Gly Gln Leu Leu
625                 630                 635                 640 agt aat ccc aag gca tct aag aag atg aac agt gac tct gag gag cta        1968
Ser Asn Pro Lys Ala Ser Lys Lys Met Asn Ser Asp Ser Glu Glu Leu
                645                 650                 655 aca cag aga tgg gat tct ctg gtt cag aga ctc gaa gac tct tct aac        2016
Thr Gln Arg Trp Asp Ser Leu Val Gln Arg Leu Glu Asp Ser Ser Asn
            660                 665                 670 cag gtg act cag gcg gta gcg aag ctc ggc atg tcc cag att cca cag        2064
Gln Val Thr Gln Ala Val Ala Lys Leu Gly Met Ser Gln Ile Pro Gln
            675                 680                 685 aag gac cta ttg gag acc gtt cat gtg aga gaa caa ggg atg gtg aag        2112
Lys Asp Leu Leu Glu Thr Val His Val Arg Glu Gln Gly Met Val Lys
        690                 695                 700 aag ccc aag cag gaa ctg cct cct cct ccc cca cca aag aag aga cag        2160
Lys Pro Lys Gln Glu Leu Pro Pro Pro Pro Pro Pro Lys Lys Arg Gln
705                 710                 715                 720 att cac gtg gac gtg gag gcc aag aaa aag ttt gat gct ata agt aca        2208
Ile His Val Asp Val Glu Ala Lys Lys Lys Phe Asp Ala Ile Ser Thr
                725                 730                 735 gag ctg ctg aac tgg att ttg aaa tca aag act gcc att cag aac aca        2256
Glu Leu Leu Asn Trp Ile Leu Lys Ser Lys Thr Ala Ile Gln Asn Thr
            740                 745                 750 gag atg aaa gaa tat aag aag tcg cag gag acc tca gga atg aaa aag        2304
```

```
Glu Met Lys Glu Tyr Lys Lys Ser Gln Glu Thr Ser Gly Met Lys Lys
            755                 760                 765 aaa ttg aag gga tta gag aaa gaa cag aag gaa aat ctg ccc cga ctg        2352
Lys Leu Lys Gly Leu Glu Lys Glu Gln Lys Glu Asn Leu Pro Arg Leu
        770                 775                 780 gac gaa ctg aat caa acc gga caa acc ctc cgg gag caa atg gga aaa        2400
Asp Glu Leu Asn Gln Thr Gly Gln Thr Leu Arg Glu Gln Met Gly Lys
785                 790                 795                 800 gaa ggc ctt cca ctg aaa gaa gta aac gat gtt ctg gaa agg gtt tcg        2448
Glu Gly Leu Pro Leu Lys Glu Val Asn Asp Val Leu Glu Arg Val Ser
                805                 810                 815 ttg gag tgg aag atg ata tct cag cag cta gaa gat ctg gga agg aag        2496
Leu Glu Trp Lys Met Ile Ser Gln Gln Leu Glu Asp Leu Gly Arg Lys
            820                 825                 830 atc cag ctg cag gaa gat ata aat gct tat ttt aag cag ctt gat gcc        2544
Ile Gln Leu Gln Glu Asp Ile Asn Ala Tyr Phe Lys Gln Leu Asp Ala
        835                 840                 845 att gag gag acc atc aag gag aag gaa gag tgg ctg agg ggc aca ccc        2592
Ile Glu Glu Thr Ile Lys Glu Lys Glu Glu Trp Leu Arg Gly Thr Pro
850                 855                 860 att tct gaa tcg ccc cgg cag ccc ttg cca ggc tta aag gat tct tgc        2640
Ile Ser Glu Ser Pro Arg Gln Pro Leu Pro Gly Leu Lys Asp Ser Cys
865                 870                 875                 880 cag agg gaa ctg aca gat ctc ctt ggc ctt cac ccc aga att gag acg        2688
Gln Arg Glu Leu Thr Asp Leu Leu Gly Leu His Pro Arg Ile Glu Thr
                885                 890                 895 ctg tgt gca agc tgt tca gcc ctg aag tct cag ccc tgt gtc cca ggt        2736
Leu Cys Ala Ser Cys Ser Ala Leu Lys Ser Gln Pro Cys Val Pro Gly
            900                 905                 910 ttt gtc cag cag ggt ttt gac gac ctt cga cat cat tac cag gct gtt        2784
Phe Val Gln Gln Gly Phe Asp Asp Leu Arg His His Tyr Gln Ala Val
        915                 920                 925 gcg aag gct tta gag gaa tac caa caa caa cta gaa aat gag ctg aag        2832
Ala Lys Ala Leu Glu Glu Tyr Gln Gln Gln Leu Glu Asn Glu Leu Lys
    930                 935                 940 agc cag cct gga ccc gag tat ttg gac aca ctg aat acc ctg aaa aaa        2880
Ser Gln Pro Gly Pro Glu Tyr Leu Asp Thr Leu Asn Thr Leu Lys Lys
945                 950                 955                 960 atg cta agc gag tca gaa aag gcg gcc cag gcc tct ctg aat gcc ctg        2928
Met Leu Ser Glu Ser Glu Lys Ala Ala Gln Ala Ser Leu Asn Ala Leu
                965                 970                 975 aac gat ccc ata gcg gtg gag cag gcc ctg cag gag aaa aag gcc ctt        2976
Asn Asp Pro Ile Ala Val Glu Gln Ala Leu Gln Glu Lys Lys Ala Leu
            980                 985                 990 gat gaa acc ctt gag aat cag aaa  cat acg tta cat aag  ctt tca gaa     3024
Asp Glu Thr Leu Glu Asn Gln Lys His Thr Leu His Lys Leu Ser Glu
        995                 1000                1005 gaa acg aag act ttg gag aaa  aat atg ctt cct gat  gtg ggg aaa         3069
Glu Thr Lys Thr Leu Glu Lys Asn Met Leu Pro Asp Val Gly Lys
    1010                1015                1020 atg tat aaa caa gaa ttt gat  gat gtc caa ggc aga  tgg aat aaa         3114
Met Tyr Lys Gln Glu Phe Asp Asp Val Gln Gly Arg Trp Asn Lys
    1025                1030                1035 gta aag acc aag gtt tcc aga  gac tta cac ttg ctc  gag gaa atc         3159
Val Lys Thr Lys Val Ser Arg Asp Leu His Leu Leu Glu Glu Ile
    1040                1045                1050 gcc cac aga gat ttt ggg cca  tct tct caa cac ttt  ctg tcc act         3204
Ala His Arg Asp Phe Gly Pro Ser Ser Gln His Phe Leu Ser Thr
    1055                1060                1065
```

```
tca gtc cag ctg ccg tgg cag aga tcc att tca cat aat aaa gtg     3249
Ser Val Gln Leu Pro Trp Gln Arg Ser Ile Ser His Asn Lys Val
    1070            1075                1080 ccc tat tac atc aac cat caa aca cag aca acc tgt tgg gat cat     3294
Pro Tyr Tyr Ile Asn His Gln Thr Gln Thr Thr Cys Trp Asp His
    1085            1090                1095 cct aaa atg act gag ctc ttc caa tcc ctt gct gat ctg aat aat     3339
Pro Lys Met Thr Glu Leu Phe Gln Ser Leu Ala Asp Leu Asn Asn
    1100            1105                1110 gta cgt ttc tct gcc tac cgc aca gca atc aaa att cga agg ctg     3384
Val Arg Phe Ser Ala Tyr Arg Thr Ala Ile Lys Ile Arg Arg Leu
    1115            1120                1125 caa aaa gca tta tgt ctg gat ctc tta gag ctg aat acg acg aat     3429
Gln Lys Ala Leu Cys Leu Asp Leu Leu Glu Leu Asn Thr Thr Asn
    1130            1135                1140 gaa gtt ttc aag cag cac aaa ctg aac caa aat gat cag ctc ctg     3474
Glu Val Phe Lys Gln His Lys Leu Asn Gln Asn Asp Gln Leu Leu
    1145            1150                1155 agt gtc cca gac gtc atc aac tgt ctg acc acc act tac gat ggg     3519
Ser Val Pro Asp Val Ile Asn Cys Leu Thr Thr Thr Tyr Asp Gly
    1160            1165                1170 ctt gag cag ctg cac aag gac ttg gtc aat gtt cca ctc tgc gtc     3564
Leu Glu Gln Leu His Lys Asp Leu Val Asn Val Pro Leu Cys Val
    1175            1180                1185 gat atg tgt ctc aac tgg ctg ctc aac gta tac gac acg ggc cgg     3609
Asp Met Cys Leu Asn Trp Leu Leu Asn Val Tyr Asp Thr Gly Arg
    1190            1195                1200 act gga aaa att cgg gta cag agt ctg aag att gga ttg atg tct     3654
Thr Gly Lys Ile Arg Val Gln Ser Leu Lys Ile Gly Leu Met Ser
    1205            1210                1215 ctc tcc aaa ggc ctc tta gaa gag aaa tac aga tgt ctc ttt aag     3699
Leu Ser Lys Gly Leu Leu Glu Glu Lys Tyr Arg Cys Leu Phe Lys
    1220            1225                1230 gag gtg gca ggg cca act gag atg tgt gac cag cgg cag ctt ggc     3744
Glu Val Ala Gly Pro Thr Glu Met Cys Asp Gln Arg Gln Leu Gly
    1235            1240                1245 ctg cta ctt cac gat gcc atc cag atc cct agg cag ctg ggg gaa     3789
Leu Leu Leu His Asp Ala Ile Gln Ile Pro Arg Gln Leu Gly Glu
    1250            1255                1260 gta gca gcc ttt ggg ggc agt aac att gag ccc agt gtc cgc agc     3834
Val Ala Ala Phe Gly Gly Ser Asn Ile Glu Pro Ser Val Arg Ser
    1265            1270                1275 tgc ttc cag cag aat aac aac aag cca gaa atc agt gtg aag gag     3879
Cys Phe Gln Gln Asn Asn Asn Lys Pro Glu Ile Ser Val Lys Glu
    1280            1285                1290 ttt ata gac tgg atg cat ttg gaa ccc agt ccc atg gtg tgg ttg     3924
Phe Ile Asp Trp Met His Leu Glu Pro Gln Ser Met Val Trp Leu
    1295            1300                1305 ccg gtt ctg cat cgg gtc gca gct gct gag act gca aaa cat cag     3969
Pro Val Leu His Arg Val Ala Ala Ala Glu Thr Ala Lys His Gln
    1310            1315                1320 gcc aaa tgc aac atc tgc aaa gaa tgc ccg att gtt ggg ttc aga     4014
Ala Lys Cys Asn Ile Cys Lys Glu Cys Pro Ile Val Gly Phe Arg
    1325            1330                1335 tac agg agc cta aag cat ttt aat tat gat gtc tgc cag agt tgc     4059
Tyr Arg Ser Leu Lys His Phe Asn Tyr Asp Val Cys Gln Ser Cys
    1340            1345                1350 ttc ttt tct gga aga aca gca aag ggc cac aag tta cat tac ccg     4104
Phe Phe Ser Gly Arg Thr Ala Lys Gly His Lys Leu His Tyr Pro
    1355            1360                1365
```

-continued

| | |
|---|---|
| atg gta gaa tac tgc ata ccg aca aca tct ggg gaa gat gtg aga<br>Met Val Glu Tyr Cys Ile Pro Thr Thr Ser Gly Glu Asp Val Arg<br>1370                          1375                              1380 | 4149 |
| gat ttc act aag gtg ctg aag aac aag ttc agg tcc aag aaa tat<br>Asp Phe Thr Lys Val Leu Lys Asn Lys Phe Arg Ser Lys Lys Tyr<br>1385                          1390                            1395 | 4194 |
| ttt gcc aaa cat cct cgg ctt ggc tac ctg cct gtc cag acc gtg<br>Phe Ala Lys His Pro Arg Leu Gly Tyr Leu Pro Val Gln Thr Val<br>1400                          1405                          1410 | 4239 |
| ctg gaa ggg gac aac tta gaa act cct atc acg ctc atc agt atg<br>Leu Glu Gly Asp Asn Leu Glu Thr Pro Ile Thr Leu Ile Ser Met<br>1415                          1420                          1425 | 4284 |
| tgg cca gag cac tat gac ccc tcc cag tcc cct cag ctg ttt cat<br>Trp Pro Glu His Tyr Asp Pro Ser Gln Ser Pro Gln Leu Phe His<br>1430                          1435                          1440 | 4329 |
| gat gac acc cac tca aga ata gag caa tac gct aca cga ctg gcc<br>Asp Asp Thr His Ser Arg Ile Glu Gln Tyr Ala Thr Arg Leu Ala<br>1445                          1450                          1455 | 4374 |
| cag atg gaa agg aca aac ggg tcc ttc cta act gat agc agc tct<br>Gln Met Glu Arg Thr Asn Gly Ser Phe Leu Thr Asp Ser Ser Ser<br>1460                          1465                          1470 | 4419 |
| aca aca gga agc gtg gag gat gag cat gcc ctc atc cag cag tac<br>Thr Thr Gly Ser Val Glu Asp Glu His Ala Leu Ile Gln Gln Tyr<br>1475                          1480                          1485 | 4464 |
| tgc cag acc ctg ggc ggg gag tca cct gtg agt cag ccg cag agt<br>Cys Gln Thr Leu Gly Gly Glu Ser Pro Val Ser Gln Pro Gln Ser<br>1490                          1495                          1500 | 4509 |
| cca gct cag atc ctg aag tcc gtg gag agg gaa gag cgt ggg gaa<br>Pro Ala Gln Ile Leu Lys Ser Val Glu Arg Glu Glu Arg Gly Glu<br>1505                          1510                          1515 | 4554 |
| ctg gag cgg atc att gct gac ttg gag gaa gag caa aga aat ctg<br>Leu Glu Arg Ile Ile Ala Asp Leu Glu Glu Glu Gln Arg Asn Leu<br>1520                          1525                          1530 | 4599 |
| cag gtg gag tat gag cag ctg aag gag cag cac cta aga agg ggt<br>Gln Val Glu Tyr Glu Gln Leu Lys Glu Gln His Leu Arg Arg Gly<br>1535                          1540                          1545 | 4644 |
| ctc cct gtg ggc tcc cct cca gac tcc atc gta tct cct cac cac<br>Leu Pro Val Gly Ser Pro Pro Asp Ser Ile Val Ser Pro His His<br>1550                          1555                          1560 | 4689 |
| aca tct gag gac tca gaa ctt ata gca gaa gct aaa ctc ctg cgg<br>Thr Ser Glu Asp Ser Glu Leu Ile Ala Glu Ala Lys Leu Leu Arg<br>1565                          1570                          1575 | 4734 |
| cag cac aaa ggg cgg ctg gag gcg agg atg caa att ttg gaa gat<br>Gln His Lys Gly Arg Leu Glu Ala Arg Met Gln Ile Leu Glu Asp<br>1580                          1585                          1590 | 4779 |
| cac aat aaa cag ctg gag tct cag ctg cac cgc ctc aga cag ctc<br>His Asn Lys Gln Leu Glu Ser Gln Leu His Arg Leu Arg Gln Leu<br>1595                          1600                          1605 | 4824 |
| ctg gag cag cct gac tct gac tcc cgc atc aat ggt gtc tcc ccc<br>Leu Glu Gln Pro Asp Ser Asp Ser Arg Ile Asn Gly Val Ser Pro<br>1610                          1615                          1620 | 4869 |
| tgg gct tcc cca cag cat tct gca ttg agc tac tca ctt gac act<br>Trp Ala Ser Pro Gln His Ser Ala Leu Ser Tyr Ser Leu Asp Thr<br>1625                          1630                          1635 | 4914 |
| gac cca ggc cca cag ttc cac cag gca gca tct gag gac ctg ctg<br>Asp Pro Gly Pro Gln Phe His Gln Ala Ala Ser Glu Asp Leu Leu<br>1640                          1645                          1650 | 4959 |
| gcc cca cct cac gac act agc acg gac ctc acg gac gtg atg gag<br>Ala Pro Pro His Asp Thr Ser Thr Asp Leu Thr Asp Val Met Glu | 5004 |

-continued

```
                  1655                1660                1665
cag atc  aac agc acg ttt  ccc  tct tgc agc tca  aat  gtc ccc agc         5049
Gln Ile  Asn Ser Thr Phe  Pro  Ser Cys Ser Ser  Asn  Val Pro Ser
    1670                 1675                1680 agg cca  cag gca atg tga                                                 5067
Arg Pro  Gln Ala Met
    1685
```

<210> SEQ ID NO 21
<211> LENGTH: 1688
<212> TYPE: PRT
<213> ORGANISM: Mus musculus

<400> SEQUENCE: 21

```
Met Asp Tyr Lys Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
                20                  25                  30

Val Pro Asp Tyr Ala Gly Ser Met Ala Lys Tyr Gly Asp Leu Glu Ala
            35                  40                  45

Arg Pro Asp Asp Gly Gln Asn Glu Phe Ser Asp Ile Ile Lys Ser Arg
        50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305                 310                 315                 320

Ile His Ile Gln Ser Ala Val Leu Ala Glu Glu Gly Gln Ser Pro Arg
```

|  |  |  |  |  |  |  |  |  |  |  |  |  |  |  |
|---|---|---|---|---|---|---|---|---|---|---|---|---|---|---|

```
                    325                 330                 335
Ala Glu Thr Pro Ser Thr Val Thr Glu Val Asp Met Asp Leu Asp Ser
                340                 345                 350

Tyr Gln Ile Ala Leu Glu Glu Val Leu Thr Trp Leu Leu Ser Ala Glu
            355                 360                 365

Asp Thr Phe Gln Glu Gln His Asp Ile Ser Asp Val Glu Glu Val
        370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
        675                 680                 685

Lys Asp Leu Leu Glu Thr Val His Val Arg Glu Gln Gly Met Val Lys
    690                 695                 700

Lys Pro Lys Gln Glu Leu Pro Pro Pro Pro Lys Lys Arg Gln
705                 710                 715                 720

Ile His Val Asp Val Glu Ala Lys Lys Phe Asp Ala Ile Ser Thr
                725                 730                 735

Glu Leu Leu Asn Trp Ile Leu Lys Ser Lys Thr Ala Ile Gln Asn Thr
            740                 745                 750
```

-continued

```
Glu Met Lys Glu Tyr Lys Lys Ser Gln Glu Thr Ser Gly Met Lys Lys
            755                 760                 765
Lys Leu Lys Gly Leu Glu Lys Glu Gln Lys Glu Asn Leu Pro Arg Leu
        770                 775                 780
Asp Glu Leu Asn Gln Thr Gly Gln Thr Leu Arg Glu Gln Met Gly Lys
785                 790                 795                 800
Glu Gly Leu Pro Leu Lys Glu Val Asn Asp Val Leu Gly Arg Val Ser
                805                 810                 815
Leu Glu Trp Lys Met Ile Ser Gln Gln Leu Glu Asp Leu Gly Arg Lys
            820                 825                 830
Ile Gln Leu Gln Glu Asp Ile Asn Ala Tyr Phe Lys Gln Leu Asp Ala
        835                 840                 845
Ile Glu Glu Thr Ile Lys Glu Lys Glu Trp Leu Arg Gly Thr Pro
    850                 855                 860
Ile Ser Glu Ser Pro Arg Gln Pro Leu Pro Gly Leu Lys Asp Ser Cys
865                 870                 875                 880
Gln Arg Glu Leu Thr Asp Leu Leu Gly Leu His Pro Arg Ile Glu Thr
                885                 890                 895
Leu Cys Ala Ser Cys Ser Ala Leu Lys Ser Gln Pro Cys Val Pro Gly
            900                 905                 910
Phe Val Gln Gln Gly Phe Asp Asp Leu Arg His His Tyr Gln Ala Val
        915                 920                 925
Ala Lys Ala Leu Glu Glu Tyr Gln Gln Leu Glu Asn Glu Leu Lys
    930                 935                 940
Ser Gln Pro Gly Pro Glu Tyr Leu Asp Thr Leu Asn Thr Leu Lys Lys
945                 950                 955                 960
Met Leu Ser Glu Ser Glu Lys Ala Ala Gln Ala Ser Leu Asn Ala Leu
                965                 970                 975
Asn Asp Pro Ile Ala Val Glu Gln Ala Leu Gln Glu Lys Lys Ala Leu
            980                 985                 990
Asp Glu Thr Leu Glu Asn Gln Lys His Thr Leu His Lys Leu Ser Glu
        995                 1000                1005
Glu Thr Lys Thr Leu Glu Lys Asn Met Leu Pro Asp Val Gly Lys
    1010                1015                1020
Met Tyr Lys Gln Glu Phe Asp Asp Val Gln Gly Arg Trp Asn Lys
    1025                1030                1035
Val Lys Thr Lys Val Ser Arg Asp Leu His Leu Leu Glu Glu Ile
    1040                1045                1050
Ala His Arg Asp Phe Gly Pro Ser Ser Gln His Phe Leu Ser Thr
    1055                1060                1065
Ser Val Gln Leu Pro Trp Gln Arg Ser Ile Ser His Asn Lys Val
    1070                1075                1080
Pro Tyr Tyr Ile Asn His Gln Thr Gln Thr Thr Cys Trp Asp His
    1085                1090                1095
Pro Lys Met Thr Glu Leu Phe Gln Ser Leu Ala Asp Leu Asn Asn
    1100                1105                1110
Val Arg Phe Ser Ala Tyr Arg Thr Ala Ile Lys Ile Arg Arg Leu
    1115                1120                1125
Gln Lys Ala Leu Cys Leu Asp Leu Leu Glu Leu Asn Thr Thr Asn
    1130                1135                1140
Glu Val Phe Lys Gln His Lys Leu Asn Gln Asn Asp Gln Leu Leu
    1145                1150                1155
```

-continued

Ser Val Pro Asp Val Ile Asn Cys Leu Thr Thr Thr Tyr Asp Gly
1160                1165                1170

Leu Glu Gln Leu His Lys Asp Leu Val Asn Val Pro Leu Cys Val
1175                1180                1185

Asp Met Cys Leu Asn Trp Leu Asn Val Tyr Asp Thr Gly Arg
1190                1195                1200

Thr Gly Lys Ile Arg Val Gln Ser Leu Lys Ile Gly Leu Met Ser
1205                1210                1215

Leu Ser Lys Gly Leu Leu Glu Glu Lys Tyr Arg Cys Leu Phe Lys
1220                1225                1230

Glu Val Ala Gly Pro Thr Glu Met Cys Asp Gln Arg Gln Leu Gly
1235                1240                1245

Leu Leu Leu His Asp Ala Ile Gln Ile Pro Arg Gln Leu Gly Glu
1250                1255                1260

Val Ala Ala Phe Gly Gly Ser Asn Ile Glu Pro Ser Val Arg Ser
1265                1270                1275

Cys Phe Gln Gln Asn Asn Asn Lys Pro Glu Ile Ser Val Lys Glu
1280                1285                1290

Phe Ile Asp Trp Met His Leu Glu Pro Gln Ser Met Val Trp Leu
1295                1300                1305

Pro Val Leu His Arg Val Ala Ala Glu Thr Ala Lys His Gln
1310                1315                1320

Ala Lys Cys Asn Ile Cys Lys Glu Cys Pro Ile Val Gly Phe Arg
1325                1330                1335

Tyr Arg Ser Leu Lys His Phe Asn Tyr Asp Val Cys Gln Ser Cys
1340                1345                1350

Phe Phe Ser Gly Arg Thr Ala Lys Gly His Lys Leu His Tyr Pro
1355                1360                1365

Met Val Glu Tyr Cys Ile Pro Thr Thr Ser Gly Glu Asp Val Arg
1370                1375                1380

Asp Phe Thr Lys Val Leu Lys Asn Lys Phe Arg Ser Lys Lys Tyr
1385                1390                1395

Phe Ala Lys His Pro Arg Leu Gly Tyr Leu Pro Val Gln Thr Val
1400                1405                1410

Leu Glu Gly Asp Asn Leu Glu Thr Pro Ile Thr Leu Ile Ser Met
1415                1420                1425

Trp Pro Glu His Tyr Asp Pro Ser Gln Ser Pro Gln Leu Phe His
1430                1435                1440

Asp Asp Thr His Ser Arg Ile Glu Gln Tyr Ala Thr Arg Leu Ala
1445                1450                1455

Gln Met Glu Arg Thr Asn Gly Ser Phe Leu Thr Asp Ser Ser Ser
1460                1465                1470

Thr Thr Gly Ser Val Glu Asp Glu His Ala Leu Ile Gln Gln Tyr
1475                1480                1485

Cys Gln Thr Leu Gly Gly Glu Ser Pro Val Ser Gln Pro Gln Ser
1490                1495                1500

Pro Ala Gln Ile Leu Lys Ser Val Glu Arg Glu Arg Gly Glu
1505                1510                1515

Leu Glu Arg Ile Ile Ala Asp Leu Glu Glu Gln Arg Asn Leu
1520                1525                1530

Gln Val Glu Tyr Glu Gln Leu Lys Glu Gln His Leu Arg Arg Gly
1535                1540                1545

Leu Pro Val Gly Ser Pro Pro Asp Ser Ile Val Ser Pro His His

-continued

```
                       1550                1555                1560

Thr Ser  Glu Asp Ser Glu  Leu  Ile Ala Glu Ala  Lys  Leu Leu Arg
         1565                1570                1575

Gln His  Lys Gly Arg Leu  Glu  Ala Arg Met Gln  Ile  Leu Glu Asp
         1580                1585                1590

His Asn  Lys Gln Leu Glu  Ser  Gln Leu His Arg  Leu  Arg Gln Leu
         1595                1600                1605

Leu Glu  Gln Pro Asp Ser  Asp  Ser Arg Ile Asn  Gly  Val Ser Pro
         1610                1615                1620

Trp Ala  Ser Pro Gln His  Ser  Ala Leu Ser Tyr  Ser  Leu Asp Thr
         1625                1630                1635

Asp Pro  Gly Pro Gln Phe  His  Gln Ala Ala Ser  Glu  Asp Leu Leu
         1640                1645                1650

Ala Pro  Pro His Asp Thr  Ser  Thr Asp Leu Thr  Asp  Val Met Glu
         1655                1660                1665

Gln Ile  Asn Ser Thr Phe  Pro  Ser Cys Ser Ser  Asn  Val Pro Ser
         1670                1675                1680

Arg Pro  Gln Ala Met
         1685

<210> SEQ ID NO 22
<211> LENGTH: 6027
<212> TYPE: DNA
<213> ORGANISM: Mus musculus
<220> FEATURE:
<221> NAME/KEY: CDS
<222> LOCATION: (1)..(6027)
<220> FEATURE:
<221> NAME/KEY: misc_feature
<222> LOCATION: (1)..(117)

<400> SEQUENCE: 22 atg gac tac aag gac gac gat gac aag ggc tac ggc cgc aag aaa cgc        48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac        96
Arg Gln Arg Arg Arg Gly Gly Ser Thr Met Ser Gly Tyr Pro Tyr Asp
            20                  25                  30 gtc cca gac tat gct ggc tcc atg gcc aag tat ggg gac ctt gaa gcc       144
Val Pro Asp Tyr Ala Gly Ser Met Ala Lys Tyr Gly Asp Leu Glu Ala
        35                  40                  45 agg cct gat gat ggg cag aac gaa ttc agt gac atc att aag tcc aga       192
Arg Pro Asp Asp Gly Gln Asn Glu Phe Ser Asp Ile Ile Lys Ser Arg
    50                  55                  60 tct gat gaa cac aat gat gta cag aag aaa acc ttt acc aaa tgg ata       240
Ser Asp Glu His Asn Asp Val Gln Lys Lys Thr Phe Thr Lys Trp Ile
65                  70                  75                  80 aac gct cga ttt tcc aag agt ggg aaa cca ccc atc agt gat atg ttc       288
Asn Ala Arg Phe Ser Lys Ser Gly Lys Pro Pro Ile Ser Asp Met Phe
                85                  90                  95 tca gac ctc aaa gat ggg aga aag ctc ttg gat ctt ctc gaa ggc ctc       336
Ser Asp Leu Lys Asp Gly Arg Lys Leu Leu Asp Leu Leu Glu Gly Leu
            100                 105                 110 aca gga aca tca ttg cca aag gaa cgt ggt tcc aca agg gtg cat gcc       384
Thr Gly Thr Ser Leu Pro Lys Glu Arg Gly Ser Thr Arg Val His Ala
        115                 120                 125 tta aac aat gtc aac cga gtg cta cag gtt tta cat cag aac aat gtg       432
Leu Asn Asn Val Asn Arg Val Leu Gln Val Leu His Gln Asn Asn Val
    130                 135                 140
```

```
gac ttg gtg aat att gga ggc acg gac att gtg gct gga aat ccc aag    480
Asp Leu Val Asn Ile Gly Gly Thr Asp Ile Val Ala Gly Asn Pro Lys
145                 150                 155                 160 ctg act tta ggg tta ctc tgg agc atc att ctg cac tgg cag gtg aag    528
Leu Thr Leu Gly Leu Leu Trp Ser Ile Ile Leu His Trp Gln Val Lys
                165                 170                 175 gat gtc atg aaa gat atc atg tca gac ctg cag cag aca aac agc gag    576
Asp Val Met Lys Asp Ile Met Ser Asp Leu Gln Gln Thr Asn Ser Glu
            180                 185                 190 aag atc ctg ctg agc tgg gtg cgg cag acc acc agg ccc tac agt caa    624
Lys Ile Leu Leu Ser Trp Val Arg Gln Thr Thr Arg Pro Tyr Ser Gln
        195                 200                 205 gtc aac gtc ctc aac ttc acc acc agc tgg acc gat gga ctc gcg ttc    672
Val Asn Val Leu Asn Phe Thr Thr Ser Trp Thr Asp Gly Leu Ala Phe
    210                 215                 220 aac gcc gtg ctc cac cgg cac aaa cca gat ctc ttc gac tgg gac gag    720
Asn Ala Val Leu His Arg His Lys Pro Asp Leu Phe Asp Trp Asp Glu
225                 230                 235                 240 atg gtc aaa atg tcc cca att gag aga ctt gac cat gct ttt gac aag    768
Met Val Lys Met Ser Pro Ile Glu Arg Leu Asp His Ala Phe Asp Lys
                245                 250                 255 gcc cac act tct ttg gga att gaa aag ctc cta agt cct gaa act gtt    816
Ala His Thr Ser Leu Gly Ile Glu Lys Leu Leu Ser Pro Glu Thr Val
            260                 265                 270 gct gtg cat ctc cct gac aag aaa tcc ata att atg tat tta acg tct    864
Ala Val His Leu Pro Asp Lys Lys Ser Ile Ile Met Tyr Leu Thr Ser
        275                 280                 285 ctg ttt gag gtg ctt cct cag caa gtc acg ata gat gcc atc cga gag    912
Leu Phe Glu Val Leu Pro Gln Gln Val Thr Ile Asp Ala Ile Arg Glu
    290                 295                 300 gtg gag act ctc cca agg aag tat aag aaa gaa tgt gaa gag gaa gaa    960
Val Glu Thr Leu Pro Arg Lys Tyr Lys Lys Glu Cys Glu Glu Glu Glu
305                 310                 315                 320 att cat atc cag agt gca gtg ctg gca gag gaa ggc cag agt ccc cga   1008
Ile His Ile Gln Ser Ala Val Leu Ala Glu Glu Gly Gln Ser Pro Arg
                325                 330                 335 gct gag acc cct agc acc gtc act gaa gtg gac atg gat ttg gac agc   1056
Ala Glu Thr Pro Ser Thr Val Thr Glu Val Asp Met Asp Leu Asp Ser
            340                 345                 350 tac cag ata gcg cta gag gaa gtg ctg acg tgg ctg ctg tcc gcg gag   1104
Tyr Gln Ile Ala Leu Glu Glu Val Leu Thr Trp Leu Leu Ser Ala Glu
        355                 360                 365 gac acg ttc cag gag caa cat gac att tct gat gat gtc gaa gaa gtc   1152
Asp Thr Phe Gln Glu Gln His Asp Ile Ser Asp Asp Val Glu Glu Val
    370                 375                 380 aaa gag cag ttt gct acc cat gaa act ttt atg atg gag ctg aca gca   1200
Lys Glu Gln Phe Ala Thr His Glu Thr Phe Met Met Glu Leu Thr Ala
385                 390                 395                 400 cac cag agc agc gtg ggg agc gtc ctg cag gct ggc aac cag ctg atg   1248
His Gln Ser Ser Val Gly Ser Val Leu Gln Ala Gly Asn Gln Leu Met
                405                 410                 415 aca caa ggg act ctg tcc aga gag gag gag ttt gag atc cag gaa cag   1296
Thr Gln Gly Thr Leu Ser Arg Glu Glu Glu Phe Glu Ile Gln Glu Gln
            420                 425                 430 atg acc ttg ctg aat gca agg tgg gag gcg ctc cgg gtg gag agc atg   1344
Met Thr Leu Leu Asn Ala Arg Trp Glu Ala Leu Arg Val Glu Ser Met
        435                 440                 445 gag agg cag tcc cgg ctg cac gac gct ctg atg gag ctg cag aag aaa   1392
Glu Arg Gln Ser Arg Leu His Asp Ala Leu Met Glu Leu Gln Lys Lys
    450                 455                 460
```

```
cag ctg cag cag ctc tca agc tgg ctg gcc ctc aca gaa gag cgc att      1440
Gln Leu Gln Gln Leu Ser Ser Trp Leu Ala Leu Thr Glu Glu Arg Ile
465                 470                 475                 480 cag aag atg gag agc ctc ccg ctg ggt gat gac ctg ccc tcc ctg cag      1488
Gln Lys Met Glu Ser Leu Pro Leu Gly Asp Asp Leu Pro Ser Leu Gln
                485                 490                 495 aag ctg ctt caa gaa cat aaa agt ttg caa aat gac ctt gaa gct gaa      1536
Lys Leu Leu Gln Glu His Lys Ser Leu Gln Asn Asp Leu Glu Ala Glu
            500                 505                 510 cag gtg aag gta aat tcc tta act cac atg gtg gtg att gtg gat gaa      1584
Gln Val Lys Val Asn Ser Leu Thr His Met Val Val Ile Val Asp Glu
        515                 520                 525 aac agt ggg gag agt gcc aca gct ctt ctg gaa gat cag tta cag aaa      1632
Asn Ser Gly Glu Ser Ala Thr Ala Leu Leu Glu Asp Gln Leu Gln Lys
    530                 535                 540 ctg ggt gag cgc tgg aca gct gta tgc cgc tgg act gaa gaa cgt tgg      1680
Leu Gly Glu Arg Trp Thr Ala Val Cys Arg Trp Thr Glu Glu Arg Trp
545                 550                 555                 560 aac agg ttg caa gaa atc agt att ctg tgg cag gaa tta ttg gaa gag      1728
Asn Arg Leu Gln Glu Ile Ser Ile Leu Trp Gln Glu Leu Leu Glu Glu
                565                 570                 575 cag tgt ctg ttg gag gct tgg ctc acc gaa aag gaa gag gct ttg gat      1776
Gln Cys Leu Leu Glu Ala Trp Leu Thr Glu Lys Glu Glu Ala Leu Asp
            580                 585                 590 aaa gtt caa acc agc aac ttt aaa gac cag aag gaa cta agt gtc agt      1824
Lys Val Gln Thr Ser Asn Phe Lys Asp Gln Lys Glu Leu Ser Val Ser
        595                 600                 605 gtc cgg cgt ctg gct ata ttg aag gaa gac atg gaa atg aag agg cag      1872
Val Arg Arg Leu Ala Ile Leu Lys Glu Asp Met Glu Met Lys Arg Gln
    610                 615                 620 act ctg gat caa ctg agt gag att ggc cag gat gtg ggc caa tta ctc      1920
Thr Leu Asp Gln Leu Ser Glu Ile Gly Gln Asp Val Gly Gln Leu Leu
625                 630                 635                 640 agt aat ccc aag gca tct aag aag atg aac agt gac tct gag gag cta      1968
Ser Asn Pro Lys Ala Ser Lys Lys Met Asn Ser Asp Ser Glu Glu Leu
                645                 650                 655 aca cag aga tgg gat tct ctg gtt cag aga ctc gaa gac tct tct aac      2016
Thr Gln Arg Trp Asp Ser Leu Val Gln Arg Leu Glu Asp Ser Ser Asn
            660                 665                 670 cag gtg act cag gcg gta gcg aag ctc ggc atg tcc cag att cca cag      2064
Gln Val Thr Gln Ala Val Ala Lys Leu Gly Met Ser Gln Ile Pro Gln
        675                 680                 685 aag gac cta ttg gag acc gtt cat gtg aga gaa caa ggg atg gtg aag      2112
Lys Asp Leu Leu Glu Thr Val His Val Arg Glu Gln Gly Met Val Lys
    690                 695                 700 aag ccc aag cag gaa ctg cct cct cct ccc cca cca aag aag aga cag      2160
Lys Pro Lys Gln Glu Leu Pro Pro Pro Pro Pro Lys Lys Arg Gln
705                 710                 715                 720 att cac gtg gac gtg gag gcc aag aaa aag ttt gat gct ata agt aca      2208
Ile His Val Asp Val Glu Ala Lys Lys Lys Phe Asp Ala Ile Ser Thr
                725                 730                 735 gag ctg ctg aac tgg att ttg aaa tca aag act gcc att cag aac aca      2256
Glu Leu Leu Asn Trp Ile Leu Lys Ser Lys Thr Ala Ile Gln Asn Thr
            740                 745                 750 gag atg aaa gaa tat aag aag tcg cag gag acc tca gga atg aaa aag      2304
Glu Met Lys Glu Tyr Lys Lys Ser Gln Glu Thr Ser Gly Met Lys Lys
        755                 760                 765 aaa ttg aag gga tta gag aaa gaa cag aag gaa aat ctg ccc cga ctg      2352
Lys Leu Lys Gly Leu Glu Lys Glu Gln Lys Glu Asn Leu Pro Arg Leu
```

```
                        770                 775                 780
gac gaa ctg aat caa acc gga caa acc ctc cgg gag caa atg gga aaa    2400
Asp Glu Leu Asn Gln Thr Gly Gln Thr Leu Arg Glu Gln Met Gly Lys
785                 790                 795                 800 gaa ggc ctt cca ctg aaa gaa gta aac gat gtt ctg gaa agg gtt tcg    2448
Glu Gly Leu Pro Leu Lys Glu Val Asn Asp Val Leu Glu Arg Val Ser
            805                 810                 815 ttg gag tgg aag atg ata tct cag cag cta gaa gat ctg gga agg aag    2496
Leu Glu Trp Lys Met Ile Ser Gln Gln Leu Glu Asp Leu Gly Arg Lys
        820                 825                 830 atc cag ctg cag gaa gat ata aat gct tat ttt aag cag ctt gat gcc    2544
Ile Gln Leu Gln Glu Asp Ile Asn Ala Tyr Phe Lys Gln Leu Asp Ala
    835                 840                 845 att gag gag acc atc aag gag aag gaa gag tgg ctg agg ggc aca ccc    2592
Ile Glu Glu Thr Ile Lys Glu Lys Glu Glu Trp Leu Arg Gly Thr Pro
850                 855                 860 att tct gaa tcg ccc cgg cag ccc ttg cca ggc tta aag gat tct tgc    2640
Ile Ser Glu Ser Pro Arg Gln Pro Leu Pro Gly Leu Lys Asp Ser Cys
865                 870                 875                 880 cag agg gaa ctg aca gat ctc ctt ggc ctt cac ccc aga att gag acg    2688
Gln Arg Glu Leu Thr Asp Leu Leu Gly Leu His Pro Arg Ile Glu Thr
            885                 890                 895 ctg tgt gca agc tgt tca gcc ctg aag tct cag ccc tgt gtc cca ggt    2736
Leu Cys Ala Ser Cys Ser Ala Leu Lys Ser Gln Pro Cys Val Pro Gly
        900                 905                 910 ttt gtc cag cag ggt ttt gac gac ctt cga cat cat tac cag gct gtt    2784
Phe Val Gln Gln Gly Phe Asp Asp Leu Arg His His Tyr Gln Ala Val
    915                 920                 925 gcg aag gct tta gag gaa tac caa caa caa cta gaa aat gag ctg aag    2832
Ala Lys Ala Leu Glu Glu Tyr Gln Gln Gln Leu Glu Asn Glu Leu Lys
930                 935                 940 agc cag cct gga ccc gag tat ttg gac aca ctg aat acc ctg aaa aaa    2880
Ser Gln Pro Gly Pro Glu Tyr Leu Asp Thr Leu Asn Thr Leu Lys Lys
945                 950                 955                 960 atg cta agc gag tca gaa aag gcg gcc cag gcc tct ctg aat gcc ctg    2928
Met Leu Ser Glu Ser Glu Lys Ala Ala Gln Ala Ser Leu Asn Ala Leu
            965                 970                 975 aac gat ccc ata gcg gtg gag cag gcc ctg cag gag aaa aag gcc ctt    2976
Asn Asp Pro Ile Ala Val Glu Gln Ala Leu Gln Glu Lys Lys Ala Leu
        980                 985                 990 gat gaa acc ctt gag aat cag aaa  cat acg tta cat aag  ctt tca gaa  3024
Asp Glu Thr Leu Glu Asn Gln Lys  His Thr Leu His Lys  Leu Ser Glu
    995                 1000                1005 gaa acg  aag act ttg gag aaa  aat atg ctt cct gat  gtg ggg aaa     3069
Glu Thr  Lys Thr Leu Glu Lys  Asn Met Leu Pro Asp  Val Gly Lys
1010                 1015                1020 atg tat  aaa caa gaa ttt gat  gat gtc caa ggc aga  tgg aat aaa     3114
Met Tyr  Lys Gln Glu Phe Asp  Asp Val Gln Gly Arg  Trp Asn Lys
1025                 1030                1035 gta aag  acc aag gtt tcc aga  gac tta cac ttg ctc  gag gaa atc     3159
Val Lys  Thr Lys Val Ser Arg  Asp Leu His Leu Leu  Glu Glu Ile
1040                 1045                1050 acc ccc  aga ctc cga gat ttt  gag gct gat tca gaa  gtc att gag     3204
Thr Pro  Arg Leu Arg Asp Phe  Glu Ala Asp Ser Glu  Val Ile Glu
1055                 1060                1065 aag tgg  gtg agt ggc atc aaa  gac ttc ctc atg aaa  gaa cag gct     3249
Lys Trp  Val Ser Gly Ile Lys  Asp Phe Leu Met Lys  Glu Gln Ala
1070                 1075                1080 gcc caa  gga gac gct gct gcg  cag agc cag ctt gac  caa tgt gct     3294
```

-continued

```
    Ala Gln Gly Asp Ala Ala Ala Gln Ser Gln Leu Asp Gln Cys Ala
        1085                1090                1095 acg ttt gct aat gaa atc gaa acc atc gag tca tct ctg aag aac      3339
Thr Phe Ala Asn Glu Ile Glu Thr Ile Glu Ser Ser Leu Lys Asn
1100                1105                1110 atg agg gaa gta gag act agc ctt cag agg tgt cca gtc act gga      3384
Met Arg Glu Val Glu Thr Ser Leu Gln Arg Cys Pro Val Thr Gly
    1115                1120                1125 gtc aag aca tgg gta cag gca aga cta gtg gat tac caa tcc caa      3429
Val Lys Thr Trp Val Gln Ala Arg Leu Val Asp Tyr Gln Ser Gln
    1130                1135                1140 ctg gag aaa ttc agc aaa gag att gct att caa aaa agc agg ctg      3474
Leu Glu Lys Phe Ser Lys Glu Ile Ala Ile Gln Lys Ser Arg Leu
    1145                1150                1155 tta gat agt caa gaa aaa gcc ctg aac ttg aaa aag gat ttg gct      3519
Leu Asp Ser Gln Glu Lys Ala Leu Asn Leu Lys Lys Asp Leu Ala
    1160                1165                1170 gag atg cag gag tgg atg gca cag gct gaa gag gac tac ctg gag      3564
Glu Met Gln Glu Trp Met Ala Gln Ala Glu Glu Asp Tyr Leu Glu
1175                1180                1185 agg gac ttc gag tac aaa tct cca gaa gaa ctc gag agt gcg gtg      3609
Arg Asp Phe Glu Tyr Lys Ser Pro Glu Glu Leu Glu Ser Ala Val
    1190                1195                1200 gag gaa atg aag agg gca aaa gag gat gtg ctg cag aag gag gtg      3654
Glu Glu Met Lys Arg Ala Lys Glu Asp Val Leu Gln Lys Glu Val
1205                1210                1215 agg gtg aaa att ctg aag gac agc atc aag ctg gtg gct gcc aag      3699
Arg Val Lys Ile Leu Lys Asp Ser Ile Lys Leu Val Ala Ala Lys
    1220                1225                1230 gtg ccc tct ggt ggc cag gag ttg acg tcg gaa ttc aac gag gtg      3744
Val Pro Ser Gly Gly Gln Glu Leu Thr Ser Glu Phe Asn Glu Val
    1235                1240                1245 ctg gag agc tac cag ctt ctg tgc aat aga att cga ggg aag tgc      3789
Leu Glu Ser Tyr Gln Leu Leu Cys Asn Arg Ile Arg Gly Lys Cys
    1250                1255                1260 cac aca ctg gag gag gtc tgg tct tgc tgg gtg gag ctg ctt cac      3834
His Thr Leu Glu Glu Val Trp Ser Cys Trp Val Glu Leu Leu His
    1265                1270                1275 tat ctg gac ctg gag acc acg tgg ttg aac acc ttg gag gag cgc      3879
Tyr Leu Asp Leu Glu Thr Thr Trp Leu Asn Thr Leu Glu Glu Arg
1280                1285                1290 gtg agg agc acg gag gcc ctg cct gag agg gca gaa gct gtt cat      3924
Val Arg Ser Thr Glu Ala Leu Pro Glu Arg Ala Glu Ala Val His
    1295                1300                1305 gaa gct ctg gag tct ctt gag tct gtt ttg cgc cat cca gcg gat      3969
Glu Ala Leu Glu Ser Leu Glu Ser Val Leu Arg His Pro Ala Asp
    1310                1315                1320 aat cgc acc cag att cgg gaa ctt ggg cag act ctg att gat ggt      4014
Asn Arg Thr Gln Ile Arg Glu Leu Gly Gln Thr Leu Ile Asp Gly
    1325                1330                1335 gga atc ctg gat gac ata atc agc gag aag ctg gag gct ttt aac      4059
Gly Ile Leu Asp Asp Ile Ile Ser Glu Lys Leu Glu Ala Phe Asn
1340                1345                1350 agc cgc tac gaa gag ctg agt cac ttg gcg gag agc aaa cag att      4104
Ser Arg Tyr Glu Glu Leu Ser His Leu Ala Glu Ser Lys Gln Ile
    1355                1360                1365 tct ttg gag aag caa gcc cac aga gat ttt ggg cca tct tct caa      4149
Ser Leu Glu Lys Gln Ala His Arg Asp Phe Gly Pro Ser Ser Gln
    1370                1375                1380
```

```
cac ttt ctg tcc act tca gtc cag ctg ccg tgg cag aga tcc att    4194
His Phe Leu Ser Thr Ser Val Gln Leu Pro Trp Gln Arg Ser Ile
1385             1390                 1395 tca cat aat aaa gtg ccc tat tac atc aac cat caa aca cag aca    4239
Ser His Asn Lys Val Pro Tyr Tyr Ile Asn His Gln Thr Gln Thr
1400             1405                 1410 acc tgt tgg gat cat cct aaa atg act gag ctc ttc caa tcc ctt    4284
Thr Cys Trp Asp His Pro Lys Met Thr Glu Leu Phe Gln Ser Leu
1415             1420                 1425 gct gat ctg aat aat gta cgt ttc tct gcc tac cgc aca gca atc    4329
Ala Asp Leu Asn Asn Val Arg Phe Ser Ala Tyr Arg Thr Ala Ile
1430             1435                 1440 aaa att cga agg ctg caa aaa gca tta tgt ctg gat ctc tta gag    4374
Lys Ile Arg Arg Leu Gln Lys Ala Leu Cys Leu Asp Leu Leu Glu
1445             1450                 1455 ctg aat acg acg aat gaa gtt ttc aag cag cac aaa ctg aac caa    4419
Leu Asn Thr Thr Asn Glu Val Phe Lys Gln His Lys Leu Asn Gln
1460             1465                 1470 aat gat cag ctc ctg agt gtc cca gac gtc atc aac tgt ctg acc    4464
Asn Asp Gln Leu Leu Ser Val Pro Asp Val Ile Asn Cys Leu Thr
1475             1480                 1485 acc act tac gat ggg ctt gag cag ctg cac aag gac ttg gtc aat    4509
Thr Thr Tyr Asp Gly Leu Glu Gln Leu His Lys Asp Leu Val Asn
1490             1495                 1500 gtt cca ctc tgc gtc gat atg tgt ctc aac tgg ctg ctc aac gta    4554
Val Pro Leu Cys Val Asp Met Cys Leu Asn Trp Leu Leu Asn Val
1505             1510                 1515 tac gac acg ggc cgg act gga aaa att cgg gta cag agt ctg aag    4599
Tyr Asp Thr Gly Arg Thr Gly Lys Ile Arg Val Gln Ser Leu Lys
1520             1525                 1530 att gga ttg atg tct ctc tcc aaa ggc ctc tta gaa gag aaa tac    4644
Ile Gly Leu Met Ser Leu Ser Lys Gly Leu Leu Glu Glu Lys Tyr
1535             1540                 1545 aga tgt ctc ttt aag gag gtg gca ggg cca act gag atg tgt gac    4689
Arg Cys Leu Phe Lys Glu Val Ala Gly Pro Thr Glu Met Cys Asp
1550             1555                 1560 cag cgg cag ctt ggc ctg cta ctt cac gat gcc atc cag atc cct    4734
Gln Arg Gln Leu Gly Leu Leu Leu His Asp Ala Ile Gln Ile Pro
1565             1570                 1575 agg cag ctg ggg gaa gta gca gcc ttt ggg ggc agt aac att gag    4779
Arg Gln Leu Gly Glu Val Ala Ala Phe Gly Gly Ser Asn Ile Glu
1580             1585                 1590 ccc agt gtc cgc agc tgc ttc cag cag aat aac aac aag cca gaa    4824
Pro Ser Val Arg Ser Cys Phe Gln Gln Asn Asn Asn Lys Pro Glu
1595             1600                 1605 atc agt gtg aag gag ttt ata gac tgg atg cat ttg gaa ccc cag    4869
Ile Ser Val Lys Glu Phe Ile Asp Trp Met His Leu Glu Pro Gln
1610             1615                 1620 tcc atg gtg tgg ttg ccg gtt ctg cat cgg gtc gca gct gct gag    4914
Ser Met Val Trp Leu Pro Val Leu His Arg Val Ala Ala Ala Glu
1625             1630                 1635 act gca aaa cat cag gcc aaa tgc aac atc tgc aaa gaa tgc ccg    4959
Thr Ala Lys His Gln Ala Lys Cys Asn Ile Cys Lys Glu Cys Pro
1640             1645                 1650 att gtt ggg ttc aga tac agg agc tta aag cat ttt aat tat gat    5004
Ile Val Gly Phe Arg Tyr Arg Ser Leu Lys His Phe Asn Tyr Asp
1655             1660                 1665 gtc tgc cag agt tgc ttc ttt tct gga aga aca gca aag ggc cac    5049
Val Cys Gln Ser Cys Phe Phe Ser Gly Arg Thr Ala Lys Gly His
1670             1675                 1680
```

-continued

```
aag tta cat tac ccg atg gta gaa tac tgc ata ccg aca aca tct      5094
Lys Leu His Tyr Pro Met Val Glu Tyr Cys Ile Pro Thr Thr Ser
    1685            1690                1695 ggg gaa gat gtg aga gat ttc act aag gtg ctg aag aac aag ttc      5139
Gly Glu Asp Val Arg Asp Phe Thr Lys Val Leu Lys Asn Lys Phe
1700                1705                1710 agg tcc aag aaa tat ttt gcc aaa cat cct cgg ctt ggc tac ctg      5184
Arg Ser Lys Lys Tyr Phe Ala Lys His Pro Arg Leu Gly Tyr Leu
    1715                1720                1725 cct gtc cag acc gtg ctg gaa ggg gac aac tta gaa act cct atc      5229
Pro Val Gln Thr Val Leu Glu Gly Asp Asn Leu Glu Thr Pro Ile
1730                1735                1740 acg ctc atc agt atg tgg cca gag cac tat gac ccc tcc cag tcc      5274
Thr Leu Ile Ser Met Trp Pro Glu His Tyr Asp Pro Ser Gln Ser
    1745                1750                1755 cct cag ctg ttt cat gat gac acc cac tca aga ata gag caa tac      5319
Pro Gln Leu Phe His Asp Asp Thr His Ser Arg Ile Glu Gln Tyr
1760                1765                1770 gct aca cga ctg gcc cag atg gaa agg aca aac ggg tcc ttc cta      5364
Ala Thr Arg Leu Ala Gln Met Glu Arg Thr Asn Gly Ser Phe Leu
    1775                1780                1785 act gat agc agc tct aca aca gga agc gtg gag gat gag cat gcc      5409
Thr Asp Ser Ser Ser Thr Thr Gly Ser Val Glu Asp Glu His Ala
1790                1795                1800 ctc atc cag cag tac tgc cag acc ctg ggc ggg gag tca cct gtg      5454
Leu Ile Gln Gln Tyr Cys Gln Thr Leu Gly Gly Glu Ser Pro Val
    1805                1810                1815 agt cag ccg cag agt cca gct cag atc ctg aag tcc gtg gag agg      5499
Ser Gln Pro Gln Ser Pro Ala Gln Ile Leu Lys Ser Val Glu Arg
1820                1825                1830 gaa gag cgt ggg gaa ctg gag cgg atc att gct gac ttg gag gaa      5544
Glu Glu Arg Gly Glu Leu Glu Arg Ile Ile Ala Asp Leu Glu Glu
    1835                1840                1845 gag caa aga aat ctg cag gtg gag tat gag cag ctg aag gag cag      5589
Glu Gln Arg Asn Leu Gln Val Glu Tyr Glu Gln Leu Lys Glu Gln
1850                1855                1860 cac cta aga agg ggt ctc cct gtg ggc tcc cct cca gac tcc atc      5634
His Leu Arg Arg Gly Leu Pro Val Gly Ser Pro Pro Asp Ser Ile
    1865                1870                1875 gta tct cct cac cac aca tct gag gac tca gaa ctt ata gca gaa      5679
Val Ser Pro His His Thr Ser Glu Asp Ser Glu Leu Ile Ala Glu
1880                1885                1890 gct aaa ctc ctg cgg cag cac aaa ggg cgg ctg gag gcg agg atg      5724
Ala Lys Leu Leu Arg Gln His Lys Gly Arg Leu Glu Ala Arg Met
    1895                1900                1905 caa att ttg gaa gat cac aat aaa cag ctg gag tct cag ctg cac      5769
Gln Ile Leu Glu Asp His Asn Lys Gln Leu Glu Ser Gln Leu His
1910                1915                1920 cgc ctc aga cag ctc ctg gag cag cct gac tct gac tcc cgc atc      5814
Arg Leu Arg Gln Leu Leu Glu Gln Pro Asp Ser Asp Ser Arg Ile
    1925                1930                1935 aat ggt gtc tcc ccc tgg gct tcc cca cag cat tct gca ttg agc      5859
Asn Gly Val Ser Pro Trp Ala Ser Pro Gln His Ser Ala Leu Ser
1940                1945                1950 tac tca ctt gac act gac cca ggc cca cag ttc cac cag gca gca      5904
Tyr Ser Leu Asp Thr Asp Pro Gly Pro Gln Phe His Gln Ala Ala
    1955                1960                1965 tct gag gac ctg ctg gcc cca cct cac gac act agc acg gac ctc      5949
Ser Glu Asp Leu Leu Ala Pro Pro His Asp Thr Ser Thr Asp Leu
```

```
                1970              1975              1980
acg gac  gtg atg gag cag atc  aac agc acg ttt ccc  tct tgc agc    5994
Thr Asp  Val Met Glu Gln Ile  Asn Ser Thr Phe Pro  Ser Cys Ser
1985                      1990                  1995 tca aat  gtc ccc agc agg cca  cag gca atg tga                     6027
Ser Asn  Val Pro Ser Arg Pro  Gln Ala Met
    2000                  2005
```

<210> SEQ ID NO 23
<211> LENGTH: 2008
<212> TYPE: PRT
<213> ORGANISM: Mus musculus

<400> SEQUENCE: 23

```
Met Asp Tyr Lys Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65              70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145             150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225             230                 235                 240

Met Val Lys Met Ser Pro Ile Glu Arg Leu Asp His Ala Phe Asp Lys
                245                 250                 255

Ala His Thr Ser Leu Gly Ile Glu Lys Leu Leu Ser Pro Glu Thr Val
            260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
    290                 295                 300

Val Glu Thr Leu Pro Arg Lys Tyr Lys Lys Glu Cys Glu Glu Glu Glu
305             310                 315                 320

Ile His Ile Gln Ser Ala Val Leu Ala Glu Glu Gly Gln Ser Pro Arg
```

-continued

```
              325                 330                 335
Ala Glu Thr Pro Ser Thr Val Thr Glu Val Asp Met Asp Leu Asp Ser
            340                 345                 350
Tyr Gln Ile Ala Leu Glu Glu Val Leu Thr Trp Leu Leu Ser Ala Glu
            355                 360                 365
Asp Thr Phe Gln Glu Gln His Asp Ile Ser Asp Val Glu Glu Val
        370                 375                 380
Lys Glu Gln Phe Ala Thr His Glu Thr Phe Met Met Glu Leu Thr Ala
385                 390                 395                 400
His Gln Ser Ser Val Gly Ser Val Leu Gln Ala Gly Asn Gln Leu Met
                405                 410                 415
Thr Gln Gly Thr Leu Ser Arg Glu Glu Phe Glu Ile Gln Glu Gln
            420                 425                 430
Met Thr Leu Leu Asn Ala Arg Trp Glu Ala Leu Arg Val Glu Ser Met
                435                 440                 445
Glu Arg Gln Ser Arg Leu His Asp Ala Leu Met Glu Leu Gln Lys Lys
            450                 455                 460
Gln Leu Gln Gln Leu Ser Ser Trp Leu Ala Leu Thr Glu Glu Arg Ile
465                 470                 475                 480
Gln Lys Met Glu Ser Leu Pro Leu Gly Asp Asp Leu Pro Ser Leu Gln
                485                 490                 495
Lys Leu Leu Gln Glu His Lys Ser Leu Gln Asn Asp Leu Glu Ala Glu
            500                 505                 510
Gln Val Lys Val Asn Ser Leu Thr His Met Val Val Ile Val Asp Glu
        515                 520                 525
Asn Ser Gly Glu Ser Ala Thr Ala Leu Leu Glu Asp Gln Leu Gln Lys
        530                 535                 540
Leu Gly Glu Arg Trp Thr Ala Val Cys Arg Trp Thr Glu Glu Arg Trp
545                 550                 555                 560
Asn Arg Leu Gln Glu Ile Ser Ile Leu Trp Gln Glu Leu Leu Glu Glu
                565                 570                 575
Gln Cys Leu Leu Glu Ala Trp Leu Thr Glu Lys Glu Glu Ala Leu Asp
            580                 585                 590
Lys Val Gln Thr Ser Asn Phe Lys Asp Gln Lys Glu Leu Ser Val Ser
            595                 600                 605
Val Arg Arg Leu Ala Ile Leu Lys Glu Asp Met Glu Met Lys Arg Gln
        610                 615                 620
Thr Leu Asp Gln Leu Ser Glu Ile Gly Gln Asp Val Gly Gln Leu Leu
625                 630                 635                 640
Ser Asn Pro Lys Ala Ser Lys Lys Met Asn Ser Asp Ser Glu Glu Leu
                645                 650                 655
Thr Gln Arg Trp Asp Ser Leu Val Gln Arg Leu Glu Asp Ser Ser Asn
            660                 665                 670
Gln Val Thr Gln Ala Val Ala Lys Leu Gly Met Ser Gln Ile Pro Gln
        675                 680                 685
Lys Asp Leu Leu Glu Thr Val His Val Arg Glu Gln Gly Met Val Lys
        690                 695                 700
Lys Pro Lys Gln Glu Leu Pro Pro Pro Pro Pro Lys Lys Arg Gln
705                 710                 715                 720
Ile His Val Asp Val Glu Ala Lys Lys Phe Asp Ala Ile Ser Thr
                725                 730                 735
Glu Leu Leu Asn Trp Ile Leu Lys Ser Lys Thr Ala Ile Gln Asn Thr
            740                 745                 750
```

-continued

```
Glu Met Lys Glu Tyr Lys Lys Ser Gln Glu Thr Ser Gly Met Lys Lys
            755                 760                 765
Lys Leu Lys Gly Leu Glu Lys Glu Gln Lys Glu Asn Leu Pro Arg Leu
        770                 775                 780
Asp Glu Leu Asn Gln Thr Gly Gln Thr Leu Arg Glu Gln Met Gly Lys
785                 790                 795                 800
Glu Gly Leu Pro Leu Lys Glu Val Asn Asp Val Leu Glu Arg Val Ser
                805                 810                 815
Leu Glu Trp Lys Met Ile Ser Gln Gln Leu Glu Asp Leu Gly Arg Lys
            820                 825                 830
Ile Gln Leu Gln Glu Asp Ile Asn Ala Tyr Phe Lys Gln Leu Asp Ala
        835                 840                 845
Ile Glu Glu Thr Ile Lys Glu Lys Glu Trp Leu Arg Gly Thr Pro
        850                 855                 860
Ile Ser Glu Ser Pro Arg Gln Pro Leu Pro Gly Leu Lys Asp Ser Cys
865                 870                 875                 880
Gln Arg Glu Leu Thr Asp Leu Leu Gly Leu His Pro Arg Ile Glu Thr
                885                 890                 895
Leu Cys Ala Ser Cys Ser Ala Leu Lys Ser Gln Pro Cys Val Pro Gly
            900                 905                 910
Phe Val Gln Gln Gly Phe Asp Asp Leu Arg His His Tyr Gln Ala Val
        915                 920                 925
Ala Lys Ala Leu Glu Glu Tyr Gln Gln Gln Leu Glu Asn Glu Leu Lys
        930                 935                 940
Ser Gln Pro Gly Pro Glu Tyr Leu Asp Thr Leu Asn Thr Leu Lys Lys
945                 950                 955                 960
Met Leu Ser Glu Ser Glu Lys Ala Ala Gln Ala Ser Leu Asn Ala Leu
                965                 970                 975
Asn Asp Pro Ile Ala Val Glu Gln Ala Leu Gln Glu Lys Lys Ala Leu
            980                 985                 990
Asp Glu Thr Leu Glu Asn Gln Lys  His Thr Leu His Lys  Leu Ser Glu
        995                 1000                1005
Glu Thr  Lys Thr Leu Glu Lys  Asn Met Leu Pro Asp  Val Gly Lys
        1010                1015                1020
Met Tyr  Lys Gln Glu Phe Asp  Asp Val Gln Gly Arg  Trp Asn Lys
        1025                1030                1035
Val Lys  Thr Lys Val Ser Arg  Asp Leu His Leu Leu  Glu Glu Ile
        1040                1045                1050
Thr Pro  Arg Leu Arg Asp Phe  Glu Ala Asp Ser Glu  Val Ile Glu
        1055                1060                1065
Lys Trp  Val Ser Gly Ile Lys  Asp Phe Leu Met Lys  Glu Gln Ala
        1070                1075                1080
Ala Gln  Gly Asp Ala Ala Gln Ser Gln Leu Asp  Gln Cys Ala
        1085                1090                1095
Thr Phe  Ala Asn Glu Ile Glu  Thr Ile Glu Ser Ser  Leu Lys Asn
        1100                1105                1110
Met Arg  Glu Val Glu Thr Ser  Leu Gln Arg Cys Pro  Val Thr Gly
        1115                1120                1125
Val Lys  Thr Trp Val Gln Ala  Arg Leu Val Asp Tyr  Gln Ser Gln
        1130                1135                1140
Leu Glu  Lys Phe Ser Lys Glu  Ile Ala Ile Gln Lys  Ser Arg Leu
        1145                1150                1155
```

```
Leu Asp Ser Gln Glu Lys Ala Leu Asn Leu Lys Lys Asp Leu Ala
1160                1165                1170

Glu Met Gln Glu Trp Met Ala Gln Ala Glu Glu Asp Tyr Leu Glu
1175                1180                1185

Arg Asp Phe Glu Tyr Lys Ser Pro Glu Glu Leu Glu Ser Ala Val
1190                1195                1200

Glu Glu Met Lys Arg Ala Lys Glu Asp Val Leu Gln Lys Glu Val
1205                1210                1215

Arg Val Lys Ile Leu Lys Asp Ser Ile Lys Leu Val Ala Ala Lys
1220                1225                1230

Val Pro Ser Gly Gly Gln Glu Leu Thr Ser Glu Phe Asn Glu Val
1235                1240                1245

Leu Glu Ser Tyr Gln Leu Leu Cys Asn Arg Ile Arg Gly Lys Cys
1250                1255                1260

His Thr Leu Glu Glu Val Trp Ser Cys Trp Val Glu Leu Leu His
1265                1270                1275

Tyr Leu Asp Leu Glu Thr Thr Trp Leu Asn Thr Leu Glu Glu Arg
1280                1285                1290

Val Arg Ser Thr Glu Ala Leu Pro Glu Arg Ala Glu Ala Val His
1295                1300                1305

Glu Ala Leu Glu Ser Leu Glu Ser Val Leu Arg His Pro Ala Asp
1310                1315                1320

Asn Arg Thr Gln Ile Arg Glu Leu Gly Gln Thr Leu Ile Asp Gly
1325                1330                1335

Gly Ile Leu Asp Asp Ile Ile Ser Glu Lys Leu Glu Ala Phe Asn
1340                1345                1350

Ser Arg Tyr Glu Glu Leu Ser His Leu Ala Glu Ser Lys Gln Ile
1355                1360                1365

Ser Leu Glu Lys Gln Ala His Arg Asp Phe Gly Pro Ser Ser Gln
1370                1375                1380

His Phe Leu Ser Thr Ser Val Gln Leu Pro Trp Gln Arg Ser Ile
1385                1390                1395

Ser His Asn Lys Val Pro Tyr Tyr Ile Asn His Gln Thr Gln Thr
1400                1405                1410

Thr Cys Trp Asp His Pro Lys Met Thr Glu Leu Phe Gln Ser Leu
1415                1420                1425

Ala Asp Leu Asn Asn Val Arg Phe Ser Ala Tyr Arg Thr Ala Ile
1430                1435                1440

Lys Ile Arg Arg Leu Gln Lys Ala Leu Cys Leu Asp Leu Leu Glu
1445                1450                1455

Leu Asn Thr Thr Asn Glu Val Phe Lys Gln His Lys Leu Asn Gln
1460                1465                1470

Asn Asp Gln Leu Leu Ser Val Pro Asp Val Ile Asn Cys Leu Thr
1475                1480                1485

Thr Thr Tyr Asp Gly Leu Glu Gln Leu His Lys Asp Leu Val Asn
1490                1495                1500

Val Pro Leu Cys Val Asp Met Cys Leu Asn Trp Leu Leu Asn Val
1505                1510                1515

Tyr Asp Thr Gly Arg Thr Gly Lys Ile Arg Val Gln Ser Leu Lys
1520                1525                1530

Ile Gly Leu Met Ser Leu Ser Lys Gly Leu Leu Glu Glu Lys Tyr
1535                1540                1545

Arg Cys Leu Phe Lys Glu Val Ala Gly Pro Thr Glu Met Cys Asp
```

-continued

```
            1550                    1555                    1560
Gln Arg Gln Leu Gly Leu Leu His Asp Ala Ile Gln Ile Pro
    1565                1570                1575

Arg Gln Leu Gly Glu Val Ala Ala Phe Gly Gly Ser Asn Ile Glu
    1580                1585                1590

Pro Ser Val Arg Ser Cys Phe Gln Gln Asn Asn Asn Lys Pro Glu
    1595                1600                1605

Ile Ser Val Lys Glu Phe Ile Asp Trp Met His Leu Glu Pro Gln
    1610                1615                1620

Ser Met Val Trp Leu Pro Val Leu His Arg Val Ala Ala Ala Glu
    1625                1630                1635

Thr Ala Lys His Gln Ala Lys Cys Asn Ile Cys Lys Glu Cys Pro
    1640                1645                1650

Ile Val Gly Phe Arg Tyr Arg Ser Leu Lys His Phe Asn Tyr Asp
    1655                1660                1665

Val Cys Gln Ser Cys Phe Phe Ser Gly Arg Thr Ala Lys Gly His
    1670                1675                1680

Lys Leu His Tyr Pro Met Val Glu Tyr Cys Ile Pro Thr Thr Ser
    1685                1690                1695

Gly Glu Asp Val Arg Asp Phe Thr Lys Val Leu Lys Asn Lys Phe
    1700                1705                1710

Arg Ser Lys Lys Tyr Phe Ala Lys His Pro Arg Leu Gly Tyr Leu
    1715                1720                1725

Pro Val Gln Thr Val Leu Glu Gly Asp Asn Leu Glu Thr Pro Ile
    1730                1735                1740

Thr Leu Ile Ser Met Trp Pro Glu His Tyr Asp Pro Ser Gln Ser
    1745                1750                1755

Pro Gln Leu Phe His Asp Asp Thr His Ser Arg Ile Glu Gln Tyr
    1760                1765                1770

Ala Thr Arg Leu Ala Gln Met Glu Arg Thr Asn Gly Ser Phe Leu
    1775                1780                1785

Thr Asp Ser Ser Ser Thr Thr Gly Ser Val Glu Asp Glu His Ala
    1790                1795                1800

Leu Ile Gln Gln Tyr Cys Gln Thr Leu Gly Gly Glu Ser Pro Val
    1805                1810                1815

Ser Gln Pro Gln Ser Pro Ala Gln Ile Leu Lys Ser Val Glu Arg
    1820                1825                1830

Glu Glu Arg Gly Glu Leu Glu Arg Ile Ile Ala Asp Leu Glu Glu
    1835                1840                1845

Glu Gln Arg Asn Leu Gln Val Glu Tyr Glu Gln Leu Lys Glu Gln
    1850                1855                1860

His Leu Arg Arg Gly Leu Pro Val Gly Ser Pro Pro Asp Ser Ile
    1865                1870                1875

Val Ser Pro His His Thr Ser Glu Asp Ser Glu Leu Ile Ala Glu
    1880                1885                1890

Ala Lys Leu Leu Arg Gln His Lys Gly Arg Leu Glu Ala Arg Met
    1895                1900                1905

Gln Ile Leu Glu Asp His Asn Lys Gln Leu Glu Ser Gln Leu His
    1910                1915                1920

Arg Leu Arg Gln Leu Leu Glu Gln Pro Asp Ser Asp Ser Arg Ile
    1925                1930                1935

Asn Gly Val Ser Pro Trp Ala Ser Pro Gln His Ser Ala Leu Ser
    1940                1945                1950
```

-continued

```
Tyr Ser Leu Asp Thr Asp Pro Gly Pro Gln Phe His Gln Ala Ala
    1955                1960                1965

Ser Glu Asp Leu Leu Ala Pro Pro His Asp Thr Ser Thr Asp Leu
    1970                1975                1980

Thr Asp Val Met Glu Gln Ile Asn Ser Thr Phe Pro Ser Cys Ser
    1985                1990                1995

Ser Asn Val Pro Ser Arg Pro Gln Ala Met
    2000                2005

<210> SEQ ID NO 24
<211> LENGTH: 6321
<212> TYPE: DNA
<213> ORGANISM: Mus musculus
<220> FEATURE:
<221> NAME/KEY: CDS
<222> LOCATION: (1)..(6321)
<220> FEATURE:
<221> NAME/KEY: misc_feature
<222> LOCATION: (1)..(117)
<223> OTHER INFORMATION: TAT and epitope tag coding sequence

<400> SEQUENCE: 24 atg gac tac aag gac gac gat gac aag ggc tac ggc cgc aag aaa cgc     48
Met Asp Tyr Lys Asp Asp Asp Asp Lys Gly Tyr Gly Arg Lys Lys Arg
1               5                   10                  15 cgc cag cgc cgc cgc ggt gga tcc acc atg tcc ggc tat cca tat gac     96
Arg Gln Arg Arg Arg Gly Gly Ser Thr Met Ser Gly Tyr Pro Tyr Asp
                20                  25                  30 gtc cca gac tat gct ggc tcc atg gcc aag tat ggg gac ctt gaa gcc    144
Val Pro Asp Tyr Ala Gly Ser Met Ala Lys Tyr Gly Asp Leu Glu Ala
            35                  40                  45 agg cct gat gat ggg cag aac gaa ttc agt gac atc att aag tcc aga    192
Arg Pro Asp Asp Gly Gln Asn Glu Phe Ser Asp Ile Ile Lys Ser Arg
        50                  55                  60 tct gat gaa cac aat gat gta cag aag aaa acc ttt acc aaa tgg ata    240
Ser Asp Glu His Asn Asp Val Gln Lys Lys Thr Phe Thr Lys Trp Ile
65                  70                  75                  80 aac gct cga ttt tcc aag agt ggg aaa cca ccc atc agt gat atg ttc    288
Asn Ala Arg Phe Ser Lys Ser Gly Lys Pro Pro Ile Ser Asp Met Phe
                85                  90                  95 tca gac ctc aaa gat ggg aga aag ctc ttg gat ctt ctc gaa ggc ctc    336
Ser Asp Leu Lys Asp Gly Arg Lys Leu Leu Asp Leu Leu Glu Gly Leu
                100                 105                 110 aca gga aca tca ttg cca aag gaa cgt ggt tcc aca agg gtg cat gcc    384
Thr Gly Thr Ser Leu Pro Lys Glu Arg Gly Ser Thr Arg Val His Ala
            115                 120                 125 tta aac aat gtc aac cga gtg cta cag gtt tta cat cag aac aat gtg    432
Leu Asn Asn Val Asn Arg Val Leu Gln Val Leu His Gln Asn Asn Val
        130                 135                 140 gac ttg gtg aat att gga ggc acg gac att gtg gct gga aat ccc aag    480
Asp Leu Val Asn Ile Gly Gly Thr Asp Ile Val Ala Gly Asn Pro Lys
145                 150                 155                 160 ctg act tta ggg tta ctc tgg agc atc att ctg cac tgg cag gtg aag    528
Leu Thr Leu Gly Leu Leu Trp Ser Ile Ile Leu His Trp Gln Val Lys
                165                 170                 175 gat gtc atg aaa gat atc atg tca gac ctg cag cag aca aac agc gag    576
Asp Val Met Lys Asp Ile Met Ser Asp Leu Gln Gln Thr Asn Ser Glu
                180                 185                 190 aag atc ctg ctg agc tgg gtg cgg cag acc acc agg ccc tac agt caa    624
Lys Ile Leu Leu Ser Trp Val Arg Gln Thr Thr Arg Pro Tyr Ser Gln
            195                 200                 205
```

-continued

| | |
|---|---|
| gtc aac gtc ctc aac ttc acc acc agc tgg acc gat gga ctc gcg ttc<br>Val Asn Val Leu Asn Phe Thr Thr Ser Trp Thr Asp Gly Leu Ala Phe<br>210                           215                           220 | 672 |
| aac gcc gtg ctc cac cgg cac aaa cca gat ctc ttc gac tgg gac gag<br>Asn Ala Val Leu His Arg His Lys Pro Asp Leu Phe Asp Trp Asp Glu<br>225                       230                       235                     240 | 720 |
| atg gtc aaa atg tcc cca att gag aga ctt gac cat gct ttt gac aag<br>Met Val Lys Met Ser Pro Ile Glu Arg Leu Asp His Ala Phe Asp Lys<br>                      245                     250                     255 | 768 |
| gcc cac act tct ttg gga att gaa aag ctc cta agt cct gaa act gtt<br>Ala His Thr Ser Leu Gly Ile Glu Lys Leu Leu Ser Pro Glu Thr Val<br>        260                     265                     270 | 816 |
| gct gtg cat ctc cct gac aag aaa tcc ata att atg tat tta acg tct<br>Ala Val His Leu Pro Asp Lys Lys Ser Ile Ile Met Tyr Leu Thr Ser<br>275                       280                     285 | 864 |
| ctg ttt gag gtg ctt cct cag caa gtc acg ata gat gcc atc cga gag<br>Leu Phe Glu Val Leu Pro Gln Gln Val Thr Ile Asp Ala Ile Arg Glu<br>290                       295                     300 | 912 |
| gtg gag act ctc cca agg aag tat aag aaa gaa tgt gaa gag gaa gaa<br>Val Glu Thr Leu Pro Arg Lys Tyr Lys Lys Glu Cys Glu Glu Glu Glu<br>305                       310                     315                     320 | 960 |
| att cat atc cag agt gca gtg ctg gca gag gaa ggc cag agt ccc cga<br>Ile His Ile Gln Ser Ala Val Leu Ala Glu Glu Gly Gln Ser Pro Arg<br>                      325                     330                     335 | 1008 |
| gct gag acc cct agc acc gtc act gaa gtg gac atg gat ttg gac agc<br>Ala Glu Thr Pro Ser Thr Val Thr Glu Val Asp Met Asp Leu Asp Ser<br>        340                     345                     350 | 1056 |
| tac cag ata gcg cta gag gaa gtg ctg acg tgg ctg ctg tcc gcg gag<br>Tyr Gln Ile Ala Leu Glu Glu Val Leu Thr Trp Leu Leu Ser Ala Glu<br>                      355                     360                     365 | 1104 |
| gac acg ttc cag gag caa cat gac att tct gat gat gtc gaa gaa gtc<br>Asp Thr Phe Gln Glu Gln His Asp Ile Ser Asp Asp Val Glu Glu Val<br>370                       375                     380 | 1152 |
| aaa gag cag ttt gct acc cat gaa act ttt atg atg gag ctg aca gca<br>Lys Glu Gln Phe Ala Thr His Glu Thr Phe Met Met Glu Leu Thr Ala<br>385                       390                     395                     400 | 1200 |
| cac cag agc agc gtg ggg agc gtc ctg cag gct ggc aac cag ctg atg<br>His Gln Ser Ser Val Gly Ser Val Leu Gln Ala Gly Asn Gln Leu Met<br>                      405                     410                     415 | 1248 |
| aca caa ggg act ctg tcc aga gag gag gag ttt gag atc cag gaa cag<br>Thr Gln Gly Thr Leu Ser Arg Glu Glu Glu Phe Glu Ile Gln Glu Gln<br>        420                     425                     430 | 1296 |
| atg acc ttg ctg aat gca agg tgg gag gcg ctc cgg gtg gag agc atg<br>Met Thr Leu Leu Asn Ala Arg Trp Glu Ala Leu Arg Val Glu Ser Met<br>               435                     440                     445 | 1344 |
| gag agg cag tcc cgg ctg cac gac gct ctg atg gag ctg cag aag aaa<br>Glu Arg Gln Ser Arg Leu His Asp Ala Leu Met Glu Leu Gln Lys Lys<br>        450                     455                     460 | 1392 |
| cag ctg cag cag ctc tca agc tgg ctg gcc ctc aca gaa gag cgc att<br>Gln Leu Gln Gln Leu Ser Ser Trp Leu Ala Leu Thr Glu Glu Arg Ile<br>465                       470                     475                     480 | 1440 |
| cag aag atg gag agc ctc ccg ctg ggt gat gac ctg ccc tcc ctg cag<br>Gln Lys Met Glu Ser Leu Pro Leu Gly Asp Asp Leu Pro Ser Leu Gln<br>                      485                     490                     495 | 1488 |
| aag ctg ctt caa gaa cat aaa agt ttg caa aat gac ctt gaa gct gaa<br>Lys Leu Leu Gln Glu His Lys Ser Leu Gln Asn Asp Leu Glu Ala Glu<br>                      500                     505                     510 | 1536 |
| cag gtg aag gta aat tcc tta act cac atg gtg gtg att gtg gat gaa<br>Gln Val Lys Val Asn Ser Leu Thr His Met Val Val Ile Val Asp Glu | 1584 |

-continued

```
             515                 520                 525
aac agt ggg gag agt gcc aca gct ctt ctg gaa gat cag tta cag aaa        1632
Asn Ser Gly Glu Ser Ala Thr Ala Leu Leu Glu Asp Gln Leu Gln Lys
        530                 535                 540 ctg ggt gag cgc tgg aca gct gta tgc cgc tgg act gaa gaa cgt tgg        1680
Leu Gly Glu Arg Trp Thr Ala Val Cys Arg Trp Thr Glu Glu Arg Trp
545                 550                 555                 560 aac agg ttg caa gaa atc agt att ctg tgg cag gaa tta ttg gaa gag        1728
Asn Arg Leu Gln Glu Ile Ser Ile Leu Trp Gln Glu Leu Leu Glu Glu
                565                 570                 575 cag tgt ctg ttg gag gct tgg ctc acc gaa aag gaa gag gct ttg gat        1776
Gln Cys Leu Leu Glu Ala Trp Leu Thr Glu Lys Glu Glu Ala Leu Asp
            580                 585                 590 aaa gtt caa acc agc aac ttt aaa gac cag aag gaa cta agt gtc agt        1824
Lys Val Gln Thr Ser Asn Phe Lys Asp Gln Lys Glu Leu Ser Val Ser
        595                 600                 605 gtc cgg cgt ctg gct ata ttg aag gaa gac atg gaa atg aag agg cag        1872
Val Arg Arg Leu Ala Ile Leu Lys Glu Asp Met Glu Met Lys Arg Gln
    610                 615                 620 act ctg gat caa ctg agt gag att ggc cag gat gtg ggc caa tta ctc        1920
Thr Leu Asp Gln Leu Ser Glu Ile Gly Gln Asp Val Gly Gln Leu Leu
625                 630                 635                 640 agt aat ccc aag gca tct aag aag atg aac agt gac tct gag gag cta        1968
Ser Asn Pro Lys Ala Ser Lys Lys Met Asn Ser Asp Ser Glu Glu Leu
                645                 650                 655 aca cag aga tgg gat tct ctg gtt cag aga ctc gaa gac tct tct aac        2016
Thr Gln Arg Trp Asp Ser Leu Val Gln Arg Leu Glu Asp Ser Ser Asn
            660                 665                 670 cag gtg act cag gcg gta gcg aag ctc ggc atg tcc cag att cca cag        2064
Gln Val Thr Gln Ala Val Ala Lys Leu Gly Met Ser Gln Ile Pro Gln
        675                 680                 685 aag gac cta ttg gag acc gtt cat gtg aga gaa caa ggg atg gtg aag        2112
Lys Asp Leu Leu Glu Thr Val His Val Arg Glu Gln Gly Met Val Lys
    690                 695                 700 aag ccc aag cag gaa ctg cct cct cct ccc cca cca aag aag aga cag        2160
Lys Pro Lys Gln Glu Leu Pro Pro Pro Pro Pro Pro Lys Lys Arg Gln
705                 710                 715                 720 att cac gtg gac gtg gag gcc aag aaa aag ttt gat gct ata agt aca        2208
Ile His Val Asp Val Glu Ala Lys Lys Lys Phe Asp Ala Ile Ser Thr
                725                 730                 735 gag ctg ctg aac tgg att ttg aaa tca aag act gcc att cag aac aca        2256
Glu Leu Leu Asn Trp Ile Leu Lys Ser Lys Thr Ala Ile Gln Asn Thr
            740                 745                 750 gag atg aaa gaa tat aag aag tcg cag gag acc tca gga atg aaa aag        2304
Glu Met Lys Glu Tyr Lys Lys Ser Gln Glu Thr Ser Gly Met Lys Lys
        755                 760                 765 aaa ttg aag gga tta gag aaa gaa cag aag gaa aat ctg ccc cga ctg        2352
Lys Leu Lys Gly Leu Glu Lys Glu Gln Lys Glu Asn Leu Pro Arg Leu
    770                 775                 780 gac gaa ctg aat caa acc gga caa acc ctc cgg gag caa atg gga aaa        2400
Asp Glu Leu Asn Gln Thr Gly Gln Thr Leu Arg Glu Gln Met Gly Lys
785                 790                 795                 800 gaa ggc ctt cca ctg aaa gaa gta aac gat gtt ctg gaa agg gtt tcg        2448
Glu Gly Leu Pro Leu Lys Glu Val Asn Asp Val Leu Glu Arg Val Ser
                805                 810                 815 ttg gag tgg aag atg ata tct cag cag cta gaa gat ctg gga agg aag        2496
Leu Glu Trp Lys Met Ile Ser Gln Gln Leu Glu Asp Leu Gly Arg Lys
            820                 825                 830 atc cag ctg cag gaa gat ata aat gct tat ttt aag cag ctt gat gcc        2544
```

-continued

```
                Ile Gln Leu Gln Glu Asp Ile Asn Ala Tyr Phe Lys Gln Leu Asp Ala
                        835                 840                 845 att gag gag acc atc aag gag aag gaa gag tgg ctg agg ggc aca ccc          2592
Ile Glu Glu Thr Ile Lys Glu Lys Glu Glu Trp Leu Arg Gly Thr Pro
        850                 855                 860 att tct gaa tcg ccc cgg cag ccc ttg cca ggc tta aag gat tct tgc          2640
Ile Ser Glu Ser Pro Arg Gln Pro Leu Pro Gly Leu Lys Asp Ser Cys
865                 870                 875                 880 cag agg gaa ctg aca gat ctc ctt ggc ctt cac ccc aga att gag acg          2688
Gln Arg Glu Leu Thr Asp Leu Leu Gly Leu His Pro Arg Ile Glu Thr
                885                 890                 895 ctg tgt gca agc tgt tca gcc ctg aag tct cag ccc tgt gtc cca ggt          2736
Leu Cys Ala Ser Cys Ser Ala Leu Lys Ser Gln Pro Cys Val Pro Gly
            900                 905                 910 ttt gtc cag cag ggt ttt gac gac ctt cga cat cat tac cag gct gtt          2784
Phe Val Gln Gln Gly Phe Asp Asp Leu Arg His His Tyr Gln Ala Val
            915                 920                 925 gcg aag gct tta gag gaa tac caa caa caa cta gaa aat gag ctg aag          2832
Ala Lys Ala Leu Glu Glu Tyr Gln Gln Gln Leu Glu Asn Glu Leu Lys
        930                 935                 940 agc cag cct gga ccc gag tat ttg gac aca ctg aat acc ctg aaa aaa          2880
Ser Gln Pro Gly Pro Glu Tyr Leu Asp Thr Leu Asn Thr Leu Lys Lys
945                 950                 955                 960 atg cta agc gag tca gaa aag gcg gcc cag gcc tct ctg aat gcc ctg          2928
Met Leu Ser Glu Ser Glu Lys Ala Ala Gln Ala Ser Leu Asn Ala Leu
                965                 970                 975 aac gat ccc ata gcg gtg gag cag gcc ctg cag gag aaa aag gcc ctt          2976
Asn Asp Pro Ile Ala Val Glu Gln Ala Leu Gln Glu Lys Lys Ala Leu
            980                 985                 990 gat gaa acc ctt gag aat cag aaa cat acg tta cat aag ctt tca gaa          3024
Asp Glu Thr Leu Glu Asn Gln Lys His Thr Leu His Lys Leu Ser Glu
        995                 1000                1005 gaa acg aag act ttg gag aaa aat atg ctt cct gat gtg ggg aaa              3069
Glu Thr Lys Thr Leu Glu Lys Asn Met Leu Pro Asp Val Gly Lys
    1010                1015                1020 atg tat aaa caa gaa ttt gat gat gtc caa ggc aga tgg aat aaa              3114
Met Tyr Lys Gln Glu Phe Asp Asp Val Gln Gly Arg Trp Asn Lys
    1025                1030                1035 gta aag acc aag gtt tcc aga gac tta cac ttg ctc gag gaa atc              3159
Val Lys Thr Lys Val Ser Arg Asp Leu His Leu Leu Glu Glu Ile
    1040                1045                1050 acc ccc aga ctc cga gat ttt gag gct gat tca gaa gtc att gag              3204
Thr Pro Arg Leu Arg Asp Phe Glu Ala Asp Ser Glu Val Ile Glu
    1055                1060                1065 aag tgg gtg agt ggc atc aaa gac ttc ctc atg aaa gaa cag gct              3249
Lys Trp Val Ser Gly Ile Lys Asp Phe Leu Met Lys Glu Gln Ala
    1070                1075                1080 gcc caa gga gac gct gct gcg cag agc cag ctt gac caa tgt gct              3294
Ala Gln Gly Asp Ala Ala Ala Gln Ser Gln Leu Asp Gln Cys Ala
    1085                1090                1095 acg ttt gct aat gaa atc gaa acc atc gag tca tct ctg aag aac              3339
Thr Phe Ala Asn Glu Ile Glu Thr Ile Glu Ser Ser Leu Lys Asn
    1100                1105                1110 atg agg gaa gta gag act agc ctt cag agg tgt cca gtc act gga              3384
Met Arg Glu Val Glu Thr Ser Leu Gln Arg Cys Pro Val Thr Gly
    1115                1120                1125 gtc aag aca tgg gta cag gca aga cta gtg gat tac caa tcc caa              3429
Val Lys Thr Trp Val Gln Ala Arg Leu Val Asp Tyr Gln Ser Gln
    1130                1135                1140
```

-continued

| | | |
|---|---|---|
| ctg gag aaa ttc agc aaa gag att gct att caa aaa agc agg ctg<br>Leu Glu Lys Phe Ser Lys Glu Ile Ala Ile Gln Lys Ser Arg Leu<br>1145                        1150                        1155 | 3474 |
| tta gat agt caa gaa aaa gcc ctg aac ttg aaa aag gat ttg gct<br>Leu Asp Ser Gln Glu Lys Ala Leu Asn Leu Lys Lys Asp Leu Ala<br>     1160                        1165                       1170 | 3519 |
| gag atg cag gag tgg atg gca cag gct gaa gag gac tac ctg gag<br>Glu Met Gln Glu Trp Met Ala Gln Ala Glu Glu Asp Tyr Leu Glu<br>1175                        1180                        1185 | 3564 |
| agg gac ttc gag tac aaa tct cca gaa gaa ctc gag agt gcg gtg<br>Arg Asp Phe Glu Tyr Lys Ser Pro Glu Glu Leu Glu Ser Ala Val<br>     1190                        1195                       1200 | 3609 |
| gag gaa atg aag agg gca aaa gag gat gtg ctg cag aag gag gtg<br>Glu Glu Met Lys Arg Ala Lys Glu Asp Val Leu Gln Lys Glu Val<br>1205                        1210                        1215 | 3654 |
| agg gtg aaa att ctg aag gac agc atc aag ctg gtg gct gcc aag<br>Arg Val Lys Ile Leu Lys Asp Ser Ile Lys Leu Val Ala Ala Lys<br>     1220                        1225                       1230 | 3699 |
| gtg ccc tct ggt ggc cag gag ttg acg tcg gaa ttc aac gag gtg<br>Val Pro Ser Gly Gly Gln Glu Leu Thr Ser Glu Phe Asn Glu Val<br>1235                        1240                        1245 | 3744 |
| ctg gag agc tac cag ctt ctg tgc aat aga att cga ggg aag tgc<br>Leu Glu Ser Tyr Gln Leu Leu Cys Asn Arg Ile Arg Gly Lys Cys<br>     1250                        1255                       1260 | 3789 |
| cac aca ctg gag gag gtc tgg tct tgc tgg gtg gag ctg ctt cac<br>His Thr Leu Glu Glu Val Trp Ser Cys Trp Val Glu Leu Leu His<br>1265                        1270                        1275 | 3834 |
| tat ctg gac ctg gag acc acg tgg ttg aac acc ttg gag gag cgc<br>Tyr Leu Asp Leu Glu Thr Thr Trp Leu Asn Thr Leu Glu Glu Arg<br>     1280                        1285                       1290 | 3879 |
| gtg agg agc acg gag gcc ctg cct gag agg gca gaa gct gtt cat<br>Val Arg Ser Thr Glu Ala Leu Pro Glu Arg Ala Glu Ala Val His<br>1295                        1300                        1305 | 3924 |
| gaa gct ctg gag tct ctt gag tct gtt ttg cgc cat cca gcg gat<br>Glu Ala Leu Glu Ser Leu Glu Ser Val Leu Arg His Pro Ala Asp<br>     1310                        1315                       1320 | 3969 |
| aat cgc acc cag att cgg gaa ctt ggg cag act ctg att gat ggt<br>Asn Arg Thr Gln Ile Arg Glu Leu Gly Gln Thr Leu Ile Asp Gly<br>1325                        1330                        1335 | 4014 |
| gga atc ctg gat gac ata atc agc gag aag ctg gag gct ttt aac<br>Gly Ile Leu Asp Asp Ile Ile Ser Glu Lys Leu Glu Ala Phe Asn<br>     1340                        1345                       1350 | 4059 |
| agc cgc tac gaa gag ctg agt cac ttg gcg gag agc aaa cag att<br>Ser Arg Tyr Glu Glu Leu Ser His Leu Ala Glu Ser Lys Gln Ile<br>1355                        1360                        1365 | 4104 |
| tct ttg gag aag caa ctc cag gtc ctc cgc gaa act gac cac atg<br>Ser Leu Glu Lys Gln Leu Gln Val Leu Arg Glu Thr Asp His Met<br>     1370                        1375                       1380 | 4149 |
| ctt cag gtg ctg aag gag agc ctg ggg gag ctg gac aaa cag ctt<br>Leu Gln Val Leu Lys Glu Ser Leu Gly Glu Leu Asp Lys Gln Leu<br>1385                        1390                        1395 | 4194 |
| acc aca tac ctg acg gac agg atc gat gcc ttc caa ctg cca cag<br>Thr Thr Tyr Leu Thr Asp Arg Ile Asp Ala Phe Gln Leu Pro Gln<br>     1400                        1405                       1410 | 4239 |
| gaa gct cag aag atc caa gcc gaa atc tca gcc cat gag ctc acc<br>Glu Ala Gln Lys Ile Gln Ala Glu Ile Ser Ala His Glu Leu Thr<br>1415                        1420                        1425 | 4284 |
| ctg gag gag ctg agg aag aat gtg cgc tcc cag ccc ccg acg tcc<br>Leu Glu Glu Leu Arg Lys Asn Val Arg Ser Gln Pro Pro Thr Ser<br>     1430                        1435                       1440 | 4329 |

```
cct gag ggc agg gcc acc aga gga gga agt cag atg gac atg cta     4374
Pro Glu Gly Arg Ala Thr Arg Gly Gly Ser Gln Met Asp Met Leu
    1445                1450                1455 cag agg aaa ctt cga gag gtc tcc acc aaa ttc cag ctt gcc cac     4419
Gln Arg Lys Leu Arg Glu Val Ser Thr Lys Phe Gln Leu Ala His
1460                1465                1470 aga gat ttt ggg cca tct tct caa cac ttt ctg tcc act tca gtc     4464
Arg Asp Phe Gly Pro Ser Ser Gln His Phe Leu Ser Thr Ser Val
            1475                1480                1485 cag ctg ccg tgg cag aga tcc att tca cat aat aaa gtg ccc tat     4509
Gln Leu Pro Trp Gln Arg Ser Ile Ser His Asn Lys Val Pro Tyr
        1490                1495                1500 tac atc aac cat caa aca cag aca acc tgt tgg gat cat cct aaa     4554
Tyr Ile Asn His Gln Thr Gln Thr Thr Cys Trp Asp His Pro Lys
    1505                1510                1515 atg act gag ctc ttc caa tcc ctt gct gat ctg aat aat gta cgt     4599
Met Thr Glu Leu Phe Gln Ser Leu Ala Asp Leu Asn Asn Val Arg
1520                1525                1530 ttc tct gcc tac cgc aca gca atc aaa att cga agg ctg caa aaa     4644
Phe Ser Ala Tyr Arg Thr Ala Ile Lys Ile Arg Arg Leu Gln Lys
            1535                1540                1545 gca tta tgt ctg gat ctc tta gag ctg aat acg acg aat gaa gtt     4689
Ala Leu Cys Leu Asp Leu Leu Glu Leu Asn Thr Thr Asn Glu Val
        1550                1555                1560 ttc aag cag cac aaa ctg aac caa aat gat cag ctc ctg agt gtc     4734
Phe Lys Gln His Lys Leu Asn Gln Asn Asp Gln Leu Leu Ser Val
    1565                1570                1575 cca gac gtc atc aac tgt ctg acc acc act tac gat ggg ctt gag     4779
Pro Asp Val Ile Asn Cys Leu Thr Thr Thr Tyr Asp Gly Leu Glu
1580                1585                1590 cag ctg cac aag gac ttg gtc aat gtt cca ctc tgc gtc gat atg     4824
Gln Leu His Lys Asp Leu Val Asn Val Pro Leu Cys Val Asp Met
            1595                1600                1605 tgt ctc aac tgg ctg ctc aac gta tac gac acg ggc cgg act gga     4869
Cys Leu Asn Trp Leu Leu Asn Val Tyr Asp Thr Gly Arg Thr Gly
        1610                1615                1620 aaa att cgg gta cag agt ctg aag att gga ttg atg tct ctc tcc     4914
Lys Ile Arg Val Gln Ser Leu Lys Ile Gly Leu Met Ser Leu Ser
    1625                1630                1635 aaa ggc ctc tta gaa gag aaa tac aga tgt ctc ttt aag gag gtg     4959
Lys Gly Leu Leu Glu Glu Lys Tyr Arg Cys Leu Phe Lys Glu Val
1640                1645                1650 gca ggg cca act gag atg tgt gac cag cgg cag ctt ggc ctg cta     5004
Ala Gly Pro Thr Glu Met Cys Asp Gln Arg Gln Leu Gly Leu Leu
            1655                1660                1665 ctt cac gat gcc atc cag atc cct agg cag ctg ggg gaa gta gca     5049
Leu His Asp Ala Ile Gln Ile Pro Arg Gln Leu Gly Glu Val Ala
        1670                1675                1680 gcc ttt ggg ggc agt aac att gag ccc agt gtc cgc agc tgc ttc     5094
Ala Phe Gly Gly Ser Asn Ile Glu Pro Ser Val Arg Ser Cys Phe
    1685                1690                1695 cag cag aat aac aac aag cca gaa atc agt gtg aag gag ttt ata     5139
Gln Gln Asn Asn Asn Lys Pro Glu Ile Ser Val Lys Glu Phe Ile
1700                1705                1710 gac tgg atg cat ttg gaa ccc cag tcc atg gtg tgg ttg ccg gtt     5184
Asp Trp Met His Leu Glu Pro Gln Ser Met Val Trp Leu Pro Val
            1715                1720                1725 ctg cat cgg gtc gca gct gct gag act gca aaa cat cag gcc aaa     5229
Leu His Arg Val Ala Ala Ala Glu Thr Ala Lys His Gln Ala Lys
```

```
                                                   -continued
           1730              1735              1740
tgc aac atc tgc aaa gaa tgc ccg att gtt ggg ttc aga tac agg       5274
Cys Asn Ile Cys Lys Glu Cys Pro Ile Val Gly Phe Arg Tyr Arg
    1745              1750              1755 agc cta aag cat ttt aat tat gat gtc tgc cag agt tgc ttc ttt       5319
Ser Leu Lys His Phe Asn Tyr Asp Val Cys Gln Ser Cys Phe Phe
    1760              1765              1770 tct gga aga aca gca aag ggc cac aag tta cat tac ccg atg gta       5364
Ser Gly Arg Thr Ala Lys Gly His Lys Leu His Tyr Pro Met Val
    1775              1780              1785 gaa tac tgc ata ccg aca aca tct ggg gaa gat gtg aga gat ttc       5409
Glu Tyr Cys Ile Pro Thr Thr Ser Gly Glu Asp Val Arg Asp Phe
    1790              1795              1800 act aag gtg ctg aag aac aag ttc agg tcc aag aaa tat ttt gcc       5454
Thr Lys Val Leu Lys Asn Lys Phe Arg Ser Lys Lys Tyr Phe Ala
    1805              1810              1815 aaa cat cct cgg ctt ggc tac ctg cct gtc cag acc gtg ctg gaa       5499
Lys His Pro Arg Leu Gly Tyr Leu Pro Val Gln Thr Val Leu Glu
    1820              1825              1830 ggg gac aac tta gaa act cct atc acg ctc atc agt atg tgg cca       5544
Gly Asp Asn Leu Glu Thr Pro Ile Thr Leu Ile Ser Met Trp Pro
    1835              1840              1845 gag cac tat gac ccc tcc cag tcc cct cag ctg ttt cat gat gac       5589
Glu His Tyr Asp Pro Ser Gln Ser Pro Gln Leu Phe His Asp Asp
    1850              1855              1860 acc cac tca aga ata gag caa tac gct aca cga ctg gcc cag atg       5634
Thr His Ser Arg Ile Glu Gln Tyr Ala Thr Arg Leu Ala Gln Met
    1865              1870              1875 gaa agg aca aac ggg tcc ttc cta act gat agc agc tct aca aca       5679
Glu Arg Thr Asn Gly Ser Phe Leu Thr Asp Ser Ser Ser Thr Thr
    1880              1885              1890 gga agc gtg gag gat gag cat gcc ctc atc cag cag tac tgc cag       5724
Gly Ser Val Glu Asp Glu His Ala Leu Ile Gln Gln Tyr Cys Gln
    1895              1900              1905 acc ctg ggc ggg gag tca cct gtg agt cag ccg cag agt cca gct       5769
Thr Leu Gly Gly Glu Ser Pro Val Ser Gln Pro Gln Ser Pro Ala
    1910              1915              1920 cag atc ctg aag tcc gtg gag agg gaa gag cgt ggg gaa ctg gag       5814
Gln Ile Leu Lys Ser Val Glu Arg Glu Glu Arg Gly Glu Leu Glu
    1925              1930              1935 cgg atc att gct gac ttg gag gaa gag caa aga aat ctg cag gtg       5859
Arg Ile Ile Ala Asp Leu Glu Glu Glu Gln Arg Asn Leu Gln Val
    1940              1945              1950 gag tat gag cag ctg aag gag cag cac cta aga agg ggt ctc cct       5904
Glu Tyr Glu Gln Leu Lys Glu Gln His Leu Arg Arg Gly Leu Pro
    1955              1960              1965 gtg ggc tcc cct cca gac tcc atc gta tct cct cac cac aca tct       5949
Val Gly Ser Pro Pro Asp Ser Ile Val Ser Pro His His Thr Ser
    1970              1975              1980 gag gac tca gaa ctt ata gca gaa gct aaa ctc ctg cgg cag cac       5994
Glu Asp Ser Glu Leu Ile Ala Glu Ala Lys Leu Leu Arg Gln His
    1985              1990              1995 aaa ggg cgg ctg gag gcg agg atg caa att ttg gaa gat cac aat       6039
Lys Gly Arg Leu Glu Ala Arg Met Gln Ile Leu Glu Asp His Asn
    2000              2005              2010 aaa cag ctg gag tct cag ctg cac cgc ctc aga cag ctc ctg gag       6084
Lys Gln Leu Glu Ser Gln Leu His Arg Leu Arg Gln Leu Leu Glu
    2015              2020              2025 cag cct gac tct gac tcc cgc atc aat ggt gtc tcc ccc tgg gct       6129
```

-continued

```
Gln Pro Asp Ser Asp Ser Arg Ile Asn Gly Val Ser Pro Trp Ala
    2030                2035                2040 tcc cca cag cat tct gca ttg agc tac tca ctt gac act gac cca      6174
Ser Pro Gln His Ser Ala Leu Ser Tyr Ser Leu Asp Thr Asp Pro
    2045                2050                2055 ggc cca cag ttc cac cag gca gca tct gag gac ctg ctg gcc cca      6219
Gly Pro Gln Phe His Gln Ala Ala Ser Glu Asp Leu Leu Ala Pro
    2060                2065                2070 cct cac gac act agc acg gac ctc acg gac gtg atg gag cag atc      6264
Pro His Asp Thr Ser Thr Asp Leu Thr Asp Val Met Glu Gln Ile
    2075                2080                2085 aac agc acg ttt ccc tct tgc agc tca aat gtc ccc agc agg cca      6309
Asn Ser Thr Phe Pro Ser Cys Ser Ser Asn Val Pro Ser Arg Pro
    2090                2095                2100 cag gca atg tga                                                   6321
Gln Ala Met
    2105

<210> SEQ ID NO 25
<211> LENGTH: 2106
<212> TYPE: PRT
<213> ORGANISM: Mus musculus

<400> SEQUENCE: 25

Met Asp Tyr Lys Asp Asp Asp Lys Gly Tyr Gly Arg Lys Lys Arg
1               5                   10                  15

Arg Gln Arg Arg Arg Gly Gly Ser Thr Met Ser Gly Tyr Pro Tyr Asp
            20                  25                  30

Val Pro Asp Tyr Ala Gly Ser Met Ala Lys Tyr Gly Asp Leu Glu Ala
        35                  40                  45

Arg Pro Asp Gly Gln Asn Glu Phe Ser Asp Ile Ile Lys Ser Arg
    50                  55                  60

Ser Asp Glu His Asn Asp Val Gln Lys Lys Thr Phe Thr Lys Trp Ile
65                  70                  75                  80

Asn Ala Arg Phe Ser Lys Ser Gly Lys Pro Pro Ile Ser Asp Met Phe
                85                  90                  95

Ser Asp Leu Lys Asp Gly Arg Lys Leu Leu Asp Leu Leu Glu Gly Leu
            100                 105                 110

Thr Gly Thr Ser Leu Pro Lys Glu Arg Gly Ser Thr Arg Val His Ala
        115                 120                 125

Leu Asn Asn Val Asn Arg Val Leu Gln Val Leu His Gln Asn Asn Val
    130                 135                 140

Asp Leu Val Asn Ile Gly Gly Thr Asp Ile Val Ala Gly Asn Pro Lys
145                 150                 155                 160

Leu Thr Leu Gly Leu Leu Trp Ser Ile Ile Leu His Trp Gln Val Lys
                165                 170                 175

Asp Val Met Lys Asp Ile Met Ser Asp Leu Gln Gln Thr Asn Ser Glu
            180                 185                 190

Lys Ile Leu Leu Ser Trp Val Arg Gln Thr Thr Arg Pro Tyr Ser Gln
        195                 200                 205

Val Asn Val Leu Asn Phe Thr Thr Ser Trp Thr Asp Gly Leu Ala Phe
    210                 215                 220

Asn Ala Val Leu His Arg His Lys Pro Asp Leu Phe Asp Trp Asp Glu
225                 230                 235                 240

Met Val Lys Met Ser Pro Ile Glu Arg Leu Asp His Ala Phe Asp Lys
                245                 250                 255
```

-continued

```
Ala His Thr Ser Leu Gly Ile Glu Lys Leu Leu Ser Pro Glu Thr Val
        260                 265                 270

Ala Val His Leu Pro Asp Lys Lys Ser Ile Ile Met Tyr Leu Thr Ser
        275                 280                 285

Leu Phe Glu Val Leu Pro Gln Gln Val Thr Ile Asp Ala Ile Arg Glu
        290                 295                 300

Val Glu Thr Leu Pro Arg Lys Tyr Lys Glu Cys Glu Glu Glu Glu
305                 310                 315                 320

Ile His Ile Gln Ser Ala Val Leu Ala Glu Glu Gly Gln Ser Pro Arg
                325                 330                 335

Ala Glu Thr Pro Ser Thr Val Thr Glu Val Asp Met Asp Leu Asp Ser
            340                 345                 350

Tyr Gln Ile Ala Leu Glu Glu Val Leu Thr Trp Leu Leu Ser Ala Glu
                355                 360                 365

Asp Thr Phe Gln Glu Gln His Asp Ile Ser Asp Asp Val Glu Glu Val
        370                 375                 380

Lys Glu Gln Phe Ala Thr His Glu Thr Phe Met Met Glu Leu Thr Ala
385                 390                 395                 400

His Gln Ser Ser Val Gly Ser Val Leu Gln Ala Gly Asn Gln Leu Met
                405                 410                 415

Thr Gln Gly Thr Leu Ser Arg Glu Glu Glu Phe Glu Ile Gln Glu Gln
            420                 425                 430

Met Thr Leu Leu Asn Ala Arg Trp Glu Ala Leu Arg Val Glu Ser Met
        435                 440                 445

Glu Arg Gln Ser Arg Leu His Asp Ala Leu Met Glu Leu Gln Lys Lys
    450                 455                 460

Gln Leu Gln Gln Leu Ser Ser Trp Leu Ala Leu Thr Glu Glu Arg Ile
465                 470                 475                 480

Gln Lys Met Glu Ser Leu Pro Leu Gly Asp Asp Leu Pro Ser Leu Gln
                485                 490                 495

Lys Leu Leu Gln Glu His Lys Ser Leu Gln Asn Asp Leu Glu Ala Glu
            500                 505                 510

Gln Val Lys Val Asn Ser Leu Thr His Met Val Val Ile Val Asp Glu
        515                 520                 525

Asn Ser Gly Glu Ser Ala Thr Ala Leu Leu Glu Asp Gln Leu Gln Lys
    530                 535                 540

Leu Gly Glu Arg Trp Thr Ala Val Cys Arg Trp Thr Glu Glu Arg Trp
545                 550                 555                 560

Asn Arg Leu Gln Glu Ile Ser Ile Leu Trp Gln Glu Leu Leu Glu Glu
                565                 570                 575

Gln Cys Leu Leu Glu Ala Trp Leu Thr Glu Lys Glu Glu Ala Leu Asp
            580                 585                 590

Lys Val Gln Thr Ser Asn Phe Lys Asp Gln Lys Glu Leu Ser Val Ser
        595                 600                 605

Val Arg Arg Leu Ala Ile Leu Lys Glu Asp Met Glu Met Lys Arg Gln
    610                 615                 620

Thr Leu Asp Gln Leu Ser Glu Ile Gly Gln Asp Val Gly Gln Leu Leu
625                 630                 635                 640

Ser Asn Pro Lys Ala Ser Lys Lys Met Asn Ser Asp Ser Glu Glu Leu
                645                 650                 655

Thr Gln Arg Trp Asp Ser Leu Val Gln Arg Leu Glu Asp Ser Ser Asn
            660                 665                 670

Gln Val Thr Gln Ala Val Ala Lys Leu Gly Met Ser Gln Ile Pro Gln
```

-continued

```
            675                 680                 685
Lys Asp Leu Leu Glu Thr Val His Val Arg Glu Gln Gly Met Val Lys
            690                 695                 700
Lys Pro Lys Gln Glu Leu Pro Pro Pro Pro Pro Lys Lys Arg Gln
705                 710                 715                 720
Ile His Val Asp Val Glu Ala Lys Lys Phe Asp Ala Ile Ser Thr
                    725                 730                 735
Glu Leu Leu Asn Trp Ile Leu Lys Ser Lys Thr Ala Ile Gln Asn Thr
                740                 745                 750
Glu Met Lys Glu Tyr Lys Lys Ser Gln Glu Thr Ser Gly Met Lys Lys
                755                 760                 765
Lys Leu Lys Gly Leu Glu Lys Glu Gln Lys Glu Asn Leu Pro Arg Leu
                770                 775                 780
Asp Glu Leu Asn Gln Thr Gly Gln Thr Leu Arg Glu Gln Met Gly Lys
785                 790                 795                 800
Glu Gly Leu Pro Leu Lys Glu Val Asn Asp Val Leu Glu Arg Val Ser
                    805                 810                 815
Leu Glu Trp Lys Met Ile Ser Gln Gln Leu Glu Asp Leu Gly Arg Lys
                820                 825                 830
Ile Gln Leu Gln Glu Asp Ile Asn Ala Tyr Phe Lys Gln Leu Asp Ala
                835                 840                 845
Ile Glu Glu Thr Ile Lys Glu Lys Glu Glu Trp Leu Arg Gly Thr Pro
850                 855                 860
Ile Ser Glu Ser Pro Arg Gln Pro Leu Pro Gly Leu Lys Asp Ser Cys
865                 870                 875                 880
Gln Arg Glu Leu Thr Asp Leu Leu Gly Leu His Pro Arg Ile Glu Thr
                    885                 890                 895
Leu Cys Ala Ser Cys Ser Ala Leu Lys Ser Gln Pro Cys Val Pro Gly
                900                 905                 910
Phe Val Gln Gln Gly Phe Asp Asp Leu Arg His His Tyr Gln Ala Val
                915                 920                 925
Ala Lys Ala Leu Glu Glu Tyr Gln Gln Gln Leu Glu Asn Glu Leu Lys
                930                 935                 940
Ser Gln Pro Gly Pro Glu Tyr Leu Asp Thr Leu Asn Thr Leu Lys Lys
945                 950                 955                 960
Met Leu Ser Glu Ser Glu Lys Ala Ala Gln Ala Ser Leu Asn Ala Leu
                    965                 970                 975
Asn Asp Pro Ile Ala Val Glu Gln Ala Leu Gln Glu Lys Lys Ala Leu
                980                 985                 990
Asp Glu Thr Leu Glu Asn Gln Lys His Thr Leu His Lys Leu Ser Glu
                995                 1000                1005
Glu Thr Lys Thr Leu Glu Lys Asn Met Leu Pro Asp Val Gly Lys
    1010                1015                1020
Met Tyr Lys Gln Glu Phe Asp Asp Val Gln Gly Arg Trp Asn Lys
    1025                1030                1035
Val Lys Thr Lys Val Ser Arg Asp Leu His Leu Leu Glu Glu Ile
    1040                1045                1050
Thr Pro Arg Leu Arg Asp Phe Glu Ala Asp Ser Glu Val Ile Glu
    1055                1060                1065
Lys Trp Val Ser Gly Ile Lys Asp Phe Leu Met Lys Glu Gln Ala
    1070                1075                1080
Ala Gln Gly Asp Ala Ala Ala Gln Ser Gln Leu Asp Gln Cys Ala
    1085                1090                1095
```

```
Thr Phe Ala Asn Glu Ile Glu Thr Ile Glu Ser Ser Leu Lys Asn
    1100                1105                1110

Met Arg Glu Val Glu Thr Ser Leu Gln Arg Cys Pro Val Thr Gly
    1115                1120                1125

Val Lys Thr Trp Val Gln Ala Arg Leu Val Asp Tyr Gln Ser Gln
    1130                1135                1140

Leu Glu Lys Phe Ser Lys Glu Ile Ala Ile Gln Lys Ser Arg Leu
    1145                1150                1155

Leu Asp Ser Gln Glu Lys Ala Leu Asn Leu Lys Lys Asp Leu Ala
    1160                1165                1170

Glu Met Gln Glu Trp Met Ala Gln Ala Glu Glu Asp Tyr Leu Glu
    1175                1180                1185

Arg Asp Phe Glu Tyr Lys Ser Pro Glu Glu Leu Glu Ser Ala Val
    1190                1195                1200

Glu Glu Met Lys Arg Ala Lys Glu Asp Val Leu Gln Lys Glu Val
    1205                1210                1215

Arg Val Lys Ile Leu Lys Asp Ser Ile Lys Leu Val Ala Ala Lys
    1220                1225                1230

Val Pro Ser Gly Gly Gln Glu Leu Thr Ser Glu Phe Asn Glu Val
    1235                1240                1245

Leu Glu Ser Tyr Gln Leu Leu Cys Asn Arg Ile Arg Gly Lys Cys
    1250                1255                1260

His Thr Leu Glu Glu Val Trp Ser Cys Trp Val Glu Leu Leu His
    1265                1270                1275

Tyr Leu Asp Leu Glu Thr Thr Trp Leu Asn Thr Leu Glu Glu Arg
    1280                1285                1290

Val Arg Ser Thr Glu Ala Leu Pro Glu Arg Ala Glu Ala Val His
    1295                1300                1305

Glu Ala Leu Glu Ser Leu Glu Ser Val Leu Arg His Pro Ala Asp
    1310                1315                1320

Asn Arg Thr Gln Ile Arg Glu Leu Gly Gln Thr Leu Ile Asp Gly
    1325                1330                1335

Gly Ile Leu Asp Asp Ile Ile Ser Glu Lys Leu Glu Ala Phe Asn
    1340                1345                1350

Ser Arg Tyr Glu Glu Leu Ser His Leu Ala Glu Ser Lys Gln Ile
    1355                1360                1365

Ser Leu Glu Lys Gln Leu Gln Val Leu Arg Glu Thr Asp His Met
    1370                1375                1380

Leu Gln Val Leu Lys Glu Ser Leu Gly Glu Leu Asp Lys Gln Leu
    1385                1390                1395

Thr Thr Tyr Leu Thr Asp Arg Ile Asp Ala Phe Gln Leu Pro Gln
    1400                1405                1410

Glu Ala Gln Lys Ile Gln Ala Glu Ile Ser Ala His Glu Leu Thr
    1415                1420                1425

Leu Glu Glu Leu Arg Lys Asn Val Arg Ser Gln Pro Pro Thr Ser
    1430                1435                1440

Pro Glu Gly Arg Ala Thr Arg Gly Gly Ser Gln Met Asp Met Leu
    1445                1450                1455

Gln Arg Lys Leu Arg Glu Val Ser Thr Lys Phe Gln Leu Ala His
    1460                1465                1470

Arg Asp Phe Gly Pro Ser Ser Gln His Phe Leu Ser Thr Ser Val
    1475                1480                1485
```

```
Gln Leu Pro Trp Gln Arg Ser Ile Ser His Asn Lys Val Pro Tyr
    1490            1495                1500

Tyr Ile Asn His Gln Thr Gln Thr Thr Cys Trp Asp His Pro Lys
    1505            1510                1515

Met Thr Glu Leu Phe Gln Ser Leu Ala Asp Leu Asn Asn Val Arg
    1520            1525                1530

Phe Ser Ala Tyr Arg Thr Ala Ile Lys Ile Arg Arg Leu Gln Lys
    1535            1540                1545

Ala Leu Cys Leu Asp Leu Leu Glu Leu Asn Thr Thr Asn Glu Val
    1550            1555                1560

Phe Lys Gln His Lys Leu Asn Gln Asn Asp Gln Leu Leu Ser Val
    1565            1570                1575

Pro Asp Val Ile Asn Cys Leu Thr Thr Thr Tyr Asp Gly Leu Glu
    1580            1585                1590

Gln Leu His Lys Asp Leu Val Asn Val Pro Leu Cys Val Asp Met
    1595            1600                1605

Cys Leu Asn Trp Leu Leu Asn Val Tyr Asp Thr Gly Arg Thr Gly
    1610            1615                1620

Lys Ile Arg Val Gln Ser Leu Lys Ile Gly Leu Met Ser Leu Ser
    1625            1630                1635

Lys Gly Leu Leu Glu Glu Lys Tyr Arg Cys Leu Phe Lys Glu Val
    1640            1645                1650

Ala Gly Pro Thr Glu Met Cys Asp Gln Arg Gln Leu Gly Leu Leu
    1655            1660                1665

Leu His Asp Ala Ile Gln Ile Pro Arg Gln Leu Gly Glu Val Ala
    1670            1675                1680

Ala Phe Gly Gly Ser Asn Ile Glu Pro Ser Val Arg Ser Cys Phe
    1685            1690                1695

Gln Gln Asn Asn Lys Pro Glu Ile Ser Val Lys Glu Phe Ile
    1700            1705                1710

Asp Trp Met His Leu Glu Pro Gln Ser Met Val Trp Leu Pro Val
    1715            1720                1725

Leu His Arg Val Ala Ala Ala Glu Thr Ala Lys His Gln Ala Lys
    1730            1735                1740

Cys Asn Ile Cys Lys Glu Cys Pro Ile Val Gly Phe Arg Tyr Arg
    1745            1750                1755

Ser Leu Lys His Phe Asn Tyr Asp Val Cys Gln Ser Cys Phe Phe
    1760            1765                1770

Ser Gly Arg Thr Ala Lys Gly His Lys Leu His Tyr Pro Met Val
    1775            1780                1785

Glu Tyr Cys Ile Pro Thr Thr Ser Gly Glu Asp Val Arg Asp Phe
    1790            1795                1800

Thr Lys Val Leu Lys Asn Lys Phe Arg Ser Lys Lys Tyr Phe Ala
    1805            1810                1815

Lys His Pro Arg Leu Gly Tyr Leu Pro Val Gln Thr Val Leu Glu
    1820            1825                1830

Gly Asp Asn Leu Glu Thr Pro Ile Thr Leu Ile Ser Met Trp Pro
    1835            1840                1845

Glu His Tyr Asp Pro Ser Gln Ser Pro Gln Leu Phe His Asp Asp
    1850            1855                1860

Thr His Ser Arg Ile Glu Gln Tyr Ala Thr Arg Leu Ala Gln Met
    1865            1870                1875

Glu Arg Thr Asn Gly Ser Phe Leu Thr Asp Ser Ser Ser Thr Thr
```

```
        1880                1885                1890

Gly Ser  Val Glu Asp Glu  His  Ala Leu Ile Gln Gln  Tyr Cys Gln
    1895                 1900                1905

Thr Leu  Gly Gly Glu Ser  Pro  Val Ser Gln Pro Gln  Ser Pro Ala
    1910                 1915                1920

Gln Ile  Leu Lys Ser Val  Glu  Arg Glu Arg Gly Glu  Leu Glu
    1925                 1930                1935

Arg Ile  Ile Ala Asp Leu  Glu  Glu Gln Arg Asn Leu  Gln Val
    1940                 1945                1950

Glu Tyr  Glu Gln Leu Lys  Glu  Gln His Leu Arg Arg  Gly Leu Pro
    1955                 1960                1965

Val Gly  Ser Pro Pro Asp  Ser  Ile Val Ser Pro His  His Thr Ser
    1970                 1975                1980

Glu Asp  Ser Glu Leu Ile  Ala  Glu Ala Lys Leu Leu  Arg Gln His
    1985                 1990                1995

Lys Gly  Arg Leu Glu Ala  Arg  Met Gln Ile Leu Glu  Asp His Asn
    2000                 2005                2010

Lys Gln  Leu Glu Ser Gln  Leu  His Arg Leu Arg Gln  Leu Leu Glu
    2015                 2020                2025

Gln Pro  Asp Ser Asp Ser  Arg  Ile Asn Gly Val Ser  Pro Trp Ala
    2030                 2035                2040

Ser Pro  Gln His Ser Ala  Leu  Ser Tyr Ser Leu Asp  Thr Asp Pro
    2045                 2050                2055

Gly Pro  Gln Phe His Gln  Ala  Ala Ser Glu Asp Leu  Leu Ala Pro
    2060                 2065                2070

Pro His  Asp Thr Ser Thr  Asp  Leu Thr Asp Val Met  Glu Gln Ile
    2075                 2080                2085

Asn Ser  Thr Phe Pro Ser  Cys  Ser Ser Asn Val Pro  Ser Arg Pro
    2090                 2095                2100

Gln Ala  Met
    2105

<210> SEQ ID NO 26
<211> LENGTH: 59
<212> TYPE: DNA
<213> ORGANISM: Artificial Sequence
<220> FEATURE:
<223> OTHER INFORMATION: PCR primer

<400> SEQUENCE: 26
gcggccgcac accatggact acaaggacga cgatgacaag ggctacggcc gcaagaaac      59

<210> SEQ ID NO 27
<211> LENGTH: 32
<212> TYPE: DNA
<213> ORGANISM: Artificial Sequence
<220> FEATURE:
<223> OTHER INFORMATION: PCR primer

<400> SEQUENCE: 27
ggagatgcac agcaacagtt tcaggactta gg                                   32

<210> SEQ ID NO 28
<211> LENGTH: 4
<212> TYPE: PRT
```

```
-continued

<213> ORGANISM: Artificial
<220> FEATURE:
<223> OTHER INFORMATION: Artificial polypeptide/FLAG fragment

<400> SEQUENCE: 28

Asp Tyr Lys Asp
1
```

US 7,863,017 B2

TAT-UTROPHIN AS A PROTEIN THERAPY FOR DYSTROPHINOPATHIES

CROSS-REFERENCE TO RELATED APPLICATIONS

Priority is hereby claimed to provisional application Ser. No. 60/868,119, filed Dec. 1, 2006, which is incorporated herein by reference.

FEDERAL FUNDING STATEMENT

This invention was made with United States government support awarded by the following agency: NIH Grant AR042423. The United States goverment has certain rights in this invention.

FIELD OF THE INVENTION

The invention is directed to a fusion protein comprising a full-length TAT-utrophin or an anti-dystrophinopathic fragment thereof, a method of treating dystrophinopathies (including Duchenne muscular dystrophy) using the fusion protein and a pharmaceutical composition for treating dystrophinopathies in mammals comprising the fusion protein.

BACKGROUND

Duchenne muscular dystrophy (DMD) is the most prevalent and severe form of human muscular dystrophy. DMD occurs with an incidence of 1 in 4000 male births. Onset of DMD is typically between 3 and 6 years of age with skeletal muscle weakness preferentially affecting the large proximal muscle groups. The disease is invariably progressive, leading to loss of ambulation by 11 to 13 years, and death typically in the 20's. Significant laboratory findings include grossly elevated serum CK-MM levels. Skeletal muscle biopsy samples reveal a dystrophic pattern of muscle degeneration and regeneration with fiber-size variation, increased central nuclei, and progressive interstitial fibrosis.

Becker muscular dystrophy (BMD) was long considered to be a potentially allelic disorder because of its clinical similarities to DMD and a common pattern of X-linked inheritance. The shared genetic basis for DMD and BMD was confirmed after the identification of the protein dystrophin; both DMD and BMD patients were shown to have dystrophin gene mutations. Typically, patients with DMD lack any detectable dystrophin expression in their skeletal muscles, and this is correlated with deletion mutations that disrupt the translational reading frame or point mutations that create stop codons. In contrast, muscle from patients with BMD contains mutated dystrophins having an altered size and/or reduced abundance secondary to deletion mutations that maintain the reading frame.

While clinical descriptions of DMD date back to the 1850's, over 100 years passed before evidence suggested that the muscle cell plasma membrane, or sarcolemma, is compromised in DMD muscle. The molecular basis for DMD and its associated sarcolemmal instability became more clear with landmark studies published in the mid-to-late 1980's which identified the gene encoding dystrophin as being defective in DMD (O'Brien and Kunkel, 2001). The DMD locus spans over 2.5 million bases distinguishing it as the largest gene in the human genome. The array of transcripts expressed from the DMD gene is complex due to the presence of multiple promoters and alternative splicing. The largest transcripts encode dystrophin, a four-domain protein with a predicted molecular weight of 427,000. Dystrophin is the predominant DMD transcript expressed in striated muscle. DMD gene mutations, deletions, or duplications most frequently result in a loss of dystrophin expression in muscle of patients afflicted with DMD. Based on its localization to the cytoplasmic face of the sarcolemma, and its sequence similarity with domains/motifs common to proteins of the actin-based cytoskeleton, dystrophin was hypothesized early on to play a mechanical role in anchoring the sarcolemma to the underlying cytoskeleton It has also been hypothesized that dystrophin plays a role in protecting the sarcolemma against stress imposed during muscle contraction or stretch.

Biochemical studies aimed at confirming the hypothesized structure and function of dystrophin revealed its tight association with a multi-subunit complex, the so-named dystrophin-glycoprotein complex. See FIG. 1, which is a schematic representation showing the sarcolemma and the interaction of dystrophin with the other elements of the dystrophin-glycoprotein complex. Through its cysteine-rich and C-terminal domains, dystrophin in striated muscle interacts with the integral membrane dystroglycan sub-complex and the sarcoglycan/sarcospan sub-complex, as well as the subsarcolemmal dystrobrevins and syntrophins (Cohn and Campbell, 2000; Blake et al., 2002). The N-terminal domain and a portion of middle rod domain of dystrophin act in concert to effect an extensive lateral association with actin filaments in vitro (Rybakova et al., 1996) and in vivo (Rybakova et al., 2000; Warner et al., 2002; Rybakova and Ervasti, 1997; Amann et al., 1998; Amann et al., 1999).

Utrophin is a widely expressed autosomal gene product with high sequence similarity to dystrophin (Tinsley et al., 1992). Utrophin is distributed throughout the sarcolemma in fetal and regenerating muscle, but is down-regulated in normal adult muscle and is restricted to the myotendinous and neuromuscular junctions (Blake et al., 1996). Because utrophin and dystrophin bind the same complement of proteins (Matsumura et al., 1992; Kramarcy et al., 1994; Winder et al., 1995), it was hypothesized that utrophin may be capable of compensating for dystrophin deficiency. Indeed, continued utrophin expression in adult mdx mice partially attenuates the phenotype associated with dystrophin deficiency. In short, mice lacking both dystrophin and utrophin exhibit a more severe phenotype similar to that seen in human DMD patients (Deconinck et al., 1997a; Grady et al., 1997). Moreover, transgenic overexpression of full-length utrophin completely rescued the dystrophic phenotype in mdx mice (Tinsley et al., 1998).

Methods to express and purify full-length utrophin using a baculovirus system has been demonstrated (Rybakova et al., 2002 and 2006). It has also been shown that purified recombinant utrophin is a soluble, rod-shaped monomer with the expected molecular weight of 400,000 Da. Recombinant utrophin-bound actin filaments display an affinity ($K_d$=0.2 µM) similar to that measured for purified dystrophin-glycoprotein complex (Rybakova et al., 2002). Recombinant utrophin-bound F-actin displays a stoichiometry of 1 utrophin per 14 actin monomers, which implies a more extensive lateral association with actin filaments than anticipated from studies with isolated fragments, but a less extensive lateral association than the 1 per 24 stoichiometry measured for purified recombinant dystrophin (Rybakova et al., 2006). Like the dystrophin-glycoprotein complex, recombinant utrophin protected actin filaments from forced depolymerization in a concentration-dependent manner that saturated at molar ratios equal to or greater than 1 utrophin per 14 actin monomers. Also different from purified dystrophin-glycoprotein complex, the binding of recombinant utrophin to actin filaments was completely insensitive to increasing ionic strength up to 0.8 M. These results (Rybakova et al., 2002) (Rybakova et al., 2006) indicate that dystrophin and utrophin both bind laterally alongside actin filaments through contributions by the spectrin-like repeats of the rod domain, but that the rod domain epitopes involved differ between the two proteins. Utrophin appears to bind laterally along actin filaments through a contribution of the first 10 acidic spectrin-like repeats (Rybakova et al., 2002) rather than a cluster of basic repeats as employed by dystrophin (Rybakova et al., 1996; Amann et al., 1998); (Rybakova et al., 2006).

Most viruses, including the human immunodeficiency viruses (HIV), encode proteins for regulating genome transcription. In HIV, the tat gene plays a role in driving the transcription of the HIV genetic code. The tat gene encodes a small nuclear protein of from 86 to 101 amino acids, depending upon the viral strain. Both the tat gene and its encoded protein, TAT, are known. The protein itself is designated TAT, for "transactivator protein." The typical HIV-1 laboratory strains HXB2 and NL4-3 express an 86 amino acid-long TAT protein, while other HIV strains express a 101 amino acid-long TAT protein. See, for example, Kuppuswamy et al., 1989.

Despite all that is now known, and despite continuing efforts by many laboratories around the world (Gregorevic and Chamberlain, 2003), there is presently no cure or effective treatment to alleviate the devastating progression of DMD.

SUMMARY OF THE INVENTION

The primary object of the present invention is a method of treating dystrophinopathies in mammals, including humans. The method comprises administering an anti-dystrophinopathic-effective amount of a chimeric protein (i.e., a fusion protein) encoding TAT-utrophin. The chimeric protein is administered in an amount effective to transduce skeletal muscle cells and thereby to correct the pathologies associated with dystrophin deficiency. The chimeric protein may comprise a full-length TAT protein (e.g., 86 amino acids long or 101 amino acids long) or a fragment thereof, such as the HIV-1 TAT protein transduction sequence (see SEQ. ID. NO: 5). Similarly, the chimeric protein may comprise a full-length utrophin protein or an anti-dystrophinopathic-effective fragment thereof. (For purposes of brevity, both full-length and fragmented versions of the chimeric protein will be referred to herein as the "TAT-utrophin chimeric (or fusion) protein.") Utrophin fragments can be evaluated for their anti-dystrophinopathic effects by transgenically over-expressing the putative anti-dystrophinopathic fragment in mdx mice in the same fashion as Tinsley et al., 1998 and observing whether the dystrophic phenotype in the mdx mice is ameliorated or eliminated. Alternatively, the TAT-utrophin chimeras can be tested on mdx mice as described herein below for their anti-dystrophinopathic efficacy.

The invention is also directed to a baculovirus construct that drives the expression of the TAT-utrophin chimeric protein, the chimeric protein encoding TAT-utrophin itself, as well as a pharmaceutical composition for treating dystrophinopathies that comprises an anti-dystrophinopathic amount of the TAT-utrophin chimeric protein in combination with a pharmaceutically suitable carrier.

Thus, one version of the invention is directed to a fusion protein comprising a first protein region which is effective to transduce the fusion protein into mammalian muscle cells. The first protein region preferably comprises an HIV TAT protein or a transduction-effective fragment thereof. The first protein region is operationally linked to a second protein region comprising a full-length utrophin protein or an anti-dystrophinopathic fragment thereof. Also included within the invention are pharmaceutically suitable salts of the fusion proteins.

Another version of the invention is directed to a nucleic acid construct (vector) that drives the expression of the above-noted fusion protein when the construct is transformed into a suitable host or disposed in a suitable cell-free expression system. Many cell-free expression systems are commercially available. For example, Promega (Madison, Wis.) markets a suitable cell-free expression system under the registered trademark "TNT." Promega's "TNT"®-brand systems are single-tube, coupled transcription/translation reactions for eukaryotic cell-free protein expression. To use these systems, 0.2 to 2.0 µg of circular plasmid DNA containing a T7, T3 or SP6 promoter, or a PCR-generated fragment containing a T7 promoter, is added to an aliquot of the "TNT"®-brand Quick Master Mix and incubated in a 50 µl reaction volume for 60 minutes at 30° C. Other cell-free systems are offered commercially by Qiagen (Valencia, Calif.), Invitrogen (Carlsbad, Calif.), and others.

The transformed host itself is also encompassed within the scope of the present invention.

Another version of the invention is directed to a pharmaceutical composition for treating dystrophinopathies in mammals, including humans. The pharmaceutical composition comprises a fusion protein as noted previously, or a pharmaceutically suitable salt thereof, in an anti-dystrophinopathic amount, in combination with a pharmaceutically suitable carrier.

Yet another version of the invention is directed to a method of treating dystrophinopathies, including DMD, in mammals. The method comprises administering to a mammalian subject in need thereof an anti-dystrophinopathic amount of an isolated fusion protein or a pharmaceutically suitable salt thereof, wherein the fusion protein comprises a first region which is effective to transduce the fusion protein into mammalian muscle cells. The first region is operationally linked to a second region comprising a full-length utrophin protein or an anti-dystrophinopathic fragment thereof.

As described herein, the present inventors have expressed full-length utrophin in a baculovirus system and have shown that the expressed protein can be purified as a highly soluble monomer. The monomer has actin-binding activities similar to those measured for recombinant dystrophin and purified dystrophin glycoprotein complex. The invention also encompasses a baculovirus expression construct (i.e. a "bacmid") that encodes full-length mouse utrophin fused with an amino-terminal peptide corresponding to the protein transduction domain of the HIV TAT protein. TAT-utrophin expresses to high levels in insect cells, is fully soluble, and can be rapidly purified by affinity chromatography.

Transduction of TAT-utrophin into the skeletal muscle of dystrophin-deficient mdx mice corrects the dystrophic phenotype displayed by the mdx mice.

BRIEF DESCRIPTION OF THE DRAWINGS

FIG. 2 is a graph depicting the relative lengths and actin-binding properties ($K_d$ and $B_{max}$) of serially-deleted constructs of utrophin.

FIGS. 3A, 3B, 3C, and 3D compare in various terms the actin-binding properties of recombinant dystrophin versus the actin-binding properties of utrophin. FIG. 3A shows parallel gels containing (moving from left to right) a Coomassie blue-stained gel loaded with recombinant utrophin (rUTR) and recombinant dystrophin (rDYS), western blots stained with rabbit 31 antibodies (Rab31) specific for dystrophin, and DRP2 antibodies specific against utrophin. FIG. 3B is a graph depicting F-actin co-sedimentation data for rDYS (lower trace) and rUTR (upper trace); the X-axis plots concentration in μM, the Y-axis plots bound rDYS and rUTR (mol/mol actin). FIG. 3C is a graph depicting the effect of dystrophin/utrophin on depolymerization of actin filaments containing PRODAN-labeled monomers (-●-=actin, -□-=rDYS, -■-=rUTR). FIG. 3D is a graph depicting the relative lengths and actin-binding properties ($K_d$ and $B_{max}$) of the serially-deleted constructs.

FIG. 6A is a western blot that shows increased utrophin immuno-reactivity in several tissues of an mdx mouse after 6 intraperitoneal injections of TAT-UTR (+) compared to PBS-injected controls (−). FIG. 6B depicts the results of immunofluorescence analysis, which shows increased sarcolemmal HA-tag and DRP2 immunoreactivity in the TAT-UTR-treated animal (upper-left and upper-right panels, respectively) as compared to the sarcolemmal HA-tag and DRP2 immunoreactivity in PBS-injected controls (lower-left and lower-right panels, respectively).

FIGS. 7A, 7B, 7C, 7D, 7E, and 7F are a series of photographs showing greatly reduced histopathology in TAT-utrophin-treated mdx muscle versus controls. FIGS. 7A, 7B, and 7C depict TAT-utrophin-treated mdx muscle (TA and quadriceps), while FIGS. 7D, 7E, and 7F depict PBS-treated mdx muscle (TA and quadriceps). Haematoxylin and eosin stained sections revealed decreased numbers of centrally nucleated fibers and less fibrosis in TAT-UTR treated compared to PBS-injected mdx muscle.

FIG. 3B is a histogram depicting serum activity levels of the muscle enzyme creatine kinase from PBS- or TAT-utrophin-injected quadriceps from mdx mice. Creatine kinase levels were reduced 50% in 38 day-old TAT-utrophin-treated mice as compared to PBS-injected controls. (*) denotes $p<0.05$.

DETAILED DESCRIPTION OF THE INVENTION

Figure 1:
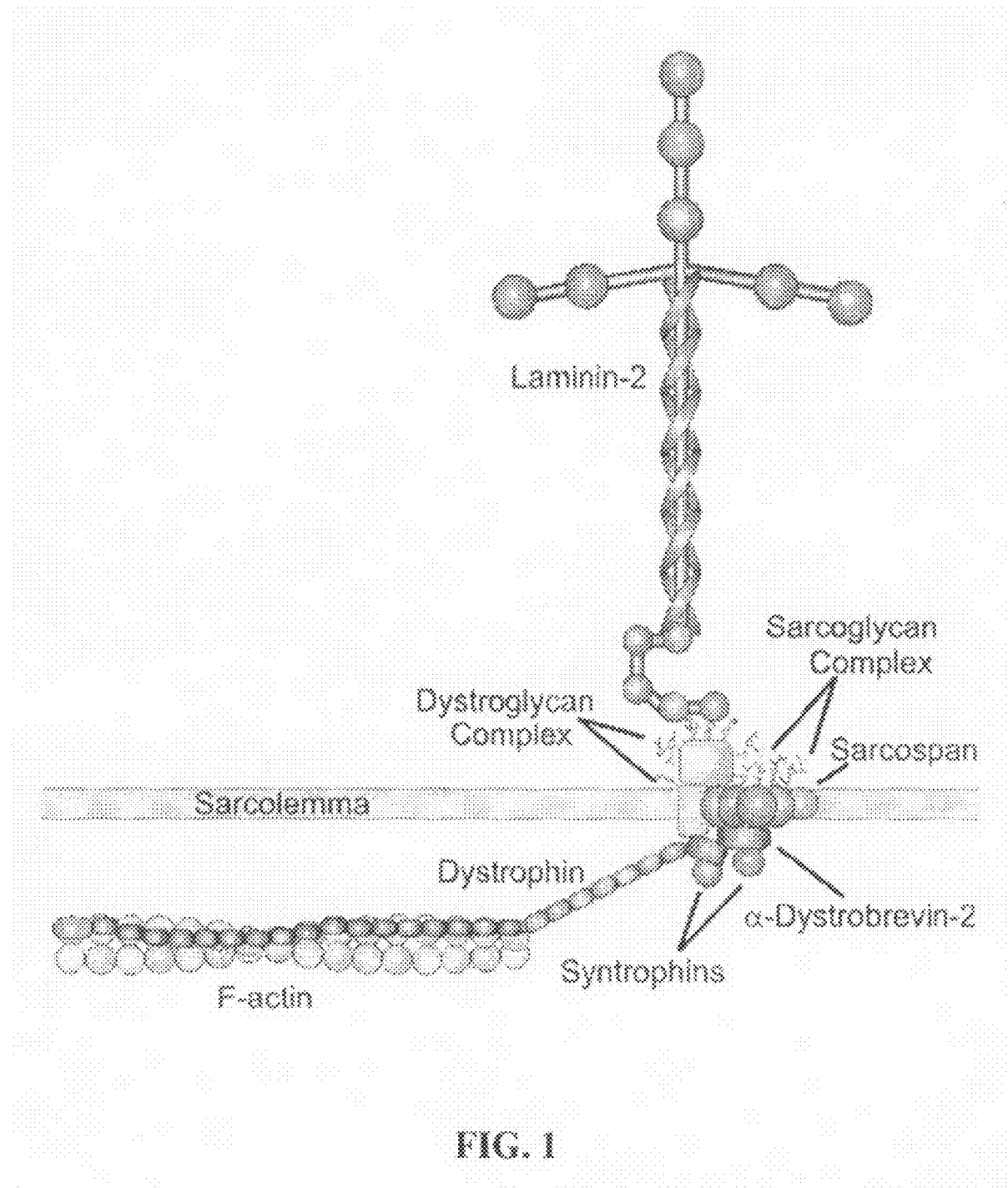
FIG. 1 is a schematic diagram of the dystrophin-glycoprotein complex.

Definitions and Abbreviations:

The following abbreviations and definitions are used throughout the specification and claims. Any terms not explicitly defined herein are to be given their accepted meanings in the fields of molecular biology, physiology, and/or biochemistry.

Affinity tag: Any moiety (typically a small oligopeptide) that can be affixed to a protein (by any means) which allows the resulting fused entity to be isolated by affinity chromatography.

Anti-dystrophinopathic fragment: a fragment of a full-length utrophin protein that functions to ameliorate dystrophinopathic symptoms when administered as part of the fusion protein described herein. Explicitly included within this definition are the utrophin fragments shown in SEQ. ID. NOS: 10-25 in the attached Sequence List. (The "delta" nomenclature used in the Sequence List reflects the number of deleted repeats. Thus, the construct "murine TAT-UTR delta 4-21" encodes a murine TAT-utrophin fusion protein deleted for repeats 4-21.) It is preferred that the fragment be no more than 75% of the mass of the full-length utrophin protein, more preferred that the fragment be no more than 50% of the mass of the full-length utrophin protein, and still more preferred that the fragment be no more than 25% of the mass of the full-length utrophin protein.

Bacmid: baculovirus shuttle vector.

BMD: Becker muscular dystrophy.

DMD: Duchenne muscular dystrophy.

Dystrophinopathy: All pathological conditions in mammals, including humans, due in full or in part to mutations in the gene(s) encoding the protein dystrophin (both now known or discovered in the future). Explicitly included within the definition of "dystrophinopathy" are BMD, DMD, EDMD, SBMA, XLDCM, elevated serum creatine kinase, and the like.

EDL: extensor digitorum longus muscle.

EDMD: Emery-Dreifuss muscular dystrophy.

"FLAG"-brand polypeptide: Generally, any polypeptide having the sequence DYKDDDDK (SEQ. ID. NO: 1), or a fragment thereof, such as the tetrapeptide DYKD (SEQ. ID. NO: 1), which can be used for isolating fusion proteins via affinity chromatography. The terms "FLAG" and "ANTI-FLAG" are registered trademarks of Sigma-Aldrich Biotechnology LP (St. Louis, Mo.). "FLAG"-brand polypeptides are available commercially from Sigma-Aldrich. See also Chubet & Brizzard (1996) "Vectors for expression and secretion of FLAG epitope-tagged proteins in mammalian cells," *Biotechniques* 20(1):136-141.

HIV-TAT or TAT: Human immunodeficiency virus transactivator protein. "Tat" is short for "transactivator," a regulatory gene that accelerates the production of more HIV virus. "TAT" designates the protein, while "tat" designates the corresponding gene that encodes the TAT protein. In its native milieu, the TAT protein binds to the start of a new HIV RNA strand. Once bound, TAT encourages the transcription of the remainder of the HIV genetic code. TAT from HIV is a protein containing from 86 to 101 amino acids, depending upon the strain of HIV. The 86 amino acid-long sequence of HIV-1 TAT is shown in SEQ. ID. NO: 2. The entire genomic sequence of the HIV-1 virus, including the tat gene (at nts 5377-5591 and 7925-7970), is shown in SEQ. ID. NO: 3. See Gaynor, R. B. (1995) Regulation of HIV-1 gene expression by the transactivator protein Tat. *Curr Top Microbiol Immunol* 193, 51-77. See also GenBank Accession No. AF033819 for a fully annotated version of the HIV-1 genomic sequence.

LGMD: Limb-Girdle muscular dystrophy.

mdx Mice: A strain of mice arising from a spontaneous mutation (mdx) in inbred C57BL mice. The mutation is X chromosome-linked and produces viable homozygous animals that lack the muscle protein dystrophin. Mdx mice have high serum levels of muscle enzymes, and possess histological lesions similar to human muscular dystrophy. The histological features, linkage, and map position of mdx make these mice a widely utilized animal model for Duchenne muscular dystrophy. Mdx mice can be purchased from several commercial suppliers, including The Jackson Laboratory, Bar Harbor, Me. (sold under the registered trademark "JAX").

Operationally linked: when referring to two or more regions of a protein or a nucleotide sequence, "operationally linked" means the two regions are physically linked either directly or indirectly via intervening amino acid residues, nucleotide bases, or any other type of linking moiety.

PBS: phosphate-buffered saline.

PCR: polymerase chain reaction.

Pharmaceutically-suitable salt: any acid or base addition salt whose counter-ions are non-toxic to the patient in pharmaceutical doses of the salts so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bishydroxynaphthoates, gentisates, isethionates, di-p-toluoyl-tartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like.

SBMA: Spinal bulbar muscular atrophy (also known as Kennedy's disease).

TA: tibialis anterior muscle.

Transduction: in general, the transfer of DNA from one cell to another; typically transduction is mediated via a bacteriophage, but any means of transferring the DNA from its original source to its ultimate destination are included within the term "transduction" as used herein.

UTR or UTRN: utrophin. The nucleotide sequence for the human utrophin gene and the corresponding amino acid sequence for the encoded human utrophin protein are shown in SEQ ID NOS: 6 and 7, respectively; the nucleotide sequence for the murine utrophin gene and the corresponding amino acid sequence for the murine utrophin protein are shown in SEQ. ID. NOS: 8 and 9, respectively.

WT: wild-type.

XLDCM: X-linked dilated cardiomyopathy.

A first version of the invention is directed to a TAT-utrophin fusion protein (TAT-UTR), and use of the TAT-UTR fusion protein to treat dystrophinopathies in mammals, including humans. To demonstrate the efficacy of the TAT-UTR to treat dystrophinopathies in mammals, the mdx mouse is used as a model to demonstrate that TAT-UTR is imported into striated muscle cells and that the TAT-UTR fusion protein eliminates or significantly reduces the dystrophic phenotype in mdx mice.

Thus, in this first version of the invention, purified TAT-utrophin is injected into dystrophin-deficient mdx mice in an anti-dystrophic-effective amount. The mdx mouse model serves to demonstrate efficacy in all mammals, including humans. Measurements are then taken to assess the extent to which the TAT-utrophin is transduced into striated muscle cells in vivo. The localization of the TAT-utrophin is then assessed to determine how much of the TAT-utrophin is localized to the sarcolemma. (As shown in FIG. 1, natural dystrophin exerts its biological effect in close conjunction with the sarcolemma.) Measurements are also taken to determine whether the TAT-UTR fusion protein becomes stably associated with other dystrophin-associated proteins. The progress of mdx mice treated with the TAT-UTR is then followed to measure the improvement of several well-established parameters of the dystrophic phenotype, such as specific force and force drop in the muscles of the treated mice versus the control mice.

A second version of the invention is directed to mini- and micro-TAT-UTR constructs and methods of using these constructs to treat dystrophinopathies in mammals, including humans. Thus, the invention also encompasses truncated mini- and micro-TAT-utrophin constructs and the use of these truncated versions of the protein to treat dystrophinopathies. Reducing the physical size of the fusion protein results in improved protein transduction in vivo. Two representative truncated constructs are described herein. These truncated fusion proteins are designed to retain full activity for all known binding partners of utrophin, but with a 40 to 50% reduction in the mass of the protein. A third construct is designed to mimic the structure of the most extensively truncated, fully-functional dystrophin micro-gene.

Using TAT-UTR as a protein-based therapy for treating dystrophinopathies is a relatively low-cost, low-risk, but high-return approach to treating these currently intractable and fatal conditions. At present, there simply is no effective treatment available to treat prevalent dystrophinopathies such as DMD.

The present invention includes a series of utrophin constructs encoding the amino-terminal, actin-binding domain alone (UTRN), or the amino-terminal domain plus 4, 7, 10, or 11 spectrin-like repeats. FIG. 2 depicts the relative lengths of these constructs and their binding characteristics. As shown in FIG. 2, the constructs are designated herein as UTRN-R3, UTRN-R6, UTRN-R9, and UTRN-R10, respectively. Interestingly, the UTRN-R10 protein bound to actin filaments with essentially the same properties as full-length recombinant utrophin (rUTR), which suggests UTRN-R10 encodes the complete actin-binding region of utrophin (see FIG. 2). The UTRN-R9, UTRN-R6, and UTRN-R3 proteins each bound to actin filaments with progressively lower affinity and stoichiometry as compared to full-length utrophin and UTRN-R10. (See FIG. 2.) These results demonstrate that the first ten (10) spectrin-like repeats of utrophin dramatically enhance the F-actin binding affinity and lateral association of the amino-terminal domain and provide a molecular basis for the greater effectiveness of full-length utrophin in rescuing dystrophin-deficient muscle as compared to a utrophin mini-gene deleted for spectrin-like repeats 4-19.

The present inventors have also expressed and characterized full-length mouse dystrophin. Recombinant dystrophin binds to actin filaments with a $K_d$ of 0.4 µM and $B_{max}$ of 1 dystrophin molecule per 24 actin monomers (see FIG. 3D, second construct), which is remarkably close to the actin-binding properties of purified dystrophin-glycoprotein complex (Rybakova et al., 1996). In direct comparisons (see FIGS. 3A, 3B, and 3C), dystrophin and utrophin differed only in their extent of lateral association with actin filaments (1-to-24 for dystrophin and 1-to-14 for utrophin), and in the effect of increasing ionic strength on actin filament binding. These results strongly suggest that dystrophin and utrophin are both actin-binding proteins, but that the molecular epitopes important for filament binding differ between the two proteins.

While transgenic utrophin overexpression rescued all known phenotypes associated with dystrophin-deficiency in mdx mice (Tinsley et al., 1998), there remains a widespread perception that utrophin levels must greatly exceed the amount of dystrophin expressed in normal muscle in order to cause full rescue from the dystrophinopathic phenotype exhibited by mdx mice. This perception is based, at least in part, on an early quantitative estimate (Hoffman et al., 1987) of dystrophin abundance in normal muscle (0.002% of total muscle protein) and the present inventors' own measurements of utrophin expression (Rybakova et al., 2002) in normal (0.0006%) and mdx muscle (0.0013%), as well as in the Fiona line of transgenic mdx mice that overexpress utrophin to levels (0.014%) that fully corrected the mdx phenotype. (See Tinsley et al., 1998). From these measurements, it can reasonably be concluded that up to 7-fold greater levels of utrophin (0.014%/0.002%) may be necessary to compensate for dystrophin deficiency.

However, the early measurements of dystrophin levels in normal muscle used a relatively small recombinant protein fragment (Hoffman et al., 1987). While state-of-the-art at that time, the much smaller protein fragment used as the standard likely transferred to nitrocellulose more efficiently than the full-length dystrophin protein. Thus, it is possible that the previous measurements (Hoffman et al., 1987) may have significantly underestimated the abundance of dystrophin in normal muscle. Therefore, the abundance of dystrophin in normal skeletal muscle has now been measured by quantitative western blotting using full-length recombinant mouse dystrophin as the standard and iodinated secondary antibody as previously described for utrophin (Rybakova et al., 2002). The measurements (see the table shown in FIG. 4) suggest that the abundance of dystrophin in normal muscle is 10-times greater (0.021±0.003%, n=7)(Rybakova et al., 2006) than previously reported (Hoffman et al., 1987). The new measurements more closely agree with the measured abundance of dystrophin (Ohlendieck et al., 1991) in highly purified sarcolemma vesicles (2% of sarcolemmal protein) and with quantitative estimates that sarcolemmal proteins comprise 1% of total muscle protein based on the density of sodium channels in total homogenates (0.09 pmol/mg total protein) and in purified sarcolemmal vesicles (8 pmol/mg sarcolemmal protein) from rat skeletal muscle (Barchi and Weigele, 1979).

Most importantly, however, these data indicate that utrophin can fully rescue the mdx phenotype (Tinsley et al., 1998) when expressed to levels approaching that of dystrophin in normal muscle (0.014%/0.02%=70%).

The present invention is thus a method of using recombinant utrophin as a protein-based therapy for treating dystrophinopathies in general and DMD in particular. The present method uses TAT-utrophin chimeric (i.e., fusion) proteins. The TAT portion of the chimeric protein serves to mobilize the protein (i.e., transduce the protein) into muscle cells. The UTR portion of the chimeric protein serves to ameliorate or to eliminate the dystrophic condition.

One distinct benefit of the invention is that utrophin itself is not toxic. Therefore, the TAT-UTR fusion proteins can be administered in relatively high doses, thereby making it easier to transduce therapeutically effective amounts of the TAT-UTR fusion protein into muscle cells. Ubiquitous transgenic over-expression of utrophin itself caused no toxicity in a broad range of tissues (Fisher et al., 2001). Thus, in the present invention, an 11 kb full-length mammalian utrophin cDNA (mouse) (Guo et al., 1996) was cloned in-frame into the bacterial expression vector pTAT (Nagahara et al., 1998), which was kindly provided by Dr. Steven Dowdy (University of California, San Diego). A Kozak consensus sequence and a "FLAG"-brand type epitope were engineered in-frame 5' to TAT-utrophin by PCR.

Figure 10:
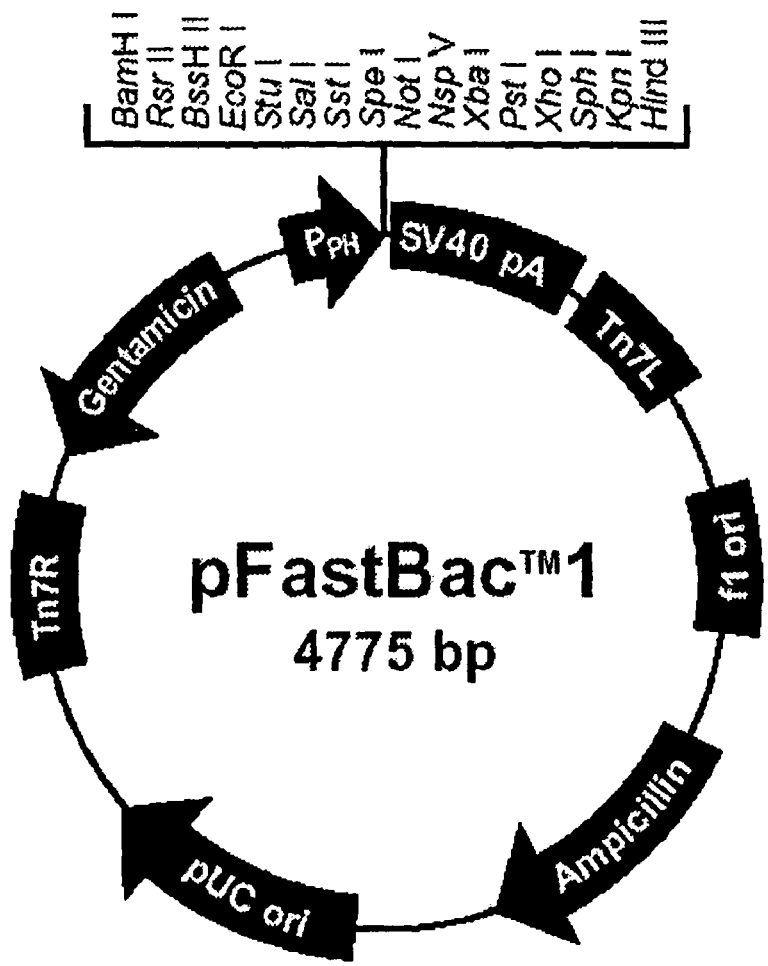
FIG. 10 is a map of the pFastBac1-brand plasmid, available commercially from Invitrogen.

The FLAG-TAT-utrophin construct was inserted into the pFastBac 1 donor plasmid (purchased commercially from Invitrogen, Carlsbad, Calif.). A map of the pFastBac1 donor plasmid is shown in FIG. 10 and the complete sequence of pFastBac1 is presented in SEQ. ID. NO: 4. Subsequent transformation into DHlOBac cells (purchased commercially from Invitrogen, catalog no. 18290-015) allowed for site-specific transposition into bMON14272 bacmid DNA. (The bMON14272 bacmid, along with the helper plasmid pMON7124, are included with the DHlOBac cells sold by Invitrogen. See Invitrogen's catalog no. 10359-016, and the product literature for Invitrogen's "BAC-TO-BAC"®-brand baculovirus expression system.)

Figures 4, 5:
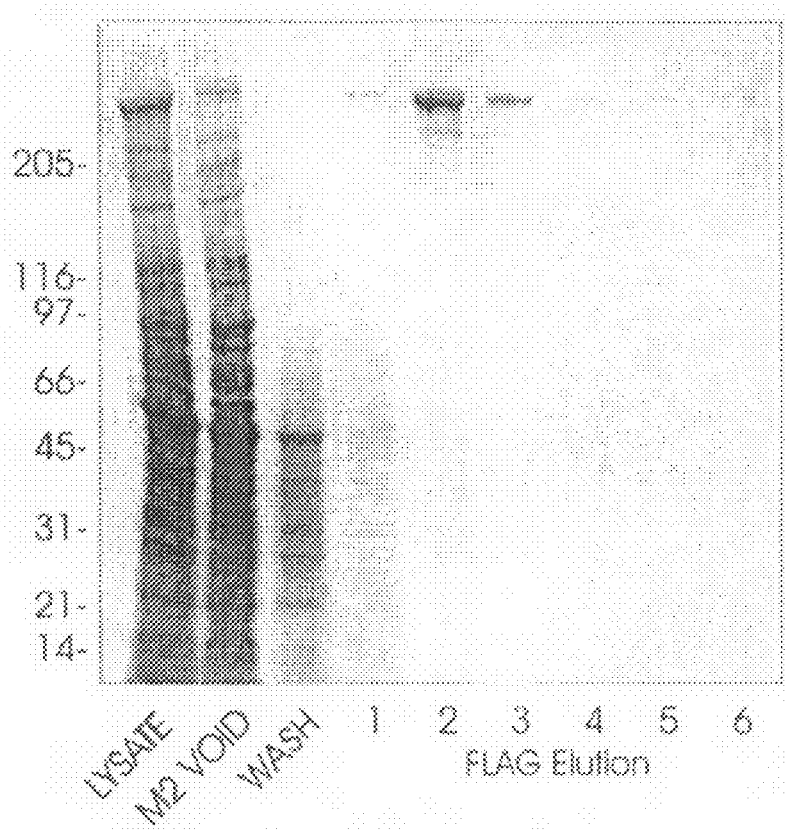
FIG. 4 is a graph depicting the quantitation of dystrophin and utrophin levels in skeletal muscle. The abundance of dystrophin and utrophin was measured in wild-type, mdx, and "Fiona" transgenic mdx mice overexpressing full-length utrophin by quantitative western blot analysis using recombinant dystrophin and utrophin as standards. Values are expressed as percent of total muscle protein and percent of dystrophin abundance in wild-type muscle.
FIG. 5 is a gel showing the expression and purification of TAT-utrophin in the baculovirus system. See the examples for lane assignments.

Colonies containing recombinant bacmid DNA were identified by blue/white screening and high titer viral stocks were used to infect Sf21 insect cells (*Spodoptera frugiperda*) for protein expression. (Sf21 cells are available commercially from a number of international suppliers, including Orbigen Inc., San Diego Calif., and Gentaur, Brussels, Belgium.) Infected Sf21 cells were harvested 72 h post-infection and TAT-utrophin was purified from cell lysates using "ANTI-FLAG"-brand M2 affinity resin (obtained commercially from Sigma-Aldrich, St. Louis, Mo.). The gel depicted in FIG. 5 shows that FLAG-TAT-utrophin is expressed as a fully soluble protein and can be easily purified by "ANTI-FLAG" M2 affinity chromatography. Thus, sufficient TAT-utrophin can easily be prepared to perform a host of experiments. Moving from left-to-right, the lanes of the gel in FIG. 5 depict the cell lysate prior to chromatography, the M2 column void volume, and the M2 column wash. The lanes numbered 1-6 then depict the elution of the M2 column to obtain the resulting fusion protein.

Figures 6A, 6B:
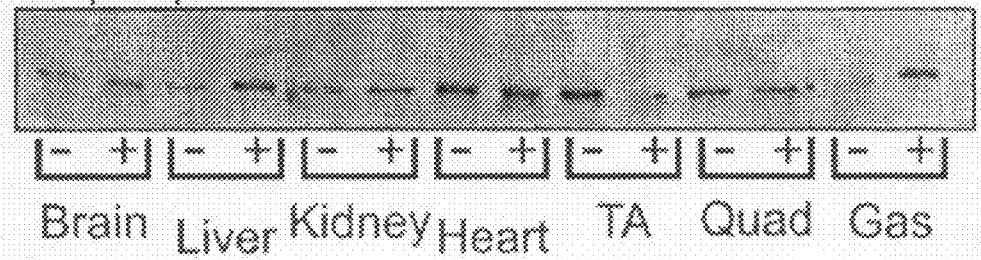
FIGS. 6A and 6B depict uptake and membrane localization of TAT-utrophin in mdx muscle.

To assess whether TAT-utrophin is measurably transduced into skeletal muscle, a 2.5 week-old mdx mouse received six intraperitoneal injections of TAT-utrophin (20 mg/kg in sterile PBS) administered biweekly. As a control, a littermate mdx mouse was sham-injected with sterile PBS in parallel. At age six weeks, both mice were euthanized, perfused with PBS, and muscle tissue was excised for western blot, immunofluorescence and histological analyses. Western blot analysis of lysates from several tissues showed increased utrophin immunoreactivity in the TAT-utrophin-treated mdx mouse compared to the PBS-injected animal. See FIG. 6A, which is a gel depicting the utrophin immunoreactivity of the treated mouse versus the untreated mouse in several different tissue types. Importantly, immunofluorescence analysis of muscle cryosections revealed both increased HA-tag and DRP2 immunoreactivity localized to the sarcolemma of muscle from the animal treated with TAT-utrophin. See FIG. 6B, where the two upper panels depict immunoreactivity in the treated mouse and the two lower panels depict immunoreactivity in the untreated mouse.

Most strikingly, light microscopic analysis of haematoxylin and eosin-stained muscle cryosections showed dramatically decreased fibrosis and numbers of centrally nucleated myofibers in the TAT-utrophin treated animal compared to PBS-injected control. Compare FIGS. 7A, 7B, and 7C (which are photos of tibialis anterior ("TA") and quadriceps ("QUAD") muscle fibers from treated mice) to FIGS. 7D, 7E, and 7F (which are corresponding photos from untreated mice). In the quadriceps, the percentage of centrally nucleated fibers was 48% in the PBS-injected control, but only 24% in the TAT-utrophin-treated animal. The combined data of FIGS. 6A, 6B, 7A, 7B, 7C, 7D, 7E, and 7F show that TAT-utrophin effectively transduced skeletal muscle cells in vivo, correctly localized to the sarcolemma, and improved the histopathology of dystrophin-deficient mdx muscle.

Figures 8A, 8B:
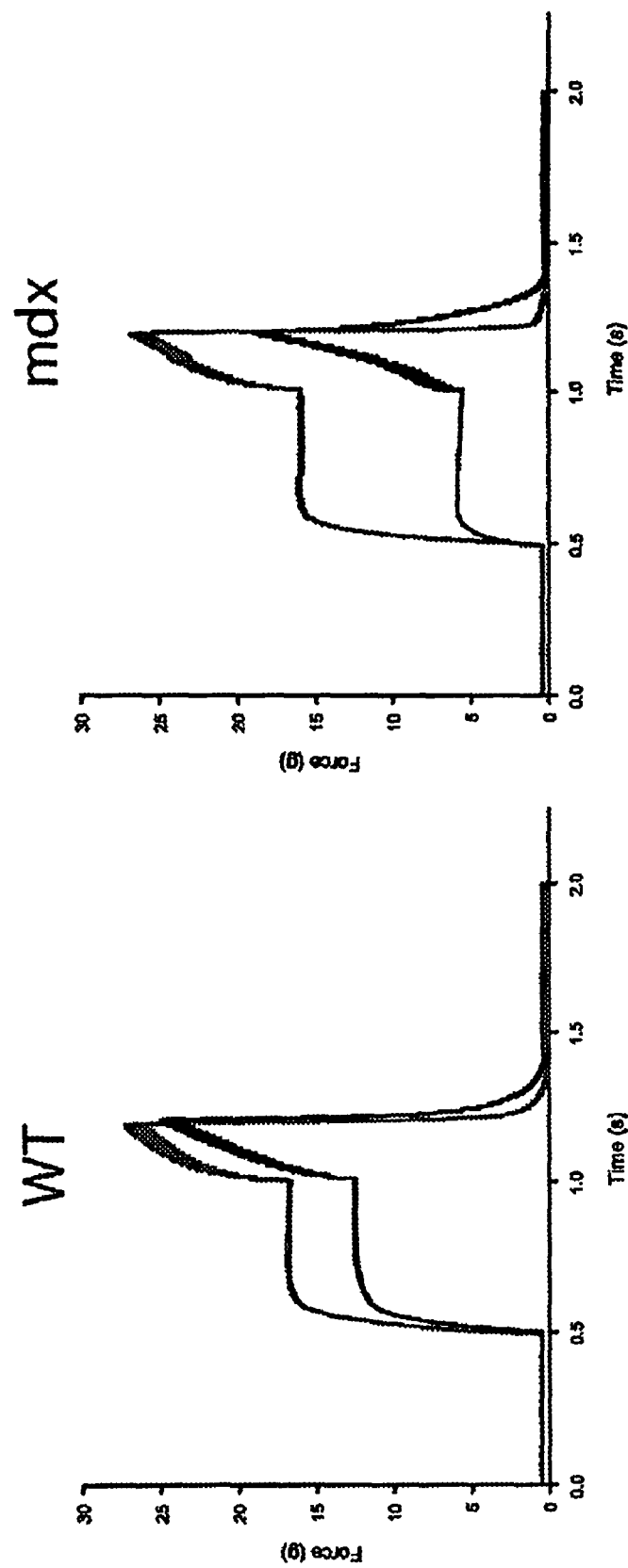
FIGS. 8A and 8B are graphs depicting the increased susceptibility of mdx muscles to eccentric contraction. Shown are tracings of maximal force versus time obtained during the first (upper trace) and fifth (lower trace) eccentric contraction imposed on isolated EDL muscle from wild-type (WT) and dystrophin-deficient mdx mice. Note the greater force drop in mdx muscle versus WT muscle as previously reported by Petrof et al. (1993) and Moens et al. (1993).

Of course, recovery of muscle function is the ultimate criterion for evaluating the efficacy of any therapy for dystrophinopathies. Several studies have demonstrated that specific force production by mdx muscle is significantly decreased. It has also been shown that mdx muscle is hypersensitive to lengthening and eccentric contraction (Petrof et al., 1993; Moens et al., 1993). Therefore, these parameters were measured in sham- and TAT-utrophin treated mdx mice. (Kind thanks are extended to Dr. Richard L. Moss for his aid in conducting these tests.) FIGS. 8A and 8B provide data demonstrating that the eccentric contraction protocol described in Petrof et al. (1993) and Moens et al. (1993) can be performed and that these tests performed by the present inventors reproduced the key findings of Petrof et al. (1993) and Moens et al. (1993).

Regarding the key utility of the present invention, the Examples presented below clearly demonstrate that dystrophinopathic mammals treated according to the present invention show a significantly increased specific force produced by their muscles as compared to untreated dystrophinopathic mammals, as well as a significantly decreased force drop. See Example 3 and FIGS. 11 and 12. Thus, the utility of the compounds, compositions, and methods of the present invention is to ameliorate the disabling effects of dystrophinopathic conditions in mammals, including DMD in humans.

As indicated above, the invention includes pharmaceutical compositions comprising the fusion protein(s) described herein and/or a pharmaceutically acceptable salt thereof together with a pharmaceutically acceptable carrier. The compositions may also include other therapeutically active substances in addition to the fusion protein and/or salt thereof. The pharmaceutical compositions of the invention comprise an amount of the fusion protein and/or a pharmaceutically suitable salt thereof that is effective to ameliorate dystrophinopathic symptoms in a mammal suffering from a dystrophinopathy. In a pharmaceutical composition of the invention, the carrier must be pharmaceutically acceptable in the sense of being compatible with other ingredients in the particular composition and not deleterious to the recipient thereof. The compositions include those suitable for oral, topical, rectal or parenteral (including subcutaneous, intramuscular, intraperitoneal, intradermal and intravenous) administration. Parenteral administration, either via the intramuscular or the intraperitoneal routes, is preferred.

In a particular version of the invention, the pharmaceutical compositions comprise the active ingredient (the fusion protein or a salt thereof) presented in a unit dosage form. The term "unit dosage" or "unit dose" is denoted to mean a predetermined amount of the active ingredient sufficient to be effective for treating dystrophinopathy. Preferred unit dosage formulations are those containing a daily dose, daily subdose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form.

Compositions of the present invention suitable for oral administration may be presented as discrete unit dosages, e.g., as capsules, cachets, tablets, boluses, lozenges and the like, each containing a predetermined amount of the active ingredient; as a powder or granules; or in liquid form, e.g., as a collyrium, suspension, solution, syrup, elixir, emulsion, dispersion and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered active compound with any suitable carrier.

Compositions suitable for parenteral administration conveniently comprise a sterile injectable preparation of the active ingredient in, for example, a solution which is preferably isotonic with the blood of the recipient. Useful formulations also comprise concentrated solutions or solids containing the active ingredient which upon dilution with an appropriate solvent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredient formulated into pharmaceutically-acceptable topical vehicles by conventional methodologies. Common formulations include drops, collyriums, aerosol sprays, lotions, gels, ointments, plasters, shampoos, transferosomes, liposomes and the like.

Compositions suitable for inhalation administration, wherein the carrier is a solid, include a micronized powder or liquid formulation having a particle size in the range of from about 5 μm or less to about 500 μm, for rapid inhalation through the nasal or oral passage from a conventional inhalation squeeze or spray container. Suitable liquid nasal compositions include conventional nasal sprays, nasal drops and the like, of aqueous solutions of the active ingredient and optional adjuvants.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants), and the like.

The amount of active ingredient required to be effective for any specific dystrphinopathy in any specific patient will, of course, vary with the individual mammal being treated and is ultimately at the discretion of the medical or veterinary practitioner. The factors to be considered include the species and sex of the mammal, the dystrophinopathic condition being treated, the route of administration, the nature of the formulation, the mammal's body weight, surface area, age and general condition, and the particular compound to be administered.

In general, the pharmaceutical compositions of this invention contain from about 0.5 to about 500 mg and, preferably, from about 5 to about 350 mg of the active ingredient, preferably in a unit dosage form, for each of the indicated activities. However, a suitable effective dose is in the range of about 0.1 to about 200 mg/kg body weight per day, preferably in the range of about 1 to about 100 mg/kg per day, calculated as the non-salt form of the fusion protein. The total daily dose may be given as a single dose, multiple doses, e.g., two to six times per day, or by intravenous or parenteral infusion for a selected duration. Dosages above or below the range cited above are within the scope of the present invention and may be administered to the individual patient if desired and necessary. In topical formulations, the subject compounds are preferably utilized at concentrations of from about 0.1% to about 5.0% by weight.

EXAMPLES

The following Examples are presented solely to provide a more complete description of the invention disclosed and claimed herein. The Examples do not limit the scope of the invention claimed herein in any fashion.

Example 1

—Expression, Purification of TAT-Utrophin; General Protocols:

1.a. Expression and Purification of TAT-Utrophin. High titer stocks of recombinant baculovirus encoding the "FLAG"-tagged TAT-utrophin chimera were used to infect Sf21 insect cells for protein expression by a shaker culture procedure described in the manufacturer's instructions. Infected Sf21 cells were harvested 72 h post-infection and resuspended in 10 ml of 50 mM Tris-HCl, pH 7.4, 150 mM NaCl, 1% Triton X-100, and a cocktail of protease inhibitors. The soluble lysate was circulated over a 2 ml "ANTI-FLAG" M2 agarose column (Sigma-Aldrich). The column was washed extensively with 10 mM Tris-HCl, pH 7.4, 150 mM NaCl and bound protein eluted with the same buffer containing 100 µg/ml "FLAG"-brand peptide (Sigma-Aldrich). Purified protein was concentrated in a Centricon 100 column (Amicon) and quantified with the Bio-Rad DC Protein Assay Kit using BSA as standard. The typical yield of pure utrophin was 700 µg when only five 177 cm$^2$ plates of cell monolayer were used as a starting material. The protocols can be easily scaled up as needed.

Quality control analysis. The data indicate that TAT-utrophin is abundantly expressed in a highly soluble form that can be readily purified by "ANTI-FLAG" affinity chromatography (see FIG. 5). It is critical to note that including the TAT sequence within the fusion protein has no adverse effect on utrophin structure/function. The purified TAT-utrophin is to be analyzed by gel permeation chromatography (Rybakova and Ervasti, 1997), velocity sedimentation analysis (Ervasti et al., 1991) and electron microscopy after rotary shadowing (Rybakova et al., 2002). These analyses yield quantitative measures for the native molecular weight, dimensions, shape, oligomeric/aggregative state as well as an assessment of proper folding.

The F-actin binding properties of TAT-utrophin are measured using the established high-speed co-sedimentation assay (see FIG. 3B) and binding data is analyzed by nonlinear regression analysis. These experiments will yield both the apparent $K_d$ and $B_{max}$ of recombinant protein binding to F-actin. See FIG. 3D. The ability of different proteins to protect actin filaments from depolymerization is measured by monitoring the time-dependent decay in fluorescence of preformed filaments seeded with PRODAN-labeled (i.e., 6-propionyl-2-(N,N-dimethyl)aminonaphthalene-labeled) monomers at Cys374 (Marriott et al., 1988; Miyata et al., 1997) as shown in FIG. 3C. All data is compared to those measured for recombinant utrophin performed in parallel.

More specifically, an 11 kb full-length murine utrophin cDNA was subcloned in-frame into the bacterial expression vector pTAT to generate PTAT-Utr. To prepare for eventual expression and purification of TAT-Utrophin in Sf21 insect cells using a baculovirus expression system, a Kozak consensus sequence and FLAG-epitope were engineered in-frame at the extreme 5' end of TAT-Utr using PCR primers KJS36 (5' gcggccgcacaccatggactacaagga-caacgatgacaaggctacggccgcaagaaac-3') (SEQ. ID. NO: 26) (FLAG-epitope is underlined) and KJS32 (5'-ggagatgcacag-caacagtttcaggacttagg-3') (SEQ. ID. NO: 27). This FLAG-TAT-utrophin construct was inserted into the bacmid donor plasmid pFastBac1 (Invitrogen, Carlsbad, Calif.) and subsequently transformed into DH10BAC (Invitrogen) bacterial cells to allow for site-specific transposition into bacmid DNA. Recombinant bacmid DNA was purified and used to transfect Sf21 cell monolayers in order to generate recombinant baculovirus. Recombinant virus infection of Sf21 monolayers and recombinant protein purification using anti-FLAG M2 affinity resin (Sigma, St. Louis, Mo.) was performed as per the manufacturer's instructions.

Elution fractions were pooled, dialyzed against phosphate buffered saline (PBS) overnight, and concentrated using a Centricon 100 (Millipore, Concord, Mass.). The purified protein was sterilized for injection by passage through a 0.22 µm filter and injected into the intraperitoneal cavity of mdx mice at a concentration of 0.5 to 1.0 mg/ml. The pure protein was stable for up to 4 days when kept on wet ice at 4° C. (assessed by a lack of degradation on Coomassie blue stained SDS-polyacrylamide gels), so a single protein preparation was utilized for up to 2 injections when possible. Otherwise, protein was prepared fresh for each injection.

1.b. Treatment Time Course. Pairs of female C57Bl/10ScSn-Dmdmdx/J (The Jackson Laboratory, Bar Harbor, Me.) littermates were treated in parallel, one of which received a dose of 20 µg TAT-utrophin/g body weight while the control mouse received equal volume injections of sterile PBS. A total of 6 biweekly injections were administered over three weeks, beginning at 18 days and culminating at 35 days of age. Three days after the final injection, serum and tissue were collected for creatine kinase, western blot, immunofluorescence, histological, and physiological analyses. Animals were housed and treated in accordance with the standards set by the University of Wisconsin Institutional Animal and Care and Use Committee.

1.c. Protein extracts and Western Blotting. Tissues were dissected from freshly killed mice and snap frozen in liquid nitrogen. Frozen tissue was pulverized with a liquid nitrogen-cooled mortar and pestle and solubilized in 1% SDS, 5 mM EGTA, and a cocktail of protease inhibitors. Samples were incubated for 2 minutes at 100° C. and centrifuged 2 min at 12000×g. The supernatant protein concentration was determined with the Bio-Rad DC protein assay kit using bovine serum albumin as standard. Equal amounts of protein was separated by SDS-PAGE and transferred to nitrocellulose. Western blot analysis of utrophin levels was performed with rabbit polyclonal antibody 103 raised against the carboxyl-terminus of utrophin (generously provided by Dr. Stanley Froehner, University of Washington) diluted 1:250 in BLOTTO (i.e., bovine lacto transfer technique optimizer, a blocking reagent made from nonfat dry milk and PBS) (5% milk in PBS, pH 7.5) and anti-FLAG monoclonal antibody M2 (Sigma) diluted 1:1000 in BLOTTO. (BLOTTO blocking reagents are also commercially available from, for example, Thermo-Fisher Scientific, Waltham, Mass., catalog no. PI-37530.)

1.d. Histological and Morphometric Analysis. Individual muscles were dissected from freshly killed mice, coated with "O.C.T." matrix solution ("TissueTek"®-brand, Sakura Finetek, Torrance, Calif.; O.C.T. refers to "optimum cutting temperature," a specimen matrix formulation comprising water-soluble glycols and resins for cryostat sectioning at temperatures of −10° C. and below), and rapidly frozen in liquid nitrogen-cooled isopentane. Ten (10) µm thick cryosections were cut on a Leica CM3050 cryostat, allowed to dry, and stained with hematoxylin and eosin-phloxine. Sections cut from the mid-belly of both the tibialis anterior and quadriceps were selected for histological assessment. Images were collected on a Zeiss Axiovert 25 microscope and compiled into montages of entire sections in CorelDraw 10 and exported to Scion Image (Scion Corporation, Frederick, Maryland) for morphometric analyses. The percentage of centrally nucleated fibers and fiber diameters were determined from one muscle of each mouse, with every fiber scored for CNF analysis and ~700 fiber diameters measured per muscle section. A Student's t-test was used to compare average CNF values and average fiber diameter. To determine statistical significance of fiber diameter variability, a student's t-test was performed on the standard deviations of individual muscle sections.

1.e. Immunofluorescence. 10 µm thick cryosections were fixed in 4% paraformaldehyde for 10 minutes, washed 3×10 minutes in PBS, and blocked in 5% goat serum for 30 minutes. Primary antibodies were applied in 5% goat serum overnight at 4° C. and washed off 3×10 minutes in PBS. "ALEXA"®-brand 488- or 568-conjugated secondary antibodies (Invitrogen) were incubated for 30 min before a final 3×10 minute wash cycle. Coverslips were applied with a drop of Anti-Fade Reagent (Molecular Probes) and confocal images obtained using a Bio-Rad MRC 1000 scan head mounted transversely to an inverted Nikon Diaphot 200 microscope at the Keck Center for Biological Imaging. Primary monoclonal antibodies used were anti-HA tag HA. 11 (BABCO, Berkeley, Calif.) 1:1000; anti-utrophin DRP2 (Novacastra, Newcastle upon Tyne, UK) 1: 10; anti-β-dystroglycan b-DG (Novacastra) 1:1000; anti-α-sarcoglycan (NCL-a-SARC; α-SG), (Novacastra) 1:1000; and anti-γ-sarcoglycan g-SARC (Novacastra) 1:1000.

1.f. Contractile Properties. All mechanical properties were adapted from Petrof et al. After rapid PBS perfusion, the extensor digitorum longus (EDL) muscles were quickly dissected tendon to tendon and immersed in an $O_2$-saturated Ringer's solution (135 mM NaCl, 4 mM KCl, 1 mM $MgCl_2$, 10 mM HEPES, 10 mM glucose, and 1.8 mM $CaCl_2$, pH 7.4) at 25° C. Suture silk (4-0) was used to attach one tendon to a rigid support and the other to a dual lever force transducer (Aurora Scientific, Ontario, Canada) and the entire apparatus was immersed in oxygenated Ringer's solution and allowed to equilibrate for 5 minutes. Muscles were stimulated through two platinum plate electrodes on either side of the muscle. A range of twitch stimulations were performed to determine $L_o$, the muscle length at which maximal twitch force was produced. After 5 minutes of recovery, the EDL was maximally activated to determine maximal tetanic tension. Data were normalized against cross-sectional area of each individual muscle.

Protection against mechanical injury was assessed by subjecting the muscle to a series of five eccentric contractions (ECC). Each ECC consisted of maximally activating the muscle for 700 ms, with a stretch of 0.5 $L_o$/s over the final 200 ms to result in a total stretch of 0.1 $L_o$. Five minutes of recovery time was allowed between each ECC. Force drop was calculated as (ECC1-ECC5)/ECC1. Data were compared using ANOVA followed by a Tukey post hoc test.

1.g. Serum CK Analysis. Retro-orbital bleeds were performed on anesthetized mice using heparinized capillary tubes. Approximately 100 µl of blood was obtained per mouse, centrifuged at 5000 rpm and the serum layer removed and stored at —80° C. for analysis. Creatine kinase levels were determined using Vitros CK DT slides (Ortho-Clinical Diagnostics, Raritan, N.J.) and analyzed using a Kodak Ektachem DT60 Analyzer as per the manufacturer's instructions. Data were collected in Units/ml and compared using a Student's T-test.

Example 2

—Effect of TAT-Utrophin on the Dystrophic Phenotype of mdx Mice:

In this Example, purified TAT-utrophin is injected into dystrophin-deficient mdx mice. The mice are then examined to assess the extent to which the TAT-utrophin is transduced into striated muscle cells in vivo. The extent of uptake is measured, and the amount of TAT-utrophin localized to the sarcolemma is determined. Optionally, it may also be determined whether the TAT-utrophin becomes stably associated with other dystrophin-associated proteins. The quantitative improvement of several well-established parameters of the dystrophic phenotype is then measured in mdx mice treated with TAT-utrophin and compared to untreated controls and placebo groups.

Administration of TAT-utrophin—Purified TAT-utrophin is dialyzed against phosphate-buffered saline and sterilized by passage through a Millex-GP 0.22 µm filter. Assuming 100% protein transduction specifically into skeletal muscle, a minimal dose of 11 µg TAT-utrophin per gram body weight is believed to compensate for dystrophin deficiency. Of course, it is likely that TAT-utrophin will distribute to all tissues and transduction efficiency will almost certainly be less than complete. Therefore, TAT-utrophin is preferably administered via intraperitoneal injection at several different concentrations ranging from 1-5 mg/ml and total injection volumes of 0.1-0.5 ml.

Measurement of TAT-Utrophin Uptake and Cellular Location - TAT-utrophin uptake into skeletal muscle and cellular localization is assessed by two methods. In the first method, mice are deeply anesthetized with avertin, the chest wall is opened, and the animals are infused for 20 minutes with phosphate-buffered saline through the left ventricle with an outflow path from the right atrium. Skeletal muscles are then dissected and used in the preparation of KCl-washed skeletal muscle membranes (Ohlendieck et al., 1991), or immediately snap-frozen in liquid nitrogen to prepare SDS total protein lysates (Rybakova et al., 2002). Both preparations are analyzed for TAT-utrophin content by quantitative western blot analysis using "ANTI-FLAG"-brand M2 antibody (Sigma-Aldrich) detected with $^{125}$I-goat anti-mouse IgG and the signals quantitated by phosphor autoradiography. Analysis of total protein lysates and KCl-washed membranes provides a measure of the fraction of TAT-utrophin stably associated with the sarcolemma. The absolute utrophin content in SDS muscle lysates of TAT-utrophin-treated mice is also quantitatively compared to the utrophin content of sham-treated mdx mice and transgenic mdx mice expressing full-length utrophin (Fiona) to levels that rescue all known phenotypes of mdx mice. These comparisons provide a quantitative assessment of the TAT-utrophin uptake relative to a fully-rescued transgenic animal model.

In the second method, anesthetized animals are infused for 2 minutes with PBS followed by a 20 minute infusion of 2% paraformaldehyde in PBS. Various skeletal muscles are dissected, post-fixed for 5 minutes in 2% paraformaldehyde, and frozen in liquid nitrogen-cooled isopentane. From 8 µm cryosections, both the uptake and cellular location of TAT-utrophin is assessed using confocal immunofluorescence microscopy.

The KCl-washed membranes, SDS lysates and cryosections prepared from TAT-utrophin-treated mdx mice are also used to detect alterations in the abundance and sarcolemmal localization of other proteins within the dystrophin-glycoprotein complex including α- and β-dystroglycan, α-, β-, γ- and δ-sarcoglycans, syntrophin and α-dystrobrevins. Relative protein abundance can be assessed by quantitative western blot analysis of total muscle SDS extracts (Rybakova et al., 2002), while cellular localization and organization can be assessed by immunofluorescence analysis of both longitudinal and transverse cryosections and mechanically peeled sarcolemma (Rybakova et al., 2000).

Assessment of costamere structure and function—To assess whether TAT-utrophin treatment can restore mechanical coupling between the sarcolemma and costameric γ-actin, confocal immunofluorescence microscopy analysis is performed on mechanically peeled sarcolemma (Rybakova et al., 2000) from sham and TAT-utrophin-treated mdx mice. Paraformaldehyde-fixed sarcolemma are blocked for 2 h at 4° C. with 5% serum in PBS and incubated with the appropriate primary antibodies overnight at 4° C. The specimens are washed with PBS, incubated with fluorescent secondary antibody for 30 min at 37° C., rinsed and sealed under coverslips in an anti-fade solution.

Assessment of Dystrophic Phenotype—Skeletal and cardiac muscle of dystrophin-deficient mdx mice exhibits several histologic and physiologic defects in common with patients suffering from Duchenne muscular dystrophy. Most notable (and easily measured) are a dramatic elevation in centrally nucleated fibers of irregular size resulting from muscle fiber necrosis/regeneration and elevated serum creatine kinase levels due to sarcolemmal instability.

For histologic analysis, 8 µm cryosections of skeletal muscle from control, sham-injected, and TAT-utrophin-injected mdx mice are stained with haematoxylin and eosin and the percentage of central nuclei and mean fiber diameter measured. Histological analyses are also performed on several different muscles to compare the effects of TAT-utrophin on different fiber types, and muscles experiencing different work loads and activities. Measurement of these parameters in C57BL/10 control and sham-injected mdx mice provides a baseline and elevated values for normal and dystrophic muscle, respectively. While the number of centrally-nucleated fibers is already quite high (~40%) in 4 week-old mdx mice (Warner et al., 2002), this parameter doubles yet again by 10-12 weeks of age (Warner et al., 2002). Therefore, it is possible to measure a decrease in the percentage of centrally nucleated fibers in mdx mice treated for 2 months with TAT-utrophin compared to sham-treated mice.

To assess for sarcolemmal damage, quantitative colorimetric analysis of serum creatine kinase levels is performed using CK DT slides (Ortho-Clinical Diagnostics) measured with a Kodak Ektachem DT 60 Analyzer. A minimum of 5 animals in each treatment regime are measured at several time points post-injection. Evans blue infiltration is also assessed, which has been shown to accumulate significantly in dystrophin deficient mdx cardiac and skeletal muscle (Straub et al., 1997). Evans blue dye in sterile PBS is injected into the tail veins of control and knockout littermates and the animals sacrificed 3-6 h after dye administration. After skinning, the animals are visually inspected for macroscopic dye uptake by a blue coloration of limb muscles. 100% of mdx mice and 0% of control mice exhibit indication of membrane damage by this technique (Straub et al., 1997). In addition, 8 µm cryosections are examined by immunofluorescence microscopy to quantitate the fraction of muscle cells infiltrated by Evans blue (Straub et al., 1997).

Assessment of contractile function—Several studies have demonstrated that specific force production by mdx muscle is significantly decreased and hypersensitive to lengthening, or eccentric contraction (Petrof et al., 1993; Moens et al., 1993). Thus, the measure isometric twitch and tetanic tension in intact muscles from sham- and TAT-utrophin treated mdx mice are measured. The EDL muscle is dissected tendon to tendon and allowed to equilibrate in oxygenated mammalian Ringers' solution (Eddinger et al., 1986), and then tied into a dual mode force transducer (Aurora Scientific). The muscle length ($L_o$) at which maximal twitch tension is obtained is determined with a single pulse at a stimulation frequency of 2500 Hz at increasing muscle lengths. After a 10 minute wait, the muscle undergoes a series of 5 eccentric contractions (ECC) with the maximal tetanic tension measured for each round. The ECC protocol involves stimulation at 150 Hz at $L_o$ for 500 msec followed by lengthening the muscle by 0.5 $L_o$/sec for 200 msec before relaxing at a rate of 0.5 $L_o$/sec for 200 msec. This protocol results in a stretch equal to 10% $L_o$. There is a 5 minute wait in between each ECC to allow the muscle to recover. All measurements are recorded and analyzed using Dynamic Muscle Control and Analysis Software (Aurora Scientific).

Example 3

—Generation of Mini- and Micro-TAT-Utrophin Constructs:

In parallel with the experiments described in Example 1, the invention also encompasses fusion proteins wherein the utrophin portion of the fusion protein has been truncated (to lower the molecular weight of the fusion protein), without deleteriously impacting the anti-dystrophinopathic activity of the fusion protein. Thus, the invention encompasses truncated, but fully functional mini- and micro-TAT-utrophin constructs. It is hoped that reducing the size of the chimera leads to improved protein uptake.

Figures 9A, 9B:
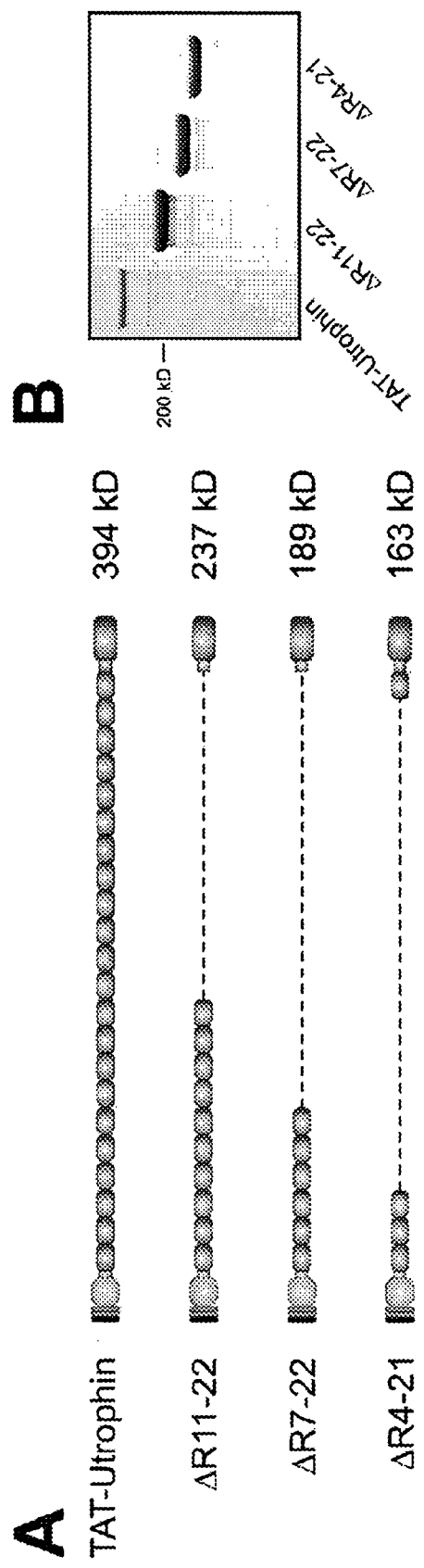
FIG. 9A is a schematic representation of mini- and micro-TAT-utrophin constructs according to the present invention.
FIG. 9B is a Coomassie Blue-stained protein gel of the truncated TAT-utrophin constructs depicted schematically in FIG. 9A.

Bacmid construction—Mini- and micro-TAT-utrophin constructs are generated with the "BAC-TO-BAC"-brand expression system (anvitrogen), which has been used to express full-length mouse utrophin (Rybakova et al., 2002), dystrophin (see FIG. 3A), and numerous truncation constructs (see FIG. 2). Briefly, all expression constructs are PCR-amplified from the TAT-utrophin construct using PfuUltra high-fidelity DNA polymerase (Stratagene) to incorporate an amino-terminal "FLAG"-brand type purification tag (DYKDDDDK) (SEQ. ID. NO: 1) followed by the HIV TAT protein transduction sequence (YGRKKRRQRRR) (SEQ. ID. NO: 5). The HIV TAT protein transduction sequence is preferred. However, any sequence that functions to transduce the fusion protein into mammalian muscle cells may be used in its place. The mini- and micro-constructs planned or actually made are shown schematically in FIG. 9. Preferably, the constructs all contain intact cysteine-rich and carboxy-terminal domains to ensure optimal β-dystroglycan binding activity (Ishikawa-Sakurai et al., 2004).

Based on actin-binding studies of serially-truncated utrophin constructs performed by the present inventors (data not shown), it is expected that TAT-UTRΔR11-22 should have near-optimal actin filament binding activity, but with a 40% reduction in molecular weight (237,000) compared to full-length utrophin (394,000). TAT-UTRΔR7-22, which is less than half the molecular weight of full-length utrophin (189,000) will also be evaluated, but at the expense of diminished actin-binding activity. TAT-UTRΔR4-21 will also be generated and tested. This construct is expected to bind actin with the lowest affinity. It is an attractive compound for incorporation into a pharmaceutical composition because based on its small size (42% of full-length utrophin), and in light of the success of the analogous dystrophin micro-gene to rescue the mdx phenotype (Harper et al., 2002).

pFASTBAC1 donor plasmids carrying each new TAT construct is transformed into DHIOBAC for site-specific transposition into bMON14272 bacmid DNA. Colonies containing recombinant bacmid DNA are identified by blue-white screening and high titer viral stocks produced for infection of Sf21 insect cells for protein expression. Protein purification, quality control and transduction efficacy are performed as described earlier.

Example 4

—Dose-Dependent Amelioration of Dystrophin-Deficient Phenotype:

To determine whether the ability of TAT-utrophin to ameliorate the dystrophin-deficient phenotype is dose-dependent, the protective effects of increased dosages of TAT-utrophin were assessed on the dystrophin-deficient mdx mouse. An initial dosage of 20 µg protein/g mouse body weight was arbitrarily designated as a dosage of "1×." A study was then performed in which littermate mdx mice were injected with 1× (20 µg protein/g body weight), 2× (40 µg protein/g body weight), and 5× (100 µg protein/g body weight) levels of TAT-utrophin. The timeline of treatment was consistent with the original 1× studies (see above) in which 2.5 week-old mdx mice received six intraperitoneal injections at the indicated dosage. The doses were administered bi-weekly. As controls, littermate mdx mice received sterile PBS injections in parallel. At six weeks of age, treated and control mice were euthanized and assessed for several functional and histological parameters of dystrophin deficiency.

Figure 11:
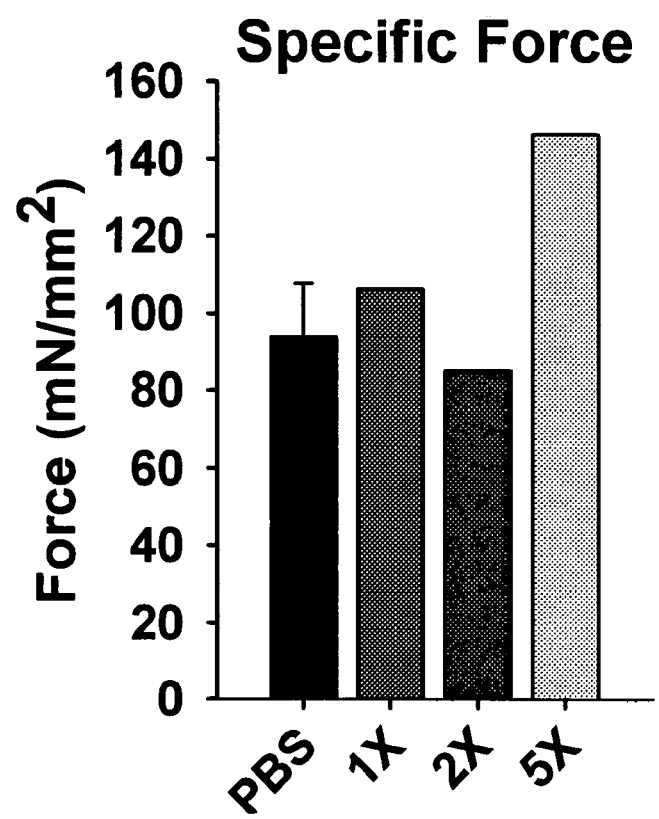
FIG. 11 is a histogram depicting the dose-dependent ability of TAT-utrophin to increase the specific force of muscle tissue in mdx mice treated with the TAT-utrophin.

Of note, the 5×-treated mdx mouse demonstrated an approximately 45% increase in specific force generation over PBS-injected mice (see FIG. 11, which depicts the results for PBS-treated versus TAT-utrophin-treated mice). Specific force is an index of maximal force generated by a muscle normalized against the cross-sectional area of the muscle; mdx muscle typically generates approximately 25-30% less specific force than wild-type mice (Petrof et al., 1993).

Figure 12:
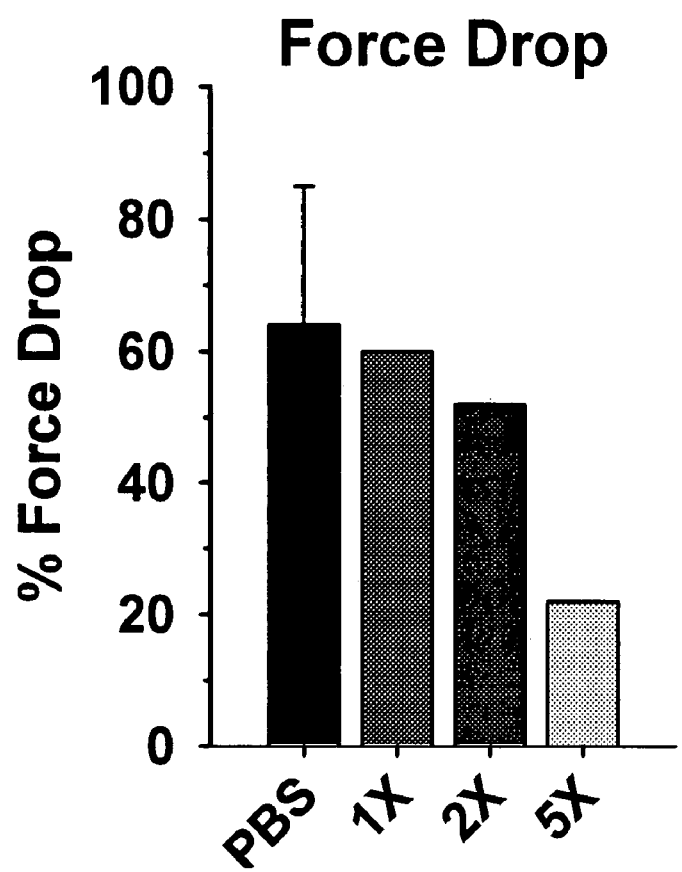
FIG. 12 is a histogram depicting the dose-dependent ability of TAT-utrophin to decrease contraction-induced injury of muscle tissue in mdx mice treated with the TAT-utrophin.

Additionally, the treated mdx mice exhibited a dose-dependent improvement in protection against contraction-induced injury (see FIG. 12, which depicts the results for PBS-treated versus TAT-utrophin-treated mice). Contraction-induced injury is a parameter quantified by the drop in maximal force generation after five (5) consecutive damaging eccentric contractions. Wild-type force drop values are typically 15-25%, while the corresponding mdx values range from 60-80% (Petrof et al., 1993). As shown in FIG. 12, the 5×-treated mdx mice had a force drop value in the range of 20%, which is well within the range for non-mdx, wild-type mice. In contrast, the PBS-treated mdx mice had a force drop value typical of mdx mice, an approximately 65% drop.

Example 5

Figures 13A, 13B:
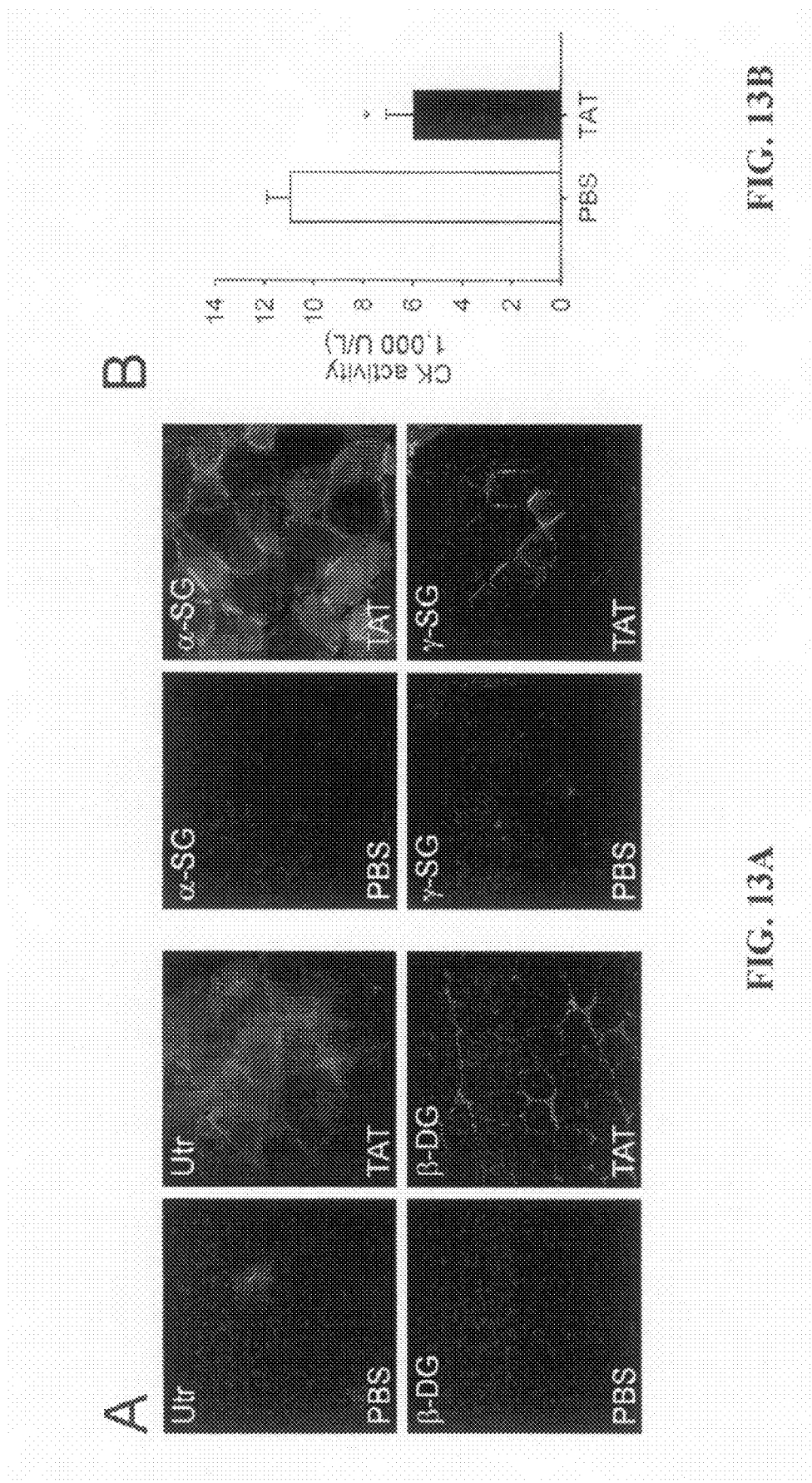
FIG. 13A depicts the results of immunofluorescence analysis on 10 μm thick cryosections from PBS- or TAT-utrophin-injected quadriceps from mdx mice. Primary antibodies to utrophin (NCL-DRP2; Utr), β-dystroglycan (NCL-b-DG; β-DG), α-sarcoglycan (NCL-a-SARC; α-SG), and γ-sarcoglycan (NCL-g-SARC; γ-SG) demonstrated peripherally localized dystrophin complex members in the TAT-utrophin-treated mice.

—Reduction of Serum Creatine Kinase in TAT-Utrophin-treated Mice:

To assess whether the protective effects of TAT-utrophin were mitigated through restoration of dystrophin complex members to the sarcolemma, immunofluorescence analyses were carried out on cryosections from TAT-utrophin and PBS-injected quadriceps. While no signal was observed on cryosections from PBS-treated muscle stained for the transmembrane glycoproteins β-dystroglycan, α-sarcoglycan, and γ-sarcoglycan, each antibody probe revealed intense staining along the periphery of muscle cells from TAT-utrophin-treated mice (FIG. 13A). Sarcolemmal integrity was also assessed by measuring serum levels of the muscle-specific enzyme creatine kinase (CK), which are typically elevated ~20 fold in mdx mice. TAT-utrophin-treated mice demonstrated a 50% reduction in serum CK activity compared to PBS-injected controls. See FIG. 13B. These results strongly indicate that TAT-utrophin not only restored dystrophin complex members to the sarcolemma but also partially protected against membrane instability.

The significance of these Examples is that they show that the TAT-utrophin constructs function to ameliorate dystrophinopathy in a dose-dependent fashion. The Examples also show the now best-known combination of transduction efficiency, size, and pharmacological activity to rescue phenotypically dystrophic mammals.

REFERENCES

Amann, K. J., Guo, W. X. A., and Ervasti, J. M. (1999). Utrophin lacks the rod domain actin binding activity of dystrophin. *J. Biol. Chem.* 274:35375-35380.

Amann, K. J., Renley, B. A., and Ervasti, J. M. (1998). A cluster of basic repeats in the dystrophin rod domain binds F-actin through an electrostatic interaction. *J. Biol. Chem.* 273:28419-28423.

Barchi, R. L. & Weigele, J. B. (1979). Characteristics of saxitoxin binding to the sodium channel of sarcolemma isolated from rat skeletal muscle. *J. Physiol.* 295:383-396.

Blake, D. J., Tinsley, J. M., and Davies, K. E. (1996). Utrophin: A structural and functional comparison to dystrophin. *Brain Pathol.* 6:37-47.

Blake, D. J., Weir, A., Newey, S. E., and Davies, K. E. (2002). Function and genetics of dystrophin and dystrophin-related proteins in muscle. *Physiol Rev.* 82:291-329.

Cohn, R. D. & Campbell, K. P. (2000). Molecular basis of muscular dystrophies. *Muscle Nerve* 23:1456-1471.

Deconinck, A. E., Rafael, J. A., Skinner, J. A., Brown, S. C., Potter, A. C., Metzinger, L., Watt, D. J., Dickson, J. G., Tinsley, J. M., and Davies, K. E. (1997a). Utrophin-dystrophin-deficient mice as a model for Duchenne muscular dystrophy. *Cell* 90:717-727.

Deconinck, N., Tinsley, J., De Backer, F., Fisher, R., Kahn, D., Phelps, S., Davies, K., and Gillis, J. M. (1997b). Expression of truncated utrophin leads to major functional improvements in dystrophin-deficient muscles of mice. *Nature Med.* 3:1216-1221.

Eddinger, T. J., Cassens, R. G., and Moss, R. L. (1986). Mechanical and histochemical characterization of skeletal muscles from senescent rats. *Am. J. Physiol.* 251 :C421-C430.

Ervasti, J. M., Kahl, S. D., and Campbell, K. P. (1991). Purification of dystrophin from skeletal muscle. *J. Biol. Chem.* 266:9161-9165.

Fisher, R., Tinsley, J. M., Phelps, S. R., Squire, S. E., Townsend, E. R., Martin, J. E., and Davies, K. E. (2001). Non-toxic ubiquitous over-expression of utrophin in the mdx mouse. *Neuromuscul. Disord.* 11:713-721.

Grady, R. M., Teng, H. B., Nichol, M. C., Cunningham, J. C., Wilkinson, R. S., and Sanes, J. R. (1997). Skeletal and cardiac myopathies in mice lacking utrophin and dystrophin: A model for Duchenne muscular dystrophy. *Cell* 90:729-738.

Gregorevic, P. and Chamberlain, J. S. (2003). Gene therapy for muscular dystrophy—a review of promising progress. *Expert. Opin. Biol. Ther.* 3:803-814.

Guo, W. X. A., Nichol, M., and Merlie, J. P. (1996). Cloning and expression of full length mouse utrophin: The differential association of utrophin and dystrophin with AChR clusters. *FEBS Lett.* 398:259-264.

Harper, S. Q., Hauser, M. A., DelloRusso, C., Duan, D., Crawford, R. W., Phelps, S. F., Harper, H. A., Robinson, A. S., Engelhardt, J. F., Brooks, S. V., and Chamberlain, J. S. (2002). Modular flexibility of dystrophin: implications for gene therapy of Duchenne muscular dystrophy. *Nat. Med.* 8:253-261.

Hoffman, E. P., Brown, R. H., and Kunkel, L. M. (1987). Dystrophin: the protein product of the Duchenne muscular dystrophy locus. *Cell* 51:919-928.

Ishikawa-Sakurai, M., Yoshida, M., Imamura, M., Davies, K. E., and Ozawa, E. (2004). ZZ domain is essentially required for the physiological binding of dystrophin and utrophin to beta-dystroglycan. *Hum. Mol. Genet.* 13:693-702.

Joliot, A. and Prochiantz, A. (2004). Transduction peptides: from technology to physiology. *Nat. Cell Biol.* 6:189-196.

Khurana, T. S. and Davies, K. E. (2003). Pharmacological strategies for muscular dystrophy. *Nat. Rev. Drug Discov.* 2:379-390.

Krag, T. O., Bogdanovich, S., Jensen, C. J., Fischer, M. D., Hansen-Schwartz, J., Javazon, E. H., Flake, A. W., Edvinsson, L., and Khurana, T. S. (2004). Heregulin ameliorates the dystrophic phenotype in mdx mice. *Proc. Natl. Acad. Sci. U.S.A.* 101:13856-13860.

Kramarcy, N. R., Vidal, A., Froehner, S. C., and Sealock, R. (1994). Association of utrophin and multiple dystrophin short forms with the mammalian $M_r$ 58,000 dystrophin-associated protein (syntrophin). *J. Biol. Chem.* 269:2870-2876.

Kuppuswamy, M., Subramanian, T., Srinivasan, A., and Chinnadurai, G. (1989). Multiple functional domains of Tat, the trans-activator of HIV-1, defined by mutational analysis. *Nucleic Acids Research,* 17(9):3551-3561.

Lindsay, M. A. (2002). Peptide-mediated cell delivery: application in protein target validation. *Curr. Opin. Pharmacol.* 2:587-594.

Marriott, G., Zechel, K., and Jovin, T. M. (1988). Spectroscopic and functional characterization of an environmentally sensitive fluorescent actin conjugate. *Biochemistry* 27:6214-6220.

Matsumura, K., Ervasti, J. M., Ohlendieck, K., Kahl, S. D., and Campbell, K. P. (1992). Association of dystrophin-related protein with dystrophin-associated proteins in mdx mouse muscle. *Nature* 360:588-591.

Miyata, H., Kinosita, K., Jr., and Marriott, G. (1997). Cooperative association of actin protomers and crosslinked actin oligomers in filaments at low ionic strength. *J. Biochem. (Tokyo)* 121:527-533.

Moens, P., Baatsen, P. H., and Marechal, G. (1993). Increased susceptibility of EDL muscles from mdx mice to damage induced by contractions with stretch. *J. Muscle Res. Cell Motil.* 14:446-451.

Nagahara, H., Vocero-Akbani, A. M., Snyder, E. L., Ho, A., Latham, D. G., Lissy, N. A., Becker-Hapak, M., Ezhevsky, S. A., and Dowdy, S. F. (1998). Transduction of full-length TAT fusion proteins into mammalian cells: TAT-p27Kipl induces cell migration. *Nat. Med.* 4:1449-1452.

O'Brien, K. F. and Kunkel, L. M. (2001). Dystrophin and muscular dystrophy: past, present, and future. *Mol. Genet. Metab.* 74:75-88.

Ohlendieck, K., Ervasti, J. M., Snook, J. B., and Campbell, K. P. (1991). Dystrophin-glycoprotein complex is highly enriched in isolated skeletal muscle sarcolemma. *J. Cell Biol.* 112:135-148.

Petrof, B. J., Shrager, J. B., Stedman, H. H., Kelly, A. M., and Sweeney, H. L. (1993). Dystrophin protects the sarcolemma from stresses developed during muscle contraction. *Proc. Natl. Acad. Sci. U.S.A.* 90:3710-3714.

Rybakova, I. N., Amann, K. J., and Ervasti, J. M. (1996). A new model for the interaction of dystrophin with F-actin. *J. Cell Biol.* 135:661-672.

Rybakova, I. N. and Ervasti, J. M. (1997). Dystrophin-glycoprotein complex is monomeric and stabilizes actin filaments in vitro through a lateral association. *J. Biol. Chem.* 272:28771-28778.

Rybakova, I. N., Patel, J. R., Davies, K. E., Yurchenco, P. D., and Ervasti, J. M. (2002). Utrophin binds laterally along actin filaments and can couple costameric actin with the sarcolemma when overexpressed in dystrophin-deficient muscle. *Mol. Biol. Cell* 13:1512-1521.

Rybakova, I. N., Patel, J. R., and Ervasti, J. M. (2000). The dystrophin complex forms a mechanically strong link between the sarcolemma and costameric actin. *J. Cell Biol.* 150:1209-1214.

Rybakova, I. N., Humston J. L., Sonnemann, K. J., Ervasti, J. M. ( 2006) Dystrophin and utrophin bind actin through distinct modes of contact. *J. Biol Chem.* 281 (15): 9996-10001.

Schwarze, S. R., Ho, A., Vocero-Akbani, A., and Dowdy, S. F. (1999). In vivo protein transduction: delivery of a biologically active protein into the mouse. *Science* 285:1569-1572.

Schwarze, S. R., Hruska, K. A., and Dowdy, S. F. (2000). Protein transduction: unrestricted delivery into all cells? *Trends Cell Biol.* 10:290-295.

Snyder, E. L. and Dowdy, S. F. (2004). Cell penetrating peptides in drug delivery. *Pharm. Res.* 21:389-393.

Straub, V., Rafael, J. A., Chamberlain, J. S., and Campbell, K. P. (1997). Animal models for muscular dystrophy show different patterns of sarcolemmal disruption. *J. Cell Biol.* 139:375-385.

Tinsley, J., Deconinck, N., Fisher, R., Kahn, D., Phelps, S., Gillis, J. M., and Davies, K. (1998). Expression of full-length utrophin prevents muscular dystrophy in mdx mice. *Nature Med.* 4:1441-1444.

Tinsley, J. M., Blake, D. J., Roche, A., Byth, B. C., Knight, A. E., Kendrick-Jones, J., Suthers, G. K., Love, D. R., Edwards, Y. H., and Davies, K. E. (1992). Primary structure of dystrophin-related protein. *Nature* 360:591-593.

Tinsley, J. M., Potter, A. C., Phelps, S. R., Fisher, R., Trickett, J. I., and Davies, K. E. (1996). Amelioration of the dystrophic phenotype of mdx mice using a truncated utrophin transgene. *Nature* 384:349-353.

Wang, B., Li, J., and Xiao, X. (2000). Adeno-associated virus vector carrying human mindystrophin genes effectively ameliorates muscular dystrophy in mdx mouse model. *Proc. Natl. Acad. Sci. U.S.A.* 97:13714-13719.

Warner, L. E., DelloRusso, C., Crawford, R. W., Rybakova, I. N., Patel, J. R., Ervasti, J. M., and Chamberlain, J. S. (2002). Expression of Dp260 in muscle tethers the actin cytoskeleton to the dystrophin-glycoprotein complex. *Hum. Mol. Genet.* 11: 1095-1105.

Winder, S. J., Hemmings, L., Maciver, S. K., Bolton, S. J., Tinsley, J. M., Davies, K. E., Critchley, D. R., and Kendrick-Jones, J. (1995). Utrophin actin binding domain: analysis of actin binding and cellular targeting. *J. Cell Sci.* 108(1):63-71.

---

What is claimed is:

1. An isolated fusion protein comprising:
   a first protein region comprising a human immunodeficiency virus transactivator protein (HIV-TAT) or a transduction-effective fragment thereof which is effective to transduce the fusion protein into mammalian muscle cells, operationally linked to;
   a second protein region comprising a full-length utrophin protein or an anti-dystrophinopathic fragment thereof.

2. The isolated fusion protein of claim 1, further comprising an affinity tag operationally linked to the fusion protein.

3. The isolated fusion protein of claim 2, wherein the affinity tag comprises an amino acid sequence DYKDDDDK (SEQ. ID. NO: 1) or a fragment thereof.

4. The isolated fusion protein of claim 2, wherein the affinity tag comprises an amino acid sequence DYKD (SEQ. ID. NO: 28).

5. The isolated fusion protein of claim 1, wherein the second protein region is an anti-dystrophinopathic utrophin fragment comprising an amino-terminal actin-binding domain of the utrophin protein, or the amino-terminal actin-binding domain domain plus 4, 7, 10, or 11 spectrin-like repeats.

6. The isolated fusion protein of claim 1, wherein the second protein region is an amino acid sequence selected from the group consisting of SEQ. ID. NOS: 7 and 9.

7. The isolated fusion protein of claim 1, which is an amino acid sequence selected from the group consisting of SEQ. ID. NOS: 11, 13, 15, 17, 19, 21, 23, and 25.

8. The isolated fusion protein of claim 1, wherein the first protein region is an amino acid sequence as shown in SEQ. ID. NO: 2.

9. The isolated fusion protein of claim 8, wherein the second protein region is an anti-dystrophinopathic utrophin fragment comprising an amino-terminal actin-binding domain of the utrophin protein, or the amino-terminal actin-binding domain domain plus 4, 7, 10, or 11 spectrin-like repeats.

10. The isolated fusion protein of claim 8, wherein the second protein region is an amino acid sequence selected from the group consisting of SEQ. ID. NOS: 7and 9.

11. The isolated fusion protein of claim 1, wherein the first protein region is an amino acid sequence as shown in SEQ. ID. NO: 5: YGRKKRRQRRR.

12. The isolated fusion protein of claim 11, wherein the second protein region is an anti-dystrophinopathic utrophin fragment comprising an amino-terminal actin-binding domain of the utrophin protein, or the amino-terminal actin-binding domain domain plus 4, 7, 10, or 11 spectrin-like repeats.

13. The isolated fusion protein of claim 11, wherein the second protein region is an amino acid sequence selected from the group consisting of SEQ. ID. NOS: 7and 9.

14. The isolated fusion protein of claim 1, wherein the second protein region is an anti-dystrophinopathic utrophin fragment comprising no more than 75% of the mass of the full-length utrophin protein.

15. The isolated fusion protein of claim 1, wherein the second protein region is an anti-dystrophinopathic utrophin fragment comprising no more than 50% of the mass of the full-length utrophin protein.

16. The isolated fusion protein of claim 1, wherein the second protein region is an anti-dystrophinopathic utrophin fragment comprising no more than 25% of the mass of the full-length utrophin protein.

17. Pharmaceutically suitable salts of the isolated fusion protein recited in claim 1.

18. A pharmaceutical composition for treating dystrophinopathies in mammals, including humans, comprising:
   an isolated fusion protein or a pharmaceutically suitable salt thereof as recited in any one of claims 1-7 and 8-17, in combination with a pharmaceutically suitable carrier.

19. A method of treating dystrophinopathies in mammals, the method comprising administering to a mammalian subject in need thereof an anti-dystrophinopathic amount of an isolated fusion protein or a pharmaceutically suitable salt thereof as recited in any one of claims 1-7 and 8-17.

20. An isolated nucleic acid expression construct encoding a fusion protein, the nucleic acid expression construct comprising:
   a first nucleic acid region that encodes a first protein region of the fusion protein, wherein the first protein region comprises a human immunodeficiency virus transactivator protein (HIV-TAT) or a transduction-effective fragment thereof which is effective to transduce the fusion protein into mammalian muscle cells, operationally linked to;
   a second nucleic acid region that encodes a second protein region of the fusion protein, wherein the second protein region comprises a full-length utrophin protein or an anti-dystrophinopathic fragment thereof;
   wherein the expression construct drives expression of the fusion protein when transformed into a suitable host cell or disposed into a suitable cell-free expression system.

21. The isolated nucleic acid expression construct of claim 2, further comprising a third nucleic acid region that encodes an affinity tag that is operationally linked to the fusion protein.

22. The isolated nucleic acid expression construct of claim 20, wherein the third nucleic acid region encodes an amino acid sequence DYKDDDDK (SEQ. ID. NO: 1) or a fragment thereof.

23. The isolated nucleic acid expression construct of claim 20, wherein the third nucleic acid region encodes an amino acid sequence DYKD (SEQ. ID. NO: 28).

24. The isolated nucleic acid expression construct of claim 20, wherein the second nucleic acid region encodes an anti-dystrophinopathic utrophin fragment comprising an amino-terminal actin-binding domain of the utrophin protein, or the amino-terminal actin-binding domain domain plus 4, 7, 10, or 11 spectrin-like repeats.

25. The isolated nucleic acid expression construct of claim 20, wherein the second nucleic acid region encodes an amino acid sequence selected from the group consisting of SEQ. ID. NOS: 7 and 9.

26. The isolated nucleic acid expression construct of claim 20, which is a nucleic acid sequence selected from the group consisting of SEQ. ID. NOS: 10, 12, 14, 16, 18, 20, 22, and 24.

27. The isolated nucleic acid expression construct of claim 20, wherein the first nucleic acid region encodes an amino acid sequence as shown in SEQ. ID. NO: 2.

28. The isolated nucleic acid expression construct of claim 27, wherein the second nucleic acid region encodes an anti-dystrophinopathic utrophin fragment comprising an amino-terminal actin-binding domain of the utrophin protein, or the amino-terminal actin-binding domain domain plus 4, 7, 10, or 11 spectrin-like repeats.

29. The isolated nucleic acid expression construct of claim 27, wherein the second nucleic acid region encodes an amino acid sequence selected from the group consisting of SEQ. ID. NOS: 7 and 9.

30. The isolated nucleic acid expression construct of claim 20, wherein the first nucleic acid region encodes an amino acid sequence as shown in SEQ. ID. NO: 5: YGRKKRRQRRR.

31. The isolated nucleic acid expression construct of claim 30, wherein the second nucleic acid region encodes an anti-dystrophinopathic utrophin fragment comprising an amino-terminal actin-binding domain of the utrophin protein, or the amino-terminal actin-binding domain domain plus 4, 7, 10, or 11 spectrin-like repeats.

32. The isolated nucleic acid expression construct of claim 30, wherein the second nucleic acid region encodes an amino acid sequence selected from the group consisting of SEQ. ID. NOS: 7 and 9.

33. The isolated nucleic acid expression construct of claim 20, wherein the second nucleic acid region encodes an anti-dystrophinopathic utrophin fragment comprising no more than 75% of the mass of the full-length utrophin protein.

34. The isolated nucleic acid expression construct of claim 20, wherein the second nucleic acid region encodes an anti-dystrophinopathic utrophin fragment comprising no more than 50% of the mass of the full-length utrophin protein.

35. The isolated nucleic acid expression construct of claim 20, wherein the second nucleic acid region encodes an anti-dystrophinopathic utrophin fragment comprising no more than 25% of the mass of the full-length utrophin protein.

* * * * *

UNITED STATES PATENT AND TRADEMARK OFFICE
CERTIFICATE OF CORRECTION

PATENT NO. : 7,863,017 B2  Page 1 of 1
APPLICATION NO. : 11/998798
DATED : January 4, 2011
INVENTOR(S) : James M. Ervasti and Kevin J. Sonnemann It is certified that error appears in the above-identified patent and that said Letters Patent is hereby corrected as shown below:

At column 1, under the heading "FEDERAL FUNDING STATEMENT" delete lines 13-16 and insert therefor:

--This invention was made with government support under AR042423 awarded by the National Institutes of Health. The government has certain rights in the invention.--

Signed and Sealed this
Twenty-second Day of March, 2011

David J. Kappos
*Director of the United States Patent and Trademark Office*